US010640534B2

(12) United States Patent
Popovici-Muller et al.

(10) Patent No.: US 10,640,534 B2
(45) Date of Patent: May 5, 2020

(54) THERAPEUTICALLY ACTIVE COMPOSITIONS AND THEIR METHODS OF USE

(71) Applicant: Agios Pharmaceuticals, Inc., Cambridge, MA (US)

(72) Inventors: Janeta Popovici-Muller, Windham, NH (US); Rene M. Lemieux, Charlestown, MA (US); Jeremy Travins, Southborough, MA (US); Zhenwei Cai, Skillman, NJ (US); Dawei Cui, Shanghai (CN); Ding Zhou, Shanghai (CN)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/809,325

(22) Filed: Nov. 10, 2017

(65) Prior Publication Data

US 2018/0194802 A1    Jul. 12, 2018

Related U.S. Application Data

(63) Continuation of application No. 15/279,146, filed on Sep. 28, 2016, now Pat. No. 9,850,277, which is a continuation of application No. 13/745,005, filed on Jan. 18, 2013, now Pat. No. 9,474,779.

(30) Foreign Application Priority Data

Jan. 19, 2012    (WO) ................ PCT/CN2012/070601

(51) Int. Cl.
*C07D 207/26* (2006.01)
*C07D 401/04* (2006.01)
*C07D 403/04* (2006.01)
*C07K 5/065* (2006.01)
*C07D 205/08* (2006.01)
*C07D 401/14* (2006.01)
*C07D 413/04* (2006.01)
*C07D 417/04* (2006.01)
*A61K 38/05* (2006.01)
*A61K 45/06* (2006.01)
*A61K 38/00* (2006.01)
*C07K 5/06* (2006.01)

(52) U.S. Cl.
CPC ........ *C07K 5/06078* (2013.01); *A61K 38/005* (2013.01); *A61K 38/05* (2013.01); *A61K 45/06* (2013.01); *C07D 205/08* (2013.01); *C07D 207/26* (2013.01); *C07D 401/04* (2013.01); *C07D 401/14* (2013.01); *C07D 403/04* (2013.01); *C07D 413/04* (2013.01); *C07D 417/04* (2013.01); *C07K 5/06191* (2013.01)

(58) Field of Classification Search
CPC ... C07D 207/26; C07D 401/04; C07D 403/04
See application file for complete search history.

(56) References Cited

U.S. PATENT DOCUMENTS

| | | |
|---|---|---|
| 2,390,529 A | 12/1945 | Friedheim |
| 3,755,322 A | 8/1973 | Winter et al. |
| 3,867,383 A | 2/1975 | Winter |
| 4,084,053 A | 4/1978 | Desai et al. |
| 5,021,421 A | 6/1991 | Hino et al. |
| 5,489,591 A | 2/1996 | Kobayashi et al. |
| 5,807,876 A | 9/1998 | Armistead et al. |
| 5,834,485 A | 11/1998 | Dyke et al. |
| 5,965,559 A | 10/1999 | Faull et al. |
| 5,965,569 A | 10/1999 | Camps Garcia et al. |
| 5,984,882 A | 11/1999 | Rosenschein et al. |
| 6,262,113 B1 | 7/2001 | Widdowson et al. |
| 6,274,620 B1 | 8/2001 | Labrecque et al. |
| 6,313,127 B1 | 11/2001 | Waterson et al. |
| 6,399,358 B1 | 6/2002 | Williams et al. |
| 6,576,235 B1 | 6/2003 | Williams et al. |
| 6,723,730 B2 | 4/2004 | Bakthavatchalam et al. |
| 6,783,965 B1 | 8/2004 | Sherman et al. |
| 6,979,675 B2 | 12/2005 | Tidmarsh |
| 7,173,025 B1 | 2/2007 | Stocker et al. |
| 7,858,782 B2 | 12/2010 | Tao et al. |
| 8,133,900 B2 | 3/2012 | Hood et al. |
| 8,465,673 B2 | 6/2013 | Yasuda et al. |
| 8,957,068 B2 | 2/2015 | Caferro et al. |
| 9,850,277 B2 | 12/2017 | Popovici-Muller et al. |
| 9,968,595 B2 | 5/2018 | Gu |
| 2002/0049310 A1 | 4/2002 | Tateishi et al. |
| 2002/0188027 A1 | 12/2002 | Robinson et al. |
| 2003/0095958 A1 | 5/2003 | Bhisetti et al. |
| 2003/0109527 A1 | 6/2003 | Jin et al. |
| 2003/0207882 A1 | 11/2003 | Stocker et al. |
| 2003/0213405 A1 | 11/2003 | Harada et al. |
| 2004/0067234 A1 | 4/2004 | Einat et al. |
| 2004/0248221 A1 | 12/2004 | Stockwell |
| 2005/0261268 A1 | 11/2005 | Amost et al. |
| 2006/0084645 A1 | 4/2006 | Pal et al. |
| 2006/0281122 A1 | 12/2006 | Bryant et al. |
| 2007/0244088 A1 | 10/2007 | Brickmann et al. |
| 2008/0132490 A1 | 6/2008 | Bergman et al. |
| 2008/0300208 A1 | 12/2008 | Einat et al. |

(Continued)

FOREIGN PATENT DOCUMENTS

| | | |
|---|---|---|
| CN | 101296909 A | 10/2008 |
| CN | 101575408 A | 11/2009 |

(Continued)

OTHER PUBLICATIONS

Aghili et al. "Hydroxyglutaric aciduria and malignant brain tumor: a case report and literature review", Journal of Neuroncology (2008) 91 pp. 233-236.

(Continued)

*Primary Examiner* — Samira J Jean-Louis
(74) *Attorney, Agent, or Firm* — Goodwin Procter LLP

(57) ABSTRACT

Provided are methods of treating a cancer characterized by the presence of a mutant allele of IDH1/2 comprising administering to a subject in need thereof a compound described here.

6 Claims, No Drawings

(56) References Cited

U.S. PATENT DOCUMENTS

| | | |
|---|---|---|
| 2009/0093526 A1 | 4/2009 | Miller et al. |
| 2009/0163508 A1 | 6/2009 | Kori et al. |
| 2009/0163545 A1 | 6/2009 | Goldfarb |
| 2009/0281089 A1 | 11/2009 | Gunzner et al. |
| 2009/0286752 A1 | 11/2009 | Etter et al. |
| 2010/0129350 A1 | 5/2010 | Zacharie et al. |
| 2010/0144722 A1 | 6/2010 | Alexander et al. |
| 2010/0273808 A1 | 10/2010 | Armitage et al. |
| 2010/0331307 A1 | 12/2010 | Salituro et al. |
| 2011/0073007 A1 | 3/2011 | Yasuda et al. |
| 2011/0086088 A1 | 4/2011 | Berry |
| 2011/0288065 A1 | 11/2011 | Fujihara et al. |
| 2012/0121515 A1 | 5/2012 | Dang et al. |
| 2012/0129865 A1 | 5/2012 | Wang et al. |
| 2012/0164143 A1 | 6/2012 | Teeling et al. |
| 2012/0202818 A1 | 8/2012 | Tao et al. |
| 2012/0238576 A1 | 9/2012 | Tao et al. |
| 2012/0277233 A1 | 11/2012 | Tao et al. |
| 2013/0035329 A1 | 2/2013 | Saunders et al. |
| 2013/0109643 A1 | 5/2013 | Riggins et al. |
| 2013/0183281 A1 | 7/2013 | Su et al. |
| 2013/0184222 A1 | 7/2013 | Popovici-Muller et al. |
| 2013/0190249 A1 | 7/2013 | Lemieux et al. |
| 2013/0190287 A1 | 7/2013 | Cianchetta et al. |
| 2013/0197106 A1 | 8/2013 | Fantin et al. |
| 2014/0094503 A1 | 4/2014 | Ma et al. |
| 2014/0187435 A1 | 7/2014 | Dang et al. |
| 2014/0206673 A1 | 7/2014 | Cao et al. |
| 2014/0213580 A1 | 7/2014 | Cao et al. |
| 2015/0018328 A1 | 1/2015 | Konteatis et al. |
| 2015/0031627 A1 | 1/2015 | Lemieux et al. |
| 2015/0044716 A1 | 2/2015 | Balss et al. |
| 2015/0087600 A1 | 3/2015 | Popovici-Muller et al. |
| 2015/0240286 A1 | 8/2015 | Dang et al. |
| 2015/0299115 A1 | 10/2015 | Popovici-Muller et al. |
| 2016/0130298 A1 | 5/2016 | Lemieux et al. |
| 2016/0264621 A1 | 9/2016 | Popovici-Muller et al. |
| 2016/0304556 A1 | 10/2016 | Popovici-Muller et al. |
| 2017/0007661 A1 | 1/2017 | Gu |
| 2017/0014396 A1 | 1/2017 | Gu |
| 2017/0057994 A1 | 3/2017 | Lemieux et al. |
| 2019/0023737 A1 | 1/2019 | Lemieux et al. |

FOREIGN PATENT DOCUMENTS

| | | |
|---|---|---|
| CN | 102659765 A | 9/2012 |
| CN | 103097340 A | 5/2013 |
| DE | 2263878 A1 | 7/1973 |
| DE | 3314663 A1 | 10/1983 |
| DE | 3512630 A1 | 10/1986 |
| EP | 0022958 A1 | 1/1981 |
| EP | 0384228 A1 | 8/1990 |
| EP | 0385237 A2 | 9/1990 |
| EP | 0945446 A1 | 9/1999 |
| EP | 1391487 A2 | 2/2004 |
| EP | 1886673 A2 | 2/2008 |
| FR | 2735127 A1 | 12/1996 |
| GB | 1033266 A | 6/1966 |
| JP | H04099768 A | 3/1992 |
| JP | H05140126 A | 6/1993 |
| JP | H09291034 A | 11/1997 |
| JP | H11158073 A | 6/1999 |
| JP | 2004107220 A | 4/2004 |
| JP | 2005264016 A | 9/2005 |
| JP | 2009237115 A | 10/2009 |
| JP | 2010079130 A | 4/2010 |
| JP | 2010181540 A | 8/2010 |
| JP | 4753336 B2 | 8/2011 |
| JP | 2013519858 A | 5/2013 |
| TW | 201028381 A | 8/2010 |
| WO | 1996030343 A1 | 10/1996 |
| WO | 9728128 A1 | 8/1997 |
| WO | 9728129 A1 | 8/1997 |
| WO | 1997044322 A1 | 11/1997 |
| WO | 9932463 A1 | 7/1999 |
| WO | 00002864 A1 | 1/2000 |
| WO | 2001016097 A1 | 3/2001 |
| WO | 2001019788 A2 | 3/2001 |
| WO | 2001019798 A2 | 3/2001 |
| WO | 0147897 A1 | 7/2001 |
| WO | 2001064642 A2 | 9/2001 |
| WO | 2001064643 A2 | 9/2001 |
| WO | 2002100822 A1 | 12/2002 |
| WO | 2002102313 A2 | 12/2002 |
| WO | 030016289 A1 | 2/2003 |
| WO | 2004009562 A1 | 1/2004 |
| WO | 2004046120 A2 | 6/2004 |
| WO | 2004050033 A2 | 6/2004 |
| WO | 2004073619 A2 | 9/2004 |
| WO | 2004074438 A2 | 9/2004 |
| WO | 2004089470 A2 | 10/2004 |
| WO | 2005035507 A2 | 4/2005 |
| WO | 2005060956 A1 | 7/2005 |
| WO | 2005065691 A1 | 7/2005 |
| WO | 2005103015 A1 | 11/2005 |
| WO | 2005120474 A2 | 12/2005 |
| WO | 2006034341 A2 | 3/2006 |
| WO | 2006038594 A1 | 4/2006 |
| WO | 2006070198 A1 | 7/2006 |
| WO | 2006079791 A1 | 8/2006 |
| WO | 2006/110761 A2 | 10/2006 |
| WO | 2007003934 A2 | 1/2007 |
| WO | 2007023186 A1 | 3/2007 |
| WO | 2008036835 A2 | 3/2008 |
| WO | 2008050168 A1 | 5/2008 |
| WO | 2008050186 A1 | 5/2008 |
| WO | 2008052190 A2 | 5/2008 |
| WO | 2008070661 A1 | 6/2008 |
| WO | 2008073670 A2 | 6/2008 |
| WO | 2008076883 A2 | 6/2008 |
| WO | 2008131547 A1 | 11/2008 |
| WO | 2008154026 A1 | 12/2008 |
| WO | 2009013126 A1 | 1/2009 |
| WO | 2009015254 A1 | 1/2009 |
| WO | 2009016410 A2 | 2/2009 |
| WO | WO-2009051910 A1 * | 4/2009 ........... A61K 31/167 |
| WO | 2009118567 A2 | 10/2009 |
| WO | 2009126863 A2 | 10/2009 |
| WO | 2009150248 A1 | 12/2009 |
| WO | 2010007756 A1 | 1/2010 |
| WO | 2010028099 A1 | 3/2010 |
| WO | 2010105243 A1 | 9/2010 |
| WO | 2010129596 A1 | 11/2010 |
| WO | 2010130638 A1 | 11/2010 |
| WO | 2010144338 A1 | 12/2010 |
| WO | 2010144404 A1 | 12/2010 |
| WO | 201105210 A1 | 1/2011 |
| WO | 2011002817 A1 | 1/2011 |
| WO | 2011/027249 A2 | 3/2011 |
| WO | 2011032169 A2 | 3/2011 |
| WO | 2011047432 A1 | 4/2011 |
| WO | 2011050210 A1 | 4/2011 |
| WO | 2011072174 A1 | 6/2011 |
| WO | 2012006506 A1 | 1/2012 |
| WO | 2012009678 A1 | 1/2012 |
| WO | 2012074999 A1 | 6/2012 |
| WO | 2012078288 A2 | 6/2012 |
| WO | 2012092442 A1 | 7/2012 |
| WO | 2012151452 A1 | 11/2012 |
| WO | 2012160034 A1 | 11/2012 |
| WO | 2012171337 A1 | 12/2012 |
| WO | 2012171506 A1 | 12/2012 |
| WO | 2012173682 A2 | 12/2012 |
| WO | 2013004332 A1 | 1/2013 |
| WO | 2013007708 A1 | 1/2013 |
| WO | 2013016206 A1 | 1/2013 |
| WO | 2013102431 A1 | 7/2013 |
| WO | 2013107291 A1 | 7/2013 |
| WO | 2013107405 A1 | 7/2013 |
| WO | 2013133367 A1 | 9/2013 |
| WO | 2014015422 A1 | 1/2014 |
| WO | 2015/003360 A2 | 1/2015 |
| WO | 2015127173 A1 | 8/2015 |
| WO | 2015138837 A1 | 9/2015 |

(56) References Cited

FOREIGN PATENT DOCUMENTS

| WO | 2015138839 A1 | 9/2015 |
|---|---|---|
| WO | 2017066566 A1 | 4/2017 |
| WO | 2017066571 A1 | 4/2017 |
| WO | 2017096309 A1 | 6/2017 |
| WO | 2017146795 A1 | 8/2017 |

OTHER PUBLICATIONS

Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Balss, "Analysis of the IDH1 codon 132 mutation in brain tumors", Acta Neuropathol (2008) vol. 116, pp. 597-602.
Benner et al, "Evolution, language and analogy in functional genomics", Trends in Genetics (2001) vol. 17, pp. 414-418.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Bleeker et al., "IDH1 mutations at residue p. R132 (IDH1 (R132)) occur frequently in high-grade 18-22 gliomas but not in other solid tumors." Hum Mutal., (2009) vol. 30, No. 1, pp. 7-11.
Braun et al. "Triazine-based polymers: 4. MALDI-MS of triazine-based polyamines" Polymer (1996) vol. 37, No. 5, pp. 777-783.
Cairns et al. "Oncogenic Isocitrate Dehydrogenase Mutations: Mechanisms, Models, and Clinical Opportunities" Cancer Discovery (2013) vol. 3, Iss 7, pp. 730-741.
Cecil Text Book of Medicine, edited by BENNET and PLUM, (1997) 20th edition, vol. 1, pp. 1004-1010.
Chan et al. "Multi-domain hydrogen-bond forming metal chelates: X-ray crystal structuresof dicyclopalladated 2,3-bis [6-(2-amino-4-phenylamino-1 ,3,5-triazinyl)]pyrazine(H2L) [Pd2Br2L] and 2,6-bis[6-(2-amino-4-phenylamino-1,3,5-triazinylium)] -pyridine dichloride" Chemical Communications (1996) No. 1, pp. 81-83.
Chapman et al. "Substituted aminopyrimidine protein kinase B (PknB) inhibitorsshow activity against Mycobacterium tuberculosis" Bioorganic & Medicinal Chemistry Letters (2012) vol. 22, pp. 3349-3353.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry (1995) vol. 32, pp. 543-545.
Dang et al., "Cancer-associated IDH1 mutations produce 2-hydroxyglutarate." Nature (2009) vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Database CA [Online] Chemical Abstracts Service. Columbus.Ohio. US; Baibulova M. S. et al:'Syntheses from pyridylguanamines"_ XP002764691. retrieved from STN Database accession No. 1990:406282 *abstract* & Bai Bulova, M. S. et al:Syntheses from pyridylguanamines", Izvestiya Akademii Nauk Kazakhskoi SSR, Seriya Khimicheskaya, (5), 40-2 CODEN: Ikakak; ISSN: 0002-3205, 1989.
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Dermer "another Anniversary for the War on Cancer" Bio/Technology (1994) vol. 12, p. 320.
Dohner et al. "Impact of Genetic Features on Treatment Decisions in AML" American Society of Hematology (2011) pp. 36-42.

Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
EP Search Report Written Opinion for EP 10825706 dated Mar. 20, 2013.
European Search Report for Application No. 10751525.6 dated Dec. 14, 2012.
Eurpoean Search Report for EP Application No. 11763425.3 dated Sep. 23, 2013.
European Search Report for European Application No. 12799802.9 dated Sep. 24, 2014.
European Search Report for European Application No. EP 12800001.5 dated Oct. 10, 2014.
Extended European Search Report for PCT/CN2014081957 dated Dec. 9, 2016.
Freshney et al. "Culture of Animal Cells, A Manual of Basic Techniques" Alan R. Liss, Inc. (1983) pp. 1-6.
Gewald et al. "Discovery of triazines as potent, selective and orally active PDE4 inhibitors" Bioorganic & medicinal Chemistry Letters (2013) vol. 23, pp. 4308-4314.
Golub et al. "Molecular Classification of Cancer: Class Discovery and Class Prediction by Gene Expression Monitoring" Science (1999) vol. 286, pp. 531-537.
Hartmann et al. "Type and Frequency of IDH1 and IDH2 mutations are related to astrocytic and oligodendroglial differentiation and age: a study of 1010 diffuse gliomas" Acta Neuropathologica (2009) vol. 118, pp. 469-474.
Ho et al., "Triazine and pyrimidine based ROCK inhibitors with efficacy in spontaneous hypertensive rat model." Bioorganic & Medicinal Chemistry Letters (2009) vol. 19, pp. 6027-6031.
Holmes et al. "750 MHz 1H NMR spectroscopy characterisation of the complex metabolic pattern of urine from patients with inborn errors of metabolism: 2-hydroxyglutaric aciduria and maple syrup urine disease" Journal of Pharmaceutical and Biomedical Analysis (1997) vol. 15, pp. 1647-1659.
Huang et al., "N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease," Bioorganic & Medicinal Chemistry Letters (2007) vol. 12, pp. 5783-5789.
International Preliminary Report on Patentability for PCT/CN2012/000841 dated Dec. 17, 2013.
International Search Report for PCT/CN2013/000068 dated Apr. 25, 2013.
International Search Report for PCT/US2010053624 dated Apr. 7, 2011.
International Search Report for PCT/US2011/067752 dated Feb. 22, 2012.
International Preliminary Report for related application No. PCT/US2010/059778 dated Jun. 12, 2012.
International Preliminary Report on Patentability for PCT/CN2012/077096 dated Dec. 17, 2013.
International Preliminary Report on Patentability for PCT/US2010/027253 dated Sep. 13, 2011.
International Preliminary Report on Patentability for Application No. PCT/US2010/053623 dated Apr. 24, 2012.
International Preliminary Report on Patentability for PCT/US2010/053624 dated Apr. 7, 2011.
International Preliminary Report on Patentability for PCT/US2011/030692 dated Oct. 2, 2012.
International Search Report & Written Opinion for PCT/CN2013/070755 dated Apr. 25, 2013.
International Search Report and Written Opinion for International Application No. PCT/CN2013/080105 dated Jul. 11, 2014.
International Search Report and Written Opinion for International Application No. PCT/CN2013/081170 dated Apr. 30, 2014.
International Search Report and Written Opinion for International Application No. PCT/CN2014/081957 dated Sep. 30, 2014.
International Search Report and Written Opinion for International Application No. PCT/CN2014/081958 dated Sep. 29, 2014.

(56) References Cited

OTHER PUBLICATIONS

International Search Report and Written Opinion for International Application No. PCT/US2014/046202 dated Sep. 30, 2014.
International Search Report and Written Opinion for International Application No. PCT/US2014/049469 dated Jan. 22, 2015.
Amary et al. "Ollier disease and Maffucci syndrome are caused by somatic mosiac mutations of IDH1 and IDH2," Nature Genetics Letters, 2011, 43(12):1262-1266.
Burger et al. "Nuclear substituted 3,4-dihydroxyphenethylamines and related derivatives," Journal of American Chemical Society, 1956, 78(17):4419-4422.
Database CA [Online] Chemical Abstracts Service, Columbus,Ohio, US; Ambartsumyan, E. N. et al: "Synthesis and transformations of chloropyrazolylazines", XP002764692, retrieved from STN Database accession No. 2012:876343 * abstract * & Ambartsumyan, E. N. et al: "Synthesis and transformations of chloropyrazolylazines", Hayastani Kimiakan Handes ( 2011 ), 64(4), 544-550 CODEN: KZARF3; ISSN: 1561-4190, 2011.
Database CA [Online] Chemical Abstracts Service. Columbus.Ohio. US; Krimmer. Hans Peter et al: "Reaction of .beta.-mercapto .alpha.-amino acids with nitriles".XP002764690.retrieved from STN Database accession No. 1988:529623* abstract* & Krimmer. Hans Peter et al: "Reaction of .beta.-mercapto .alpha.-amino acids with nitriles".Chemiker-Zeitung â€¢ 111(12). 357-61 CODEN: CMKZAT; ISSN: 0009-2894.1987.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Dohner et al. "Acute myeloid leukemia," New England Journal of Medicine, 2015, 373:1136-52.
Drew, MGB, et al. "Solvent extraction and lanthanide complexation studies with new terdentate ligands containing two 1, 3, 5-triazine moieties." Dalton Transactions 2 (2004): 244-251.
Enholm, EJ., Jed M. Hastings, and Chris Edwards. "Hydrogen-Bonded Arrays Coupled by Cross-Metathesis." Synlett Feb. 2008 (2008): 203-206.
Genetics Home Reference. "L2HGDH." accessed at <http://ghr.nlm.nih.gov/gene/L2HGDH> on Sep. 4, 2015.
Gura. "Systems for identifying new drugs are often faulty," Science, 1997, 278(5340):1041-2.
Im et al. "DNMT3A and IDH mutations in acute myeloid leukemia and other myeloid malignancies: Associations with prognosis and potential treatment strategies," Leukemia, 2014, 28:1774-1783.
Johannessen et al. "Rapid conversion of mutant IDH1 from driver to passenger in model of human gliomagenesis," Molecular Cancer Resarch, 2016, 14(10): 976-83.
Johnson et al. "Relationships between drug activity in NCI preclinical in vitro and in vivo models and early clinical trials," British Journal of Cancer, 2001, 84(10): 1424-1431.
Kumar et al. "Pharmaceutical solid dispersion technology: A strategy to improve dissolution of poorly water-soluable drugs," Recent Patents on Drug Delivery and Formulation, 2013, 7:111-121.
Lou. "IDH1: function follows form." SciBX, 2009, 1-2.
Lowe, "Good old medicinal chemistry: what can you get away with?," Blog "In the Pipeline," entry of Nov. 2, 2010.
Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.
Maison, "Multicomponent synthesis of novel amino acid-nucleobase chimeras: a versatile approach to PNA-monomers," Bioorganic & Medicinal Chemistry (2000) vol. 8, pp. 1343-1360.
Mikhailichenko, S. N., et al. "sym-triazines. 7. Hydrolysis and cyclization of 1, 3, 5-triazine series mononitriles." Chemistry of Heterocyclic Compounds 42.5 (2006): 642-647.
Mikhaylichenko, Svetlana, et al. "Synthesis and structure of new 1, 2, 3-triazolyl substituted 1, 3, 5-triazines." European Journal of Chemistry 3.1 (2012): 1-9.

Ramos et al. "Current approaches in the treatment of relapsed and refractory acute myeloid leukemia," Journal of Clinical Medicine, 2015, 4(4):665-695.
Rao et al., "Polymorphism in Drugs and its Significance in Therapeutics". Journal of Scientific & Industrial Research vol. 46 Oct. 1987 pp. 450-455.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929971-43-7.
Registry (STN) [online], Jul. 3, 2008, CAS Registration No. 1032461-94-1.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Serajuddin et al. "Solid dispersion of poorly water-soluable drugs: early promises, subsequent problems, and recent breakthroughs," Journal of Pharmaceutical Sciences, 1999, 88(10):1058-1066.
Sosnovik et al. "Emerging concepts in molecular MRI." Curr. Op. Biotech., 2007, 18, 4-10.
STN Tokyo, Registry No. 1001833-18-6, Entered STN on Feb. 6, 2008, Chemical Abstracts Index Name "1,4-Benzodioxin-6-sulfonamide, 2,3-dihydro-N-[4-[(4-methyl-1-piperazinyl)carbonyl]phenyl]—".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4-[[4-[(5-methyl-3-isoxazolyl)methyl]-I-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4-[[4-(2-pyridinyl)-1-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4-[[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4-[[4-(cyclopropylcarbonyl)-1-piperazinyl]carbonyl]phenyl]-2,3-dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4-[[4-(4-pyridinyl)-1-piperazinyl]carbonyl]phenyl]".

(56) References Cited

OTHER PUBLICATIONS

STN Tokyo, Registry No. 920822-52-2, Entered STN on Feb. 14, 2007, Chemical Abstracts Index Name "1,4-Benzodioxin-6-sulfonamide, N-[4-[[4-(4-fluoropheyl)-1-piperazinyl]carbonyl]phenyl]-2,3dihydro-".

STN Tokyo, Registry No. 920824-56-2, Entered STN on Feb. 14, 2007, Chemical Abstracts Index Name "1,4-Benzodioxin-6-sulfonamide, 2,3-dihydro-N-[4-[[4-(3-thienylmethyl)-1-piperazinyl]carbonyl]phenyl]-".

STN Tokyo, Registry No. 920847-34-3, Entered STN on Feb. 14, 2007, Chemical Abstracts Index Name "1,4-Benzodioxin-6-sulfonamide, 2,3-dihydro-N-[4-[[4-(2-methylphenyl)-1-piperazinyl]carbonyl]phenyl]-".

STN Tokyo, Registry No. 920875-39-4, Entered STN on Feb. 14, 2007, Chemical Abstracts Index Name "1,4-Benzodioxin-6-sulfonamide, 2,3-dihydro-N-[4-[[4-(2-hydroxyphenyl)-1-piperazinyl]carbonyl]phenyl]-".

STN Tokyo, Registry No. 920902-88-1, Entered STN on Feb. 14, 2007, Chemical Abstracts Index Name "1,4-Benzodioxin-6-sulfonamide, 2,3-dihydro-N-[4-[[4-(2-thienylmethyl)-1-piperazinyl]carbonyl]phenyl]-".

STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".

STN Tokyo, Registry No. 920924-42-1, Entered STN on Feb. 14, 2007, Chemical Abstracts Index Name "1,4-Benzodioxin-6-sulfonamide, 2,3-dihydro-N-[4-[[4-(2-pyridinylmethyl)-1-piperazinyl]carbonyl]phenyl]-".

STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-1-piperazinyl)carbonyl]phenyl]-".

International Search Report for PCT/CN2012/000841 dated Sep. 27, 2012.
International Search Report for PCT/CN2012/077096 dated Oct. 4, 2012.
International Search Report for PCT/CN2013/000009 dated Apr. 18, 2013.
International Search Report for International Application No. PCT/CN2013/079184 dated Jan. 12, 2015.
International Search Report for International Application No. PCT/CN2013/079200 dated Jan. 12, 2015.
International Search Report for International Application No. PCT/CN2014/082869 dated Sep. 30, 2014.
International Search Report for PCT/US2010/027253 dated Aug. 19, 2010.
International Search Report for PCT/US2010/059778 dated Mar. 17, 2011.
International Search Report for PCT/US2010/53623 dated Jan. 18, 2011.
International Search Report for PCT/US201/030692 dated Jul. 27, 2011.
International Search Report for PCT/US2011044254 dated May 10, 2011.
International Search Report for PCT/US2013/064601 dated Feb. 24, 2014.
International Search Report for International Application No. PCT/US2014/046204 dated Oct. 1, 2014.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jana et al., "Synthesis and Antibacterial Activity of Some Novel 4-Benzyl-piperazinyl-s-triazine Derivatives." Asian Journal of Chemistry (2013) vol. 25, No. 1, pp. 186-190.
Jennings et al. "Expression and mutagenesis of mammalian cytosolic NADP+-specific isocitrate dehydrogenase" Biochemistry (1997) vol. 36, pp. 13743-13747.

Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al. "Identification and Functional Characterization of a Novel, Tissue-specific NAD+-dependent Isocitrate Dehydrogenase b Subunit Isoform" JBC (1999) vol. 274, No. 52, pp. 36866-36875.
Kim et al. "Ser95, Asn97, and Thr78 are important for the catalytic function of porcine NADP-dependent isocitrate dehydrogenase" Protein Science (2005) vol. 14, pp. 140-147.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kumar et al., "4-Anilinoquinoline triazines: A novel class of hybrid antimalarial agents" European Journal of Medicinal Chemistry (2011) vol. 46, pp. 676-690.
Kumar et al., "Synthesis and bioevaluation of hybrid 4-aminoquinoline triazines as a new class of antimalarial agents," Bioorganic & Medicinal chemistry Letters (2008) vol. 18, pp. 6530-6533.
Kusakabe et al. Chemical Abstracts vol. 152, No. 191956, Abstract for WO2010007756 (2010).
Lee et al. "Combinatorial Solid-Phase Synthesis of 6-Aryl-1,3,4-triazines via Suzuki Coupling" Aust. J. Chem. (2011) vol. 64, pp. 540-544.
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
May et al. "How many species are there on earth" Science (1988) vol. 241, p. 1441.
McRobbie et al. "MRI from Picture to Proton," Cambridge University Press, 2007, pp. 307-308.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Paronikyan et al. "Synthesis and biological activity of 3-piperazinylpyrano [3,4-C] pyridines" Armyanskii Khimicheskii Zhurnal (1990) vol. 43, No. 8, pp. 518-523.
Parsons et al. "An Integrated Genomic Analysis of Human Glioblastoma Multiforme" Science (2008) vol. 321, pp. 1807-1812 and Supplemental Data.
Pitts et al., "Rapid Synthesis of Triazine Inhibitors of Inosine Monophosphate Dehydrogenase," Bioorganic & Medicinal Chemistry Letters (2002) vol. 12, pp. 2137-2140.
Pollard et al, "Cancer. Puzzling patterns of predisposition." Science (2009) vol. 324, pp. 192-194.
Popovici-Muller et al. "Discovery of the First Potent Inhibitors of Mutant IDH1 That Lower Tumor2-HG in Vivo" ACS Medicinal Chemistry Letters (2012) vol. 3, No. 10, pp. 850-855.
Pubchem CID 4078245 [online]; Sep. 13, 2005 [retrieved on Feb. 4, 2012]; retrieved from http://pubchem.ncbi.nim.nih.gov/; 2d-structure.
Pubchem CID 4854170 [online]; Sep. 17, 2005 [retrieved on Feb. 4, 2012]; retrieved from http://pubchem.ncbi.nim.nih.gov/; 2d-structure.
Raynaud et al. "Absence of R140Q Mutation of Isocitrate Dehydrogenase 2 in Gliomas and Breast Cancers" Oncology Letters (2010) vol. 1, No. 5, pp. 883-884.
Registry (STN) [online], Jul. 3, 2008, CAS Registration No. 1032470-22-6.

(56) References Cited

OTHER PUBLICATIONS

Registry (STN) [online], Jul. 4, 2008, CAS Registration No. 1032747-65-1.
Registry (STN) [online], Apr. 16, 2010, CAS Registration No. 1219379-97-1.
Registry (STN) [online], Apr. 13, 2007 [Retrieved on Jan. 29, 2016] CAS Registration No. 929819-92-1.
Reitman et al. "Isocitrate Dehydrogenase 1 and 2 Mutations in Cancer: Alterations at a Crossroads of Cellular Metabolism" Journal of the National Cancer Institute (2010) vol. 102, No. 13, pp. 932-941.
Rohle et al. "An Inhibitor of Mutant IDH1 Delays Growth and Promotes Differentiation of Glioma Cells" Science (2013) vol. 340, No. 6132, pp. 626-630.
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Search Report for SG 11201600185U dated Nov. 16, 2016.
Shahin et al., "Elaborate ligand-based modeling and subsequent synthetic exploration unveil new nanomora Ca2+/Calmodulin-dependent protein kinase II inhibitory leads" Bioorganic & Medicinal Chemistry (2012) vol. 20, pp. 377-400.
U.S. Appl. No. 13/810,410, filed Mar. 28, 2013, Janeta Popovici-Muller.
U.S. Appl. No. 15/064,874, filed Mar. 9, 2016, Janeta Popovici-Muller.
U.S. Appl. No. 13/745,005, filed Jan. 18, 2013, Rene M. Lemieux.
U.S. Appl. No. 14/988,661, filed Jan. 5, 2016, Rene M. Lemieux.
U.S. Appl. No. 15/279,146, filed Sep. 28, 2016, Janeta Popovici-Muller.
U.S. Appl. No. 15/809,325, filed Nov. 10, 2017, Janeta Popovici-Muller.
U.S. Appl. No. 14/373,154, filed Jul. 18, 2014, Janeta Popovici-Muller.
U.S. Appl. No. 15/196,842, filed Jun. 29, 2016, Janeta Popovici-Muller.
U.S. Appl. No. 14/341,426, filed Jul. 25, 2014, Rene M. Lemieux.
U.S. Appl. No. 15/347,407, filed Nov. 9, 2016, Rene M. Lemieux.
U.S. Appl. No. 15/915,213, filed Mar. 8, 2018, Rene M. Lemieux.
U.S. Appl. No. 15/125,884, filed Sep. 13, 2016, Chong-Hui Gu.
U.S. Appl. No. 15/125,880, filed Sep. 13, 2016, Chong-Hui Gu.
U.S. Appl. No. 15/767,813, filed Apr. 12, 2018, Samuel V. Agresta.
U.S. Appl. No. 15/767,822, filed Apr. 12, 2018, Samuel V. Agresta.
Shin et al. "The Role of Mutations in Epigenetic Regulators in Myeloid Malignancies" Nature Reviews Cancer (2012) vol. 12, No. 9, pp. 599-612.
Sirkanyan et al "Synthesis of new derivatives of piperazine-substituted pyrano[3,4-c]pyridines" Hayastani Kimiakan Handes—Chemical Journal of Armenia (2009) vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
STN file CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylpheny1)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts Index Name "1H-Pyrano[3,4-c]pyridine-5-carbonitrile,3,4-dihydro-3,3-dimethyl-6[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile,3,4-dihydro-3,3-dimethyl-6[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN file CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry. L23 Answer 1 of 3 (CAS No. 1038821-72-5),Database: ChemDB (University of California Irvine), Entered STN: Aug. 5, 2008 (Aug. 5, 2008).
STN Registry, L23 Answer 2 of 3 (CAS No. 1032450-21-7), Database: ASINEX Ltd.,Entered STN: Jul. 3, 2008 (Jul. 3, 2008).
Struys et al. "Investigations by mass isotopomer analysis of the formation of D-2-hydroxyglutarate by cultured lymphoblasts from two patients with D-2-hydroxyglutaric aciduria" FEBS Letters (2004) vol. 557, pp. 115-120.
Struys et al. "Mutations in the D-2-hydroxyglutarate dehydrogenase gene cause D-2-hydroxyglutaric aciduria" American Journal of Human Genetics (2005) vol. 76, pp. 358-360.
Supplementary European Search Report for EP 10751525 dated Dec. 14, 2012.
Supplementary European Search Report for EP Application No. 10825707.2 dated Jun. 28, 2013.
Supplementary Search Report for EP10794668 dated Oct. 18, 2012.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England Journal of Medicine (2009) vol. 360, No. 8, pp. 813-815.
Van Schaftingen et al. "L-2-Hydroglutaric aciduria, a disorder of metabolite repair" J Inherit. Metab. Dis. (2009) vol. 32, pp. 135-142.
Wang et al. "A novel ligand N,N'-di(2-pyridyl)-2,4-diamino-6-phenyl-1,3,5-triazine (dpdapt) and its complexes: [Cu (dpdapt)Cl2] and [Cu(dpdapt)(NO3)(H2O)] Â•NO3 Â•H2O" Polyhedron (2006) vol. 25, No. 1, pp. 195-202.
Wang et al "Facile Synthesis of 2,4-Dianiino-6-alkyi- or 6-Aryl-PyrimidineDerivatives" Journal of Heterocyclic Chemistry (2010) vol. 47 pp. 1056-1061.
Ward et al. "The Common Feature of Leukemia-Associated IDH1 and IDH2 Mutations Is a Neomorphic Enzyme Activity Converting [alpha]-Ketoglutarate to 2-Hydroxyglutarate" Cancer Cell (2010) vol. 17, No. 3 pp. 225-234.
Watanabe et al., "IDH1 Mutations Are Early Events in the Development of Astrocytomas and Oligodendrogliomas". American Journal of Pathology (2009) vol. 174, No. 4, pp. 1149-1153.
Written Opinion for PCT/US2010/027253 dated Aug. 19, 2010.
Written Opinion of Search Authority for PCT/US2010/53623 dated Jan. 18, 2011.

(56) References Cited

OTHER PUBLICATIONS

Written Opinion of the International Searching Authority for PCT/US2011/067752 dated Mar. 5, 2012.
Written Opinion for SG 11201600185U dated Nov. 16, 2016.
Written Opinion of International Search Authority for PCT/CN2013/000009 dated Apr. 18, 2013.
Yan et al., "IDH1 and IDH2 Mutations in Gliomas" The New England Journal of Medicine, 79 Feb. 18-22, 2009, vol. 360, No. 8, pp. 765-773.
Yrjola et al., "Discovery of novel cannabinoid receptor ligands by a virtual screening approach: Further development pf 2,4,6-trisubstituted 1,3,5-triazines as CB2 agonists," European Journal of Pharmaceutical Sciences (2013) vol. 48, pp. 9-20.
Zhao et al. "Glioma-derived mutations in IDH1 dominantly inhibit IDH1 catalytic activity and induce HIF-1alpha", Science (2009) vol. 324, No. 5924, pp. 261-265.
Zheng et al. "Synthesis and antitumor evaluation of a novel series of triaminotriazine derivatives" Bioorganic & Medicinal Chemistry (2007) vol. 15, pp. 1815-1827.
Struys, EA. et al. "Measurement of Urinary D- and L-2-Hydroxyglutarate Enantiomers by Stable-Isotope-Dilution LiquidChromatography-Tandem Mass Spectrometry after Derivatization with Diacetyi-L-Tartaric Anhydride." Clinical Chemistry (2004)501391-1395.
Zuo et al. "Synthesis of 4-methyl-1,2,3-thiadiazole derivatives via ugi reaction and their biological activities," Journal of Agricultural and Food Chemistry, 2010, 58(5): 2755-2762.

\* cited by examiner

THERAPEUTICALLY ACTIVE COMPOSITIONS AND THEIR METHODS OF USE

CLAIM OF PRIORITY

This application is a continuation of U.S. Ser. No. 15/279,146, filed Sep. 28, 2016, which is a continuation of U.S. Ser. No. 13/745,005, filed Jan. 18, 2013, which claims priority under 35 U.S.C. § 119 from International Application No. PCT/CN2012/070601, filed Jan. 19, 2012, each of which is incorporated herein by reference in its entirety.

BACKGROUND OF INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2,4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684 (1998); Geisbrecht et al., J. Biol. Chem. 274:30527-30533 (1999); Wiemann et al., Genome Res. 11:422-435 (2001); The MGC Project Team, Genome Res. 14:2121-2127 (2004); Lubec et al., Submitted (December 2008) to UniProtKB; Kullmann et al., Submitted (June 1996) to the EMBL/GenBank/DDBJ databases; and Sjoeblom et al., Science 314:268-274 (2006).

Non-mutant, e.g., wild type, IDH1 catalyzes the oxidative decarboxylation of isocitrate to α-ketoglutarate thereby reducing NAD (NADP$^+$) to NADH (NADPH), e.g., in the forward reaction:

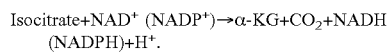

It has been discovered that mutations of IDH1 present in certain cancer cells result in a new ability of the enzyme to catalyze the NAPH-dependent reduction of α-ketoglutarate to R(−)-2-hydroxyglutarate (2HG). The production of 2HG is believed to contribute to the formation and progression of cancer (Dang, L et al, Nature 2009, 462:739-44).

The inhibition of mutant IDH1 and its neoactivity is therefore a potential therapeutic treatment for cancer. Accordingly, there is an ongoing need for inhibitors of IDH1 mutants having alpha hydroxyl neoactivity.

SUMMARY OF INVENTION

Described herein are methods of treating a cancer characterized by the presence of a mutant allele of IDH1 or IDH2. The methods comprise the step of administering to a subject in need thereof a compound of formula I, or a pharmaceutically acceptable salt, tautomer, isotopologue or hydrate thereof, wherein:

formula I

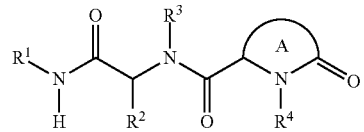

$R^1$ is optionally substituted $C_4$-$C_6$ carbocyclyl;
each $R^2$ and $R^3$ is independently selected from optionally substituted aryl or optionally substituted heteroaryl;
$R^4$ is alkyl, optionally substituted aryl, optionally substituted heteroaryl, optionally substituted aralkyl, or optionally substituted heteroaralkyl;
ring A is 4-6 membered non-aromatic ring having 0-1 additional heteroatoms selected from N, O or S, wherein ring A is optionally substituted with one or two $R^5$ groups;
each $R^5$ is independently halo; —$CF_3$; —CN; —$OR^6$; —$N(R^6)_2$; —C(O)$C_1$-$C_4$ alkyl; $C_1$-$C_4$ haloalkyl; $C_1$-$C_4$ alkyl optionally substituted with —$OR^6$ or —$N(R^6)_2$; —O—$C_1$-$C_4$ alkyl optionally substituted with halo, —$OR^6$ or —$N(R^6)_2$; —$SO_2N(R^6)_2$; —$SO_2(C_1$-$C_4$ alkyl); —$NR^6SO_2R^6$; $C_3$-$C_5$ carbocyclyl optionally substituted with one or two $R^6$ groups; —O—($C_3$-$C_6$ carbocyclyl optionally substituted with one or two $R^6$ groups); 5-6 membered heteroaryl; —$C_1$-$C_4$ alkyl-C(O)O—$C_1$-$C_4$ alkyl; or —C(O)O—$C_1$-$C_4$ alkyl; or
each $R^6$ is independently H or $C_1$-$C_3$ alkyl.

The compound of formula I inhibits mutant IDH1/2, particularly mutant IDH1 having alpha hydroxyl neoactivity. Also described herein are pharmaceutical compositions comprising a compound of formula I.

DETAILED DESCRIPTION OF THE INVENTION

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Arylalkyl or aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups. The terms "heteroarylalkyl" or "heteroaralkyl" refer to an alkyl moiety in which an alkyl hydrogen atom is replaced by a heteroaryl group. Heteroarylalkyl or heteroaralkyl includes groups in which more than one hydrogen atom has been replaced by a heteroaryl group.

The term "alkylene" refers to a divalent alkyl, e.g., —CH$_2$—, —CH$_2$CH$_2$—, and —CH$_2$CH$_2$CH$_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkoxy" refers to an —O-alkyl radical. The term "haloalkoxy" refers to an alkoxy in which one or more hydrogen atoms are replaced by halo, and includes alkoxy moieties in which all hydrogens have been replaced by halo (e.g., perfluoroalkoxy).

The term "carbocyclyl" refers to a monocyclic, bicyclic or tricyclic, hydrocarbon ring system that is not fully aromatic, wherein any ring atom capable of substitution can be substituted by one or more substituents. A carbocyclyl can be fully or partially saturated. A bicyclic or tricyclic carbocyclyl may contain one (in the case of a bicycle) or up to two (in the case of a tricycle) aromatic rings, as long as at least one ring in the carbocyclyl is non-aromatic. Unless otherwise specified, any ring atom capable of substitution in a carbocyclyl can be substituted by one or more substituents.

The term "aryl" refers to a fully aromatic monocyclic, bicyclic, or tricyclic hydrocarbon ring system. Examples of aryl moieties are phenyl, naphthyl, and anthracenyl. Unless otherwise specified, any ring atom in an aryl can be substituted by one or more substituents.

The term "cycloalkyl" as employed herein refers to a saturated cyclic, bicyclic, tricyclic, or polycyclic hydrocarbon group. Unless otherwise specified, any ring atom can be substituted by one or more substituents. The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl. Unless otherwise specified, any ring atom can be substituted by one or more substituents.

The term "heterocyclyl" refers to a monocyclic, bicyclic or tricyclic, ring structure that is not fully aromatic and includes one to four heteroatoms independently selected from N, O, or S in one or more of the rings. A heterocyclyl can be fully or partially saturated. A bicyclic or tricyclic heterocyclyl may contain one (in the case of a bicycle) or up to two (in the case of a tricycle) aromatic rings, as long as at least one ring in the heterocyclyl is non-aromatic. Unless otherwise specified, any ring atom capable of substitution in a heterocyclyl can be substituted by one or more substituents. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like.

The term "heteroaryl" refers to a monocyclic, bicyclic, or tricyclic ring system having 1-3 heteroatoms if monocyclic, 1-6 heteroatoms if bicyclic, or 1-9 heteroatoms if tricyclic, said heteroatoms independently selected from O, N, or S, wherein each ring in a heteroaryl is fully aromatic. Unless otherwise specified, any ring atom capable of substitution in a heteroaryl can be substituted by one or more substituents. The terms "hetaralkyl" and "heteroaralkyl", as used herein, refers to an alkyl group substituted with a heteroaryl group. The ring heteroatoms of the compounds provided herein include N—O, S(O), and S(O)$_2$.

The term "substituted" refers to the replacement of a hydrogen atom with another moiety. Typical substituents include alkyl (e.g., C1, C2, C3, C4, C5, C6, C7, C8, C9, C10, C11, C12 straight or branched chain alkyl), cycloalkyl, haloalkyl (e.g., perfluoroalkyl such as CF$_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as OCF$_3$), halo, hydroxy, carboxy, carboxylate, cyano, nitro, amino, alkyl amino, SO$_3$H, sulfate, phosphate, methylenedioxy (—O—CH$_2$—O— wherein oxygens are attached to vicinal atoms), ethylenedioxy, oxo (not a substituent on heteroaryl), thioxo (e.g., C=S) (not a substituent on heteroaryl), imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "tautomer" refers to each of two or more isomers of a compound (e.g., a compound described herein) that exist together in equilibrium, and are readily interchangeable by migration of a hydrogen atom or proton, accompanied by a switch of a single bond and an adjacent double bond.

As used herein, the term "elevated levels of 2HG" means 10%, 20% 30%, 50%, 75%, 100%, 200%, 500% or more 2HG than is present in a subject that does not carry a mutant IDH1 or IDH2 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit.

The term "treat" means decrease, suppress, attenuate, diminish, arrest, or stabilize the development or progression of a cancer (e.g., a cancer delineated herein), lessen the severity of the cancer or improve the symptoms associated with the cancer.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compounds

Provided is a compound having formula I or a pharmaceutically acceptable salt, tautomer, isotopologue or hydrate thereof, wherein:

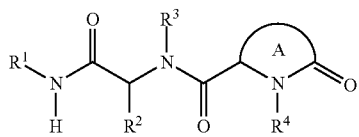

formula I $R^1$ is optionally substituted $C_4$-$C_6$ carbocyclyl;

each $R^2$ and $R^3$ is independently selected from optionally substituted aryl or optionally substituted heteroaryl;

$R^4$ is alkyl, optionally substituted aryl, optionally substituted heteroaryl, optionally substituted aralkyl, or optionally substituted heteroaralkyl;

ring A is 4-6 membered non-aromatic ring having 0-1 additional heteroatoms selected from N, O or S, wherein ring A is optionally substituted with one or two $R^5$ groups;

each $R^5$ is independently halo; —$CF_3$; —CN; —$OR^6$; —$N(R^6)_2$; —$C(O)C_1$-$C_4$ alkyl; $C_1$-$C_4$ haloalkyl; $C_1$-$C_4$ alkyl optionally substituted with —$OR^6$ or —$N(R^6)_2$; —O—$C_1$-$C_4$ alkyl optionally substituted with halo, —$OR^6$ or —$N(R^6)_2$; —$SO_2N(R^6)_2$; —$SO_2(C_1$-$C_4$ alkyl); —$NR^6SO_2R^6$; $C_3$-$C_5$ carbocyclyl optionally substituted with one or two $R^6$ groups; —O—($C_3$-$C_6$ carbocyclyl optionally substituted with one or two $R^6$ groups); 5-6 membered heteroaryl; —$C_1$-$C_4$ alkyl-C(O)O—$C_1$-$C_4$ alkyl; or —C(O)O—$C_1$-$C_4$ alkyl; or each $R^6$ is independently H or $C_1$-$C_3$ alkyl.

Provided is also a compound having formula I or a pharmaceutically acceptable salt or hydrate thereof, wherein:

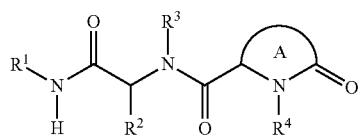

formula I $R^1$ is optionally substituted $C_4$-$C_6$ carbocyclyl;

each $R^2$ and $R^3$ is independently selected from optionally substituted aryl or optionally substituted heteroaryl;

$R^4$ is alkyl, optionally substituted aryl, optionally substituted heteroaryl, optionally substituted aralkyl, or optionally substituted heteroaralkyl;

ring A is 4-6 membered non-aromatic ring having 0-1 additional heteroatoms selected from N, O or S, wherein ring A is optionally substituted with one or two $R^5$ groups;

each $R^5$ is independently halo, —$CF_3$, —CN, —$OR^6$, —$N(R^6)_2$, —$C(O)CH_3$; $C_1$-$C_3$ haloalkyl, $C_1$-$C_3$ alkyl optionally substituted with —$OR^6$ or —$N(R^6)_2$; or each $R^6$ is independently H or $C_1$-$C_3$ alkyl.

Provided is also a compound having formula I or a pharmaceutically acceptable salt, tautomer, isotopologue or hydrate thereof, wherein:

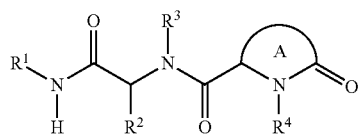

formula I $R^1$ is $C_4$-$C_6$ carbocyclyl optionally substituted with one to three $R^7$ groups;

each $R^2$ and $R^3$ is independently selected from aryl or heteroaryl, wherein said aryl or heteroaryl is independently optionally substituted with one to three $R^7$ groups;

$R^4$ is alkyl, aryl, heteroaryl, aralkyl, or heteroaralkyl, wherein said aryl, heteroaryl, aralkyl, and heteroaralkyl are each independently optionally substituted with one to three $R^7$ groups;

ring A is 4-6 membered non-aromatic ring having 0-1 additional heteroatoms selected from N, O or S, wherein ring A is optionally substituted with one or two $R^5$ groups;

each $R^5$ and $R^7$ is independently halo; —$CF_3$; —CN; —$OR^6$; —$N(R^6)_2$; —$C(O)C_1$-$C_4$ alkyl; $C_1$-$C_4$ haloalkyl; $C_1$-$C_4$ alkyl optionally substituted with —$OR^6$ or —$N(R^6)_2$; —O—$C_1$-$C_4$ alkyl optionally substituted with halo, —$OR^6$ or —$N(R^6)_2$; —$SO_2N(R^6)_2$; —$SO_2(C_1$-$C_4$ alkyl); —S(O)—$C_{1-4}$ alkyl, —$NR^6SO_2R^6$; $C_3$-$C_5$ carbocyclyl optionally substituted with one or two $R^6$ groups; —O—($C_3$-$C_6$ carbocyclyl optionally substituted with one or two $R^6$ groups); 5-6 membered heteroaryl; —$C_1$-$C_4$ alkyl-C(O)O—$C_1$-$C_4$ alkyl; or —C(O)O—$C_1$-$C_4$ alkyl; or each $R^6$ is independently H or $C_1$-$C_4$ alkyl.

Provided is also a compound having formula I or a pharmaceutically acceptable salt, tautomer, isotopologue or hydrate thereof, wherein:

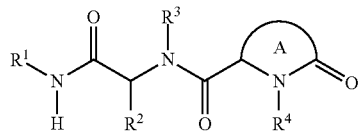

formula I $R^1$ is $C_4$-$C_6$ carbocyclyl optionally substituted with one to three $R^7$ groups;

each $R^2$ and $R^3$ is independently selected from aryl or heteroaryl, wherein said aryl or heteroaryl is independently optionally substituted with one to three $R^7$ groups;

$R^4$ is alkyl, aryl, heteroaryl, aralkyl, or heteroaralkyl, wherein said aryl, heteroaryl, aralkyl, and heteroaralkyl are each independently optionally substituted with one to three $R^7$ groups;

ring A is 4-6 membered non-aromatic ring having 0-1 additional heteroatoms selected from N, O or S, wherein ring A is optionally substituted with one or two $R^5$ groups;

each $R^5$ and $R^7$ is independently halo, —$CF_3$, —CN, —$OR^6$, —$N(R^6)_2$, —$C(O)CH_3$; $C_1$-$C_3$ haloalkyl, $C_1$-$C_3$ alkyl optionally substituted with $OR^6$ or —$N(R^6)_2$; or each $R^6$ is independently H or $C_1$-$C_3$ alkyl.

In one embodiment, $R^1$ is optionally substituted $C_4$-$C_6$ cycloalkyl. In one aspect of this embodiment, $R^1$ is $C_4$-$C_6$ cycloalkyl optionally substituted with one to three $R^7$ groups. In another aspect of this embodiment, $R^1$ is $C_4$, $C_5$, or $C_6$ cycloalkyl optionally substituted with one to two $R^7$ groups and $R^7$ is halo. In another aspect of this embodiment, $R^1$ is $C_4$ or $C_6$ cycloalkyl optionally substituted with one to two $R^7$ groups and $R^7$ is halo. In yet another aspect of this embodiment, $R^1$ is

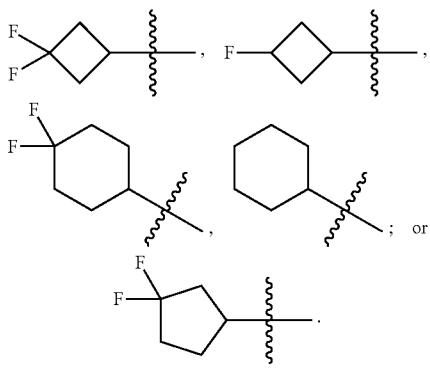

In yet another aspect of this embodiment, $R^1$ is

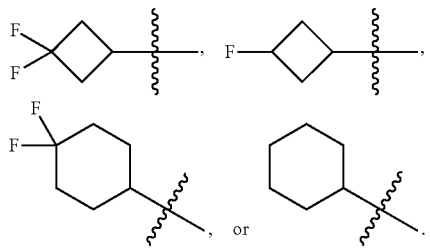

In another embodiment, $R^2$ is optionally substituted aryl. In one aspect of this embodiment, $R^2$ is aryl optionally substituted with one to three $R^7$ groups. In another aspect of this embodiment, $R^2$ is phenyl optionally substituted with one to two $R^7$ groups and $R^7$ is —Cl.

In another embodiment, $R^3$ is optionally substituted aryl or optionally substituted aryl heteroaryl. In one aspect of this embodiment, $R^3$ is optionally substituted heteroaryl. In another aspect of this embodiment, $R^3$ is heteroaryl optionally substituted with one to three $R^7$ group. In yet another aspect of this embodiment, $R^3$ is pyridinyl, indazolyl, benzoimidazolyl, indolyl, or N-methylindolyl, wherein each $R^3$ is optionally substituted with one $R^7$ wherein $R^7$ is —F. In another aspect of this embodiment, $R^3$ is optionally substituted aryl. In another aspect of this embodiment, $R^3$ is aryl optionally substituted with one to three $R^7$ groups. In yet another aspect of this embodiment, $R^3$ is phenyl optionally substituted with one $R^7$ wherein $R^7$ is —F. In yet another aspect of this embodiment, $R^3$ is phenyl optionally substituted with one or two $R^7$s wherein each $R^7$ is independently halo; —CN; —$N(R^6)_2$; $C_1$-$C_4$ alkyl optionally substituted with —$OR^6$; —O—$C_1$-$C_4$ alkyl optionally substituted with halo, or —$OR^6$; —$SO_2N(R^6)_2$; —$SO_2(C_1$-$C_4$ alkyl); —$S(O)$—$C_{1-4}$ alkyl, —$NR^6SO_2R^6$; $C_3$-$C_5$ carbocyclyl optionally substituted with one $R^6$; —O—($C_3$-$C_6$ carbocyclyl); 5-membered heteroaryl. In yet another aspect of this embodiment, $R^3$ is phenyl optionally substituted with one or two $R^7$s wherein each $R^7$ is independently —F, —$SO_2NH_2$, —$SO_2CH_3$, —$S(O)CH_3$, —CN, methoxy, —$OCH_2OH$, —$CH_2OH$, —$SO_2N(CH_3)_2$, —$SO_2NHCH_3$, —$NHSO_2CH_3$, —$CH_2CH_2OH$, —$N(CH_3)_2$, t-butyl, cyclopropyl, —$C(OH)(CH_3)_2$, —$OCF_3$, —$OCHF_2$, —O— cyclopropyl, -1-methyl-cyclopropyl, or pyrazolyl.

In another embodiment, $R^4$ is optionally substituted aryl, optionally substituted heteroaryl, optionally substituted aralkyl, or optionally substituted heteroaralkyl. In one aspect of this embodiment, $R^4$ is aryl, heteroaryl, aralkyl, or heteroaralkyl, wherein said aryl, heteroaryl, aralkyl, and heteroaralkyl are each independently optionally substituted with one to three $R^7$ groups. In another aspect of this embodiment, $R^4$ is aryl or heteroaryl, each aryl or heteroaryl is optionally substituted with one to three $R^7$ groups. In another aspect of this embodiment, $R^4$ is 6-membered aryl or 5-6 membered heteroaryl, wherein said aryl or heteroaryl is optionally substituted with one to three $R^7$ groups. In yet another aspect of this embodiment, $R^4$ is:

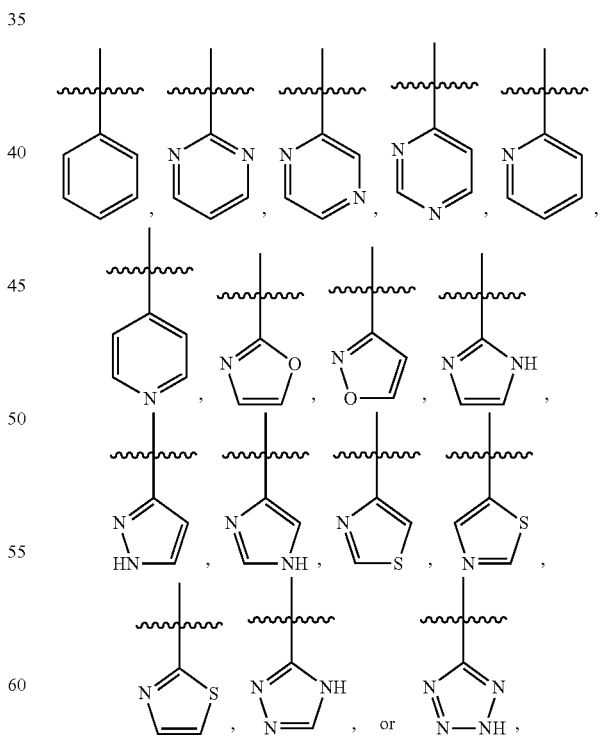

wherein each member of $R^4$ is optionally substituted with one or two $R^7$ groups and each $R^7$ is independently F, Cl, methyl, $CF_3$, CN, OMe, or $N(R^6)_2$. In yet another aspect of this embodiment, $R^4$ is:

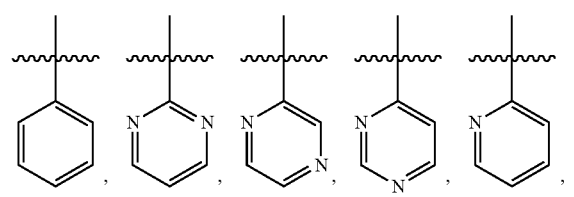
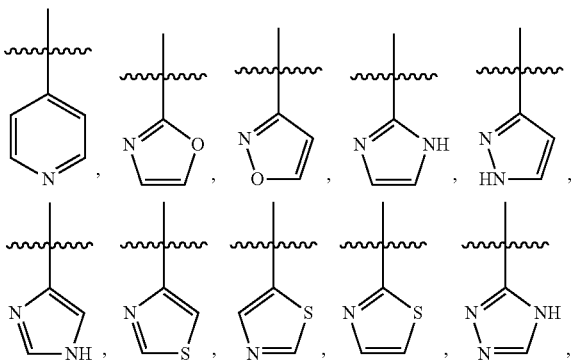
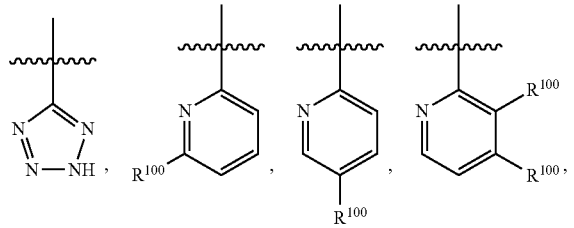
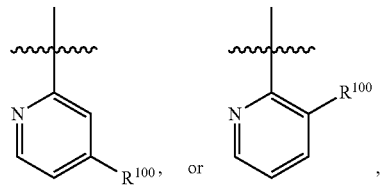
wherein each $R^{100}$ is independently H, methyl, F, Cl, CF$_3$, CN, OCH$_3$, or N(R$^6$)$_2$. In yet another aspect of this embodiment, R$^4$ is:
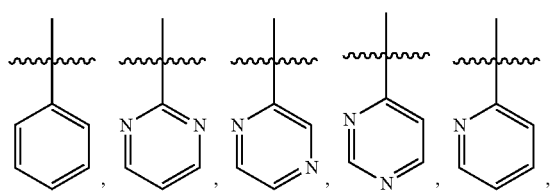
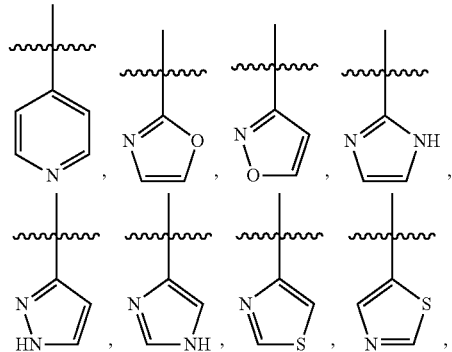
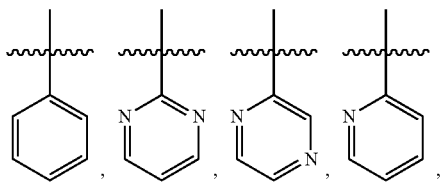
wherein $R^{100}$ is H, methyl, F, Cl, CF$_3$, CN, OCH$_3$, or N(R$^6$)$_2$. In yet another embodiment, R$^4$ is:
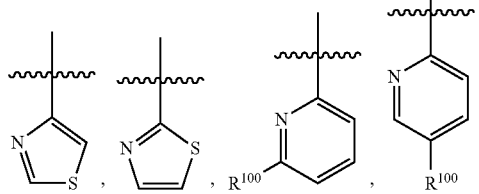
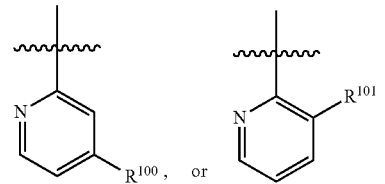
wherein $R^{100}$ is H, methyl, Cl, CF$_3$, CN, OCH$_3$, or N(R$^6$)$_2$ and $R^{101}$ is H, F or methyl.
In another embodiment, ring A is
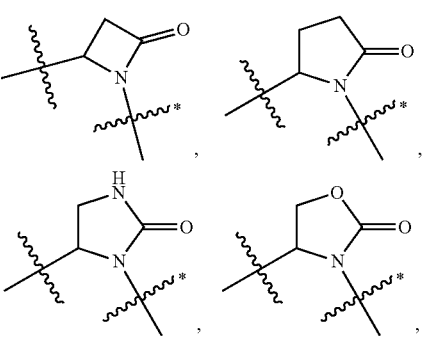

-continued

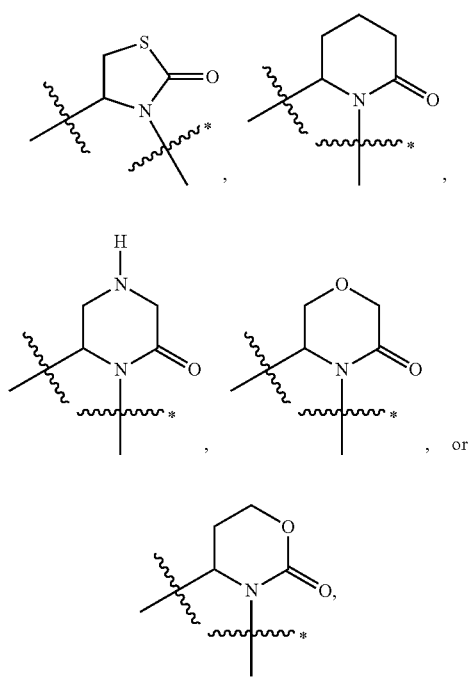

wherein

denotes ring A's attachment to the amide moiety of formula and

denotes ring A's attachment to R⁴; and each member of ring A is optionally substituted with one or two R⁵ groups. In another embodiment, ring A is

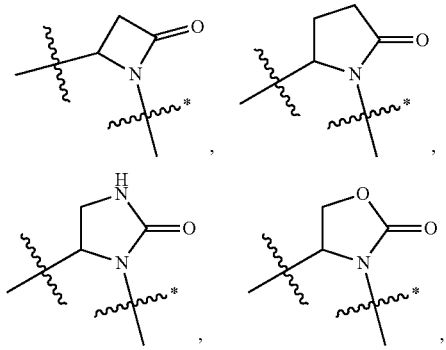

-continued

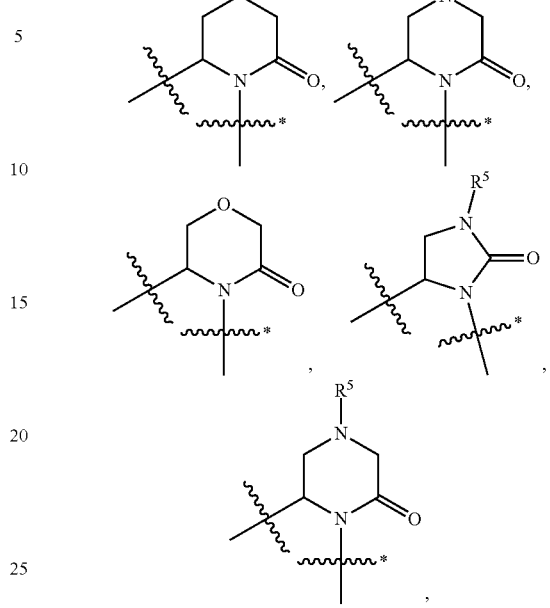

wherein

denotes ring A's attachment to the amide moiety of formula and

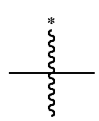

denotes ring A's attachment to R⁴; and each member of ring A is optionally substituted with one or two R⁵ groups. In one aspect of this embodiment, each R⁵ is independently halo; —OR⁶; —C(O)C₁-C₄ alkyl; C₁-C₄ alkyl optionally substituted with —OR⁶; —C₃-C₅ carbocyclyl optionally substituted with one or two R⁶ groups; —C₁-C₄ alkyl-C(O)O—C₁-C₄ alkyl; or —C(O)O—C₁-C₄ alkyl. In one aspect of this embodiment, each R⁵ is independently —OH, —F, —CH₂CH₂OH, —CH₂C(O)OCH₂CH₃, —C(O)O-t-butyl, cyclopropyl, methyl or —C(O)CH₃. In one aspect of this embodiment, each R⁵ is independently methyl or —C(O)CH₃. In another aspect of this embodiment, ring A is:

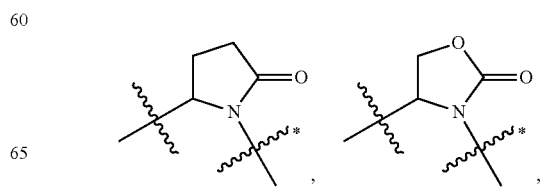

-continued

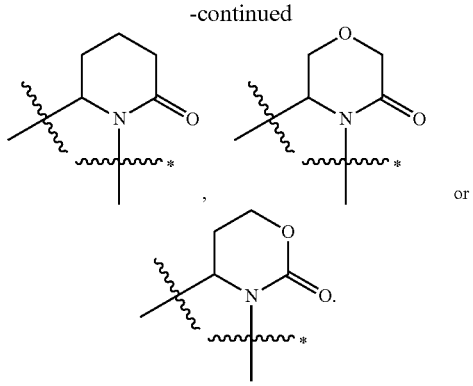

In another aspect of this embodiment, ring A is:

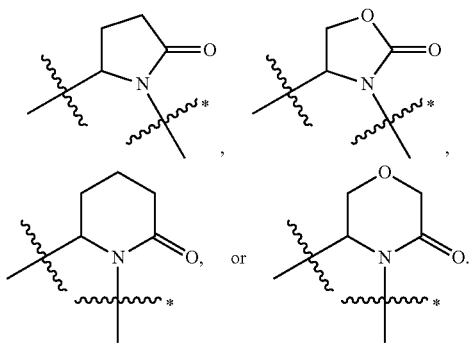

Provided is also a compound having formula II or a pharmaceutically acceptable salt or hydrate thereof, wherein $R^1$, $R^2$, $R^3$, ring A and $R^4$ are as defined in formula I or any one of the above embodiments.

formula II

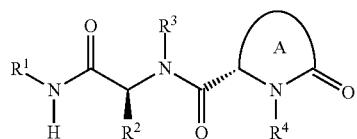

Provided is also a compound having formula II-a or a pharmaceutically acceptable salt or hydrate thereof, wherein $R^1$, $R^4$, ring A and $R^7$ are as defined in formula I or any one of the above embodiments.

formula II-a

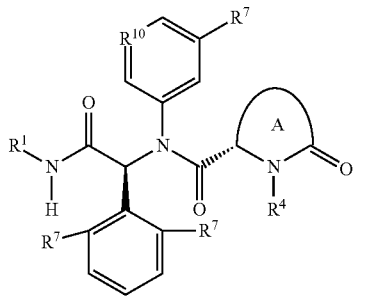

Provided is also a compound having formula II-a-1 or a pharmaceutically acceptable salt or hydrate thereof, wherein $R^1$, $R^4$, ring A and $R^7$ are as defined in formula I or any one of the above embodiments and $R^{10}$ is $CR^{11}$ or N wherein $R^{11}$ is —F, —$SO_2NH_2$, —$SO_2CH_3$, —CN, methoxy, —$OCH_2OH$, —$CH_2OH$, —$SO_2N(CH_3)_2$, —$SO_2NHCH_3$, —$NHSO_2CH_3$, —$CH_2CH_2OH$, —$N(CH_3)_2$, t-butyl, cyclopropyl, —$C(OH)(CH_3)_2$, —$OCF_3$, —$OCHF_2$, —O-cyclopropyl, -1-methyl-cyclopropyl, or pyrazolyl.

formula II-a-1

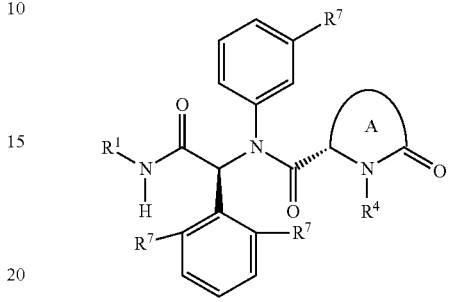

Provided is also a compound having formula II-b or a pharmaceutically acceptable salt or hydrate thereof, wherein $R^1$, $R^4$, and ring A are as defined in formula I or any one of the above embodiments; $R^{7'}$ is H or Cl; and $R^{10}$ is $CR^{11}$ or N wherein $R^{11}$ is —F, —$SO_2NH_2$, —$SO_2CH_3$, —CN, methoxy, —$OCH_2OH$, —$CH_2OH$, —$SO_2N(CH_3)_2$, —$SO_2NHCH_3$, —$NHSO_2CH_3$, —$CH_2CH_2OH$, —$N(CH_3)_2$, t-butyl, cyclopropyl, —$C(OH)(CH_3)_2$, —$OCF_3$, —$OCHF_2$, —O-cyclopropyl, -1-methyl-cyclopropyl, or pyrazolyl.

formula II-b

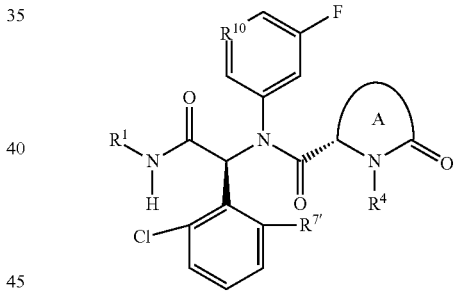

Provided is also a compound having formula II-b-1 or a pharmaceutically acceptable salt or hydrate thereof, wherein $R^1$, $R^4$, and ring A are as defined in formula I or any one of the above embodiments and $R^{7'}$ is H or Cl.

formula II-b-1

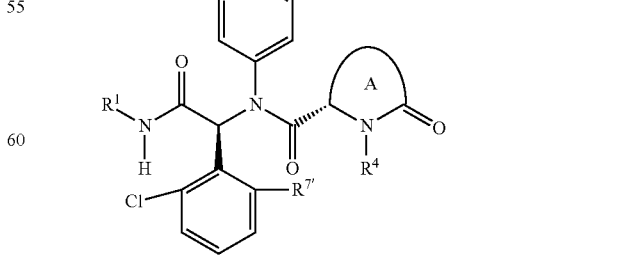

In another embodiment of formula II, II-a, II-a-1, II-b, or II-b-1, $R^1$ is:
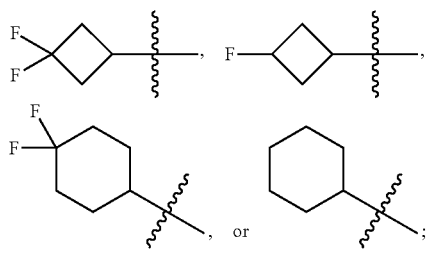
or ;
$R^4$ is:
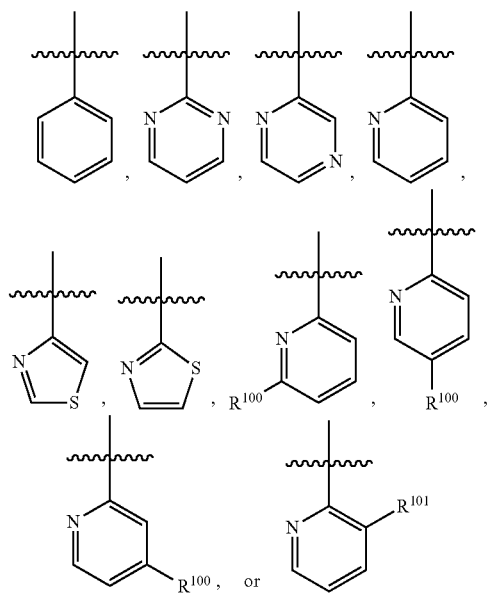
wherein $R^{100}$ is H, methyl, Cl, $CF_3$, CN, $OCH_3$, or $N(R^6)_2$ and $R^{101}$ is H, F or methyl;
ring A is:
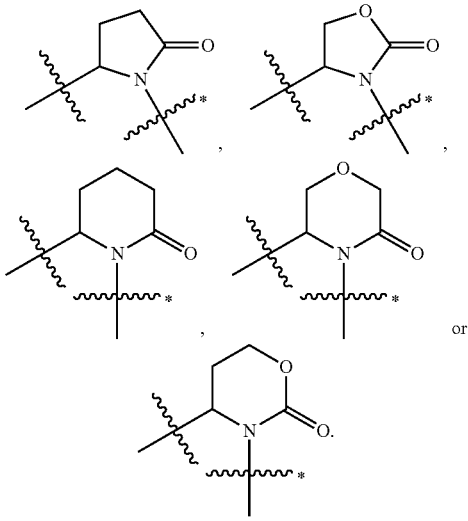
Further embodiments provided herein include combinations of one or more of the particular embodiments set forth above.
In another embodiment, exemplary compounds of formula I are depicted below in Table 1.
| Cpd No. | Structure |
|---|---|
| 1 | 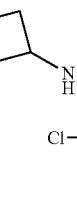 |
| 2 | 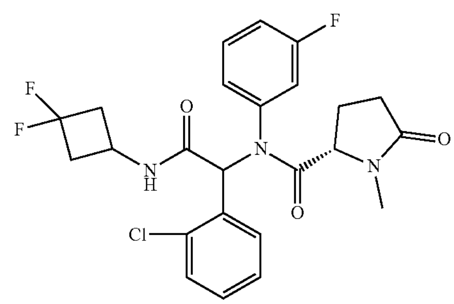 [SMILES: CN1C(=O)CC[C@H]1C(=O)N(c1cccc(F)c1)C(C(=O)NC1CC(F)(F)C1)c1ccccc1Cl] |
| 3 | 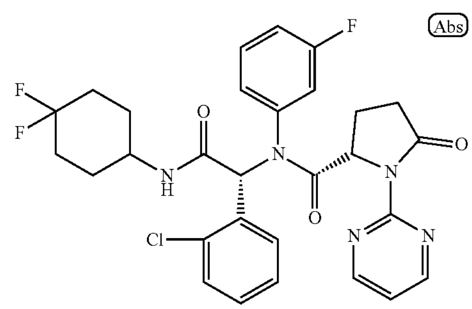 |
| 4 | 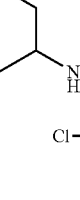 |
| 5 | 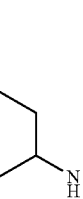 |

| Cpd No. | Structure |
|---|---|
| 6 | 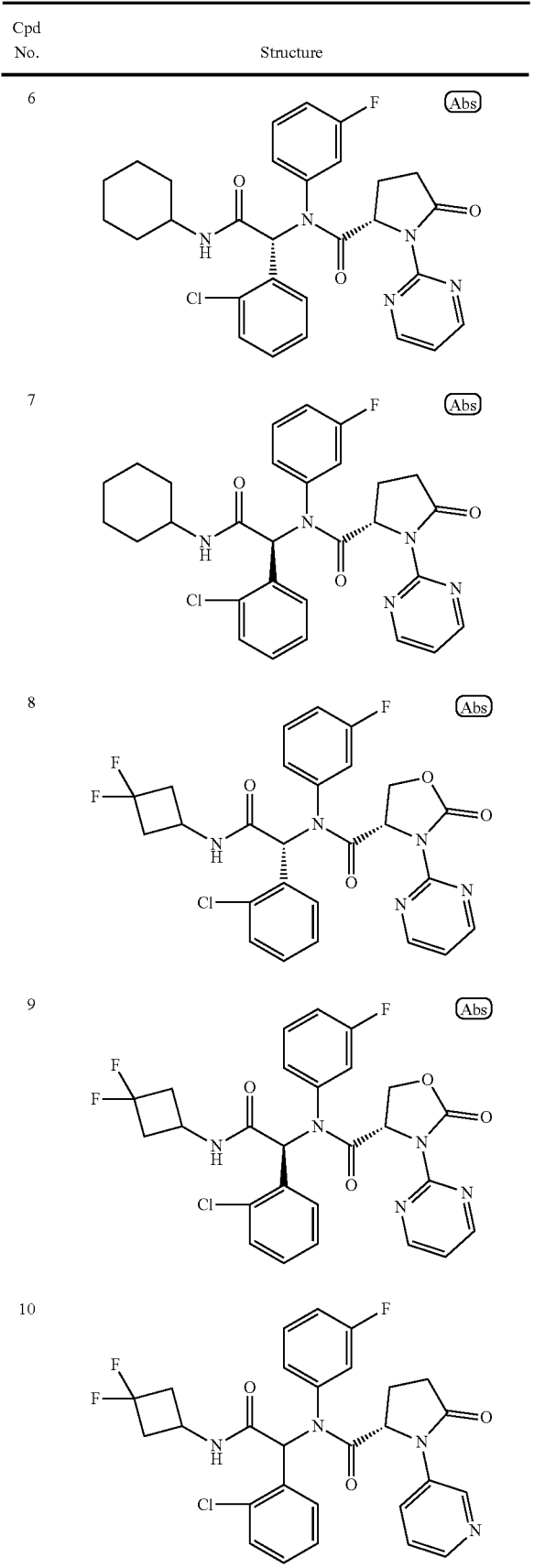 |
| 7 | |
| 8 | |
| 9 | |
| 10 | |
| Cpd No. | Structure |
|---|---|
| 11 | 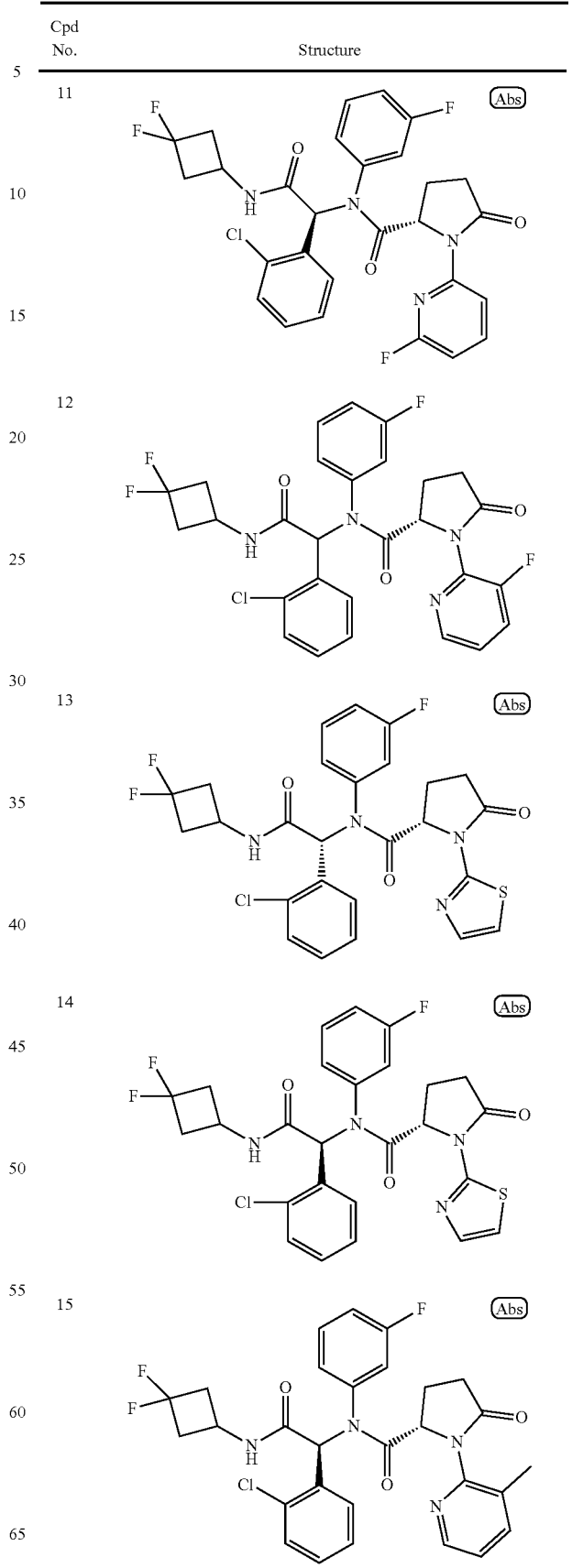 |
| 12 | |
| 13 | |
| 14 | |
| 15 | |

-continued
| Cpd No. | Structure |
|---|---|
| 16 | 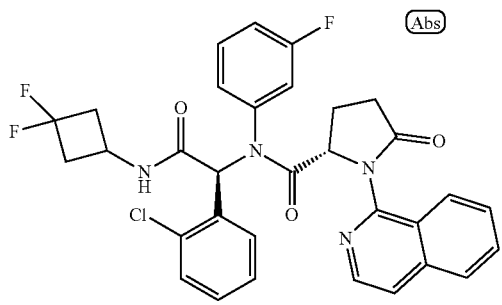 [SMILES: O=C(NC1CC(F)(F)C1)[C@H](c1ccccc1Cl)N(C(=O)[C@@H]1CCC(=O)N1c1nccc2ccccc12)c1cccc(F)c1 ; "Abs"] |
| 17 | 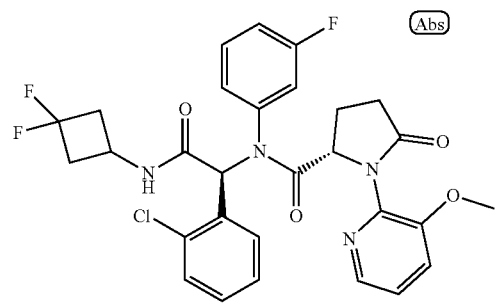 [SMILES: COc1cccnc1N1C(=O)CC[C@H]1C(=O)N(c1cccc(F)c1)[C@H](C(=O)NC1CC(F)(F)C1)c1ccccc1Cl ; "Abs"] |
| 18 | 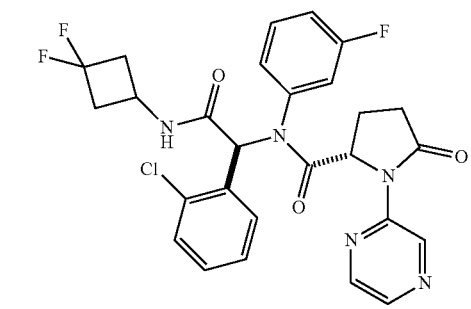 |
| 19 | 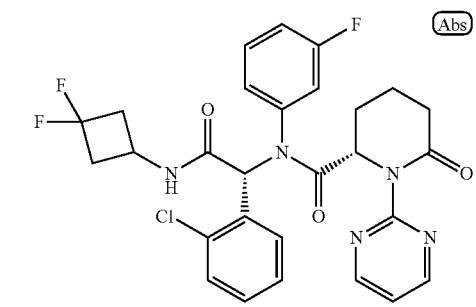 [SMILES: O=C(NC1CC(F)(F)C1)[C@@H](c1ccccc1Cl)N(C(=O)[C@@H]1CCCC(=O)N1c1ncccn1)c1cccc(F)c1 ; "Abs"] |
| 20 | 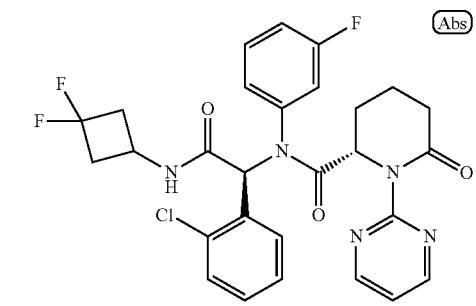 [SMILES: O=C(NC1CC(F)(F)C1)[C@H](c1ccccc1Cl)N(C(=O)[C@@H]1CCCC(=O)N1c1ncccn1)c1cccc(F)c1 ; "Abs"] |
-continued
| Cpd No. | Structure |
|---|---|
| 21 | 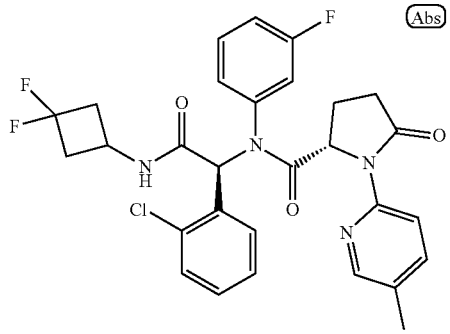 [SMILES: Cc1ccc(N2C(=O)CC[C@H]2C(=O)N(c2cccc(F)c2)[C@H](C(=O)NC2CC(F)(F)C2)c2ccccc2Cl)nc1 ; "Abs"] |
| 22 | 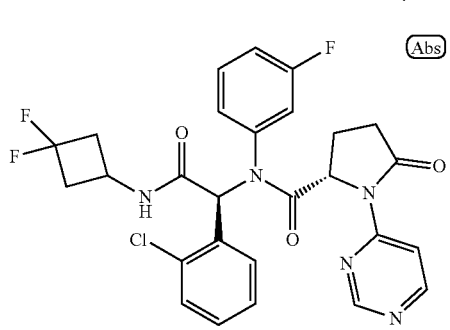 |
| 23 | 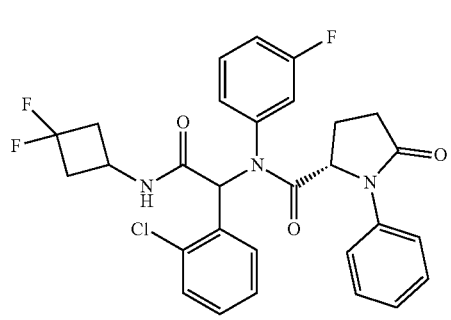 [SMILES: O=C(NC1CC(F)(F)C1)C(c1ccccc1Cl)N(C(=O)[C@@H]1CCC(=O)N1c1ccccc1)c1cccc(F)c1] |
| 24 | 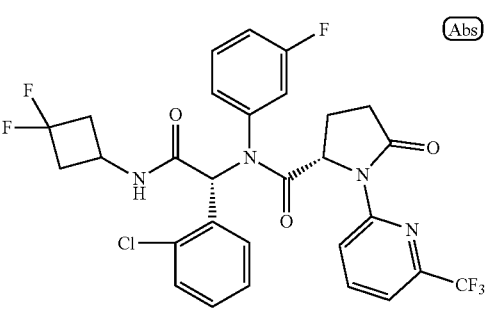 [SMILES: O=C(NC1CC(F)(F)C1)[C@@H](c1ccccc1Cl)N(C(=O)[C@@H]1CCC(=O)N1c1cccc(C(F)(F)F)n1)c1cccc(F)c1 ; "Abs"] |
| 25 | 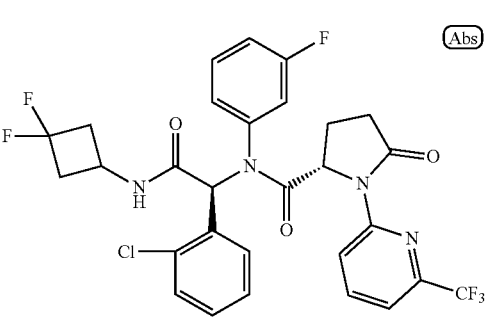 [SMILES: O=C(NC1CC(F)(F)C1)[C@H](c1ccccc1Cl)N(C(=O)[C@@H]1CCC(=O)N1c1cccc(C(F)(F)F)n1)c1cccc(F)c1 ; "Abs"] |

| Cpd No. | Structure |
|---|---|
| 26 | 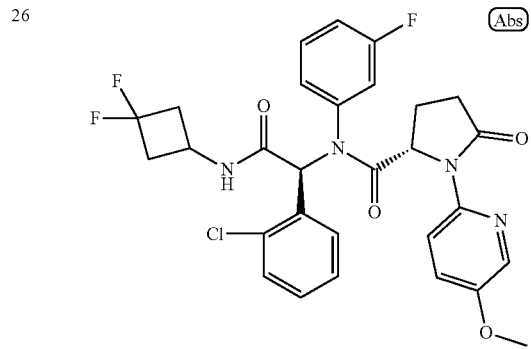 |
| 27 | 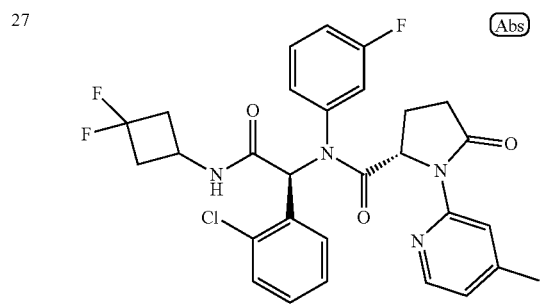 |
| 28 | 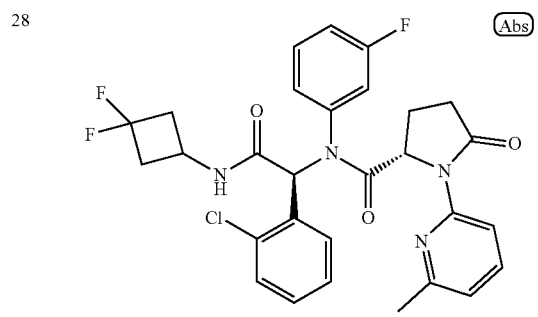 |
| 29 | 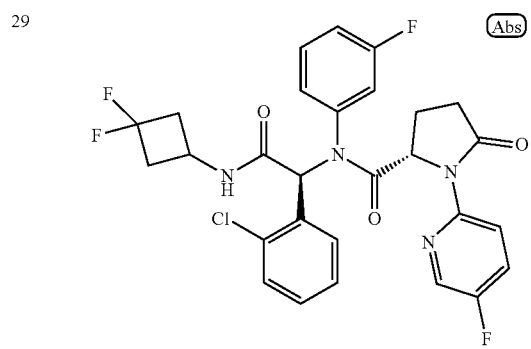 |
| 30 | 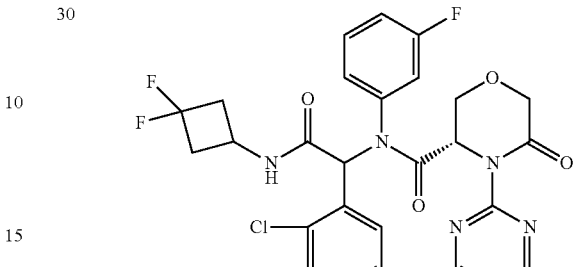 |
| 31 | 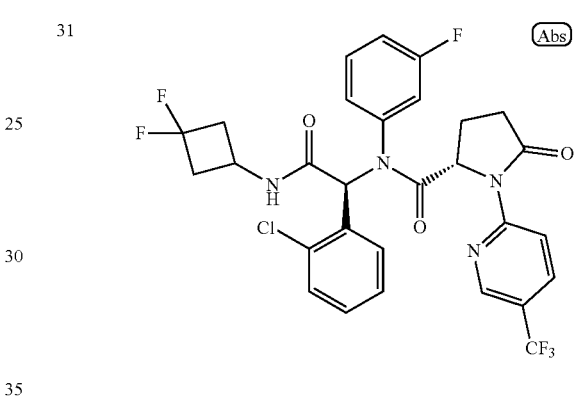 |
| 32 | 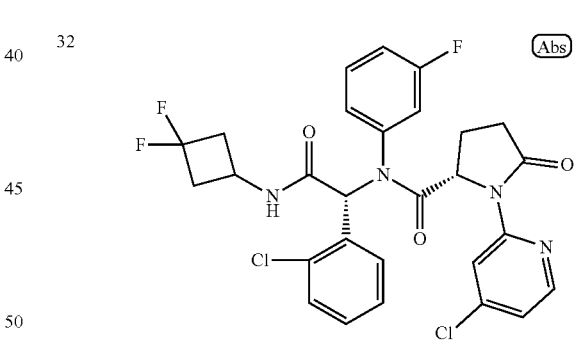 |
| 33 | 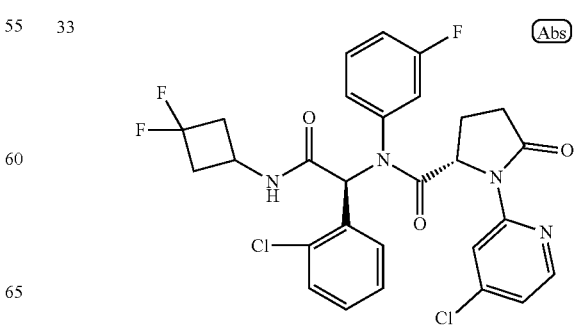 |

| Cpd No. | Structure |
|---|---|
| 34 | 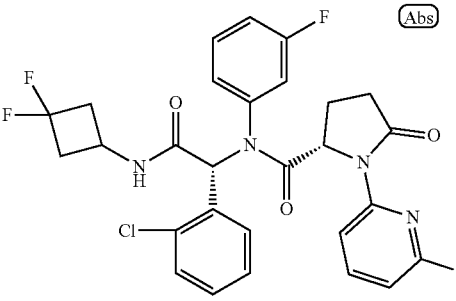 |
| 35 | 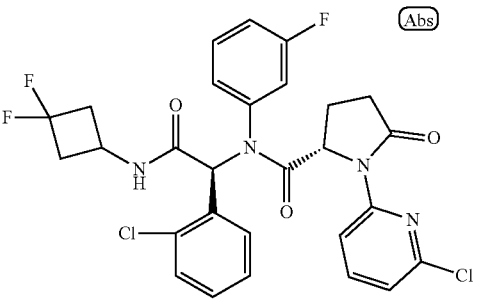 [SMILES: O=C(NC1CC(F)(F)C1)[C@H](c1ccccc1Cl)N(C(=O)[C@@H]1CCC(=O)N1c1cccc(Cl)n1)c1cccc(F)c1 ; "Abs"] |
| 36 | 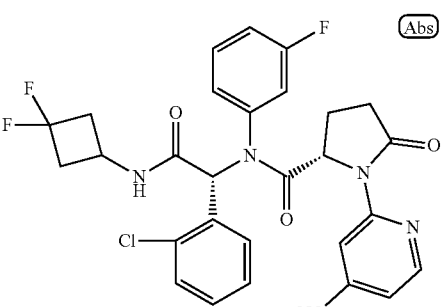 |
| 37 | 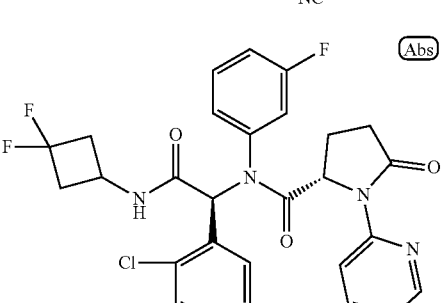 |
| 38 | 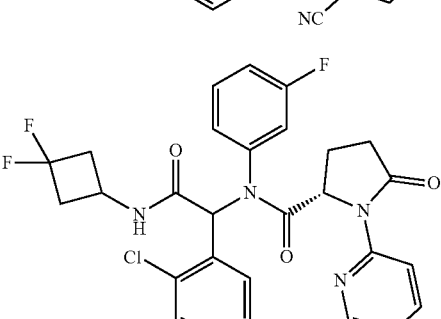 |
| Cpd No. | Structure |
|---|---|
| 39 | 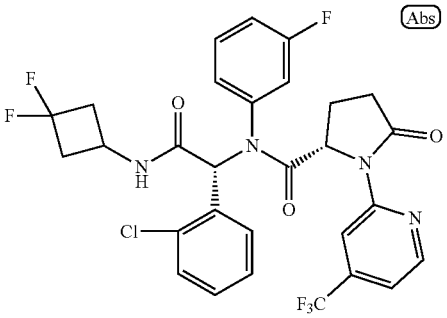 [SMILES: O=C(NC1CC(F)(F)C1)[C@@H](c1ccccc1Cl)N(C(=O)[C@@H]1CCC(=O)N1c1cc(C(F)(F)F)ccn1)c1cccc(F)c1 ; "Abs"] |
| 40 | 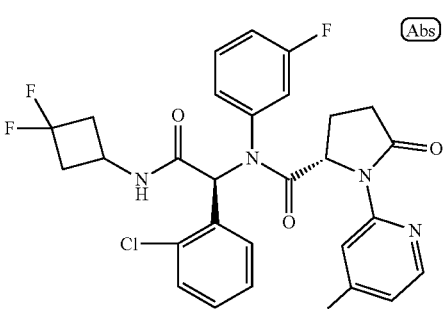 |
| 41 | 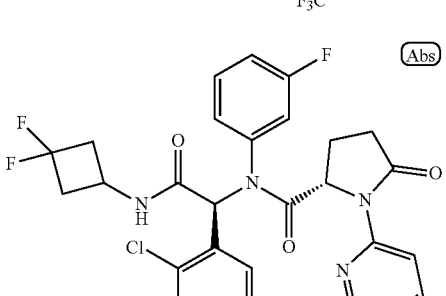 |
| 42 | 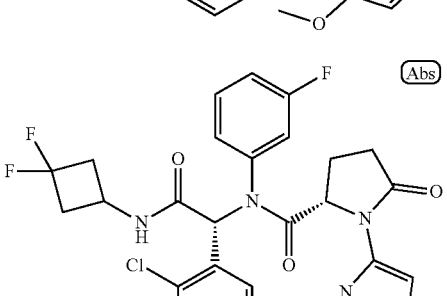 |
| 43 | 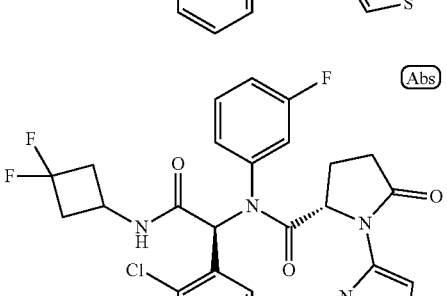 |

-continued
| Cpd No. | Structure |
|---|---|
| 44 | 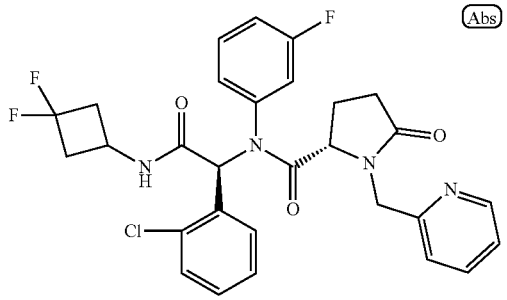 [SMILES: O=C(NC1CC(F)(F)C1)[C@H](c1ccccc1Cl)N(C(=O)[C@@H]1CCC(=O)N1Cc1ccccn1)c1cccc(F)c1 ; "Abs"] |
| 45 | 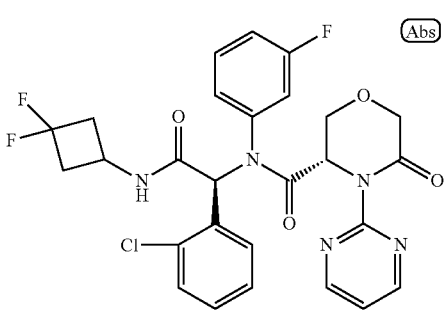 [SMILES: O=C(NC1CC(F)(F)C1)[C@H](c1ccccc1Cl)N(C(=O)[C@@H]1COCC(=O)N1c1ncccn1)c1cccc(F)c1 ; "Abs"] |
| 46 | 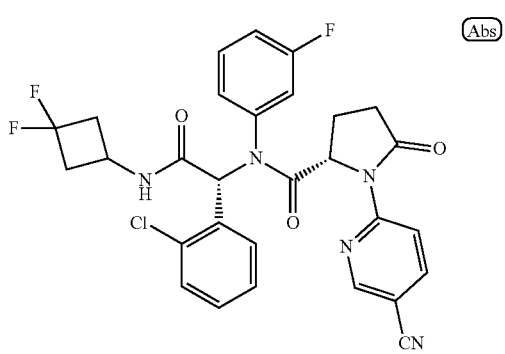 [SMILES: N#Cc1ccc(N2C(=O)CC[C@H]2C(=O)N(c2cccc(F)c2)[C@@H](C(=O)NC2CC(F)(F)C2)c2ccccc2Cl)nc1 ; "Abs"] |
| 47 | 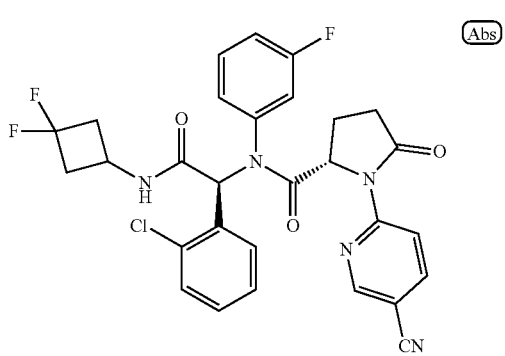 |
-continued
| Cpd No. | Structure |
|---|---|
| 48 | 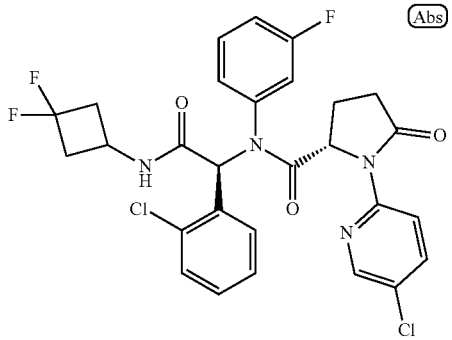 [SMILES: O=C(NC1CC(F)(F)C1)[C@H](c1ccccc1Cl)N(C(=O)[C@@H]1CCC(=O)N1c1ccc(Cl)cn1)c1cccc(F)c1 ; "Abs"] |
| 49 | 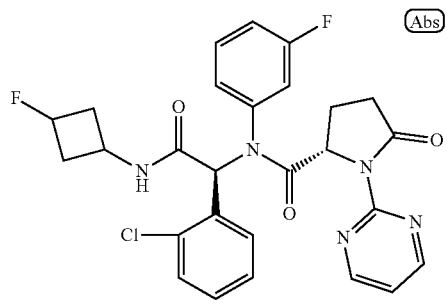 [SMILES: O=C(NC1CC(F)C1)[C@H](c1ccccc1Cl)N(C(=O)[C@@H]1CCC(=O)N1c1ncccn1)c1cccc(F)c1 ; "Abs"] |
| 50 | 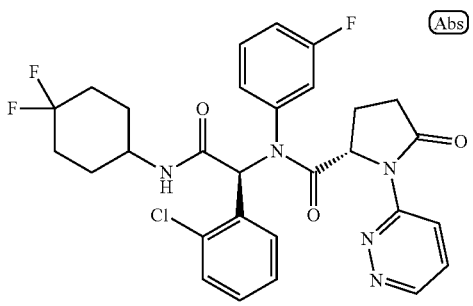 [SMILES: O=C(NC1CCC(F)(F)CC1)[C@H](c1ccccc1Cl)N(C(=O)[C@@H]1CCC(=O)N1c1cccnn1)c1cccc(F)c1 ; "Abs"] |
| 51 | 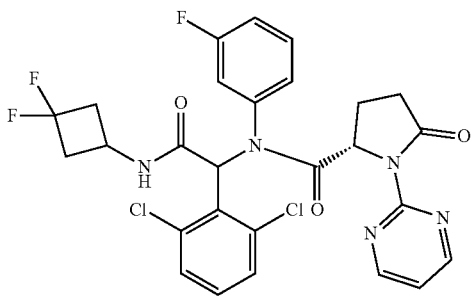 [SMILES: O=C(NC1CC(F)(F)C1)C(c1c(Cl)cccc1Cl)N(C(=O)[C@@H]1CCC(=O)N1c1ncccn1)c1cccc(F)c1] |
| 52 | 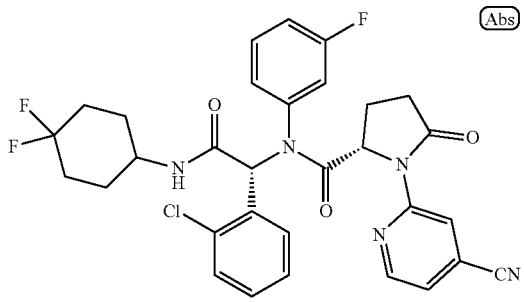 [SMILES: N#Cc1ccnc(N2C(=O)CC[C@H]2C(=O)N(c2cccc(F)c2)[C@@H](C(=O)NC2CCC(F)(F)CC2)c2ccccc2Cl)c1 ; "Abs"] |

| Cpd No. | Structure |
|---|---|
| 53 | 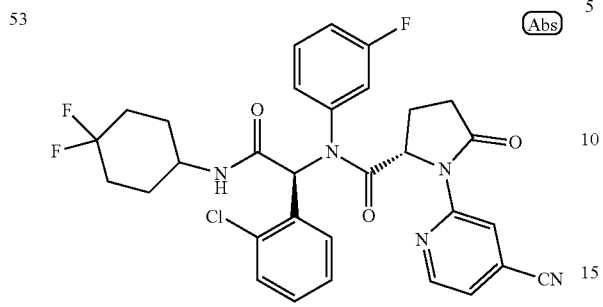 |
| 54 | 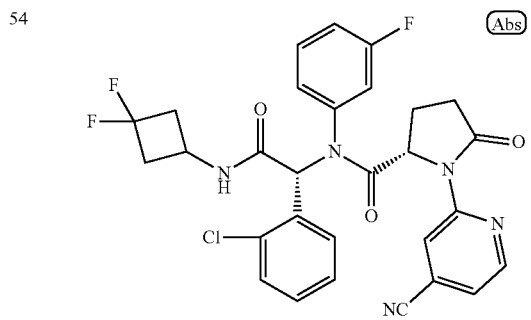 |
| 55 | 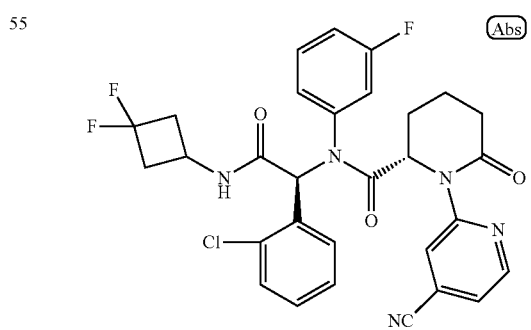 |
| 56 | 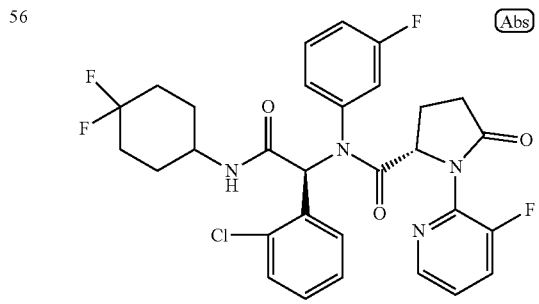 |
| 57 | 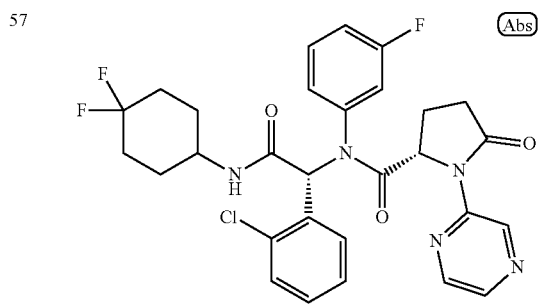 |
| Cpd No. | Structure |
|---|---|
| 58 | 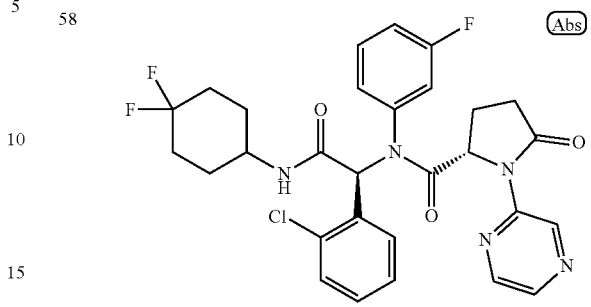 |
| 59 | 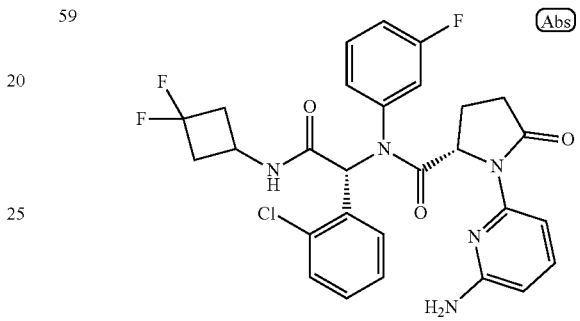 |
| 60 | 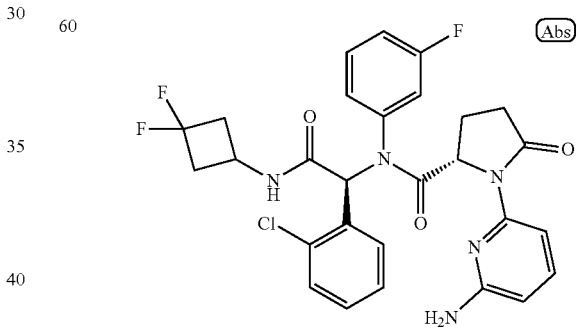 |
| 61 | 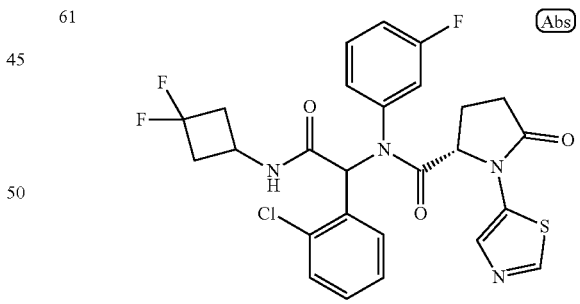 |
| 62 | 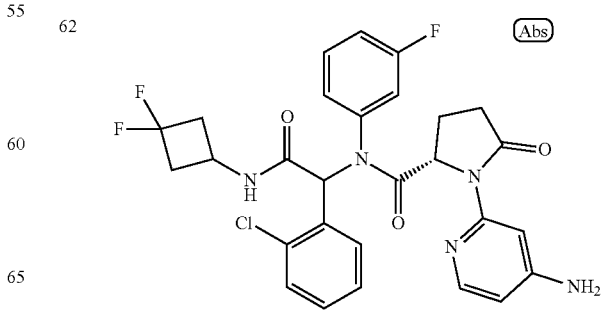 |

29
-continued
| Cpd No. | Structure |
|---|---|
| 63 | 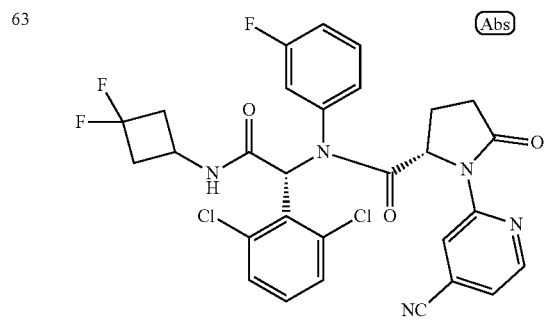 |
| 64 | 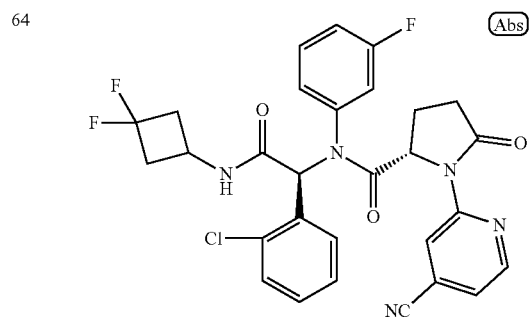 |
| 65 | 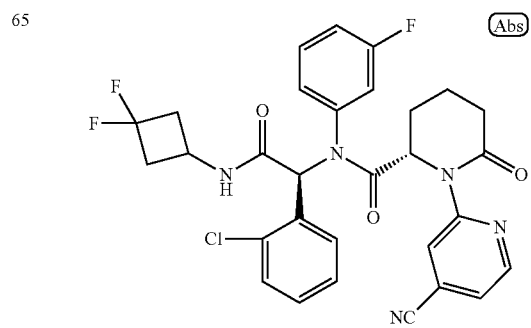 |
| 66 | 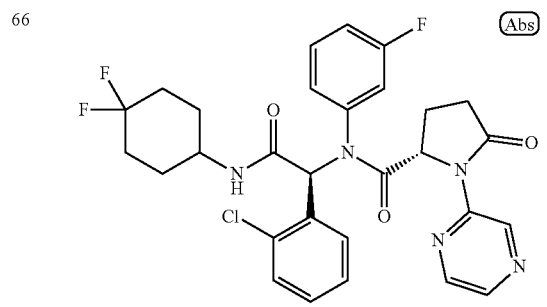 |
30
-continued
| Cpd No. | Structure |
|---|---|
| 67 | 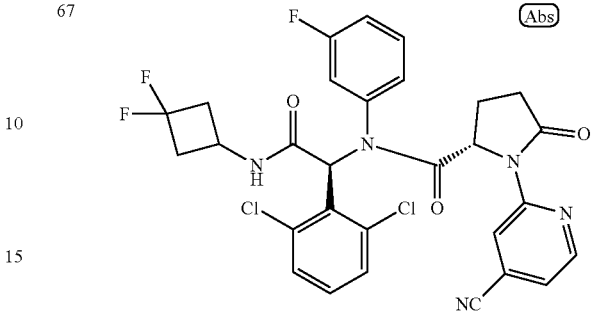 |
| 68 | 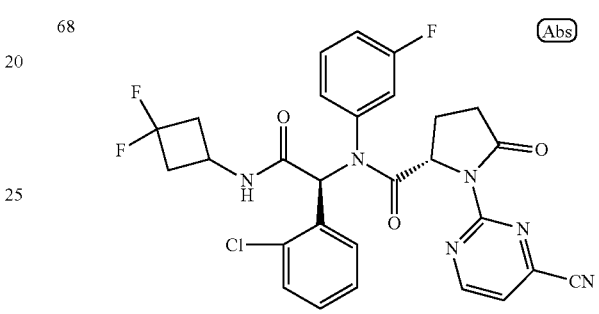 |
| 69 | 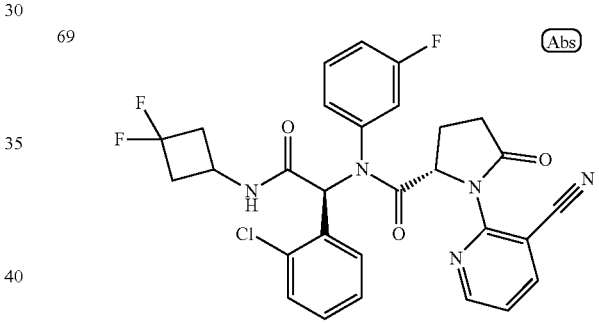 |
| 70 | 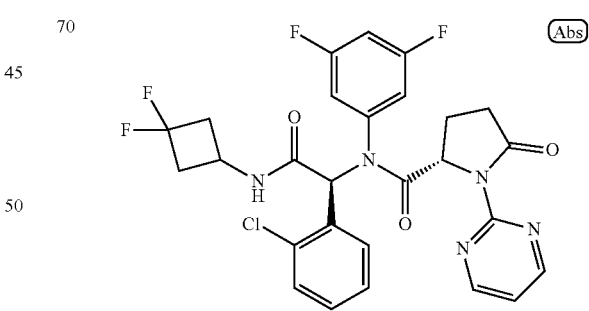 |
| 71 | 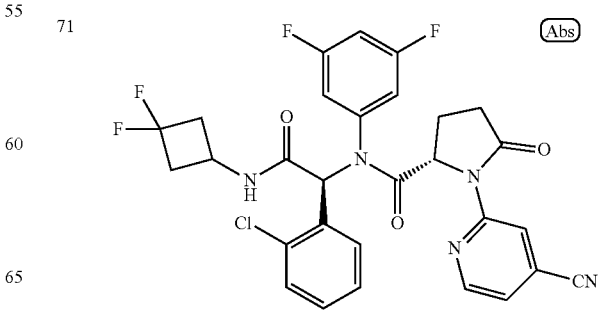 |

US 10,640,534 B2
| Cpd No. | Structure |
|---|---|
| 72 | 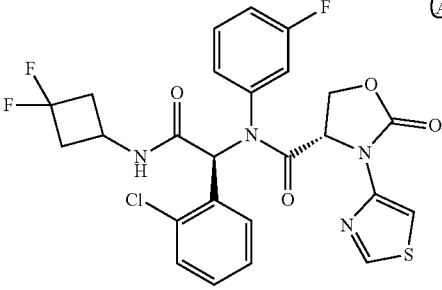 (Abs) |
| 73 | 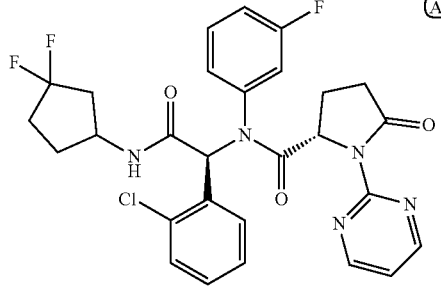 (Abs) |
| 74 | 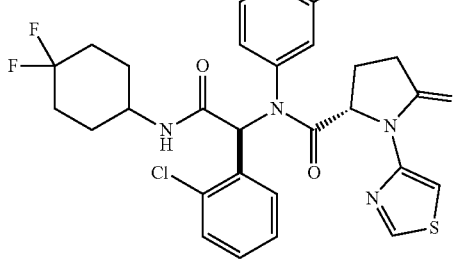 (Abs) |
| 75 | 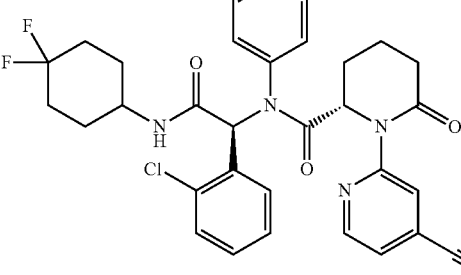 (Abs) |
| 76 | 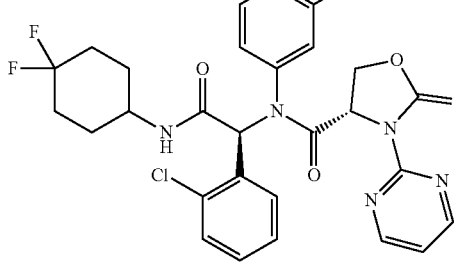 (Abs) |
| Cpd No. | Structure |
|---|---|
| 77 | 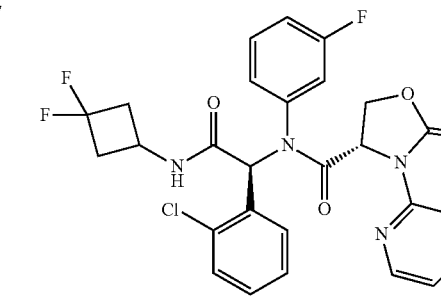 (Abs) |
| 78 | 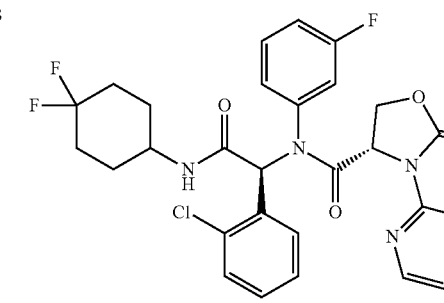 (Abs) |
| 79 | 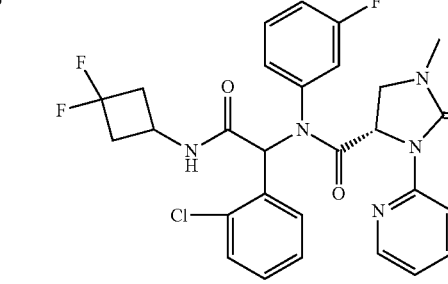 |
| 80 | 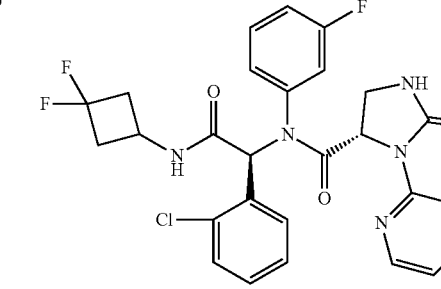 (Abs) |
| 81 | 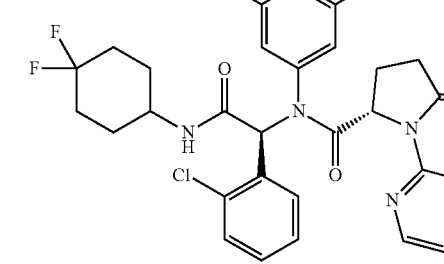 (Abs) |

| Cpd No. | Structure |
|---|---|
| 82 | 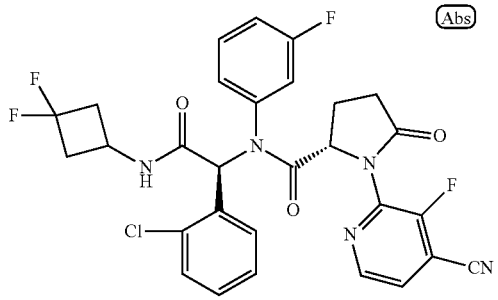 [SMILES: N#Cc1ccnc(N2C(=O)CC[C@H]2C(=O)N(c2cccc(F)c2)[C@H](C(=O)NC2CC(F)(F)C2)c2ccccc2Cl)c1F ; "Abs"] |
| 83 | 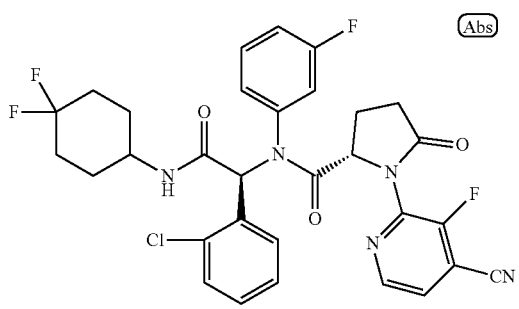 [SMILES: N#Cc1ccnc(N2C(=O)CC[C@H]2C(=O)N(c2cccc(F)c2)[C@H](C(=O)NC2CCC(F)(F)CC2)c2ccccc2Cl)c1F ; "Abs"] |
| 84 | 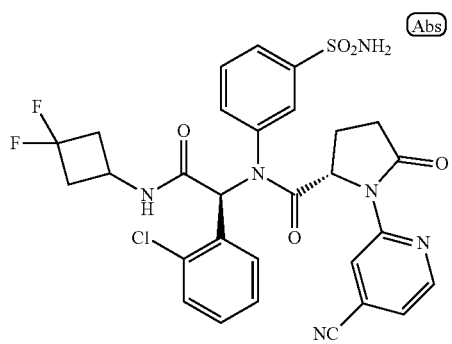 [SMILES: "Abs" ; N#Cc1ccnc(N2C(=O)CC[C@H]2C(=O)N(c2cccc(S(N)(=O)=O)c2)[C@H](C(=O)NC2CC(F)(F)C2)c2ccccc2Cl)c1] |
| 85 | 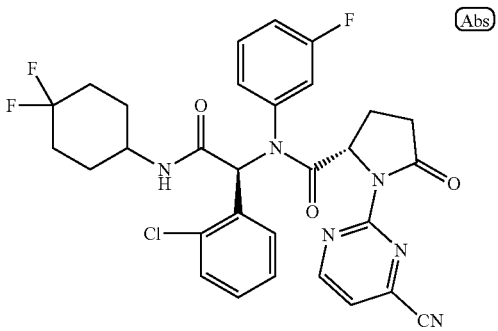 [SMILES: N#Cc1ccnc(N2C(=O)CC[C@H]2C(=O)N(c2cccc(F)c2)[C@H](C(=O)NC2CCC(F)(F)CC2)c2ccccc2Cl)n1 ; "Abs"] |
| 86 | 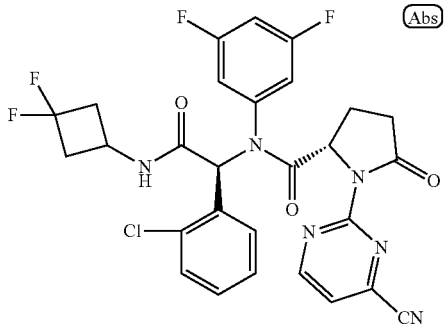 [SMILES: N#Cc1ccnc(N2C(=O)CC[C@H]2C(=O)N(c2cc(F)cc(F)c2)[C@H](C(=O)NC2CC(F)(F)C2)c2ccccc2Cl)n1 ; "Abs"] |
| 87 | 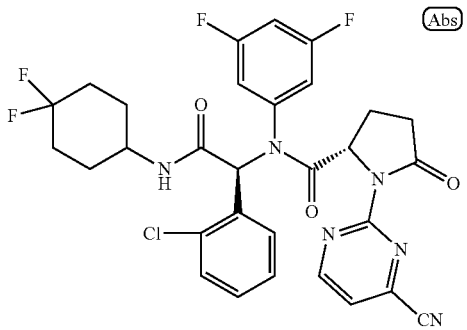 [SMILES: N#Cc1ccnc(N2C(=O)CC[C@H]2C(=O)N(c2cc(F)cc(F)c2)[C@H](C(=O)NC2CCC(F)(F)CC2)c2ccccc2Cl)n1 ; "Abs"] |
| 88 | 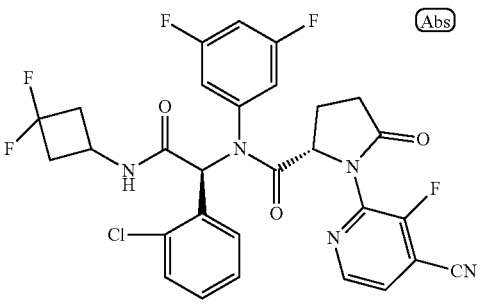 [SMILES: N#Cc1ccnc(N2C(=O)CC[C@H]2C(=O)N(c2cc(F)cc(F)c2)[C@H](C(=O)NC2CC(F)(F)C2)c2ccccc2Cl)c1F ; "Abs"] |
| 89 | 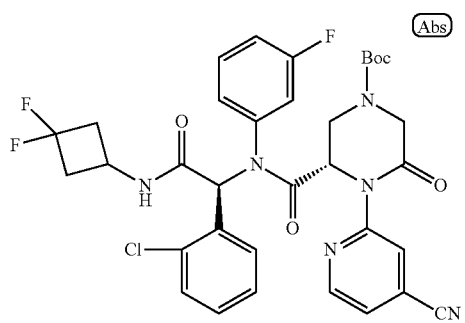 [SMILES: "Abs" ; CC(C)(C)OC(=O)N1CC(=O)N(c2cc(C#N)ccn2)[C@H](C(=O)N(c2cccc(F)c2)[C@H](C(=O)NC2CC(F)(F)C2)c2ccccc2Cl)C1] |

| Cpd No. | Structure |
|---|---|
| 90 | 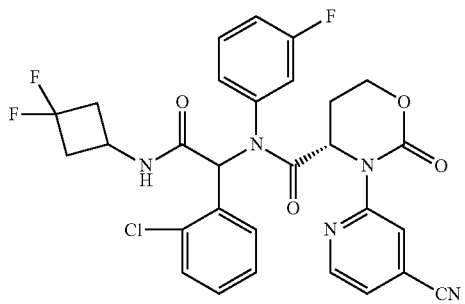 [SMILES: N#Cc1ccnc(N2C(=O)OCC[C@H]2C(=O)N(c2cccc(F)c2)C(C(=O)NC2CC(F)(F)C2)c2ccccc2Cl)c1] |
| 91 | 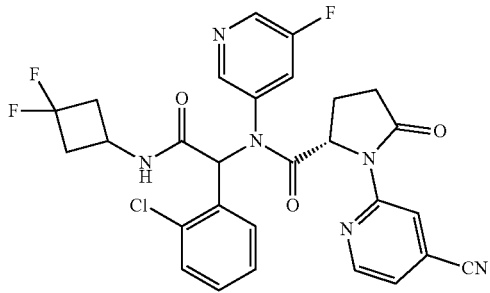 [SMILES: N#Cc1ccnc(N2C(=O)CC[C@H]2C(=O)N(c2cncc(F)c2)C(C(=O)NC2CC(F)(F)C2)c2ccccc2Cl)c1] |
| 92 | 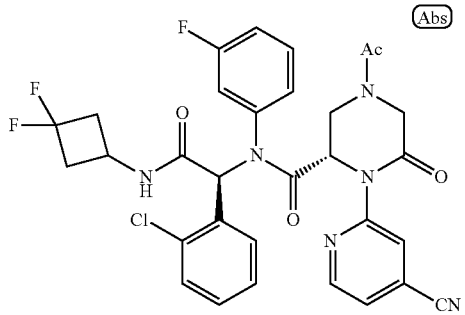 [SMILES: "Abs" ; CC(=O)N1CC(=O)N(c2cc(C#N)ccn2)[C@H](C(=O)N(c2cccc(F)c2)[C@H](C(=O)NC2CC(F)(F)C2)c2ccccc2Cl)C1] |
| 93 | 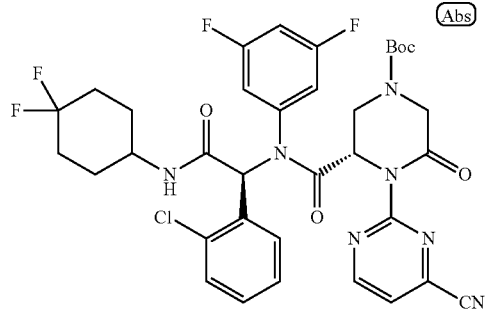 [SMILES: "Abs" ; CC(C)(C)OC(=O)N1CC(=O)N(c2nccc(C#N)n2)[C@H](C(=O)N(c2cc(F)cc(F)c2)[C@H](C(=O)NC2CCC(F)(F)CC2)c2ccccc2Cl)C1] |
| Cpd No. | Structure |
|---|---|
| 94 | 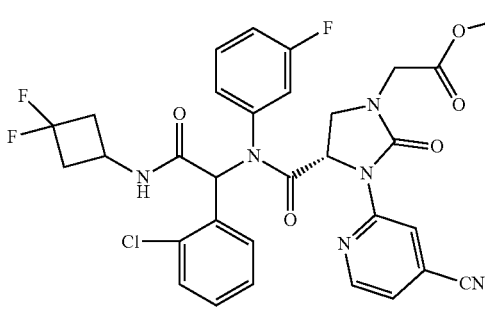 |
| 95 | 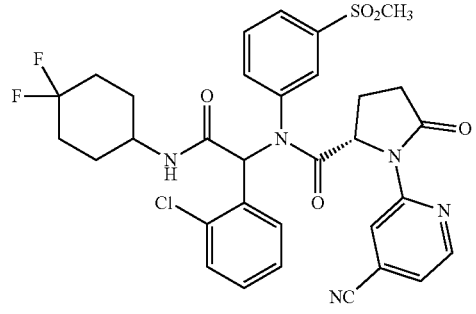 [SMILES: CS(=O)(=O)c1cccc(N(C(=O)[C@@H]2CCC(=O)N2c2cc(C#N)ccn2)C(C(=O)NC2CCC(F)(F)CC2)c2ccccc2Cl)c1] |
| 96 | 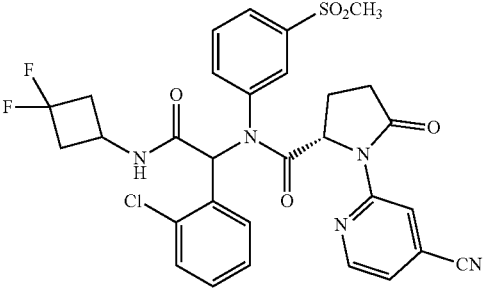 [SMILES: CS(=O)(=O)c1cccc(N(C(=O)[C@@H]2CCC(=O)N2c2cc(C#N)ccn2)C(C(=O)NC2CC(F)(F)C2)c2ccccc2Cl)c1] |
| 97 | 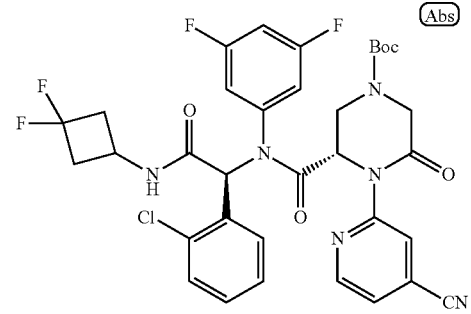 [SMILES: "Abs" ; CC(C)(C)OC(=O)N1CC(=O)N(c2cc(C#N)ccn2)[C@H](C(=O)N(c2cc(F)cc(F)c2)[C@H](C(=O)NC2CC(F)(F)C2)c2ccccc2Cl)C1] |

37
-continued
| Cpd No. | Structure |
|---|---|
| 98 | 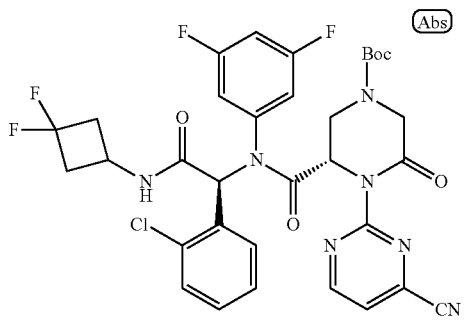 [SMILES: "Abs" ; CC(C)(C)OC(=O)N1CC(=O)N(c2nccc(C#N)n2)[C@H](C(=O)N(c2cc(F)cc(F)c2)[C@H](C(=O)NC2CC(F)(F)C2)c2ccccc2Cl)C1] |
| 99 | 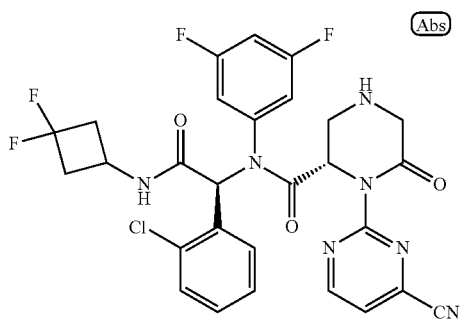 [SMILES: "Abs" ; N#Cc1ccnc(N2C(=O)CNC[C@H]2C(=O)N(c2cc(F)cc(F)c2)[C@H](C(=O)NC2CC(F)(F)C2)c2ccccc2Cl)n1] |
| 100 | 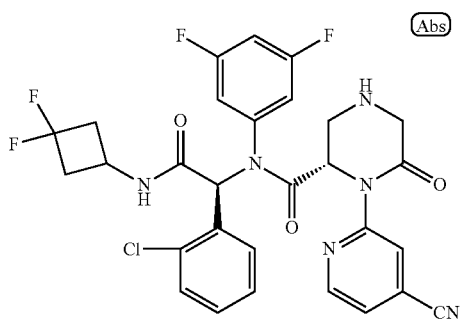 [SMILES: "Abs" ; N#Cc1ccnc(N2C(=O)CNC[C@H]2C(=O)N(c2cc(F)cc(F)c2)[C@H](C(=O)NC2CC(F)(F)C2)c2ccccc2Cl)c1] |
| 101 | 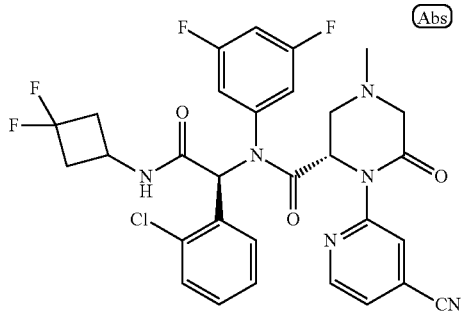 [SMILES: "Abs" ; CN1CC(=O)N(c2cc(C#N)ccn2)[C@H](C(=O)N(c2cc(F)cc(F)c2)[C@H](C(=O)NC2CC(F)(F)C2)c2ccccc2Cl)C1] |
38
-continued
| Cpd No. | Structure |
|---|---|
| 102 | 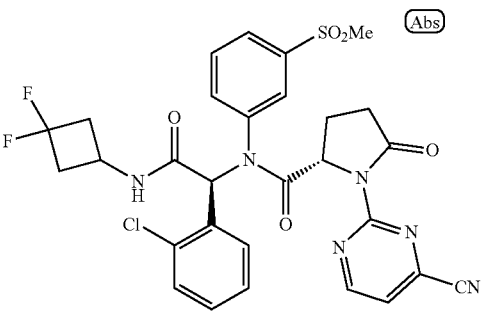 [SMILES: "Abs" ; CS(=O)(=O)c1cccc(N(C(=O)[C@@H]2CCC(=O)N2c2nccc(C#N)n2)[C@H](C(=O)NC2CC(F)(F)C2)c2ccccc2Cl)c1] |
| 103 | 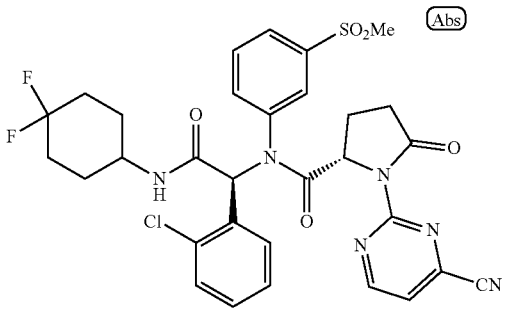 [SMILES: "Abs" ; CS(=O)(=O)c1cccc(N(C(=O)[C@@H]2CCC(=O)N2c2nccc(C#N)n2)[C@H](C(=O)NC2CCC(F)(F)CC2)c2ccccc2Cl)c1] |
| 104 | 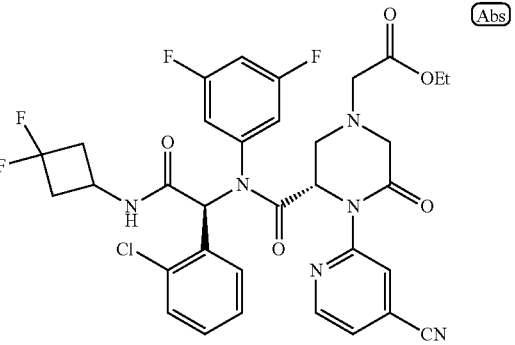 [SMILES: CCOC(=O)CN1CC(=O)N(c2cc(C#N)ccn2)[C@H](C(=O)N(c2cc(F)cc(F)c2)[C@H](C(=O)NC2CC(F)(F)C2)c2ccccc2Cl)C1 ; "Abs"] |
| 105 | 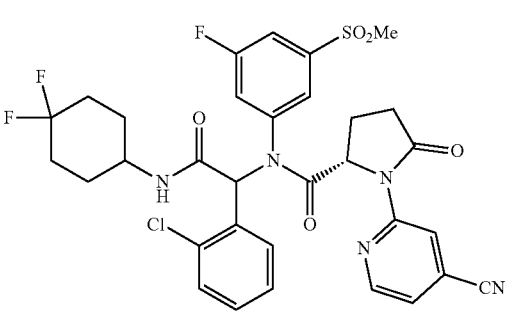 [SMILES: CS(=O)(=O)c1cc(F)cc(N(C(=O)[C@@H]2CCC(=O)N2c2cc(C#N)ccn2)C(C(=O)NC2CCC(F)(F)CC2)c2ccccc2Cl)c1] |

-continued
| Cpd No. | Structure |
|---|---|
| 106 | 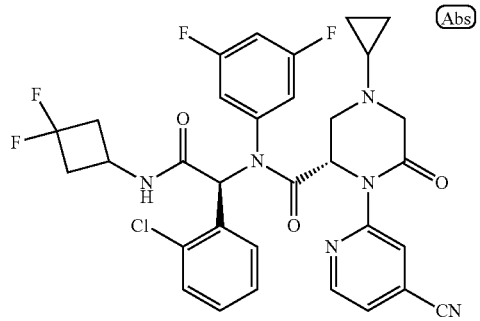 |
| 107 | 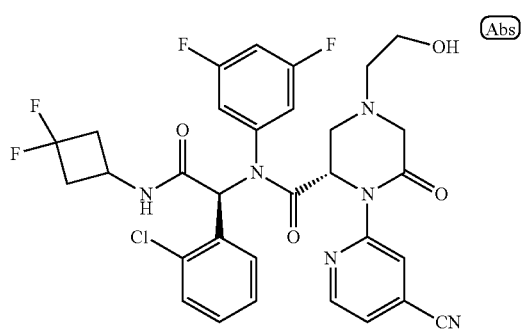 |
| 108 | 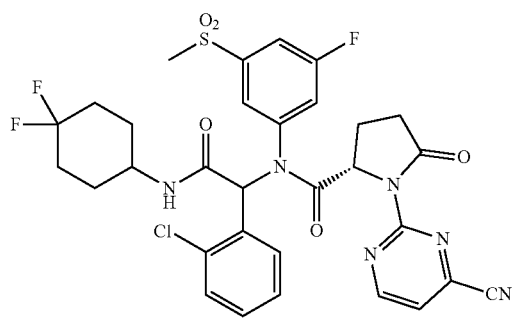 [SMILES: CS(=O)(=O)c1cc(F)cc(N(C(=O)[C@@H]2CCC(=O)N2c2nccc(C#N)n2)C(C(=O)NC2CCC(F)(F)CC2)c2ccccc2Cl)c1] |
| 109 | 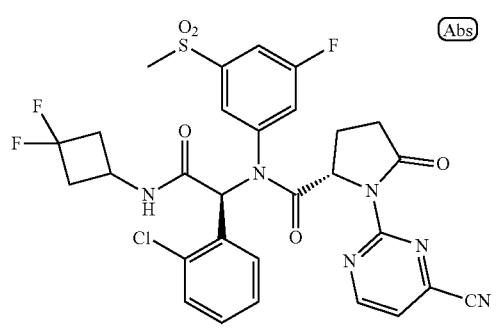 [SMILES: "Abs" ; CS(=O)(=O)c1cc(F)cc(N(C(=O)[C@@H]2CCC(=O)N2c2nccc(C#N)n2)[C@H](C(=O)NC2CC(F)(F)C2)c2ccccc2Cl)c1] |
-continued
| Cpd No. | Structure |
|---|---|
| 110 | 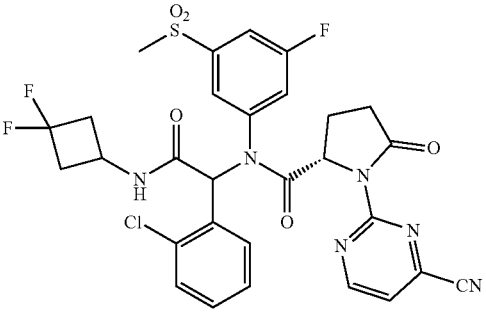 |
| 111 | 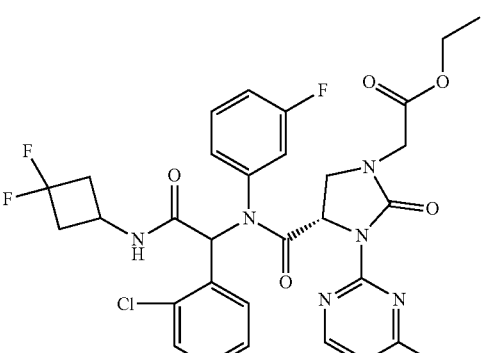 |
| 112 | 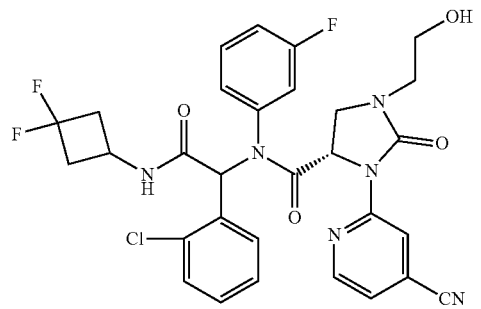 [SMILES: N#Cc1ccnc(N2C(=O)N(CCO)C[C@H]2C(=O)N(c2cccc(F)c2)C(C(=O)NC2CC(F)(F)C2)c2ccccc2Cl)c1] |
| 113 | 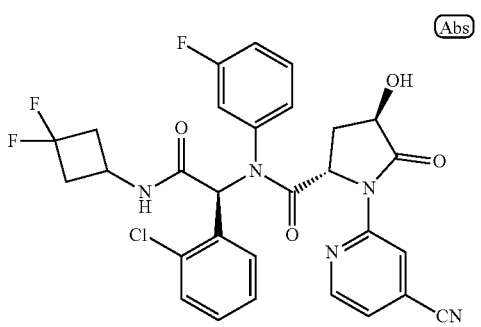 [SMILES: "Abs" ; N#Cc1ccnc(N2C(=O)[C@H](O)C[C@H]2C(=O)N(c2cccc(F)c2)[C@H](C(=O)NC2CC(F)(F)C2)c2ccccc2Cl)c1] |

| Cpd No. | Structure |
|---|---|
| 114 | 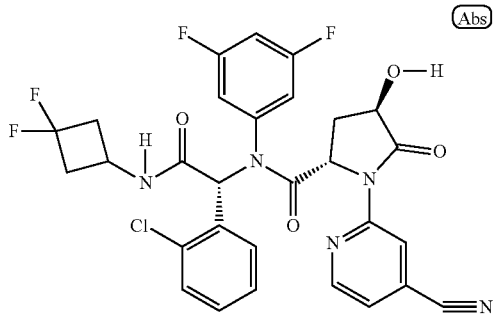 [SMILES: "Abs" ; N#Cc1ccnc(N2C(=O)[C@H](O)C[C@H]2C(=O)N(c2cc(F)cc(F)c2)[C@@H](C(=O)NC2CC(F)(F)C2)c2ccccc2Cl)c1] |
| 115 | 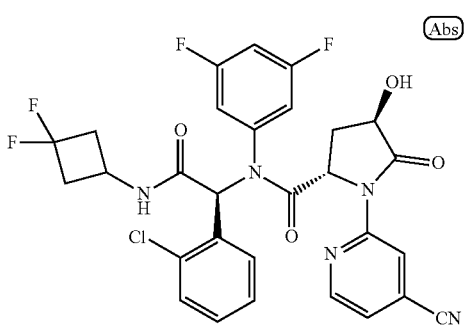 [SMILES: "Abs" ; N#Cc1ccnc(N2C(=O)[C@H](O)C[C@H]2C(=O)N(c2cc(F)cc(F)c2)[C@H](C(=O)NC2CC(F)(F)C2)c2ccccc2Cl)c1] |
| 116 | 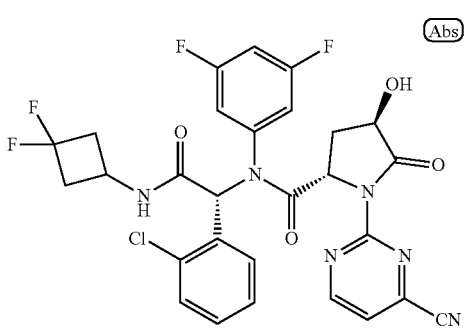 [SMILES: "Abs" ; N#Cc1ccnc(N2C(=O)[C@H](O)C[C@H]2C(=O)N(c2cc(F)cc(F)c2)[C@@H](C(=O)NC2CC(F)(F)C2)c2ccccc2Cl)n1] |
| 117 | 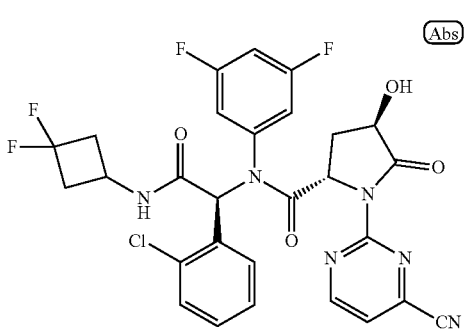 [SMILES: "Abs" ; N#Cc1ccnc(N2C(=O)[C@H](O)C[C@H]2C(=O)N(c2cc(F)cc(F)c2)[C@H](C(=O)NC2CC(F)(F)C2)c2ccccc2Cl)n1] |
| 118 | 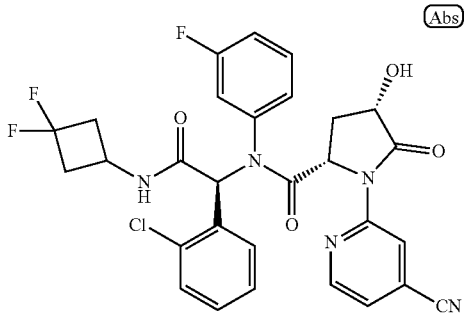 [SMILES: "Abs" ; N#Cc1ccnc(N2C(=O)[C@@H](O)C[C@H]2C(=O)N(c2cccc(F)c2)[C@H](C(=O)NC2CC(F)(F)C2)c2ccccc2Cl)c1] |
| 119 | 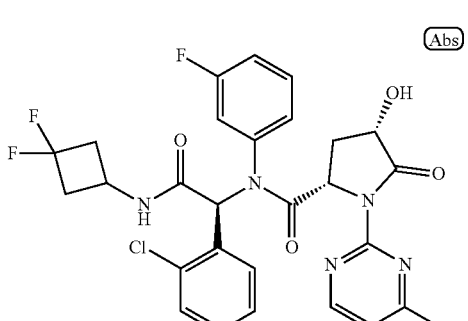 |
| 120 | 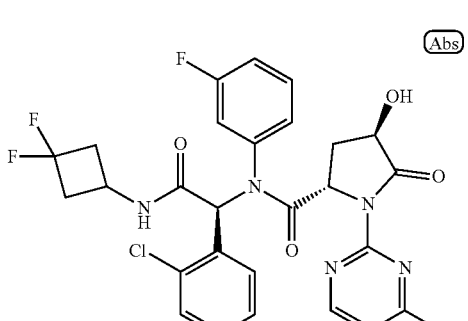 |
| 121 | 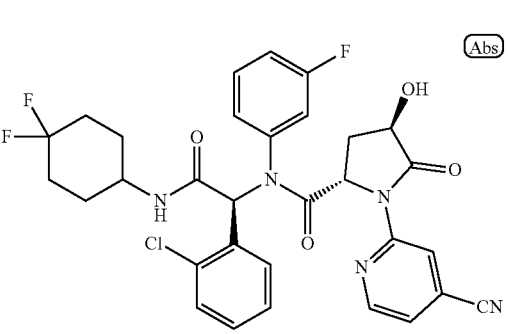 [SMILES: "Abs" ; N#Cc1ccnc(N2C(=O)[C@H](O)C[C@H]2C(=O)N(c2cccc(F)c2)[C@H](C(=O)NC2CCC(F)(F)CC2)c2ccccc2Cl)c1] |

| Cpd No. | Structure |
|---|---|
| 122 | 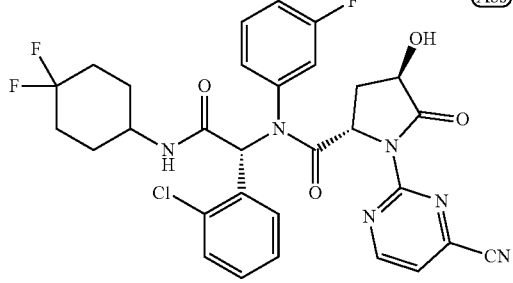 (Abs) |
| 123 | 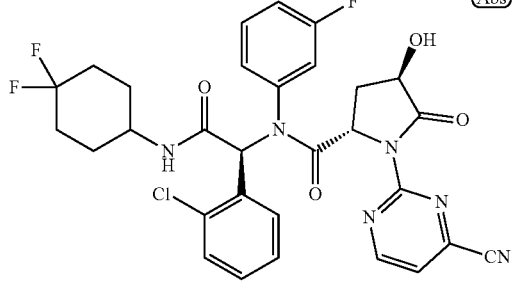 (Abs) |
| 124 | 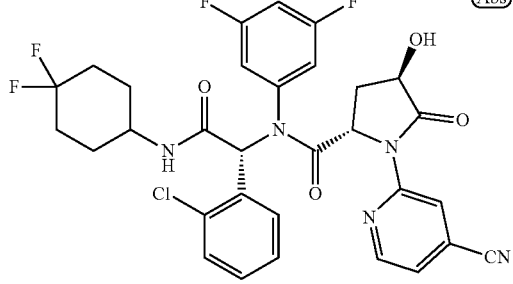 (Abs) |
| 125 | 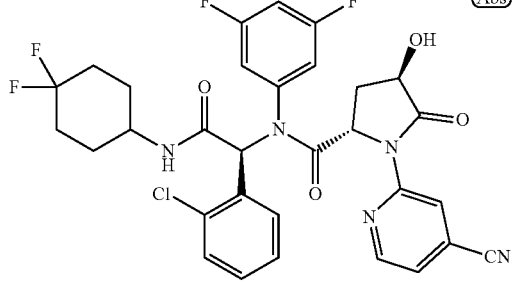 (Abs) |
| 126 | 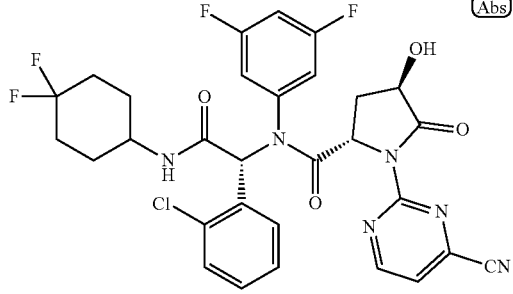 (Abs) |
| Cpd No. | Structure |
|---|---|
| 127 | 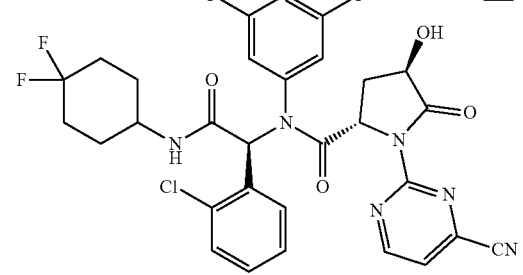 (Abs) |
| 128 | 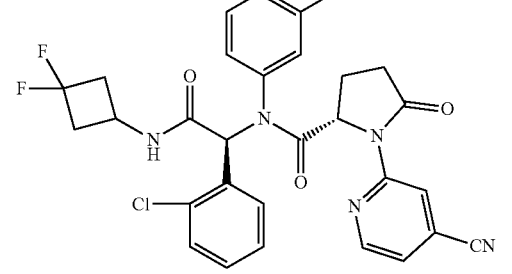 (Abs) |
| 129 | 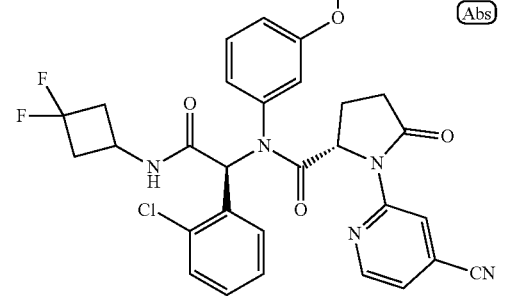 [SMILES: "Abs" ; N#Cc1cccc(N(C(=O)[C@@H]2CCC(=O)N2c2cc(C#N)ccn2)[C@H](C(=O)NC2CC(F)(F)C2)c2ccccc2Cl)c1] (Abs) |
| 130 | 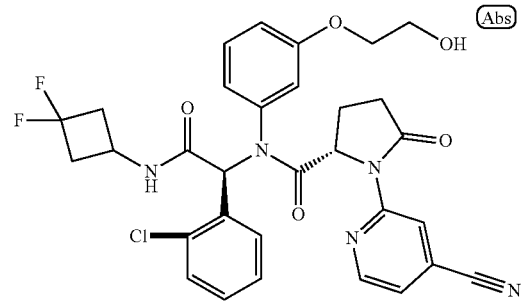 (Abs) |
| 131 | 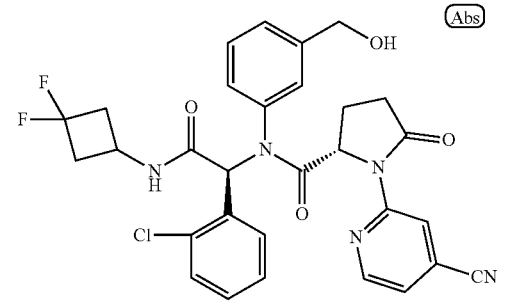 [SMILES: "Abs" ; N#Cc1ccnc(N2C(=O)CC[C@H]2C(=O)N(c2cccc(CO)c2)[C@H](C(=O)NC2CC(F)(F)C2)c2ccccc2Cl)c1] (Abs) |

-continued
| Cpd No. | Structure |
|---|---|
| 132 | 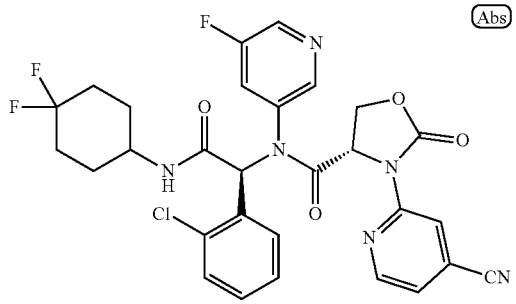 [SMILES: "Abs" ; N#Cc1ccnc(N2C(=O)OC[C@H]2C(=O)N(c2cncc(F)c2)[C@H](C(=O)NC2CCC(F)(F)CC2)c2ccccc2Cl)c1] (Abs) |
| 133 | 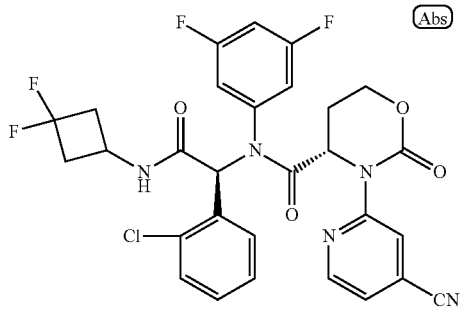 [SMILES: "Abs" ; N#Cc1ccnc(N2C(=O)OCC[C@H]2C(=O)N(c2cc(F)cc(F)c2)[C@H](C(=O)NC2CC(F)(F)C2)c2ccccc2Cl)c1] (Abs) |
| 134 | 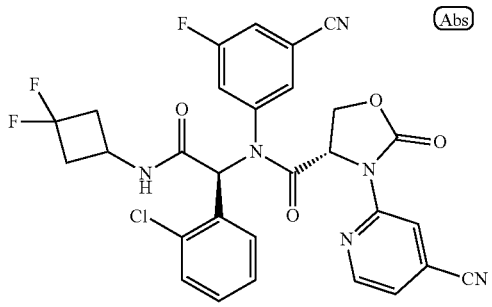 [SMILES: "Abs" ; N#Cc1cc(F)cc(N(C(=O)[C@@H]2COC(=O)N2c2cc(C#N)ccn2)[C@H](C(=O)NC2CC(F)(F)C2)c2ccccc2Cl)c1] (Abs) |
| 135 | 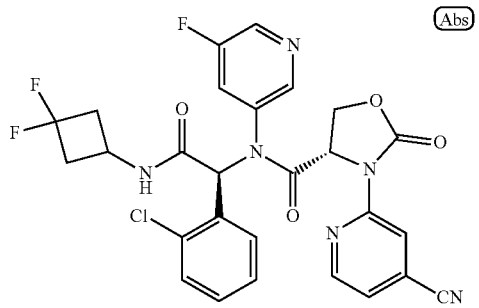 [SMILES: "Abs" ; N#Cc1ccnc(N2C(=O)OC[C@H]2C(=O)N(c2cncc(F)c2)[C@H](C(=O)NC2CC(F)(F)C2)c2ccccc2Cl)c1] (Abs) |
-continued
| Cpd No. | Structure |
|---|---|
| 136 | 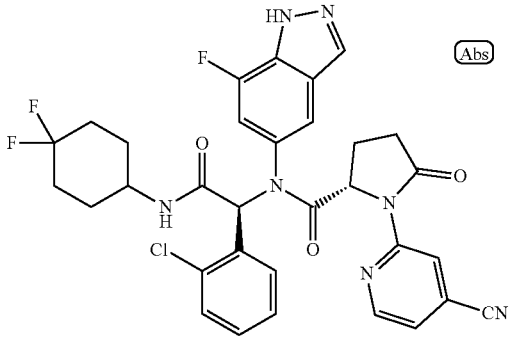 [SMILES: N#Cc1ccnc(N2C(=O)CC[C@H]2C(=O)N(c2cc(F)c3[nH]ncc3c2)[C@H](C(=O)NC2CCC(F)(F)CC2)c2ccccc2Cl)c1 ; "Abs"] (Abs) |
| 137 | 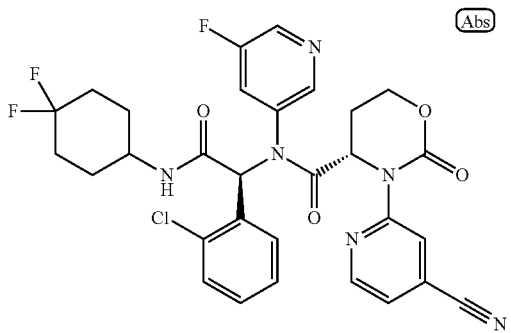 [SMILES: "Abs" ; N#Cc1ccnc(N2C(=O)OCC[C@H]2C(=O)N(c2cncc(F)c2)[C@H](C(=O)NC2CCC(F)(F)CC2)c2ccccc2Cl)c1] (Abs) |
| 138 | 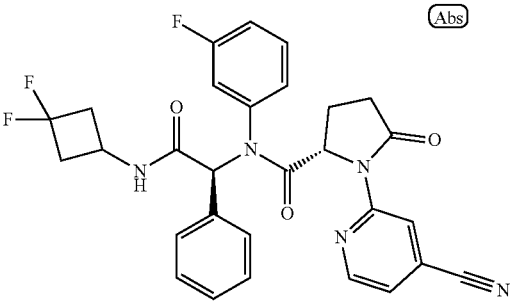 [SMILES: "Abs" ; N#Cc1ccnc(N2C(=O)CC[C@H]2C(=O)N(c2cccc(F)c2)[C@H](C(=O)NC2CC(F)(F)C2)c2ccccc2)c1] (Abs) |
| 139 | 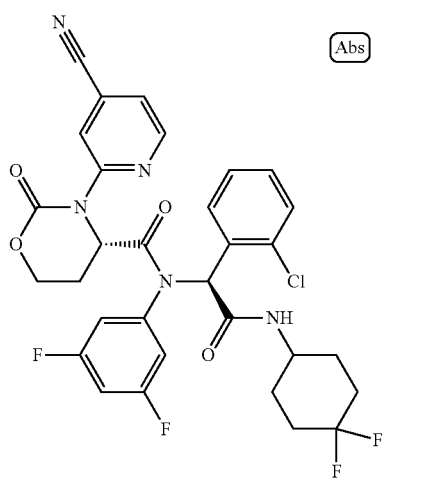 [SMILES: N#Cc1ccnc(N2C(=O)OCC[C@H]2C(=O)N(c2cc(F)cc(F)c2)[C@H](C(=O)NC2CCC(F)(F)CC2)c2ccccc2Cl)c1] (Abs) |

| Cpd No. | Structure |
|---|---|
| 140 | 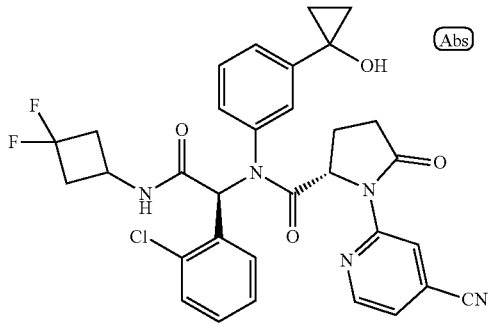 [SMILES: N#Cc1ccnc(N2C(=O)CC[C@H]2C(=O)N(c2cccc(C3(O)CC3)c2)[C@H](C(=O)NC2CC(F)(F)C2)c2ccccc2Cl)c1 ; "Abs"] |
| 141 | 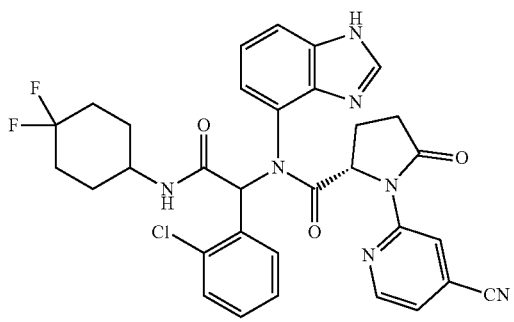 [SMILES: N#Cc1ccnc(N2C(=O)CC[C@H]2C(=O)N(c2cccc3[nH]cnc23)C(C(=O)NC2CCC(F)(F)CC2)c2ccccc2Cl)c1] |
| 142 | 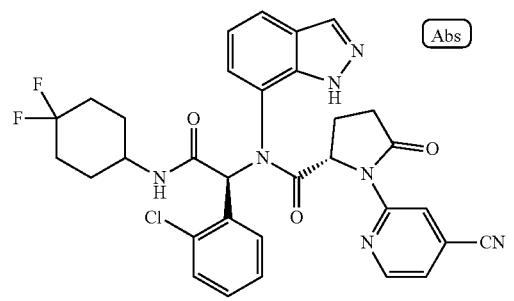 [SMILES: N#Cc1ccnc(N2C(=O)CC[C@H]2C(=O)N(c2cccc3cn[nH]c23)[C@H](C(=O)NC2CCC(F)(F)CC2)c2ccccc2Cl)c1 ; "Abs"] |
| 143 | 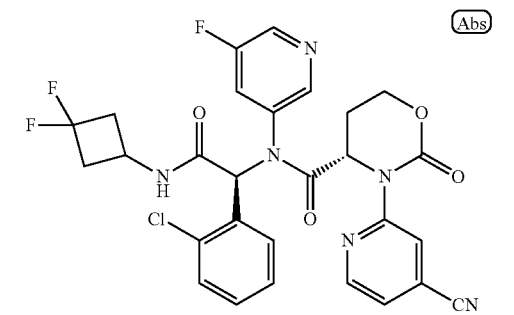 [SMILES: "Abs" ; N#Cc1ccnc(N2C(=O)OCC[C@H]2C(=O)N(c2cncc(F)c2)[C@H](C(=O)NC2CC(F)(F)C2)c2ccccc2Cl)c1] |
| 144 | 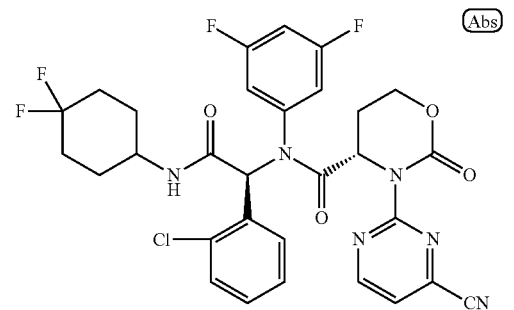 [SMILES: "Abs" ; N#Cc1ccnc(N2C(=O)OCC[C@H]2C(=O)N(c2cc(F)cc(F)c2)[C@H](C(=O)NC2CCC(F)(F)CC2)c2ccccc2Cl)n1] |
| Cpd No. | Structure |
|---|---|
| 145 | 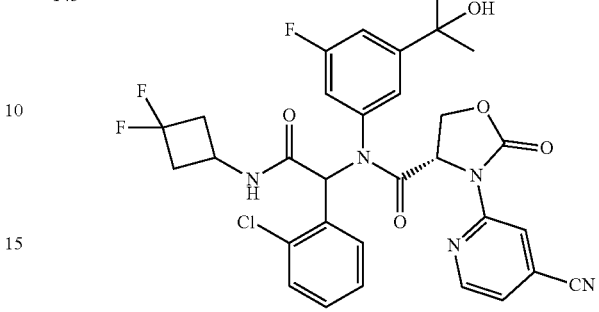 |
| 146 | 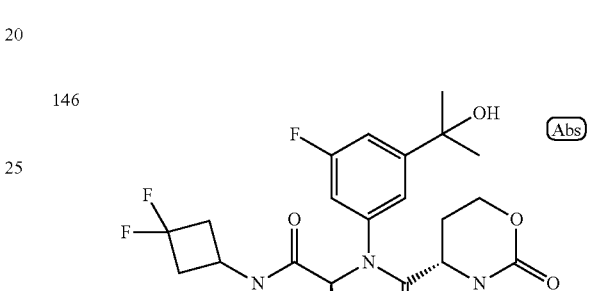 |
| 147 | 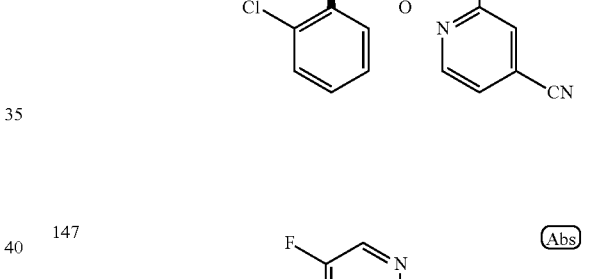 |
| 148 | 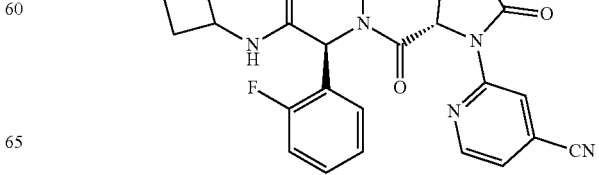 |
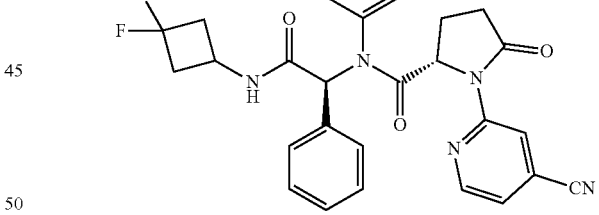
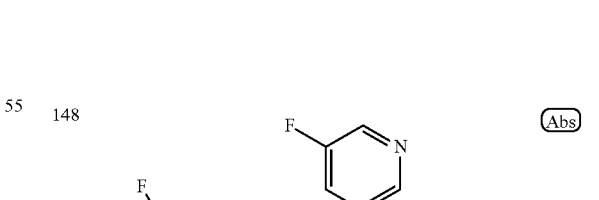

| Cpd No. | Structure |
|---|---|
| 149 | 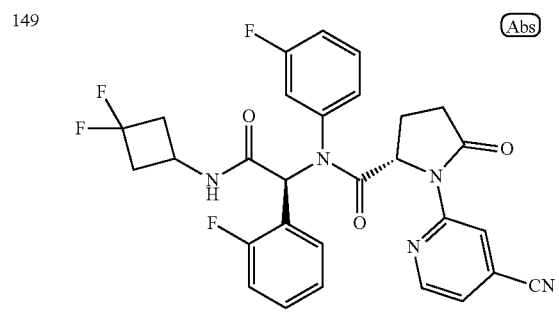 |
| 150 | 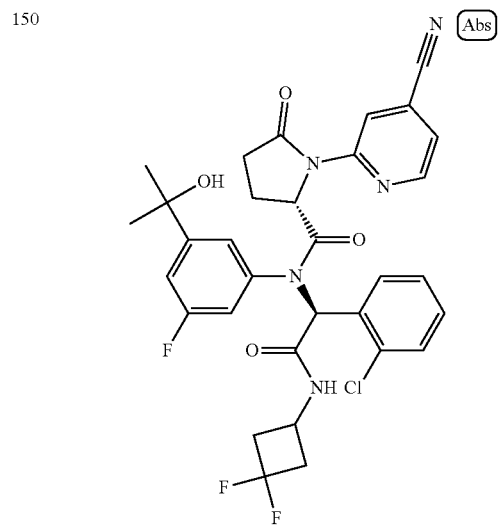 |
| 151 | 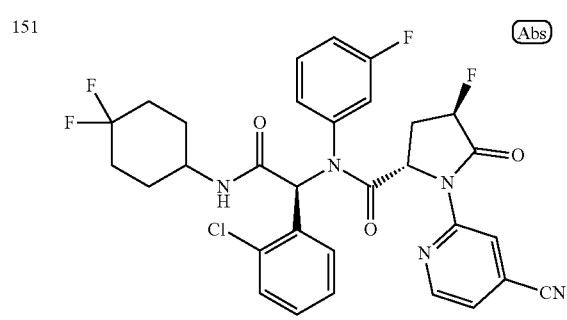 |
| 152 | 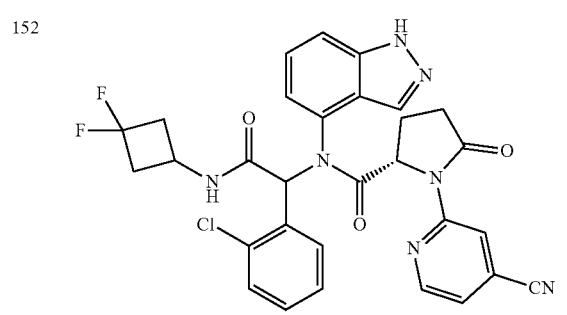 |
| Cpd No. | Structure |
|---|---|
| 153 | 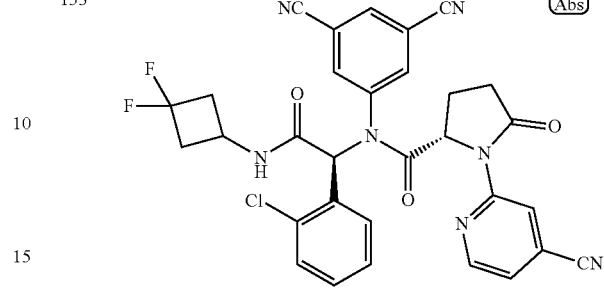 |
| 154 | 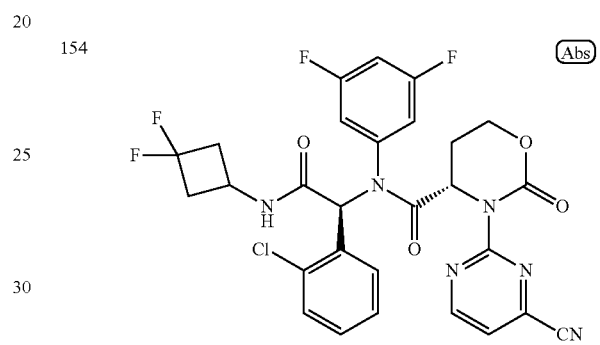 |
| 155 | 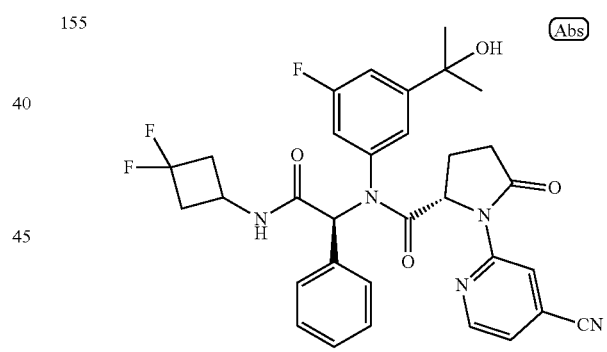 |
| 156 | 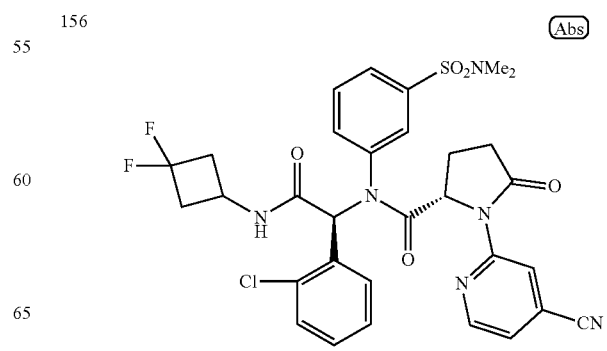 |

51
-continued
| Cpd No. | Structure |
|---|---|
| 157 | 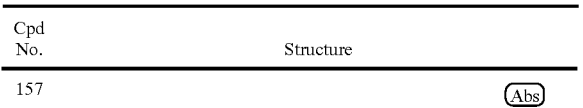 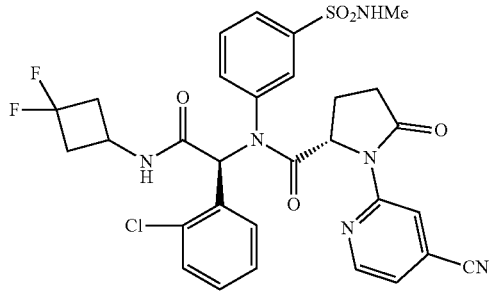 |
| 158 |  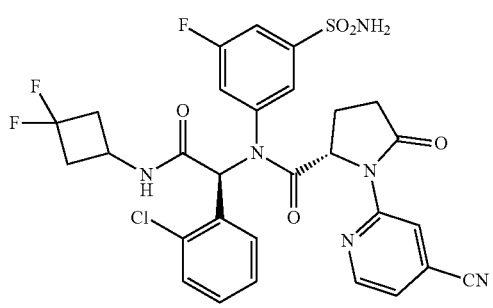 |
| 159 |  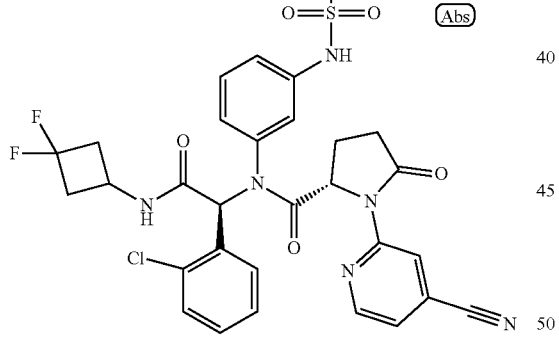 |
| 160 |  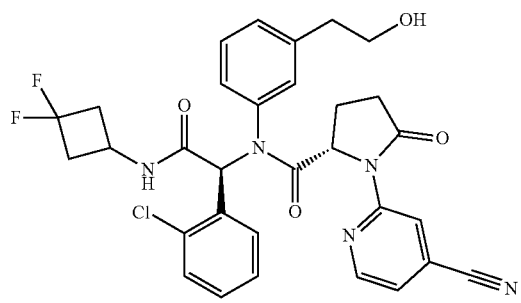 |
52
-continued
| Cpd No. | Structure |
|---|---|
| 161 | 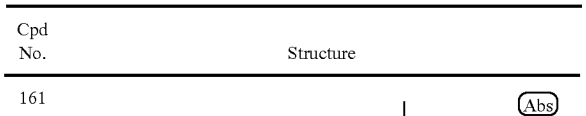 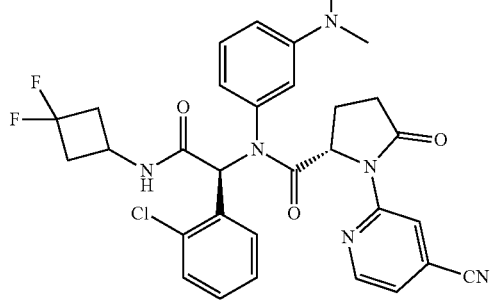 |
| 162 |  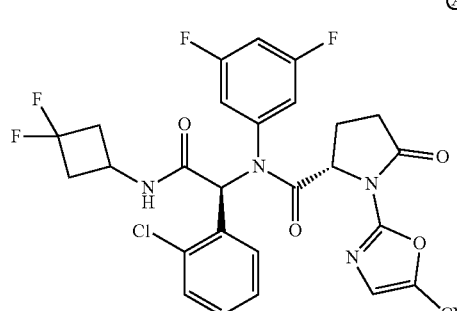 |
| 163 |  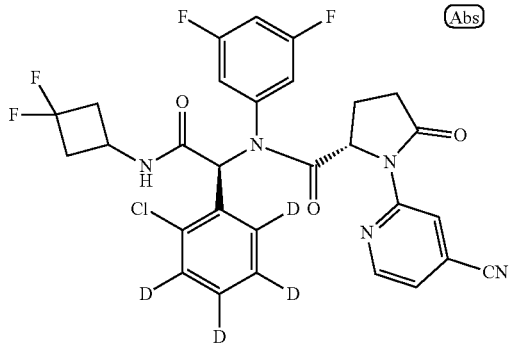 [SMILES: [2H]c1c([2H])c([2H])c([C@@H](C(=O)NC2CC(F)(F)C2)N(C(=O)[C@@H]2CCC(=O)N2c2cc(C#N)ccn2)c2cc(F)cc(F)c2)c(Cl)c1[2H] ; "Abs"] |
| 164 |  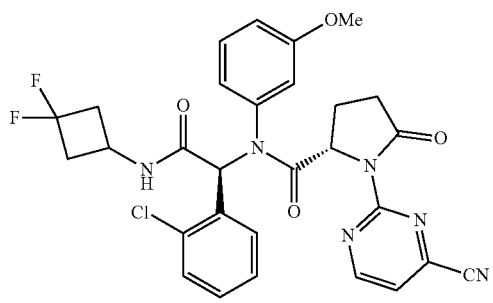 |

| Cpd No. | Structure |
|---|---|
| 165 | 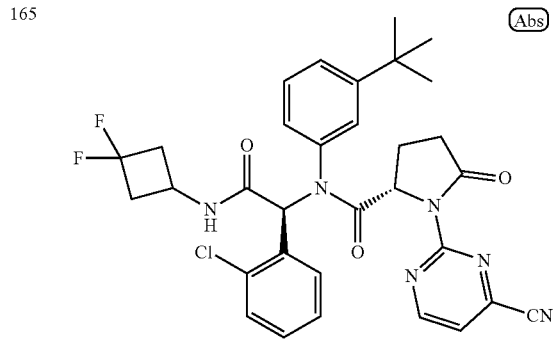 (Abs) |
| 166 | 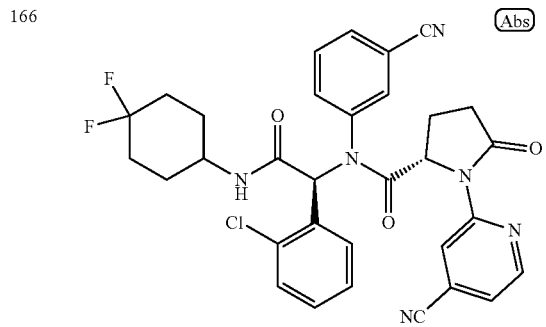 |
| 167 | 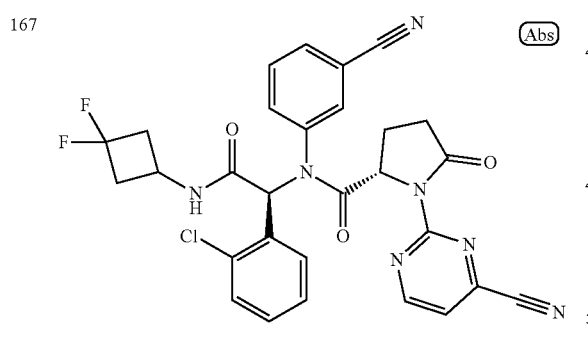 (Abs) |
| 168 | 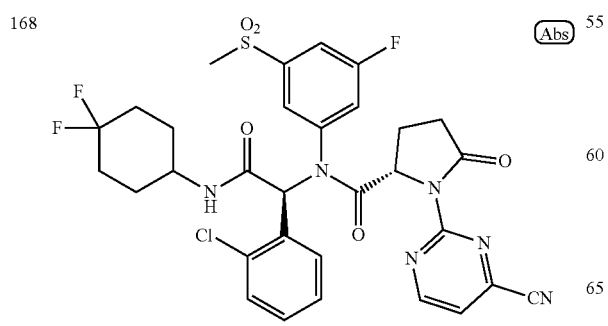 (Abs) |
| Cpd No. | Structure |
|---|---|
| 169 | 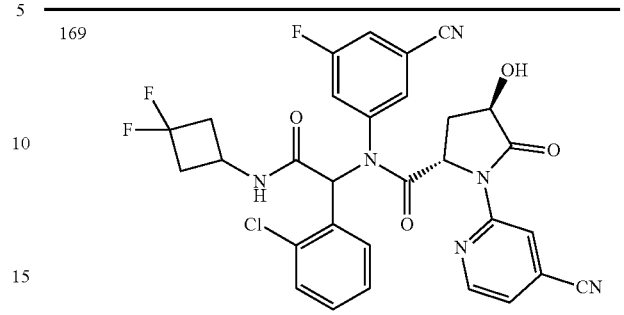 |
| 170 | 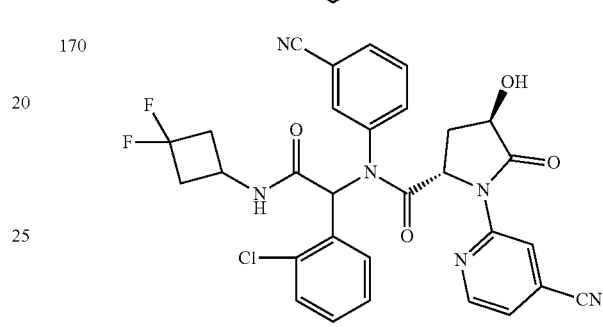 |
| 171 | 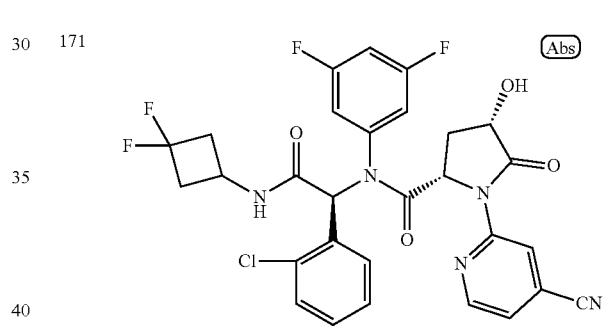 (Abs) |
| 172 | 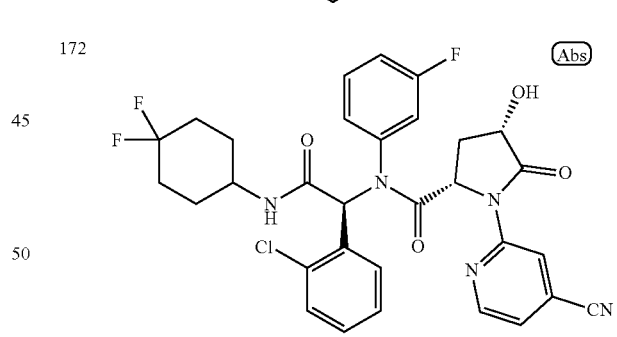 (Abs) |
| 173 | 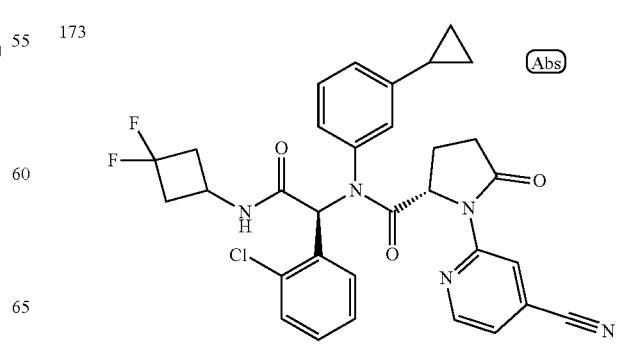 (Abs) |

US 10,640,534 B2
| 55 -continued | | 56 -continued | |
|---|---|---|---|
| Cpd No. | Structure | Cpd No. | Structure |
| 174 | 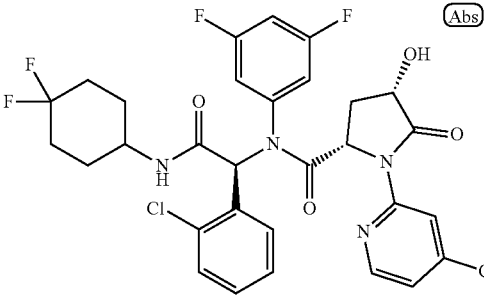 | 179 | 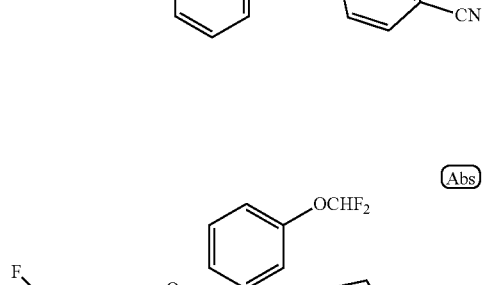 |
| 175 | 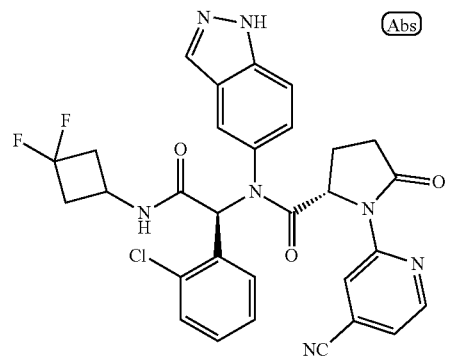 [SMILES: N#Cc1ccnc(N2C(=O)CC[C@H]2C(=O)N(c2ccc3[nH]ncc3c2)[C@H](C(=O)NC2CC(F)(F)C2)c2ccccc2Cl)c1 ; "Abs"] | 180 | 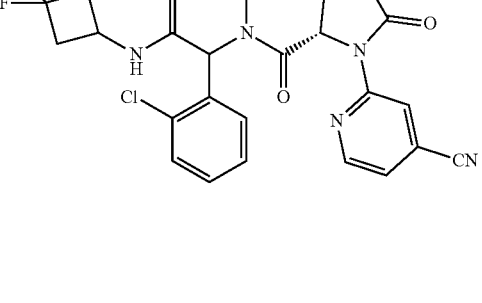 |
| 176 | 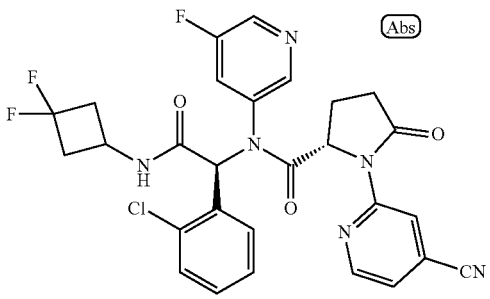 [SMILES: N#Cc1ccnc(N2C(=O)CC[C@H]2C(=O)N(c2cncc(F)c2)[C@H](C(=O)NC2CC(F)(F)C2)c2ccccc2Cl)c1 ; "Abs"] | 181 | 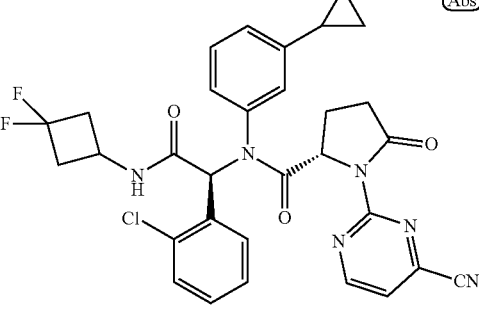 |
| 177 | 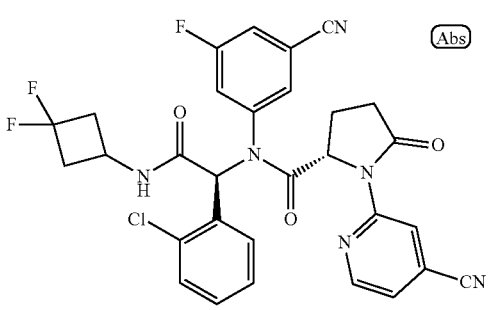 [SMILES: N#Cc1cc(F)cc(N(C(=O)[C@@H]2CCC(=O)N2c2cc(C#N)ccn2)[C@H](C(=O)NC2CC(F)(F)C2)c2ccccc2Cl)c1 ; "Abs"] | | |
| 178 | 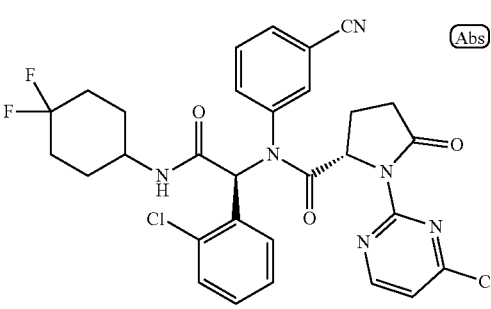 | 182 | 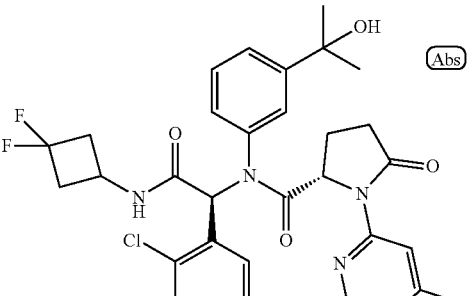 |

| Cpd No. | Structure |
|---|---|
| 183 | 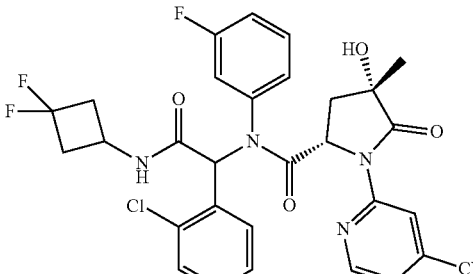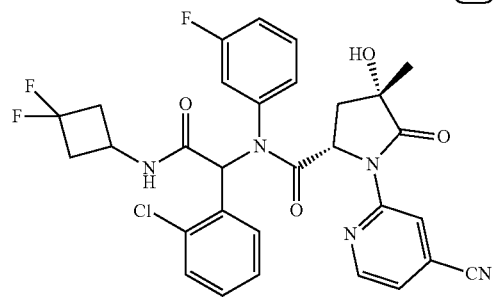 |
| 184 | 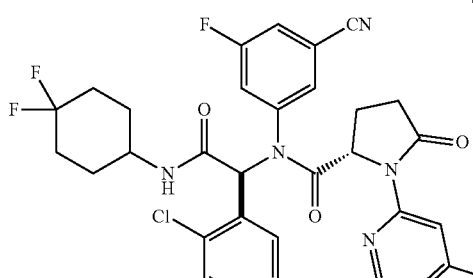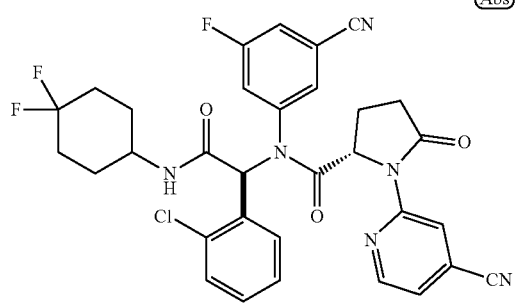 |
| 185 | 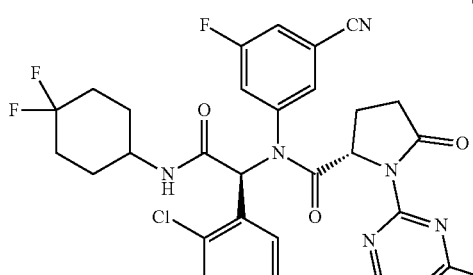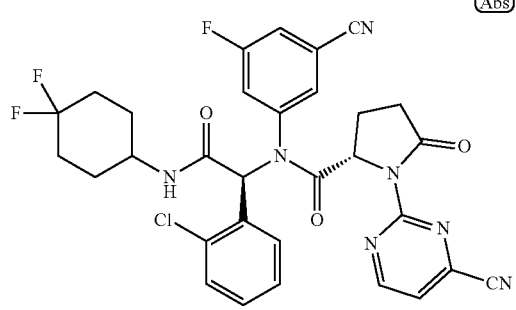 |
| 186 | 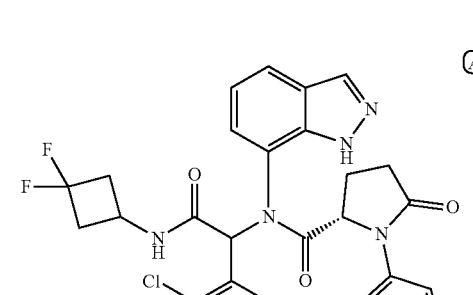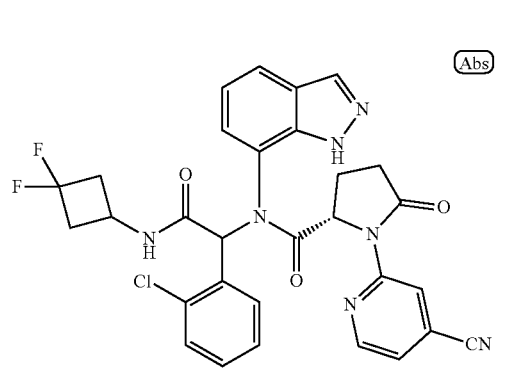 [SMILES: "Abs" ; N#Cc1ccnc(N2C(=O)CC[C@H]2C(=O)N(c2cccc3cn[nH]c23)C(C(=O)NC2CC(F)(F)C2)c2ccccc2Cl)c1] |
| Cpd No. | Structure |
|---|---|
| 187 | 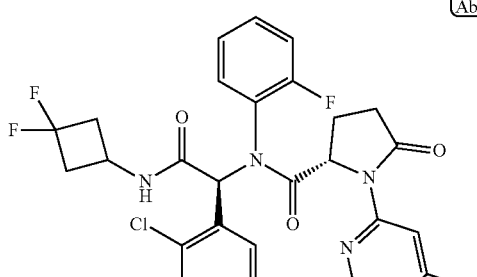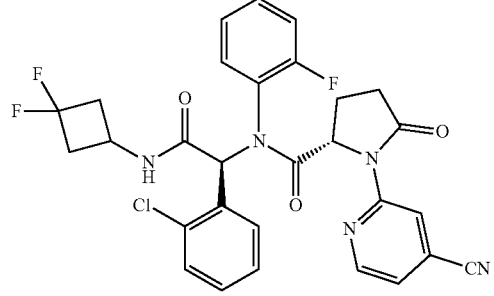 |
| 188 | 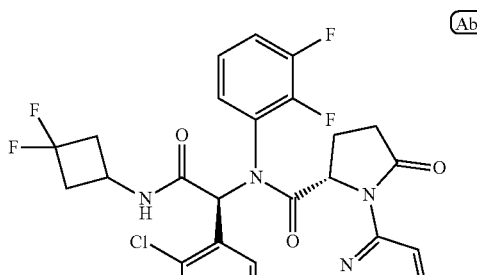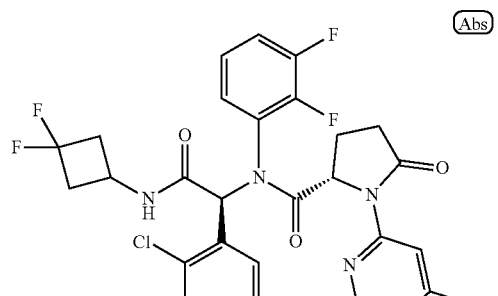 |
| 189 | 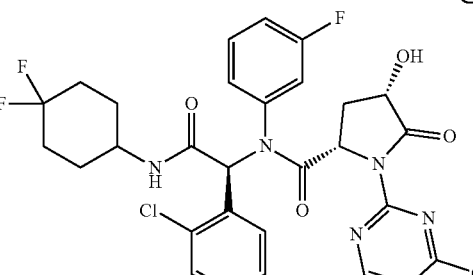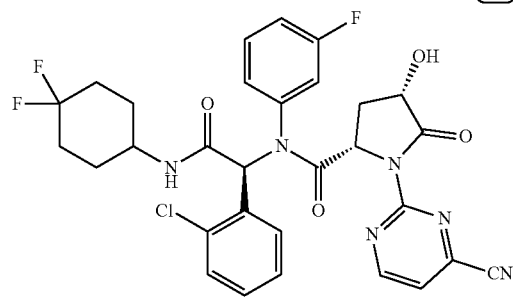 |
| 190 | 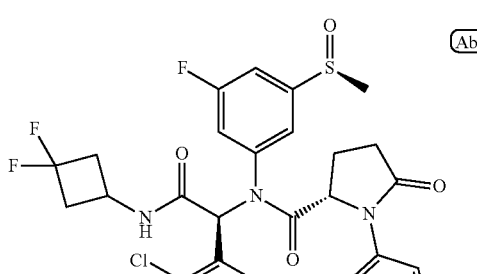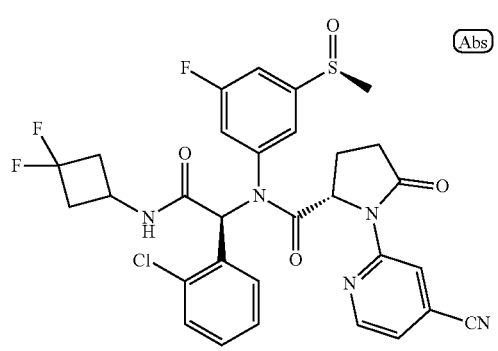 [SMILES: C[S@](=O)c1cc(F)cc(N(C(=O)[C@@H]2CCC(=O)N2c2cc(C#N)ccn2)[C@H](C(=O)NC2CC(F)(F)C2)c2ccccc2Cl)c1 ; "Abs"] |

| Cpd No. | Structure |
|---|---|
| 191 | 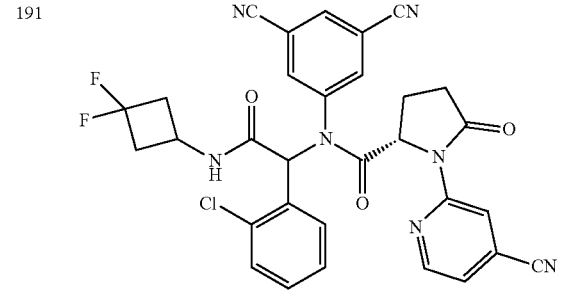 |
| 192 | 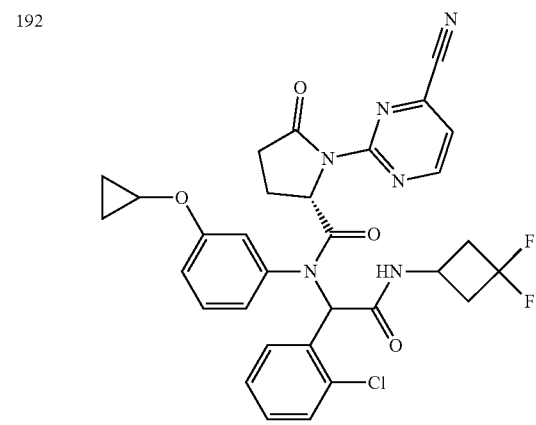 |
| 193 | 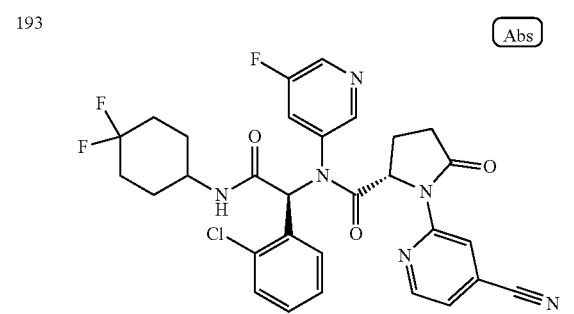 |
| 194 | 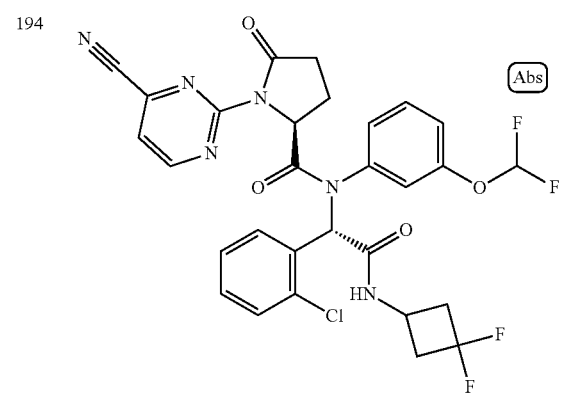 |
| Cpd No. | Structure |
|---|---|
| 195 | 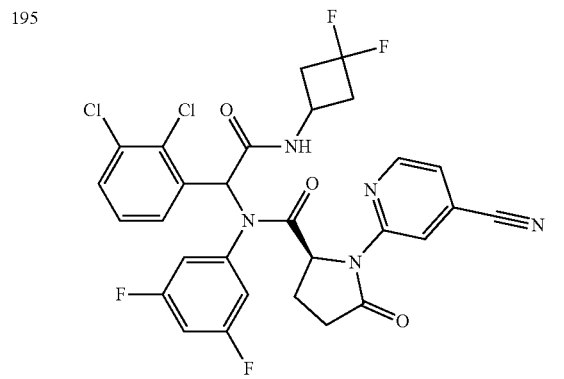 |
| 196 | 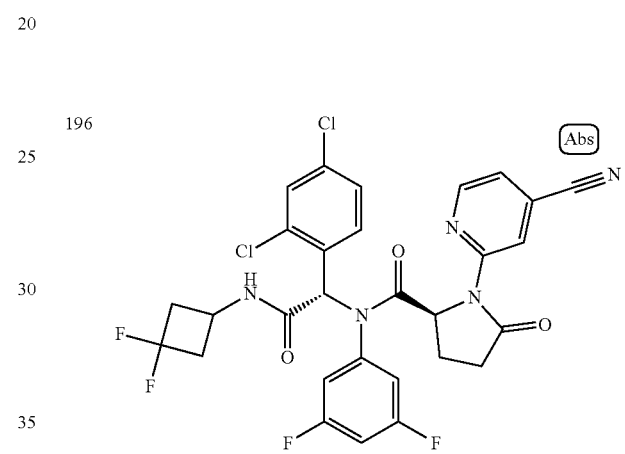 |
| 197 | 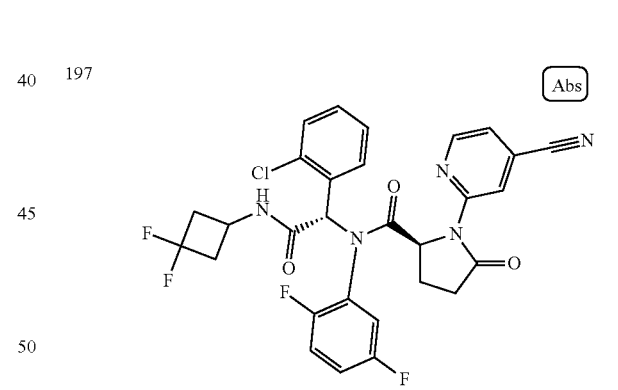 |
| 198 | 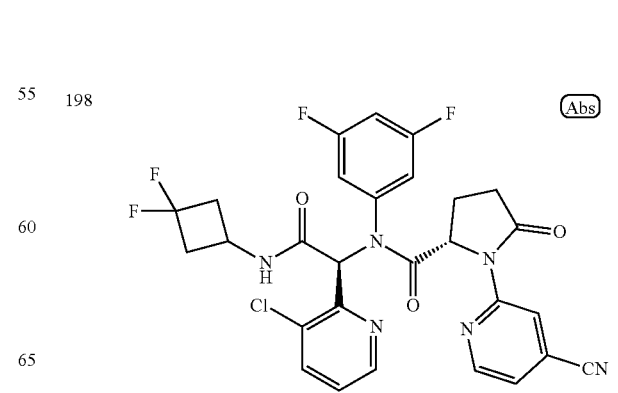 |

-continued
| Cpd No. | Structure |
|---|---|
| 199 | 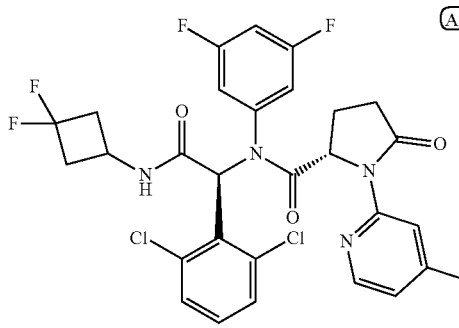 (Abs) |
| 200 | 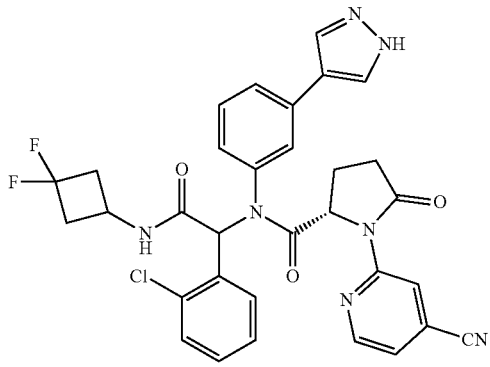 [SMILES: N#Cc1ccnc(N2C(=O)CC[C@H]2C(=O)N(c2cccc(-c3cn[nH]c3)c2)C(C(=O)NC2CC(F)(F)C2)c2ccccc2Cl)c1] |
| 201 | 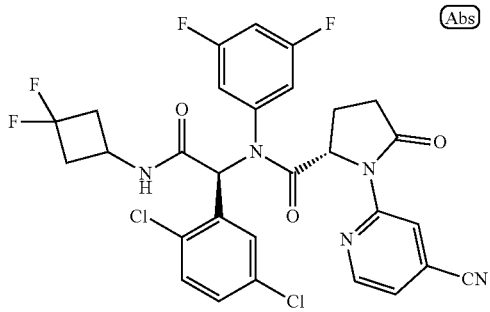 [SMILES: "Abs" ; N#Cc1ccnc(N2C(=O)CC[C@H]2C(=O)N(c2cc(F)cc(F)c2)[C@H](C(=O)NC2CC(F)(F)C2)c2cc(Cl)ccc2Cl)c1] (Abs) |
| 202 | 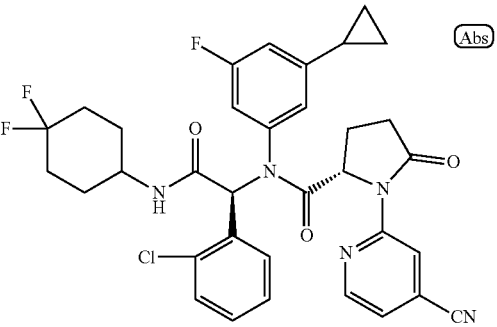 [SMILES: N#Cc1ccnc(N2C(=O)CC[C@H]2C(=O)N(c2cc(F)cc(C3CC3)c2)[C@H](C(=O)NC2CCC(F)(F)CC2)c2ccccc2Cl)c1 ; "Abs"] (Abs) |
-continued
| Cpd No. | Structure |
|---|---|
| 203 | 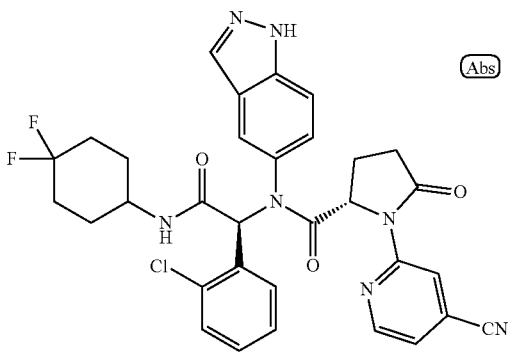 [SMILES: N#Cc1ccnc(N2C(=O)CC[C@H]2C(=O)N(c2ccc3[nH]ncc3c2)[C@H](C(=O)NC2CCC(F)(F)CC2)c2ccccc2Cl)c1 ; "Abs"] (Abs) |
| 204 | 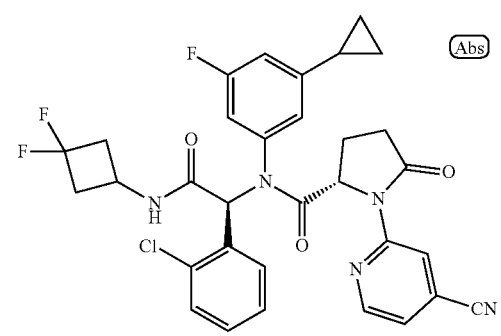 [SMILES: N#Cc1ccnc(N2C(=O)CC[C@H]2C(=O)N(c2cc(F)cc(C3CC3)c2)[C@H](C(=O)NC2CC(F)(F)C2)c2ccccc2Cl)c1 ; "Abs"] (Abs) |
| 205 | 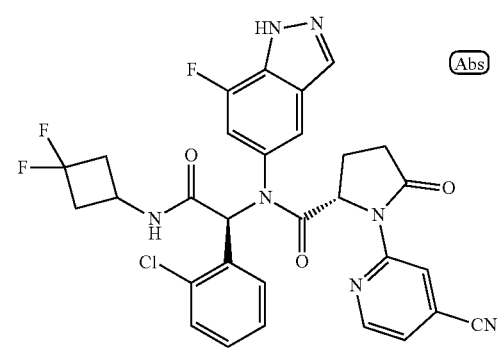 [SMILES: N#Cc1ccnc(N2C(=O)CC[C@H]2C(=O)N(c2cc(F)c3[nH]ncc3c2)[C@H](C(=O)NC2CC(F)(F)C2)c2ccccc2Cl)c1 ; "Abs"] (Abs) |
| 206 | 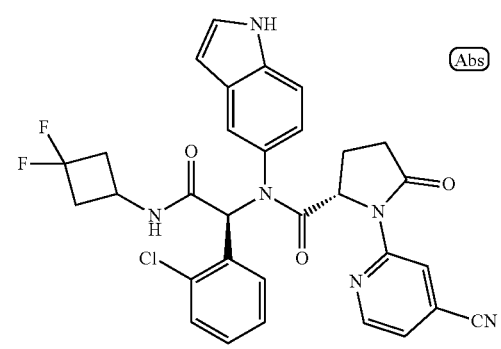 [SMILES: N#Cc1ccnc(N2C(=O)CC[C@H]2C(=O)N(c2ccc3[nH]ccc3c2)[C@H](C(=O)NC2CC(F)(F)C2)c2ccccc2Cl)c1 ; "Abs"] (Abs) |

| Cpd No. | Structure |
|---|---|
| 207 | 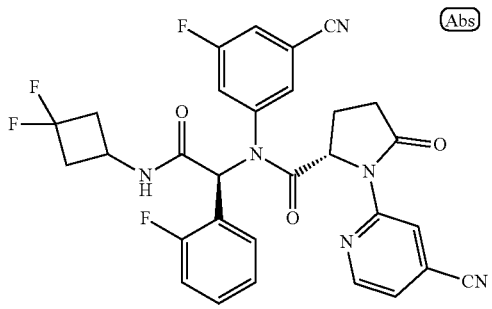 [SMILES: "Abs" ; N#Cc1cc(F)cc(N(C(=O)[C@@H]2CCC(=O)N2c2cc(C#N)ccn2)[C@H](C(=O)NC2CC(F)(F)C2)c2ccccc2F)c1] |
| 208 | 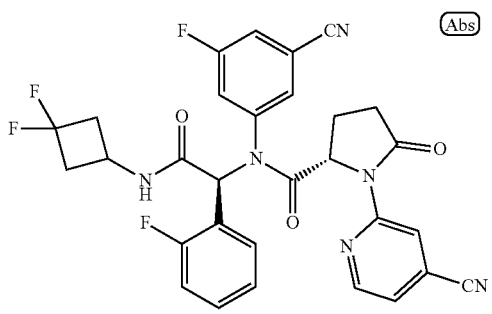 [SMILES: "Abs" ; N#Cc1cc(F)cc(N(C(=O)[C@@H]2CCC(=O)N2c2cc(C#N)ccn2)[C@H](C(=O)NC2CC(F)(F)C2)c2ccccc2F)c1] |
| 209 | 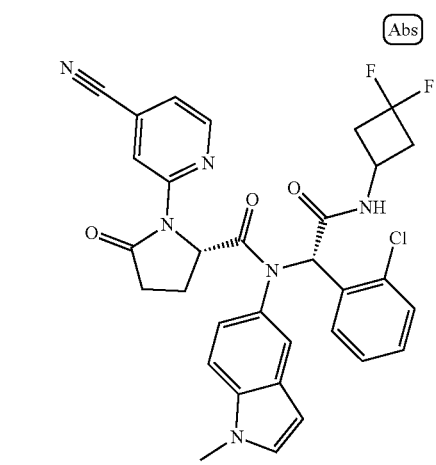 [SMILES: Cn1ccc2cc(N(C(=O)[C@@H]3CCC(=O)N3c3cc(C#N)ccn3)[C@H](C(=O)NC3CC(F)(F)C3)c3ccccc3Cl)ccc21] |
| 210 | 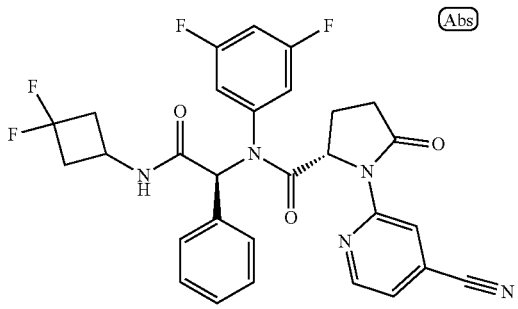 [SMILES: "Abs" ; N#Cc1ccnc(N2C(=O)CC[C@H]2C(=O)N(c2cc(F)cc(F)c2)[C@H](C(=O)NC2CC(F)(F)C2)c2ccccc2)c1] |

| Cpd No. | Structure |
|---|---|
| 211 | 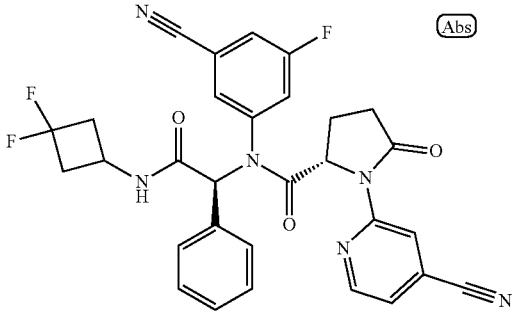 [SMILES: N#Cc1cc(F)cc(N(C(=O)[C@@H]2CCC(=O)N2c2cc(C#N)ccn2)[C@H](C(=O)NC2CC(F)(F)C2)c2ccccc2)c1 ; "Abs"] |
| 212 | 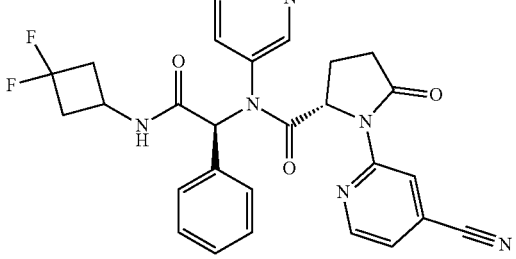 |

Included herein are also methods for making compounds of Formula I or a compound of any one of the embodiments described herein comprising reacting $R^1NC$ with $R^2CHO$, $R^3NH_2$ and

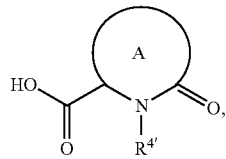

wherein $R^{4'}$ is H or $R^4$ and $R^1$, $R^2$, $R^3$, $R^4$ and ring A as defined in Formula I or in any of the embodiments described herein. In one aspect of the preceding methods, $R^4$ is alkyl.

Also included herein are methods for making compounds of Formula I or a compound of any one of the embodiments described herein comprising (1) reacting $R^1NC$ with $R^2CHO$, $R^3NH_2$ and

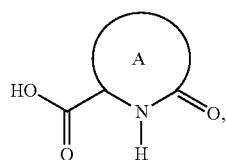

to give

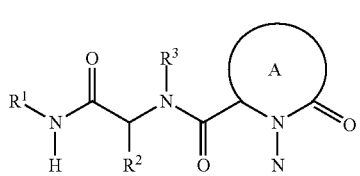

and (2) reacting

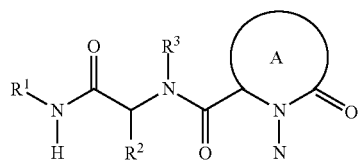

with R⁴-halide to give

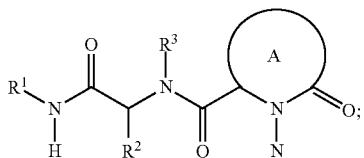

wherein R⁴ is optionally substituted aryl or optionally substituted heteroaryl; and R¹, R², R³, R⁴ and ring A as defined in Formula I or in any of the embodiments described herein. In one aspect of the preceding methods, R⁴ is aryl or heteroaryl, each independently substituted with one to three R⁷ groups. In another aspect of the preceding method, R¹, R², R³, R⁴, R⁵, R⁶, R⁷ and ring A are as defined in any of the embodiments herein.

The compounds of this invention may contain one or more asymmetric centers and thus occur as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

In one embodiment, the compound is enriched in a specific stereoisomer by at least about 60%, 65%, 70%, 75%, 80%, 85%, 90%, 95%, 96%, 97%, 98%, or 99%.

The compounds of formula I, II, II-a, II-a-1, II-b or II-b-1 may also comprise one or more isotopic substitutions. For example, H may be in any isotopic form, including ¹H, ²H (D or deuterium), and ³H (T or tritium); C may be in any isotopic form, including ¹²C, ¹³C, and ¹⁴C; O may be in any isotopic form, including ¹⁶O and ¹⁸O; and the like. For example, the compound is enriched in a specific isotopic form of H, C and/or O by at least about 60%, 65%, 70%, 75%, 80%, 85%, 90%, 95%, 96%, 97%, 98%, or 99%.

Unless otherwise indicated when a disclosed compound is named or depicted by a structure without specifying the stereochemistry and has one or more chiral centers, it is understood to represent all possible stereoisomers of the compound.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention.

Compounds described herein may be prepared following procedures detailed in the examples and other analogous methods known to one skilled in the art. Compounds produced by any of the schemes set forth below may be further modified (e.g., through the addition of substituents to rings, etc.) to produce additional compounds. The specific approaches and compounds shown herein are not intended to be limiting. The suitability of a chemical group in a compound structure for use in the synthesis of another compound is within the knowledge of one of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

It may be convenient or desirable to prepare, purify, and/or handle a corresponding salt of the active compound, for example, a pharmaceutically acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e., NH₄⁺) and substituted ammonium ions (e.g., NH₃R⁺, NH₂R²⁺, NHR³⁺, NR⁴⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group that may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Compositions and Routes of Administration

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound of formula I, II, II-a, II-a-1, II-b, or II-b-1 or a compound described in any one of the embodiments herein, may further comprise another therapeutic agent useful for treating cancer.

Methods of Use

Provided is a method for inhibiting a mutant IDH1 or IDH2 activity comprising contacting a subject in need thereof with a compound (including its tautomers and/or isotopologues) of structural formula I, II, II-a, II-a-1, II-b, or II-b-1 or a compound described in any one of the embodiments herein, or a pharmaceutically acceptable salt thereof. In one embodiment, the cancer to be treated is characterized by a mutant allele of IDH1 or IDH2 wherein the IDH1 or IDH2 mutation results in a new ability of the enzyme to catalyze the NAPH-dependent reduction of α-ketoglutarate to R(−)-2-hydroxyglutarate in a subject. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

Also provided are methods of treating a cancer characterized by the presence of a mutant allele of IDH1 comprising the step of administering to subject in need thereof (a) a compound of formula I, II, II-a, II-a-1, II-b, or II-b-1, or a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH1 wherein the IDH1 mutation results in a new ability of the enzyme to catalyze the NAPH-dependent reduction of α-ketoglutarate to R(−)-2-hydroxyglutarate in a patient. In one aspect of this embodiment, the IDH1 mutation is an R132X mutation. In another aspect of this embodiment, the R132X mutation is selected from R132H, R132C, R132L, R132V, R132S and R132G. In another aspect, the R132X mutation is R132H or R132C. A cancer can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation results in a new ability of the enzyme to catalyze the NAPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds and methods of this invention are useful to treat any type of cancer that is characterized by the presence of a mutant allele of IDH1 imparting such activity and in particular an IDH1 R132H or R132C mutation.

In one aspect of this embodiment, the efficacy of cancer treatment is monitored by measuring the levels of 2HG in the subject. Typically levels of 2HG are measured prior to treatment, wherein an elevated level is indicated for the use of the compound of formula I, II, II-a, II-a-1, II-b, or II-b-1 or a compound described in any one of the embodiments described herein to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

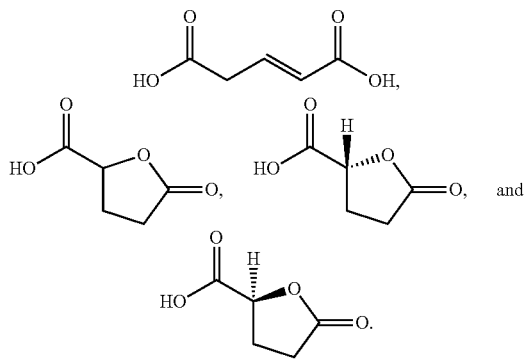

In one embodiment the cancer is a tumor wherein at least 30, 40, 50, 60, 70, 80 or 90% of the tumor cells carry an IDH1 mutation, and in particular an IDH1 R132H or R132C mutation, at the time of diagnosis or treatment.

IDH1 R132X mutations are known to occur in certain types of cancers as indicated in Table 2, below.

TABLE 2

IDH mutations associated with certain cancers

| Cancer Type | IDH1 R132X Mutation | Tumor Type |
|---|---|---|
| brain tumors | R132H | primary tumor |
| | R132C | primary tumor |
| | R132S | primary tumor |
| | R132G | primary tumor |
| | R132L | primary tumor |
| | R132V | primary tumor |
| fibrosarcoma | R132C | HT1080 fibrosarcoma cell line |
| Acute Myeloid Leukemia (AML) | R132H | primary tumor |
| | R132G | primary tumor |
| | R132C | primary tumor |
| Prostate cancer | R132H | primary tumor |
| | R132C | primary tumor |
| Acute lymphoblastic leukemia (ALL) | R132C | primary tumor |
| paragangliomas | R132C | primary tumor |

IDH1 R132H mutations have been identified in glioblastoma, acute myelogenous leukemia, sarcoma, melanoma, non-small cell lung cancer, cholangiocarcinomas, chondrosarcoma, myelodysplastic syndromes (MDS), myeloproliferative neoplasm (MPN), colon cancer, and angio-immunoblastic non-Hodgkin's lymphoma (NHL). Accordingly, in one embodiment, the methods described herein are used to treat glioma (glioblastoma), acute myelogenous leukemia, sarcoma, melanoma, non-small cell lung cancer (NSCLC) or cholangiocarcinomas, chondrosarcoma, myelodysplastic syndromes (MDS), myeloproliferative neoplasm (MPN), colon cancer, or angio-immunoblastic non-Hodgkin's lymphoma (NHL) in a patient.

Accordingly in one embodiment, the cancer is a cancer selected from any one of the cancer types listed in Table 2, and the IDH R132X mutation is one or more of the IDH1 R132X mutations listed in Table 2 for that particular cancer type.

Treatment methods described herein can additionally comprise various evaluation steps prior to and/or following treatment with a compound of formula I, II, II-a, II-a-1, II-b, or II-b-1 or a compound described in any one of the embodiments described herein.

In one embodiment, prior to and/or after treatment with a compound of Structural formula I, II, II-a, II-a-1, II-b, or II-b-1 or a compound described in any one of the embodiments described herein, the method further comprises the step of evaluating the growth, size, weight, invasiveness, stage and/or other phenotype of the cancer.

In one embodiment, prior to and/or after treatment with a compound of formula I, II, II-a, II-a-1, II-b, or II-b-1 or a compound described in any one of the embodiments described herein, the method further comprises the step of evaluating the IDH1 genotype of the cancer. This may be achieved by ordinary methods in the art, such as DNA sequencing, immuno analysis, and/or evaluation of the presence, distribution or level of 2HG.

In one embodiment, prior to and/or after treatment with a compound of formula I, II, II-a, II-a-1, II-b, or II-b-1 or a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

Combination Therapies

In some embodiments, the methods described herein comprise the additional step of co-administering to a subject in need thereof a second therapy e.g., an additional cancer therapeutic agent or an additional cancer treatment. Exemplary additional cancer therapeutic agents include for example, chemotherapy, targeted therapy, antibody therapies, immunotherapy, and hormonal therapy. Additional cancer treatments include, for example: surgery, and radiation therapy. Examples of each of these treatments are provided below.

The term "co-administering" as used herein with respect to an additional cancer therapeutic agents means that the additional cancer therapeutic agent may be administered together with a compound of this invention as part of a single dosage form (such as a composition of this invention comprising a compound of the invention and an second therapeutic agent as described above) or as separate, multiple dosage forms. Alternatively, the additional cancer therapeutic agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment. The term "co-administering" as used herein with respect to an additional cancer treatment means that the additional cancer treatment may occur prior to, consecutively with, concurrently with or following the administration of a compound of this invention.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others) and hypomethylating agents (e.g., decitabine (5-aza-deoxycytidine), zebularine, isothiocyanates, azacitidine (5-azacytidine, 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

EXAMPLES

The chemical name of each compound described below is generated by ChemBioOffice software.
DCM=dichloromethane TEA=triethylamine
DPPA=diphenyiphosphoryl azide TFA=trifluoroacetic acid
DIPEA=NA-Diisopropylethylainine TFAA=trifluoroacetic anhydride General Procedures for the Preparation of
1,1-difluoro-3-isocyanocyclobutane Method A:

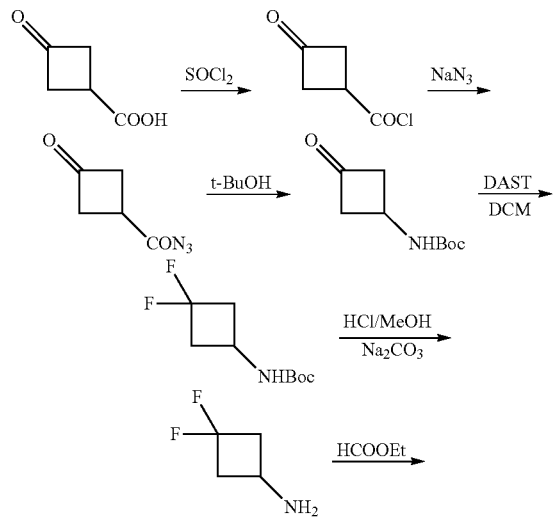

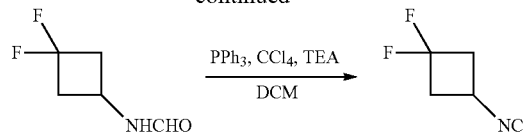

Step A: Tert-butyl 3-oxocyclobutykarbamate

To a solution of 3-oxocyclobutanecarboxylic acid (10 g, 88 mmol) in dry DCM (60 mL) at 0° C., SOCl$_2$ (20 mL) was added dropwise. The mixture was heated to reflux for 1.5 h and then evaporated in vacuo. The resulting mixture was co-evaporated twice with toluene (2×8 mL) and the residue was dissolved in acetone (30 mL), followed by adding dropwise to a solution of NaN$_3$ (12 g, 185.0 mmol) in H$_2$O (35 mL) at 0° C. After addition, the mixture was stirred for another 1 h and then quenched with ice (110 g). The resulting mixture was extracted with Et$_2$O (2×100 mL). Combined organic layers were washed with brine, dried over anhydrous Mg$_2$SO$_4$ and concentrated to about 15 mL solution. Toluene (2×30 mL) was added into the residue and the mixture was co-evaporated twice to remove Et$_2$O (about 30 mL solution left each time to avoid explosion). The resulting toluene solution was heated to 90° C. until the evolution of N$_2$ ceased. Next, 40 mL of t-BuOH was added into the reaction mixture and the resulting mixture was stirred overnight at 90° C. The mixture was cooled and concentrated. The residue was purified by column chromatography using petroleum ether/EtOAc (V:V, 7:1 to 5:1) as eluent to afford the desired product as a white solid. MS: 186.1 (M+1)$^+$.

Step B: Tert-butyl 3,3-difluorocyclobutylcarbamate

To a solution of tert-butyl-3-oxocyclobutylcarbamate (2.56 g, 111.07 mmol) in dry DCM (190 mL), DAST (diethylaminosulfur trifluoride) (41.0 mL, 222.14 mmol) was added dropwise at 0° C. under the atmosphere of N$_2$. The mixture was then allowed to warm up to r.t and stirred overnight. The resulting mixture was slowly added into a pre-cooled saturated aq. NaHCO$_3$ solution and extracted with DCM (3×200 mL). Combined organic layers were washed with brine, dried over anhydrous MgSO$_4$, and concentrated in vacuo. The residue was purified by column chromatography using petroleum ether/EtOAc (V:V, 15:1) as eluent to afford the desired product. $^1$H NMR (400 MHz, DMSO-d$_6$): δ 4.79 (s, 1H), 4.07 (s, 1H), 2.98 (s, 2H), 2.58-2.29 (m, 2H), 1.46 (s, 9H). MS: 208.1 (M+1)$^+$.

Step C: N-(3,3-difluorocyclobutyl)formamide

To a solution of MeOH (170 mL) and CH$_3$COCl (65 mL), tert-butyl 3,3-difluoro-cyclobutylcarbamate (12.1 g, 58.42 mmol) was added in one portion dropwise at 0° C. The reaction mixture was stirred at 0° C. for 20 min, and then allowed to warm up to r.t and stirred for another 1.5 h. The reaction mixture was concentrated and dissolved in H$_2$O (200 mL). The resulting mixture was extracted by Et$_2$O (150 mL) and the aqueous layer was adjusted to pH=11 with solid Na$_2$CO$_3$ and extracted by DCM (2×150 mL). The combined organic layers were dried over anhydrous MgSO$_4$, filtered and concentrated in vacuo using a cold-water bath (<20° C.). The residue was dissolved in HCOOEt (90 mL), and transferred into a sealed pressure tube. This reaction mixture was heated to 80° C. and stirred overnight. The solvent was

Step D: 1,1-Difluoro-3-isocyanocyclobutane

To a solution of N-(3,3-difluorocyclobutyl)-formamide (2.0 g, 14.81 mmol) and PPh$_3$ (4.27 g, 16.29 mmol) in DCM (35 mL) were added CCl$_4$ (1.43 mL, 14.81 mmol) and TEA (2.06 mL, 14.81 mmol). The reaction mixture was stirred at 45° C. overnight under a N$_2$ atmosphere. The resulting mixture was evaporated in vacuo at 0° C. The residue was suspended in Et$_2$O (25 mL) at 0° C. for 30 min and then filtered. The filtrate was evaporated to about 5 mL at 0° C. under reduced pressure. The residue was purified by column chromatography using Et$_2$O as eluent to afford the desired product which was used directly in the next step.
Method B:

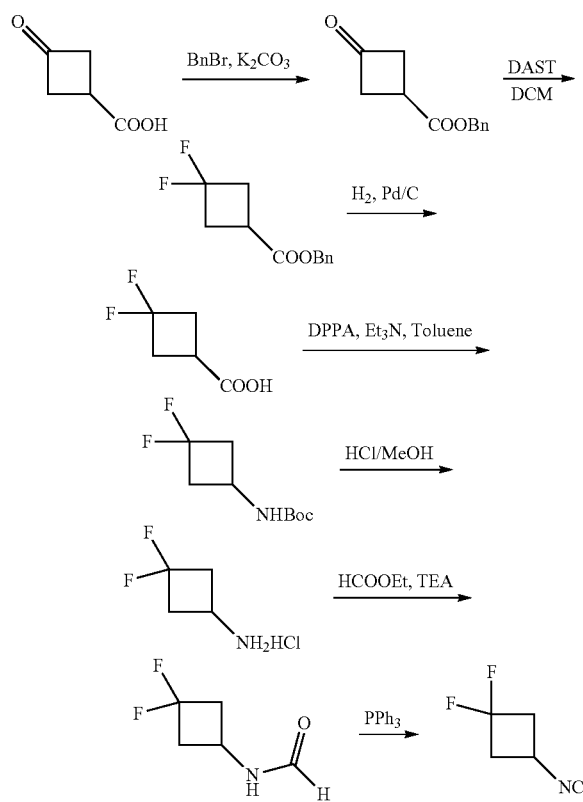

Step A: Benzyl 3-oxocyclobutanecarboxylate

A mixture of 3-oxocyclobutanecarboxylic acid (5 g, 44 mmol), potassium carbonate (12 g, 88 mmol) and benzyl bromide (11.2 g, 66 mmol) in acetone (50 mL) was refluxed for 16 h. The solvent was then removed under reduced pressure and the residue was partitioned between ethyl acetate and water. Combined organic layers were dried over anhydrous MgSO$_4$, filtered and concentrated. The residue was purified with silica gel chromatography eluting with a gradient of 100% hexane to 96% hexane/EtOAc to give the desired compound. $^1$H NMR (400 MHz, CDCl$_3$): δ 7.45-7.27 (m, 5H), 5.19 (s, 2H), 3.55-3.36 (m, 2H), 3.33-3.11 (m, 3H).

Step B: Benzyl 3,3-difluorocyclobutanecarboxylate

To a solution of benzyl 3-oxocyclobutanecarboxylate (1.23 g, 6.03 mmol) in DCM (35 mL) was added DAST (0.8 mL, 6.03 mmol) dropwise under nitrogen. The mixture was stirred at room temperature for 16 h and then diluted with DCM. After successive washes with saturated sodium bicarbonate, 1N aq. hydrochloride acid, and brine, the organic layer was dried over anhydrous sodium sulfate, filtered and concentrated. The crude product was purified by silica gel chromatography with 93% hexane/EtOAc as eluent to give the desired compound as an oil. $^1$H NMR (400 MHz, CDCl$_3$): δ 7.47-7.27 (m, 5H), 5.16 (s, 2H), 3.09-2.95 (m, 1H), 2.90-2.60 (m, 4H).

Step C: 3,3-Difluorocyclobutanecarboxylic Acid

Benzyl 3,3-difluorocyclobutanecarboxylate (0.84 g, 3.72 mol) was dissolved in ethanol (40 mL), and approximately 0.02 g palladium on activated carbon was added. The mixture was stirred at room temperature for 12 h under the atmosphere of H$_2$ and then filtered through a pad of Celite. The filtrates were concentrated and dried in vacuo to give the desired compound. $^1$H NMR (400 MHz, CDCl$_3$): δ 3.16-2.55 (m, 5H).

Step D: Tert-butyl 3,3-difluorocyclobutylcarbamate

Benzyl 3,3-difluorocyclobutanecarboxylic acid (3.7 g, 27.3 mmol), DPPA (7.87 g, 27 mmol) and TEA (2.87 g, 28.4 mmol) were dissolved in t-BuOH (25 mL). The mixture was refluxed for 5 h and then diluted with ethyl acetate (about 200 mL). The organic phase was washed twice with 5% citric acid and saturated sodium hydrogen carbonate respectively, dried over anhydrous Mg$_2$SO$_4$ and evaporated under reduced pressure. The residue was purified by silica gel chromatography with 50% hexane/EtOAc to give the desired product. MS: 208.1 (M+1)$^+$.

Step E: 3,3-Difluorocyclobutanamine hydrochloride

To a cold solution of MeOH (170 mL) and CH$_3$COCl (65 mL) was added tert-butyl 3,3-difluorocyclobutylcarbamate (12.1 g, 58.4 mmol) dropwise at 0° C. After completion of the addition, the mixture was stirred at 0° C. for 20 min and then allowed to warm up to room temperature. The reaction mixture was stirred for another 1.5 h and then concentrated to give the crude product which was precipitated in ether to give the desired product as a white solid. MS: 108.1 (M+1)$^+$.

Step F: N-(3,3-difluorocyclobutyl)formamide

The mixture of 3,3-difluorocyclobutanamine hydrochloride (6.5 g, 60.7 mmol) and TEA (3 eq) in HCOOEt (90 mL) was stirred at 80° C. overnight in a sealed pressure tube. The solvent was removed in vacuo and the residue was purified by column chromatography with 50% petroleum ether/EtOAc to 25% petroleum ether/EtOAc to give the desired product. $^1$H NMR (400 MHz, DMSO-d$_6$): δ 8.54 (s, 1H), 8.01-7.89 (m, 1H), 4.16-3.84 (m, 1H), 3.06-2.73 (m, 2H), 2.72-2.33 (m, 2H). MS: 136.1 (M+1)$^+$.

Step G: 1,1-Difluoro-3-isocyanocyclobutane

The compound was synthesized as outlined in step D of method A set forth above.

General Procedures for the Preparation of 1-fluoro-3-isocyanocyclobutane

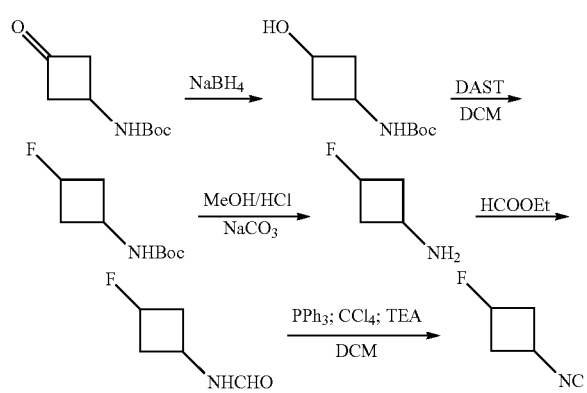

Step A: Tert-butyl 3-hydroxycyclobutylcarbamate

To a solution of tert-butyl 3-oxocyclobutylcarbamate (2 g, 10.8 mmol, 2 eq) in EtOH (20 mL) was added NaBH$_4$ (204 mg, 1 eq) at 0° C. The mixture was then allowed to warm to room temperature and stirred for 30 min. The mixture was concentrated in vacuo and the residue was purified by column chromatography using petroleum ether/EtOAc (V:V, 2:1 to pure EtOAc) as eluent to afford the desired product as a white solid. MS: 188.1 (M+1)$^+$.

Step B: Tert-butyl 3-fluorocyclobutylcarbamate

To a solution tert-butyl 3-hydroxycyclobutyl carbamate (1 g, 5.35 mmol) in dry DCM (20 mL) at −70° C. was added DAST dropwise (1 g, 0.85 mL, 1.17 eq) under the atmosphere of N$_2$. The mixture was then slowly warmed to room temperature and stirred overnight. The resulting mixture was washed with diluted aq. NaHCO$_3$. The organic layer was dried over anhydrous Mg$_2$SO$_4$ and concentrated. The residue was purified by flash chromatography using petroleum ether/EtOAc (V:V, 20:1 to 2:1) as eluent to afford a white solid as the desired product. MS: 190.1 (M+1)$^+$.

Step C: 3-Fluorocyclobutanamine

The compound was synthesized as outlined in step E of method A set forth above.

Step D: N-(3-fluorocyclobutyl)formamide

The compound was synthesized as outlined in step F of method A set forth above. $^1$H NMR (400 MHz, CDCl$_3$): δ 8.10 (s, 1H), 5.94-5.89 (brs, 1H), 5.32-5.25 (m, 0.5H), 5.18-5.11 (m, 0.5H), 4.63-4.42 (m, 1H), 2.76-2.62 (m, 2H), 2.44-2.31 (m, 2H).

Step E: 1-Fluoro-3-isocyanocyclobutane

The compound was synthesized via the general procedure as the step G in method A set forth above.

General Procedures for the Preparation of 1,1-Difluoro-4-Isocyanocyclohexane

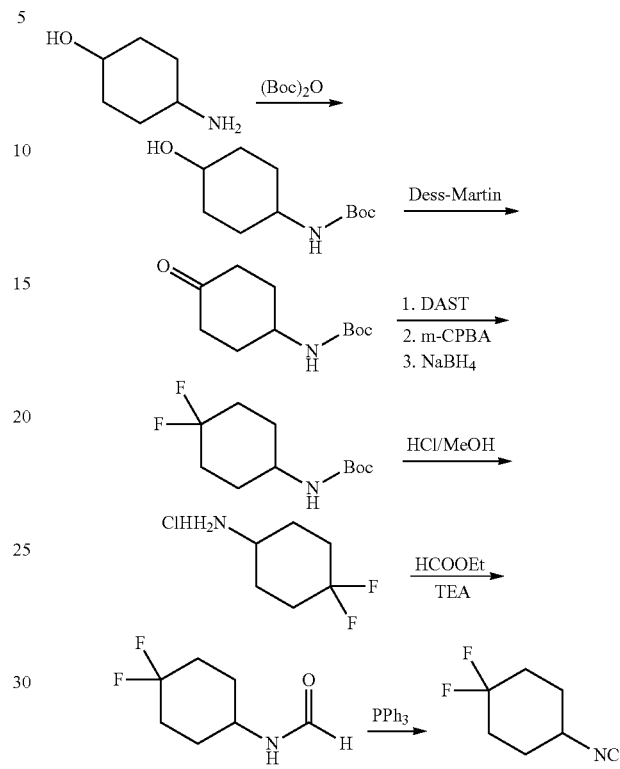

Step A: Tert-butyl 4-hydroxycyclohexylcarbamate

To a solution of 4-aminocyclohexanol (23 g, 0.2 mol) and Et$_3$N (60 g, 0.6 mol) in THF (230 mL) was added (Boc)$_2$O (87 g, 0.4 mol). The resulting solution was stirred at room temperature overnight. The solvent was removed under reduced pressure and the residue was extracted with EtOAc (3×200 mL). The combined organic layers were washed with water (2×200 mL) and brine (200 mL), dried over anhydrous Na$_2$SO$_4$ and concentrated. The residue was purified by column chromatography on silica gel using DCM/MeOH (V:V, 20:1) to afford the desired product as a white solid. MS: 216.2 (M+1)$^+$.

Step B: Tert-butyl 4-oxocyclohexylcarbamate

To a solution of tert-butyl 4-hydroxycyclohexylcarbamate (10.0 g, 46.5 mmol) in DCM (100 mL) was added Dess-Martin periodinane (39.4 g, 92.9 mmol) portionwise. The resulting solution was stirred at room temperature overnight, quenched with aq. Na$_2$S$_2$O$_3$ solution and extracted with DCM (3×100 mL). The combined organic layers were washed with water (2×100 mL) and brine (100 mL), dried over anhydrous Na$_2$SO$_4$, and concentrated. The residue was purified by column chromatography on silica gel using petroleum ether/EtOAc (V:V, 10:1) to afford desired product as a white solid.

Step C: Tert-butyl 4,4-difluorocyclohexylcarbamate

To a solution of tert-butyl 4-oxocyclohexylcarbamate (2.13 g, 10 mmol) in dry DCM (25 mL) was added DAST (2.58 g, 16 mmol) dropwise at −5° C. under nitrogen. After addition, the reaction mixture was stirred at r.t overnight. The reaction mixture was poured into ice water slowly and extracted with DCM (3×100 mL). The combined organic layers were washed with 2 N aq. NaHCO$_3$ and brine, dried over anhydrous Na$_2$SO$_4$, filtered and concentrated in vacuo. The residue was purified by column chromatography using petroleum ether/EtOAc (V:V, 5:1) as eluent to afford a mixture of the title compound (~70%) and the byproduct tert-butyl 4-fluorocyclohex-3-enylcarbamate (~30%) as a light-yellow solid.

To the above mixtures (2.52 g, 10.7 mmol) in DCM (25 mL) was added m-CPBA (2.20 g, 12.9 mmol) portionwise at 0° C. while keeping the internal temperature below 5° C. After addition, the reaction mixture was stirred at room temperature overnight. To the reaction mixture was added saturated aq. Na$_2$S$_2$O$_3$ (8.0 mL) at 0° C. The resulting mixture was stirred at 0° C. for 40 min, and then extracted by DCM (3×5.0 mL). The combined organic layers were washed with brine, dried over anhydrous Na$_2$SO$_4$, and evaporated in vacuo. The residue was used directly in the next step without further purification.

To the above residue in MeOH (15 mL) was added NaBH$_4$ (0.202 g, 5.35 mmol) at 0° C. The reaction mixture was stirred at room temperature overnight. Water (0.38 g) was added dropwise to quench the reaction at 0° C. The resulting mixture was stirred at 0° C. for 30 min, and concentrated in vacuo. The residue was purified by column chromatography using DCM as eluent to afford the pure compound as a white solid. $^1$H NMR (400 MHz, CDCl$_3$): δ 4.46 (s, 1H), 3.59 (s, 1H), 2.25-1.69 (m, 6H), 1.61-1.20 (m, 11H). MS: 236.2 (M+1)$^+$.

Step D: 4,4-Difluorocyclohexanamine hydrochloride

A mixture of tert-butyl 4,4-difluorocyclohexylcarbamate (6.0 g, 25.5 mmol) and 6 N HCl/MeOH (60 mL) was stirred at room temperature for 2 h. The reaction mixture was concentrated to give the crude product which was directly used in next step without further purification. $^1$H NMR (400 MHz, CD$_3$OD): δ 4.89 (s, 2H), 3.32-3.26 (m, 1H), 2.14-2.01 (m, 4H), 2.02-1.85 (m, 2H), 1.74-1.65 (m, 2H). MS: 136.1 (M+1)$^+$.

Step E: N-(4,4-difluorocyclohexyl)formamide

A mixture of 4,4-difluorocyclohexanamine (crude 3.4 g, 25.2 mmol), TEA (3 eq) and ethyl formate (35 mL) was stirred at 110° C. overnight in a sealed tank. The solvent was removed and the residue was purified by column chromatography using DCM/MeOH (V:V, 10:1) as eluent to afford the desired product. $^1$H NMR (400 MHz, CDCl$_3$): δ 8.14 (s, 1H), 5.98 (s, 1H), 3.93 (m, 1H), 2.54-2.19 (m, 1H), 2.15-1.39 (m, 7H). MS: 164.1 (M+1)$^+$.

Step F: 1,1-Difluoro-4-isocyanocyclohexane

A mixture of N-(4,4-difluorocyclohexyl)-formamide (2.5 g, 15.3 mmol), PPh$_3$ (4.4 g, 16.8 mmol), CCl$_4$ (2.3 g, 15.1 mmol), Et$_3$N (1.5 g, 14.9 mmol) and DCM (50 mL) was heated to 45° C. and stirred overnight. The resulting mixture was evaporated in vacuo and the residue was suspended in Et$_2$O (125 mL) at 0° C. The filtrate was concentrated and the residue was purified by column chromatography on silica gel eluting with Et$_2$O to afford the desired product as a yellow oil which was used directly in the next step.

General Procedures for the Preparation of 2-(3-aminophenoxy)ethanol

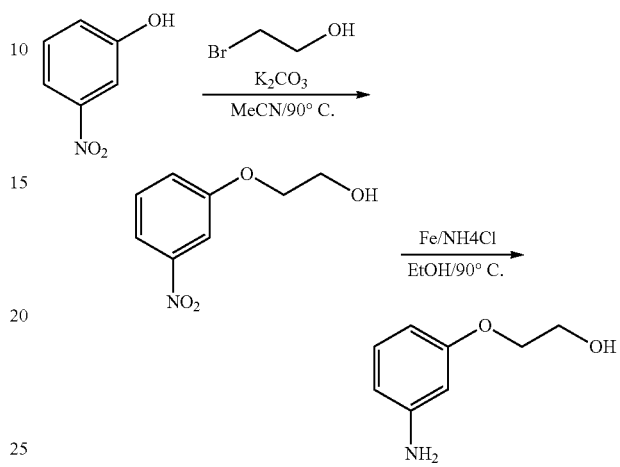

Step A: 2-(3-Nitrophenoxy)ethanol

A suspension of 3-nitrophenol (1 g, 7.2 mmol), 2-bromoethanol (1.2 g, 9.6 mmol) and K$_2$CO$_3$ (2 g, 14.4 mmol) in MeCN (12 mL) was stirred at 90° C. overnight. The precipitate was collected by filtration to give the first batch of product. The filtrate was concentrated and the residue was purified by column chromatography to afford another batch of the desired product as a yellow solid.

Step B: 2-(3-Aminophenoxy)ethanol

To a solution of 2-(3-nitrophenoxy)ethanol (500 mg, 2.7 mmol) and NH$_4$Cl (720 mg, 13.5 mmol) in EtOH (10 mL) was added iron powder (900 mg, 16.2 mmol) at room temperature. The reaction was then stirred at 90° C. for 2 hr and subsequently cooled. The mixture was filtered and the filtrate was concentrated. The resulting residue was purified by column chromatography to afford the desired product as a yellow solid. MS: 154.1 (M+1)$^+$.

General Procedures for the Preparation of 3-(1H-pyrazol-4-yl)aniline

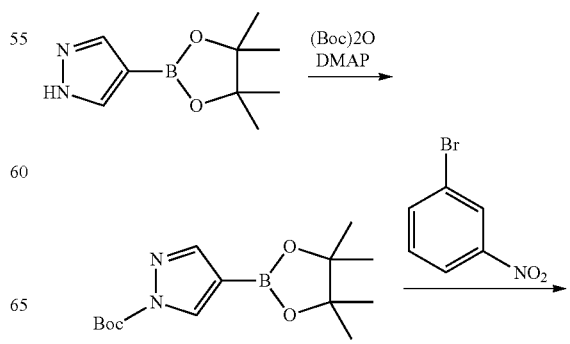

-continued

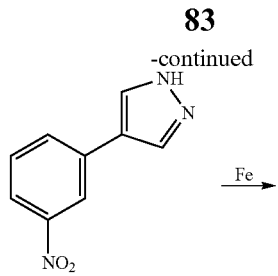

Step A: Tert-butyl 4-(4,4,5,5-tetramethyl-1,3,2-dioxaborolan-2-yl)-1H-pyrazole-1-carboxylate To a solution of 4-(4,4,5,5-tetramethyl-1,3,2-dioxaborolan-2-yl)-1H-pyrazole (500 mg, 2.57 mmol) and (Boc)$_2$O (672 mg, 3.08 mmol) in DMF (1.0 mL) was added DMAP (63 mg, 0.52 mmol) in one portion. The mixture was stirred at room temperature overnight, and then partitioned between EtOAc and saturated aq. NH$_4$Cl. The organic layer was separated, washed with brine, dried over anhydrous Na$_2$SO$_4$, and concentrated to afford the crude product.

Step B: 4-(3-Nitrophenyl)-1H-pyrazole

To a solution of tert-butyl 4-(4,4,5,5-tetramethyl-1,3,2-dioxaborolan-2-yl)-1H-pyrazole-1-carboxylate (300 mg, 0.82 mmol), 1-bromo-3-nitrobenzene (137 mg, 0.68 mmol) and Na$_2$CO$_3$ (216 mg, 2.04 mmol) in DME/H$_2$O (5 mL/1 mL) under N$_2$, was added Pd(PPh$_3$)$_2$Cl$_2$ (24 mg, 0.034 mmol). The mixture was stirred at 85° C. overnight, and then quenched with H$_2$O. The resulting mixture was extracted with EtOAc (3×25 mL). The organic layer was separated, washed with brine, dried over anhydrous Na$_2$SO$_4$, and concentrated. The resulting residue was purified by column chromatography to afford the desired product. MS: 190.2 (M+1)$^+$.

Step C: 3-(1H-pyrazol-4-yl)aniline

Iron powder (296 mg, 5.30 mmol) was added to a solution of 4-(3-nitrophenyl)-1H-pyrazole (200 mg, 1.06 mmol) in AcOH/EtOH (2 mL/3 mL). The reaction mixture was stirred at 90° C. for 2 hr and then cooled to room temperature. The reaction mixture was filtered through Celite. The filter cake was washed with H$_2$O. The filtrate was neutralized with 1 N NaOH to pH=8 and extracted with EtOAc (3×30 mL). The combined organic layers were washed with brine, dried over anhydrous Na$_2$SO$_4$, and concentrated. The resulting residue was purified by column chromatography to afford the desired product. MS: 160.2 (M+1)$^+$.

General Procedures for the Preparation of 2-(3-aminophenyl)propan-2-ol

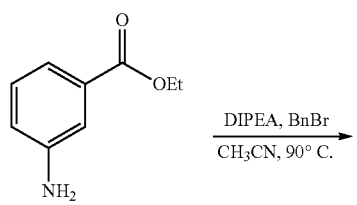

-continued

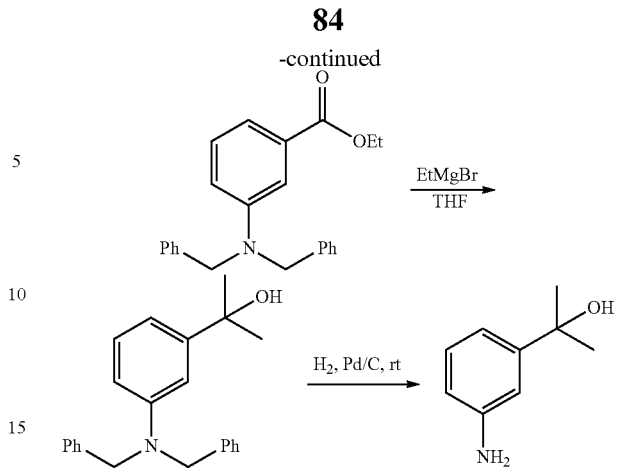

Step A: Ethyl 3-(dibenzylamino)benzoate 2

To a solution of ethyl 3-aminobenzoate (2 g, 0.012 mmol) and Et$_3$N (5.26 mL, 0.036 mmol) in CH$_3$CN (30 mL), was added BnBr (4.32 mL, 0.036 mmol) in one portion. The reaction mixture was heated to reflux for 18 hr and then cooled to room temperature. The mixture was concentrated to dryness in vacuo and the residue was purified by column chromatography (PE:EtOAc=10:1 as eluent) to afford the desired product as a white solid. MS: 346.1 (M+1)$^+$.

Step B: 2-(3-(dibenzylamino)phenyl)propan-2-ol

To a solution of ethyl 3-(dibenzylamino)benzoate (1.85 g, 5.58 mmol) in anhydrous THF (15 mL) at 0° C. under nitrogen atmosphere was added MeMgBr (3 M sol. in THF, 5.58 mL, 16.7 mmol) dropwise over 30 min. The reaction was stirred at room temperature overnight and quenched by addition of saturated NH$_4$Cl. The resulting mixture was extracted with ethyl acetate (3×50 mL). The combined organic layers were washed with NaHCO$_3$, water and brine, dried over anhydrous Na$_2$SO$_4$, filtered and then concentrated to dryness. The residue was purified by column chromatography (PE:EtOAc=2:1 as eluent) to afford the desired product as a colorless oil. MS: 332.1 (M+1)$^+$.

Step C: 2-(3-aminophenyl)propan-2-ol

To a solution of 2-(3-(dibenzylamino)phenyl)propan-2-ol (268 mg, 0.81 mmol) in MeOH (5 mL) was added 10% Pd/C (27 mg) in one portion. The reaction mixture was hydrogenated at room temperature overnight under hydrogen atmosphere. The catalyst was filtered off through Celite and the filtrate was concentrated to dryness. The residue was purified by column chromatography (PE:EtOAc=1:2 as eluent) to afford the desired product as a yellow solid. MS: 152.1 (M+1)$^+$.

General Procedures for the Preparation of 2-(3-amino-5-fluorophenyl)propan-2-ol

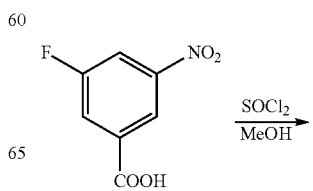

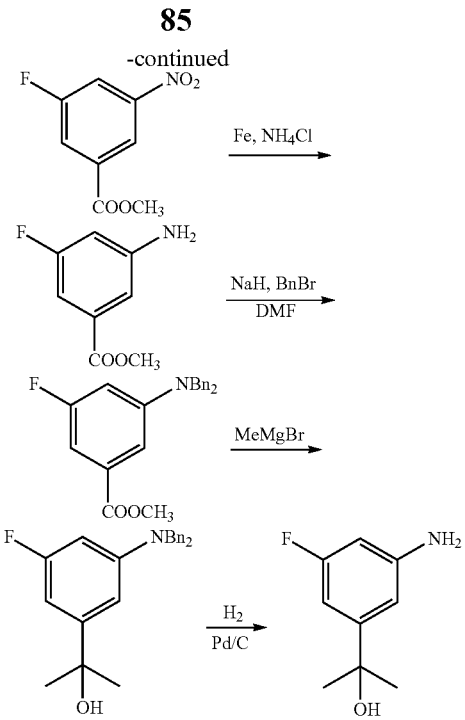

Step A. Methyl 3-fluoro-5-nitrobenzoate

Thionyl chloride (488 mg, 4.1 mmol) was added dropwise to a solution of 3-fluoro-5-nitrobenzoic acid (500 mg, 2.7 mmol) in dry methanol (10 mL) at 0° C. under nitrogen atmosphere. The reaction was warmed to room temperature and stirred for 6 hr. The reaction mixture was concentrated under reduced pressure to obtain the corresponding methyl ester hydrochloride as a waxy solid which was used directly in the next step. MS: 200 (M+1)$^+$.

Step B. Methyl 3-amino-5-fluorobenzoate

To a solution of methyl 3-fluoro-5-nitrobenzoate (400 mg, 2 mmol) in ethanol (10 mL) was added iron powder (560 mg, 10 mmol) and ammonium chloride (540 mg, 10 mmol) in one portion. The reaction mixture was stirred at 80° C. for 1 hr. After cooling the reaction, the mixture was filtered through Celite. The filtrate was concentrated under reduced pressure to give the desired product. MS: 170 (M+1)$^+$.

Step C. Methyl 3-(dibenzylamino)-5-fluorobenzoate

To a solution of methyl 3-amino-5-fluorobenzoate (440 mg, 2.6 mmol) in dry DMF (10 mL) was added NaH (187 mg, 7.8 mmol) portionwise, followed by addition of benzyl bromide (1.1 g, 6.5 mmol). The reaction mixture was stirred at 40° C. for 16 hr and concentrated. The resulting residue was purified by column chromatography to give the desired product. MS: 350 (M+1)$^+$.

Step D. 2-(3-(Dibenzylamino)-5-fluorophenyl)propan-2-ol

Methylmagnesium bromide (1 M in THF, 2.4 mL, 2.4 mmol) was dissolved in THF (5 mL) and placed in an ice-water bath. Methyl 3-(dibenzylamino)-5-fluorobenzoate (280 mg, 0.8 mmol) in THF (5 mL) was then slowly added to the reaction mixture. This mixture was stirred for 3 hr while maintaining an internal temperature range between 15 to 25° C. Then the mixture was cooled to 0° C. and treated with ammonium chloride solution, then extracted with ethyl acetate (3×30 mL). The combined organic layers were dried over anhydrous Na$_2$SO$_4$, and concentrated in vacuo. The residue was purified by column chromatography on silica gel to give the desired product. MS: 350 (M+1)$^+$.

Step E. 2-(3-Amino-5-fluorophenyl)propan-2-ol

To a solution of 2-(3-(dibenzylamino)-5-fluorophenyl)propan-2-ol (150 mg, 0.43 mmol) in ethanol (5 mL) was added 10% Pd/C (15 mg) under a hydrogen atmosphere. The reaction mixture was stirred at room temperature for 16 hr. The suspension was then filtered through Celite and the filtrate was concentrated in vacuo. The residue was purified by column chromatography to give the desired product. MS: 170 (M+1)$^+$.

General Procedures for the Preparation of ethyl 1-(3-aminophenyl)cyclopropanol

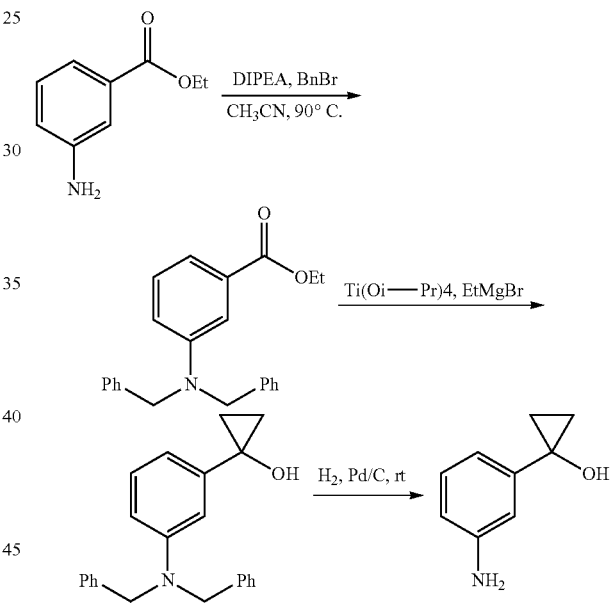

Step A. Ethyl 3-(dibenzylamino)benzoate

To a solution of ethyl 3-aminobenzoate (2 g, 0.012 mmol) and Et$_3$N (5.26 mL, 0.036 mmol) in CH$_3$CN (30 mL) was added BnBr (4.32 mL, 0.036 mmol) in one portion. The reaction mixture was heated to reflux for 18 h and cooled down to room temperature. The mixture was concentrated in vacuo and the resulting residue was purified by column chromatography to afford the desired product as a white solid. MS: 346.1 (M+1)$^+$.

Step B. 1-(3-(Dibenzylamino)phenyl)cyclopropanol

To a solution of ethyl 3-(dibenzylamino)benzoate (1.85 g, 5.58 mmol) in anhydrous THF (20 mL) at room temperature under N$_2$ was added titanium tetraisopropoxide (0.25 mL, 0.84 mmol) dropwise over 10 min. After one hour of stirring, EtMgBr (THF solution, 4.1 mL, 12.3 mmol) was added dropwise over 30 min. The reaction mixture was stirred at room temperature for 3 h. The resulting mixture was quenched by addition of saturated aq. NH$_4$Cl, and extracted with ethyl acetate (3×50 mL). The combined organic layers were washed with NaHCO$_3$, water and brine, dried over anhydrous Na$_2$SO$_4$, and concentrated in vacuo. The residue was purified by column chromatography (PE:EtOAc=5:1 as eluent) to afford the desired product as a colorless oil. $^1$H NMR (400 MHz, CDCl$_3$): δ 7.33-7.28 (m, 5H), 7.25-7.18 (m, 5H), 7.11 (t, J=8.0 Hz, 1H), 6.80-6.75 (m, 1H), 6.61-6.56 (m, 2H), 4.65 (s, 4H), 1.17-1.13 (m, 2H), 0.93-0.90 (m, 2H). MS: 330.1 (M+1)$^+$.

Step C. Ethyl 1-(3-aminophenyl)cyclopropanol

To a solution of 1-(3-(dibenzylamino)phenyl)cyclopropanol (1.8 g, 5.45 mmol) in MeOH (10 mL) at room temperature was added 10% Pd/C (200 mg) in one portion. The reaction mixture was stirred at room temperature under a hydrogen atmosphere overnight. The suspension was filtered through Celite, and the filtrate was concentrated in vacuo. The residue was purified by column chromatography (PE:EtOAc=2:1 as eluent) to afford the desired product as a yellow solid. $^1$H NMR (400 MHz, CDCl$_3$): δ 7.10 (t, J=7.8 Hz, 1H), 6.69 (t, J=2.0 Hz, 1H), 6.63-6.60 (m, 1H), 6.56-6.53 (m, 1H), 1.22-1.19 (m, 2H), 1.01-0.98 (m, 2H). MS: 150.1 (M+1)$^+$.

General Procedures for the Preparation of 3-fluoro-5-(methylthio)aniline

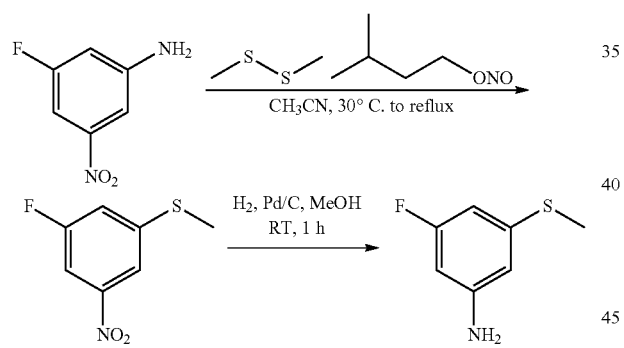

Step A. (3-Fluoro-5-nitrophenyl)(methyl)sulfane

A solution of 3-fluoro-5-nitroaniline (200 mg, 1.28 mmol), 1,2-dimethyldisulfane (121 mg, 1.29 mmol) and CH$_3$CN (3 mL) was stirred at 30° C. Neat isoamyl nitrite (150 mg, 1.28 mmol) was slowly added via syringe over 5 min. The reaction mixture was slowly heated to reflux over 10 min and maintained at a gentle reflux until N$_2$ evolution ceased (30-60 min). The reaction mixture was cooled and the solvent was removed in vacuo to afford a dark oil. The resulting oil was purified by column chromatography to give the desired product as a pale yellow solid.

Step B: 3-Fluoro-5-(methylthio)aniline

To a solution of (3-fluoro-5-nitrophenyl)(methyl)sulfane (90 mg, 0.48 mmol) in MeOH (10 mL) was added 10% Pd/C (9 mg) in one portion. The resulting mixture was purged with H$_2$ three times and stirred at room temperature for 1 h. The suspension was filtered through Celite, and the filter cake was washed with MeOH (5 mL). The filtrate was concentrated in vacuo to afford the desired product which was used directly in next step. MS: 158.0 (M+1)$^+$.

General Procedure for the Preparation of (S)-2-oxo-1,3-oxazinane-4-carboxylic Acid

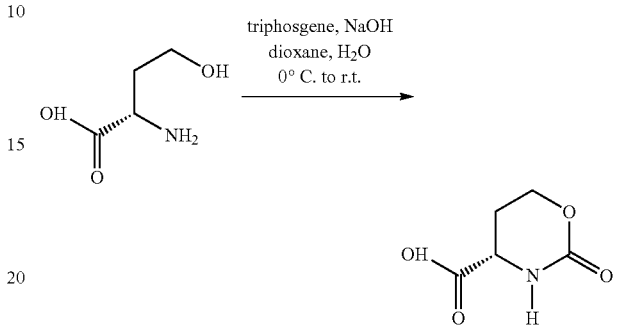

To a mixture of (S)-2-amino-4-hydroxybutanoic acid (10 g, 84.0 mmol) and 250 mL of aq. NaOH (2 mol/L, 20.4 g, 510 mmol) at 0° C. was added a solution of triphosgene in dioxane (25.3 g in 125 mL dioxane) dropwise over 1 h. The internal temperature was kept below 5° C. during the addition. The mixture was then stirred at room temperature for 2 days. The reaction mixture was then concentrated in vacuo, followed by addition of 200 mL of CH$_3$CN. The resulting mixture was then heated to 60° C. and stirred vigorously for 0.5 h. The hot mixture was filtered immediately. The filtrate was then concentrated to 100 mL and the desired product was precipitated out. The crude product was collected by filtration and used directly in the next step without further purification. MS: 146.0 (M+1)$^+$.

General Procedure for the Preparation of (S)-4-(tert-butoxycarbonyl)-6-oxopiperazine-2-carboxylic Acid

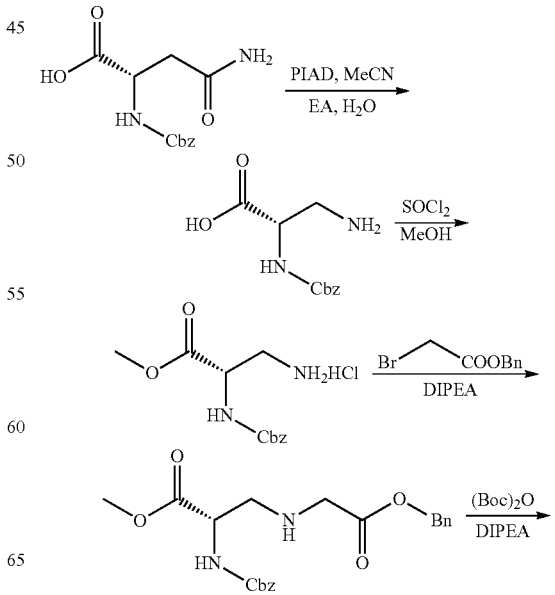

-continued

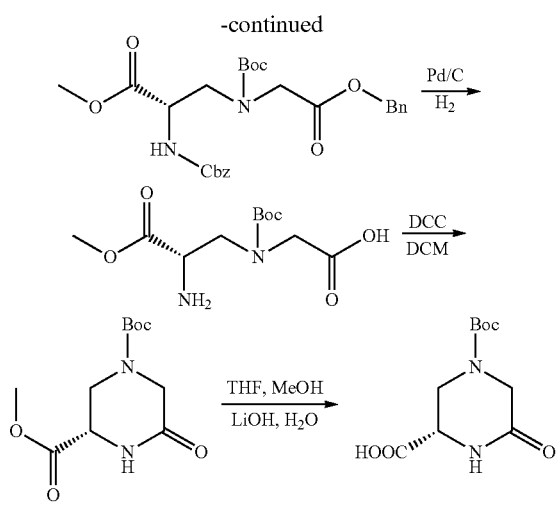

Step A: (S)-3-Amino-2-(((benzyloxy)carbonyl)amino)propanoic Acid

To a mixture of (S)-4-amino-2-(((benzyloxy)carbonyl)amino)-4-oxobutanoic acid (3 g, 11.3 mmol) in MeCN (20 mL), EtOAc (20 mL) and H₂O (10 mL), was added PIAD (4.38 g, 13.5 mmol) in one portion. The reaction mixture was stirred at room temperature overnight. The resulting mixture was filtered, and the filtrate was concentrated in vacuo to afford the desired product. MS: 239.1 (M+1)⁺.

Step B: (S)-Methyl 3-amino-2-(((benzyloxy)carbonyl)amino)propanoate hydrochloride To a stirred solution of MeOH (50 mL) was added SOCl₂ (5 mL) dropwise at 0° C. The resulting mixture was stirred at 0° C. for 0.5 h before (S)-3-amino-2-(((benzyloxy)carbonyl)amino) propanoic acid (2.6 g, 10 mmol) was added. Then the reaction mixture was stirred at room temperature overnight and concentrated in vacuo to afford the desired product. MS: 253.1 (M+1)⁺.

Step C: (S)-Methyl 3-((2-(benzyloxy)-2-oxoethyl)amino)-2-(((benzyloxy)carbonyl)amino)propaneate To a solution of (S)-methyl 3-amino-2-(((benzyloxy)carbonyl)amino)propanoate hydrochloride (2.6 g, 0.01 mol) in THF (40 mL) was added DIPEA (4.0 g, 0.03 mol) at 0° C. The mixture was stirred at 0° C. for 5 min, followed by addition of benzyl 2-bromoacetate (4.7 g, 0.02 mol). Then the mixture was allowed to warm to room temperature and stirred overnight. The reaction mixture was quenched by addition of H₂O and then extracted with EtOAc (3×40 mL). The combined organic layers were washed with brine, dried over anhydrous Na₂SO₄, and concentrated. The resulting residue was purified by column chromatography to afford the desired product. MS: 401.2 (M+1)⁺.

Step D: (S)-Methyl 3-((2-(benzyloxy)-2-oxoethyl)(tert-butoxycarbonyl)amino)-2-(((benzyloxy)carbonyl)amino)propanoate To a solution of (S)-methyl 3-((2-(benzyloxy)-2-oxoethyl)amino)-2-(((benzyloxy)carbonyl)amino)propanoate (3.0 g, 7.5 mmol) in THF (40 mL) was added DIPEA (2.9 g, 22.5 mmol) at 0° C. The mixture was stirred at 0° C. for 5 min followed by addition of di-tert-butyl dicarbonate (3.27 g, 15 mmol). Then the mixture was allowed to warm to room temperature and stirred overnight. After quenching with a saturated. NaHCO₃ solution, the resulting mixture was extracted with EtOAc (3×60 mL) and concentrated. The resulting residue was purified by column chromatography to afford the desired product. MS: 501.2 (M+1)⁺.

Step E: (S)-2-((2-Amino-3-methoxy-3-oxopropyl)(tert-butoxycarbonyl)amino)acetic Acid To a solution of (S)-methyl 3-((2-(benzyloxy)-2-oxoethyl)(tert-butoxycarbonyl)amino)-2-(((benzyl-oxy)carbonyl)amino)propanoate (2.5 g, 5 mmol) in MeOH (30 mL) was added 10% Pd/C (250 mg). The mixture was stirred under hydrogen atmosphere at room temperature overnight. The resulting suspension was filtered through Celite, and the filtrate was concentrated in vacuo to afford the desired product. MS: 277.1 (M+1)⁺.

Step E: (S)-1-tert-Butyl 3-methyl 5-oxopiperazine-1,3-dicarboxylate

To a solution of (S)-2-((2-amino-3-methoxy-3-oxopropyl)(tert-butoxycarbonyl)amino)acetic acid (1.2 g, 4 mmol) in DCM (100 mL) was added DCC (1.34 g, 6 mmol) at 5° C. The mixture was stirred at 10° C. for 4 h followed by addition of Et₃N (0.88 g, 8 mmol). The resulting mixture was stirred at room temperature for 18 h and then concentrated. The residue was added to EtOAc (20 mL) and the precipitate was filtered. The filtrate was concentrated and the residue was purified by column chromatography to afford the desired product. MS: 259.1 (M+1)⁺.

Step F: (S)-4-(tert-Butoxycarbonyl)-6-oxopiperazine-2-carboxylic Acid

To a mixture of (S)-1-tert-butyl 3-methyl 5-oxopiperazine-1,3-dicarboxylate (500 mg, 1.9 mmol) in MeOH (20 mL) and THF (20 mL) was added a solution of LiOH.H₂O (159 mg, 3.8 mmol) in H₂O (10 mL) at 0° C. The mixture was stirred at room temperature for 2 h and then partitioned between EtOAc (25 mL) and H₂O. The aqueous layer was acidified with 2N HCl to pH 3-4 and then extracted with EtOAc (3×20 mL). The combined organic layers were washed with brine, dried over anhydrous Na₂SO₄ and concentrated to afford the desired product which was used directly in the next reaction. MS: 245.1 (M+1)⁺.

General Procedure for the Preparation of 2-bromopyrimidine-4-carbonitrile

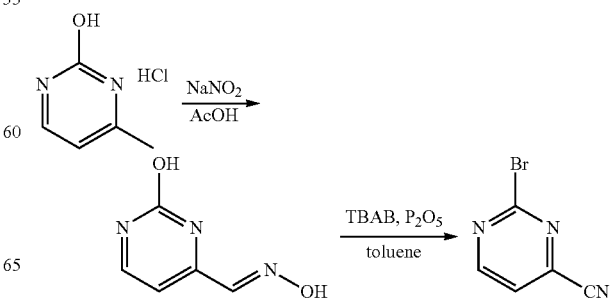

Step A: 2-Hydroxy-4-carboxyaldehyde oxime

2-Hydroxy-4-methyl pyrimidine hydrochloride (25.0 g 171 mmol) and sodium nitrate (17.7 mg, 260 mmol) were slowly added to 200 mL of 50% acetic acid at 0° C. The reaction mixture was stirred at room temperature for 3 h. The resulting suspension and the solids were filtered, washed with water and dried to afford the desired product. $^1$H NMR (400 MHz, DMSO-$d_6$): δ 12.42 (s, 1H), 11.89 (s, 1H), 7.92 (d, J=6.4 Hz, 1H), 7.75 (s, 1H), 6.43 (d, J=6.4 Hz, 1H). MS: 140.0 (M+1)$^+$.

Step B: 2-Bromopyrimidine-4-carbonitrile

A mixture of 2-hydroxy-4-carboxyaldehyde oxime (9 g, 28.8 mmol), tetrabutyl ammonium bromide (10 g, 71.9 mmol) and phosphorus pentoxide (2 g, 14.4 mmol) in toluene (300 mL) was stirred at 120° C. for 2 h. The resulting mixture was filtered and the filtrate was concentrated. The resulting residue was purified by column chromatography to give the desired compound as a yellow solid. $^1$H NMR (400 MHz, CDCl$_3$): δ 8.82 (d, J=4.8 Hz, 1H), 7.66 (d, J=4.8 Hz, 1H). MS: 185.0 (M+1)$^+$.

General Synthetic Procedures for Making Compounds of Formula I

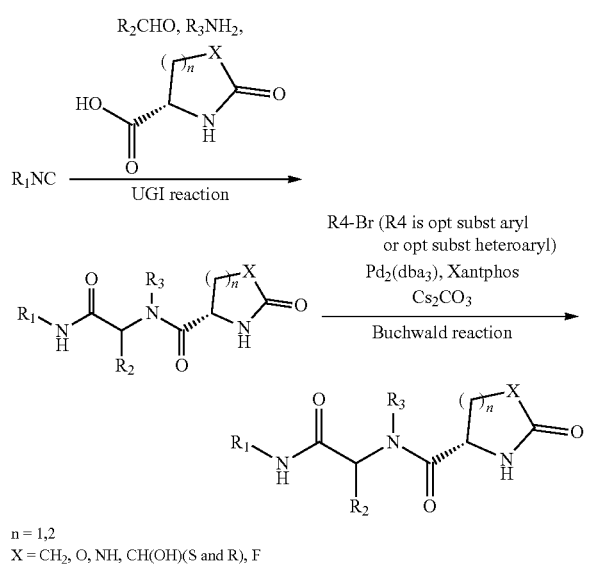

n = 1,2
X = CH$_2$, O, NH, CH(OH)(S and R), F

General Procedures for the UGI Reaction

A mixture of aldehyde (3.5 mmol) and aniline (3.5 mmol) in MeOH (8 mL) was stirred at room temperature for 30 min. Then the acid (3.5 mmol) was added and the reaction mixture was stirred for another 30 min, followed by addition of the isocyanide (3.5 mmol). The resulting mixture was then stirred at room temperature overnight and quenched with H$_2$O. The resulting mixture was partitioned between EtOAc and H$_2$O. The organic layer was washed with brine, dried over anhydrous Na$_2$SO$_4$, and then concentrated. The resulting residue was purified by a standard method to afford the desired product.

General Procedures for the Buchwald Reaction

A mixture of amine (0.30 mmol), aryl bromide (0.30 mmol), Cs$_2$CO$_3$ (129 mg, 0.39 mmol), Pd$_2$(dba)$_3$ (18 mg, 0.02 mmol) and Xant-Phos (9.4 mg, 0.02 mmol) in 1,4-dioxane (10 mL) was stirred under N$_2$ at 80° C. overnight. After filtration, the filtrate was concentrated in vacuo and the residue was purified by a standard method to give the desired products.

Example 1. Preparation of (S)-methyl 1-methyl-5-oxopyrrolidine-2-carboxylate Compound 2 was prepared according to the following scheme, using the following protocol.

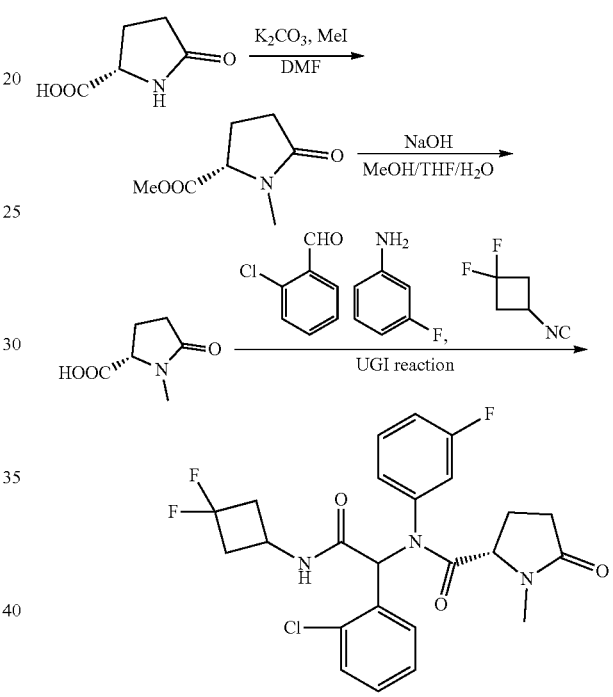

Step A: (S)-Methyl 1-methyl-5-oxopyrrolidine-2-carboxylate

To a mixture of (S)-5-oxopyrolidine-2-carboxylic acid (5.0 g, 38.8 mmol) in DMF (50 mL) were added anhydrous K$_2$CO$_3$ (16 g, 116 mmol) and iodomethane (16.4 g, 116 mmol) at room temperature The resulting mixture was warmed to 40° C., stirred for 24 h and concentrated in vacuo. The residue was precipitated with EtOAc (80 mL) and filtered. The filter cake was washed with EtOAc (2×10 mL). The combined filtrates were concentrated and the residue was purified by column chromatography on silica gel to give the desired product. $^1$H-NMR (400 MHz, CDCl$_3$): δ 4.18-4.11 (m, 1H), 3.70 (s, 3H), 2.87 (s, 3H), 2.56-2.29 (m, 3H), 2.16-2.04 (m, 1H). MS: 158.1 (M+1)$^+$.

Step B: (S)-1-Methyl-5-oxopyrrolidine-2-carboxylic Acid

To a solution of (S)-methyl 1-methyl-5-oxopyrrolidine-2-carboxylate (0.6 g, 3.8 mmol) in MeOH (6 mL) were added THF (2 mL), H$_2$O (2 mL) and NaOH (0.45 g, 11.4 mmol) at room temperature The resulting mixture was stirred at room temperature for 18 h and then acidified with 2 N HCl to pH=3-4 at 0° C. The mixture was extracted with EtOAc (3×30 mL), the combined organic layers were dried over anhydrous Na$_2$SO$_4$ and concentrated to give the crude product as a yellow solid (0.8 g) which was used directly in the next step. MS: 142.1 (M−1)$^-$.

Step C: Compound 2

2-Chlorobenzaldehyde (117 mg, 0.83 mmol), 3-fluoroaniline (92.5 mg, 0.83 mmol), crude (S)-1-methyl-5-oxopyrrolidine-2-carboxylic acid (200 mg, ~60% purity, 0.83 mmol) and 1,1-difluoro-3-isocyanocyclobutane (119 mg, 90% purity, 1.0 mmol) were used in the UGI reaction to give the desired product (diastereomeric mixture). $^1$H NMR (400 MHz, CDCl$_3$): δ 8.52 (d, J=4.9 Hz, 0.2H), 8.16 (m, 0.3H), 7.87-7.47 (m, 2H), 7.42-7.31 (m, 1H), 7.25-7.11 (m, 2H), 7.08-6.89 (m, 3.3H), 6.74 (d, J=6.0 Hz, 0.7H), 6.57 (m, 2H), 4.42-4.26 (m, 1.3H), 4.20-4.08 (m, 0.5H), 4.00 (m, 1H), 3.00 (m, 2H), 2.74 (m, 3H), 2.63-1.82 (m, 6H). MS: 494.1 (M+1)$^+$.

Example 2. Preparation of (S)—N-(1-(2-chlorophenyl)-2-((4,4-difluorocyclohexyl)amino)-2-oxoethyl)-N-(3-fluorophenyl)-5-oxopyrrolidine-2-carboxamide Compounds 3 and 4 were prepared according to the following scheme, using the following protocol.

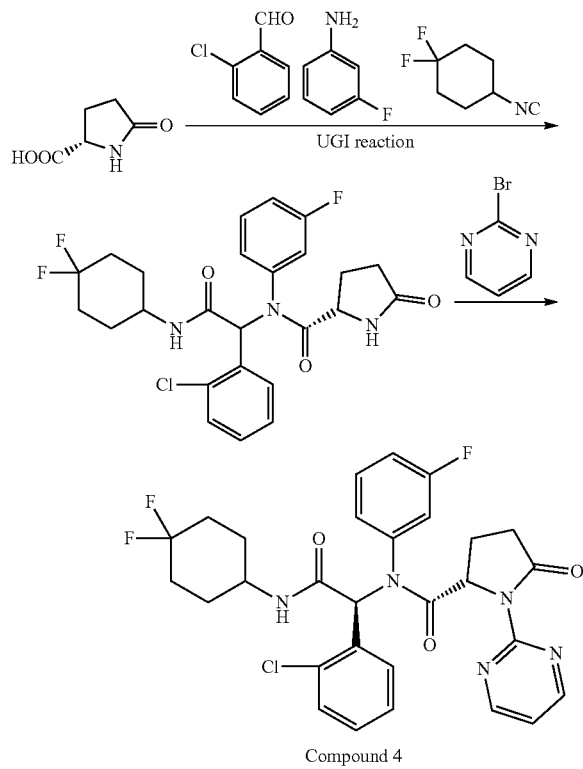

Compound 4

Step A. (S)—N-(1-(2-Chlorophenyl)-2-((4,4-difluorocyclohexyl)amino)-2-oxoethyl)-N-(3-fluorophenyl)-5-oxopyrrolidine-2-carboxamide 3-Fluoroaniline (86 mg, 0.78 mmol), 2-chlorobenzaldehyde (109 mg, 0.78 mmol), (S)-5-oxopyrrolidine-2-carboxylic acid (100 mg, 0.78 mmol) and 1,1-difluoro-4-isocyanocyclohexane (135 mg, 0.91 mmol) were used in the UGI reaction to give the desired product. MS: 508.1 (M+1)$^+$.

Step B. (S)—N—((S)-1-(2-Chlorophenyl)-2-((4,4-difluorocyclohexyl)amino)-2-oxoethyl)-N-(3-fluorophenyl)-5-oxo-1-(pyrimidin-2-yl)pyrrolidine-2-carboxamide and (S)—N—((R)-1-(2-chlorophenyl)-2-((4,4-difluorocyclohexyl)amino)-2-oxoethyl)-N-(3-fluorophenyl)-5-oxo-1-(pyrimidin-2-yl)pyrrolidine-2-carboxamide A mixture of (S)—N-(1-(2-chlorophenyl)-2-((4,4-difluorocyclohexyl)amino)-2-oxoethyl)-N-(3-fluorophenyl)-5-oxopyrrolidine-2-carboxamide (100 mg, 0.20 mmol), 2-bromopyrimidine (47 mg, 0.30 mmol), Cs$_2$CO$_3$ (129 mg, 0.39 mmol), Pd$_2$(dba)$_3$ (18 mg, 0.02 mmol) and Xant-Phos (9.4 mg, 0.02 mmol) in 1,4-dioxane (10 mL) was stirred under N$_2$ at 80° C. overnight. After filtration, the filtrate was concentrated in vacuo and the residue was purified by a standard method to give the desired products.

(S)—N—((S)-1-(2-chlorophenyl)-2-((4,4-difluorocyclohexyl)amino)-2-oxoethyl)-N-(3-fluorophenyl)-5-oxo-1-(pyrimidin-2-yl)pyrrolidine-2-carboxamide. Compound 4

$^1$H NMR (400 MHz, CDCl$_3$): δ 8.71 (d, J=4.8 Hz, 2H), 7.75 (m, 1H), 7.33 (m, 2H), 7.18 (m, 1H), 7.09-6.87 (m, 5H), 6.47 (s, 1H), 5.61 (d, J=7.6 Hz, 1H), 4.86 (d, J=6.6 Hz, 1H), 3.98 (m, 1H), 3.01-2.84 (m, 2H), 2.58 (m, 1H), 2.30-2.20 (m, 1H), 1.93 (m, 7H), 1.47 (m, 2H); MS: 586.2 (M+1)$^+$.

(S)—N—((R)-1-(2-Chlorophenyl)-2-((4,4-difluorocyclohexyl)amino)-2-oxoethyl)-N-(3-fluorophenyl)-5-oxo-1-(pyrimidin-2-yl)pyrrolidine-2-carboxamide. Compound 3

$^1$H NMR (400 MHz, CDCl$_3$): δ 8.75 (dd, J=4.8, 2.0 Hz, 2H), 7.40 (d, J=7.8 Hz, 1H), 7.23 (s, 3H), 7.08 (dt, J=11.3, 6.3 Hz, 3H), 6.99 (d, J=3.7 Hz, 1H), 6.27 (s, 1H), 6.13-5.92 (m, 1H), 5.02 (m, 1H), 4.76 (m, 1H), 3.92 (m, 1H), 2.88 (m, 1H), 2.67-2.46 (m, 1H), 2.44-2.19 (m, 2H), 2.00 (m, 8H). MS: 586.1 (M+1)$^+$.

The following analogs were synthesized via the procedures set forth above, using the appropriate aldehyde, amine, carboxylic acid, isocyanide and halo-substituted-aromatic ring or heteroaromatic ring using the reagents and solvents set forth above or similar reagents and solvents thereof, and purified via standard methods.

Compound 6

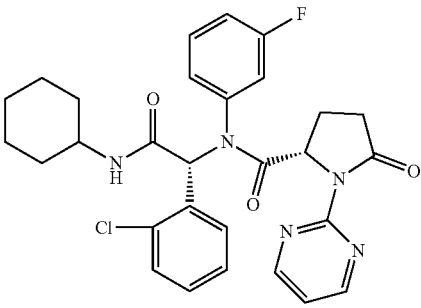

$^1$H NMR (400 MHz, CDCl$_3$): δ 8.75 (d, J=4.8 Hz, 2H), 7.35 (m, 3H), 7.25-6.81 (m, 5H), 6.28 (s, 1H), 5.84 (d, J=7.5

Hz, 1H), 4.76 (m, 1H), 3.98-3.59 (m, 1H), 2.92 (m, 1H), 2.58 (m, 1H), 2.35-2.20 (m, 1H), 2.07 (m, 1H), 1.83 (m, 2H), 1.57 (m, 4H), 1.46-1.17 (m, 4H). MS: 550.2 (M+1)$^+$.

Compound 7

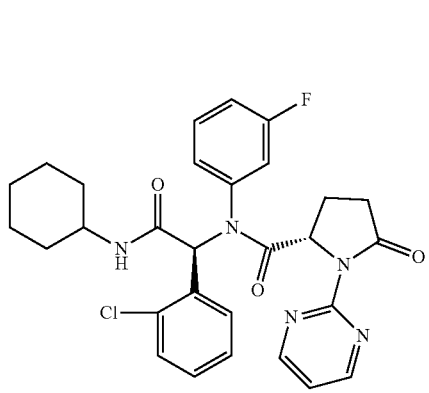

$^1$H NMR (400 MHz, CDCl$_3$): δ 8.73 (m, 2H), 7.80 (s, 1H), 7.35 (s, 1H), 7.23-6.72 (m, 6H), 6.47 (s, 1H), 5.49 (d, J=7.7 Hz, 1H), 4.87 (d, J=6.6 Hz, 1H), 4.74-4.42 (m, 1H), 3.86 (d, J=8.0 Hz, 1H), 3.19-2.77 (m, 1H), 2.56 (m, 1H), 2.44-2.21 (m, 1H), 2.13-1.73 (m, 4H), 1.60 (s, 2H), 1.26 (m, 4H). MS: 550.2 (M+1)$^+$.

Compound 5

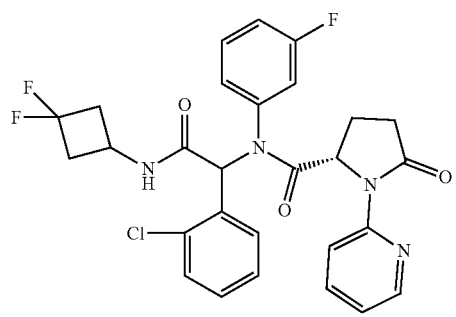

$^1$H NMR (400 MHz, CDCl$_3$): δ 8.46-8.32 (m, 1.7H), 7.78-7.61 (m, 1.5H), 7.39 (m, 1.5H), 7.23 (m, 1.6H), 7.13-6.88 (m, 4H), 6.40 (m, 1H), 6.11 (m, 1H), 5.01-4.77 (m, 1H), 4.26 (m, 1H), 3.51 (d, J=5.5 Hz, 0.3H), 3.13-2.75 (m, 3H), 2.61-2.22 (m, 3H), 2.17-1.90 (m, 1H). MS: 557.1 (M+1)$^+$.

Compound 49

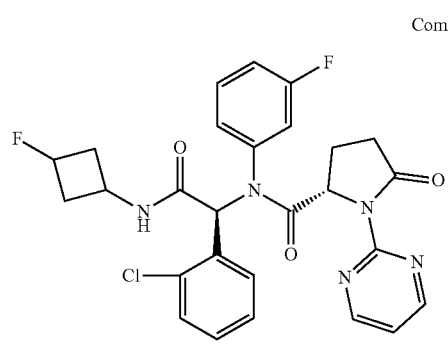

$^1$H NMR (400 MHz, CDCl$_3$): δ 8.69 (s, 2H), 7.76 (s, 1H), 7.49-6.68 (m, 7H), 6.44 (s, 1H), 6.19 (s, 1H), 4.93 (m, 3H), 2.23 (m, 8H). MS: 540.1 (M+1)$^+$.

Compound 10

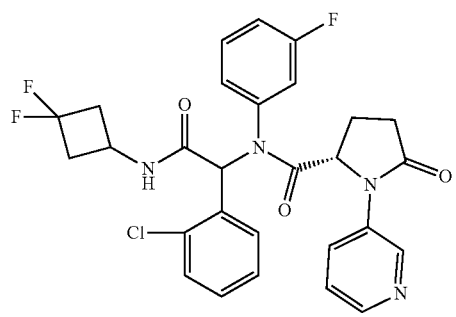

$^1$H NMR (400 MHz, CDCl$_3$): δ 8.56 (m, 2H), 8.16 (s, 1.3H), 7.74 (s, 1H), 7.36 (s, 2.6H), 7.19 (s, 1H), 7.12-6.82 (m, 3H), 6.52 (m, 2H), 6.19 (m, 1H), 4.65-4.48 (m, 1H), 4.26 (m, 1.3H), 3.90-3.82 (m, 0.3H), 2.87 (m, 3H), 2.64-1.98 (m, 6H). MS: 557.1 (M+1)$^+$.

Compound 51

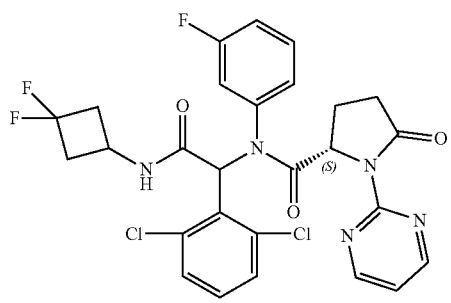

$^1$H NMR (400 MHz, CDCl$_3$): δ 8.81 (d, J=4.9 Hz, 1H), 8.66 (d, J=2.7 Hz, 1H), 8.04-7.79 (m, 1H), 7.49-7.31 (m, 1H), 7.13-6.92 (m, 6H), 6.60 (m, 1H), 6.25-5.95 (m, 1H), 5.68 (m, 1H), 4.73 (dd, J=16.0, 6.9 Hz, 1H), 4.39 (m, 1H), 2.98 (m, 3H), 2.53 (m, 4H), 2.14-1.93 (m, 1H). MS: 592.1 (M+1)$^+$.

Compound 41

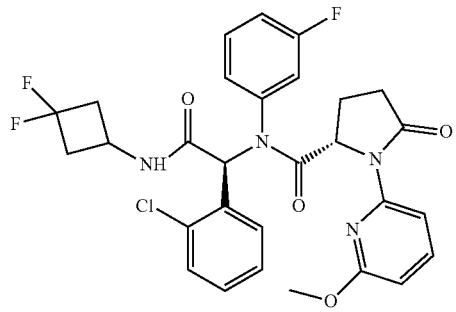

$^1$H NMR (400 MHz, CDCl$_3$): δ 7.98 (m, 1H), 7.65 (m, 2H), 7.44-7.30 (m, 2H), 7.03 (m, 6H), 6.51 (m, 1H), 6.36 (s, 1H), 5.12 (d, J=6.3 Hz, 1H), 4.33 (s, 1H), 3.97 (s, 3H), 3.10-2.63 (m, 3H), 2.60-2.00 (m, 5H). MS: 587.1 (M+1)$^+$.

Compound 26

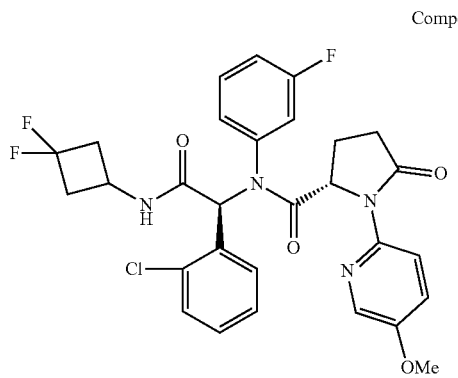

$^1$H NMR (400 MHz, CDCl$_3$): δ 8.32 (m, 1H), 8.05 (t, J=8.6 Hz, 1H), 7.69 (s, 1H), 7.45-7.30 (m, 1H), 7.25-6.78 (m, 6H), 6.38 (m, 2H), 4.88 (m, 1H), 4.33 (s, 1H), 3.89 (s, 3H), 3.11-2.72 (m, 3H), 2.66-2.29 (m, 3H), 2.23-1.86 (m, 2H). MS: 587.1 (M+1)$^+$.

Compound 21

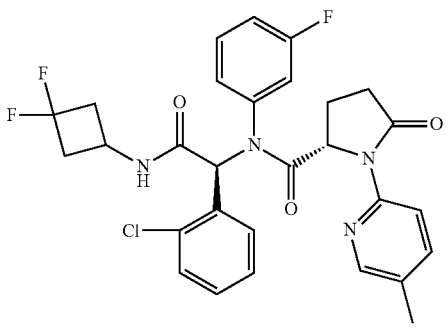

$^1$H NMR (400 MHz, CDCl$_3$): δ 8.26 (d, J=8.5 Hz, 1H), 8.15 (s, 1H), 7.64 (s, 1H), 7.48 (m, 1H), 7.32 (d, J=7.5 Hz, 1H), 7.14 (m, 2H), 7.04-6.83 (m, 3H), 6.40 (s, 1H), 6.04 (s, 1H), 4.89 (m, 1H), 4.31 (s, 1H), 2.89 (m, 3H), 2.48 (m, 2H), 2.40-2.27 (m, 3H), 2.26-1.84 (m, 3H). MS: 571.2 (M+1)$^+$.

Compound 17

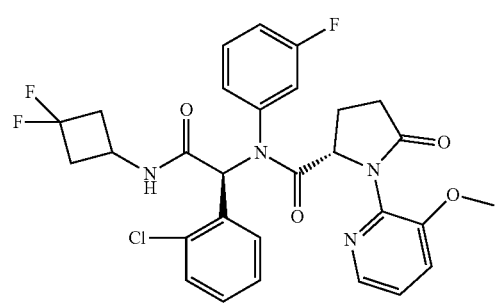

$^1$H NMR (400 MHz, CDCl$_3$): δ 7.93 (m, 1H), 7.56 (m, 2H), 7.21 (m, 3H), 7.10-6.87 (m, 3H), 6.42 (m, 3H), 5.04 (m, 1H), 4.25 (m, 1H), 3.97 (d, J=6.1 Hz, 3H), 3.10-2.69 (m, 3H), 2.60-2.15 (m, 4H), 2.12-1.87 (m, 1H). MS: 587.2 (M+1)$^+$.

Compound 27

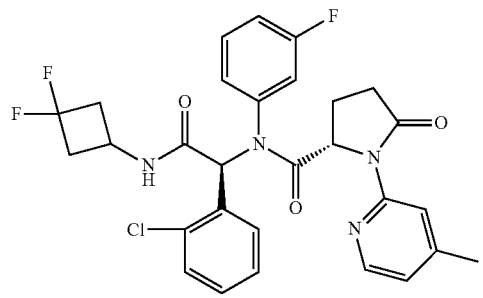

$^1$H NMR (400 MHz, CDCl$_3$): δ 8.30-8.15 (m, 2H), 7.68 (s, 1H), 7.38 (m, 1H), 7.24-6.85 (m, 6H), 6.46-6.16 (m, 2H), 4.94 (d, J=6.0 Hz, 1H), 4.32 (s, 1H), 3.10-2.74 (m, 3H), 2.60-2.43 (m, 2H), 2.36 (m, 4H), 2.23-1.91 (m, 2H). MS: 571.2 (M+1)$^+$.

Compound 28

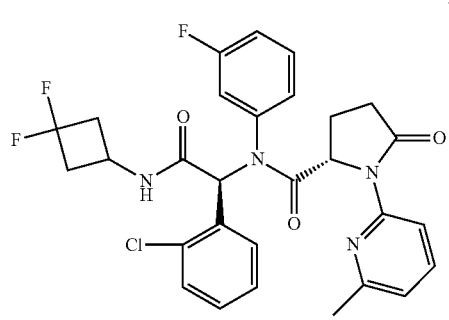

$^1$H NMR (400 MHz, CDCl$_3$): δ 8.19 (m, 1H), 7.79-7.33 (m, 3H), 7.28-7.06 (m, 4H), 7.06-6.83 (m, 4H), 6.47-6.32 (m, 2H), 5.09-4.91 (m, 1H), 4.25 (m, 1H), 3.09-2.60 (m, 4H), 2.57 (s, 3H), 2.53-1.99 (m, 5H). MS: 571.0 (M+1)$^+$.

Compound 15

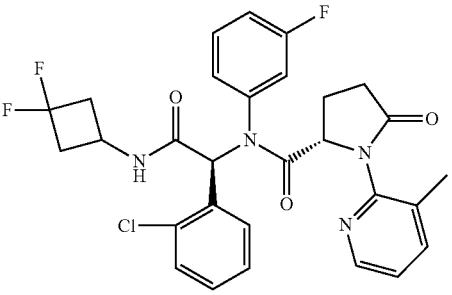

$^1$H NMR (400 MHz, CDCl$_3$): δ 8.17 (d, J=8.3 Hz, 1H), 7.56 (m, 2H), 7.25-6.96 (m, 5H), 6.89 (m, 2H), 6.42 (s, 1H), 6.21 (s, 1H), 5.12-4.96 (m, 1H), 4.31 (m, 1H), 3.14-2.74 (m, 3H), 2.55 (s, 3H), 2.51-2.28 (m, 3H), 2.20 (m, 1H), 2.05-1.87 (m, 1H). MS: 571.2 (M+1)$^+$.

1H), 6.28 (s, 1H), 4.83 (d, J=8.2 Hz, 1H), 4.12 (s, 1H), 3.10-2.62 (m, 3H), 2.56 (m, 1H), 2.36-1.84 (m, 4H). MS: 625.1 (M+1)⁺.

Compound 25

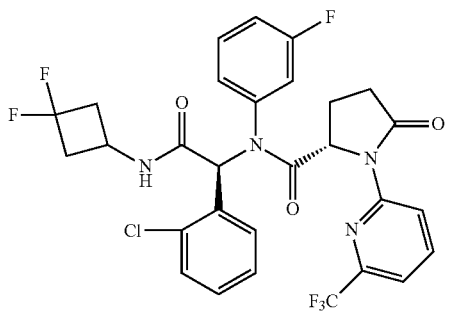

¹H NMR (400 MHz, CDCl₃): δ 8.72 (m, 1H), 7.88 (m, 1H), 7.65 (s, 1H), 7.57-7.30 (m, 2H), 7.23-7.09 (m, 2H), 7.02 (s, 2H), 6.96-6.83 (m, 1H), 6.44 (s, 1H), 6.05 (d, J=6.5 Hz, 1H), 5.31-4.93 (m, 1H), 4.33 (s, 1H), 3.02 (m, 2H), 2.86 (m, 1H), 2.63-2.45 (m, 2H), 2.44-2.23 (m, 2H), 2.01 (m, 1H). MS: 625.1 (M+1)⁺.

Compound 40

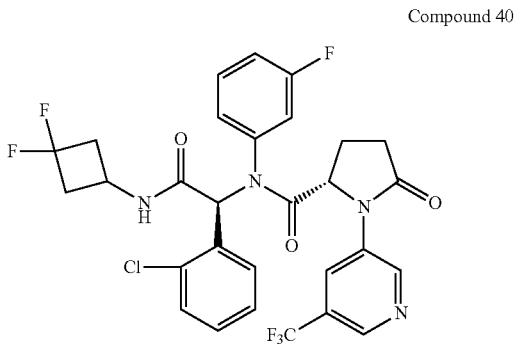 [SMILES: O=C(NC1CC(F)(F)C1)[C@H](c1ccccc1Cl)N(C(=O)[C@@H]1CCC(=O)N1c1cncc(C(F)(F)F)c1)c1cccc(F)c1]

¹H NMR (400 MHz, CDCl₃): δ 8.74 (s, 1H), 8.53 (s, 1H), 7.71 (s, 1H), 7.31 (d, J=8.3 Hz, 1H), 7.25-6.80 (m, 6H), 6.44 (s, 1H), 6.08 (s, 1H), 4.95 (m, 1H), 4.35 (s, 1H), 3.15-2.76 (m, 3H), 2.66-2.17 (m, 4H), 2.03 (s, 1H). MS: 625.1 (M+1)⁺.

Compound 31

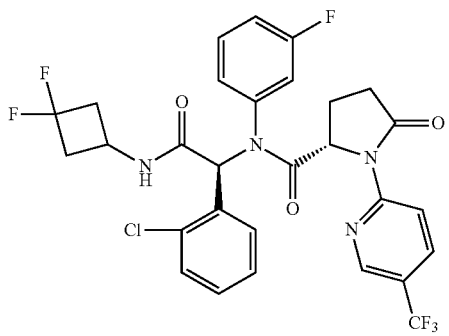

¹H NMR (400 MHz, CDCl₃): δ 8.91-8.34 (m, 2H), 8.03 (s, 1H), 7.79-7.34 (m, 3H), 7.22-6.75 (m, 5H), 6.46 (s, 1H), 6.02 (d, J=6.5 Hz, 1H), 4.95 (dd, J=9.4, 3.1 Hz, 1H), 4.35 (s, 1H), 3.13-2.76 (m, 3H), 2.68-1.83 (m, 5H). MS: 625.1 (M+1)⁺.

Compound 11

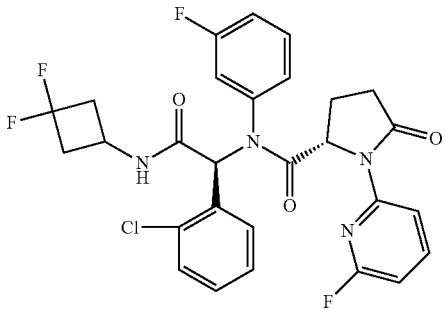

¹H NMR (400 MHz, CDCl₃): δ 8.29 (dd, J=8.1, 2.0 Hz, 1H), 7.74 (m, 2H), 7.31 (m, 2H), 7.22-7.12 (m, 2H), 7.00 (s, 2H), 6.93 (m, 1H), 6.67 (dd, J=7.9, 2.4 Hz, 1H), 6.46 (m, 1H), 6.06 (m, 1H), 4.86 (m, 1H), 4.35 (m, 1H), 2.93 (m, 3H), 2.59-2.39 (m, 2H), 2.23 (m, 1H), 2.02 (m, 1H). MS: 575.1 (M+1)⁺.

Compound 39

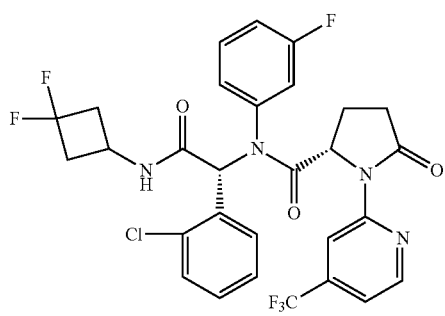

¹H NMR (400 MHz, CDCl₃): δ 8.65 (d, J=23.6 Hz, 2H), 7.87 (s, 1H), 7.59-7.29 (m, 3H), 7.26-6.71 (m, 5H), 6.59 (s,

Compound 29

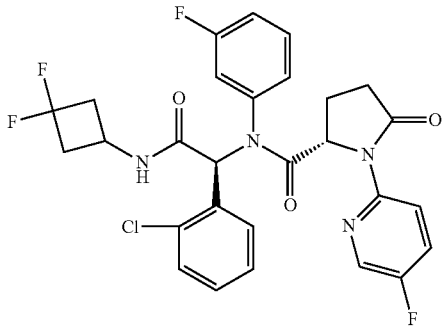

¹H NMR (400 MHz, CDCl₃): δ 8.40 (m, 1H), 8.24 (m, 1H), 7.71 (d, J=7.7 Hz, 1H), 7.49-7.30 (m, 2H), 7.28-7.21

(m, 1H), 7.12 (m, 2H), 7.04-6.88 (m, 3H), 6.67 (m, 1H), 6.42 (s, 2H), 4.90 (m, 1H), 4.27 (m, 1H), 3.07-2.76 (m, 3H), 2.58-2.29 (m, 3H). MS: 575.0 (M+1)$^+$.

Compound 12

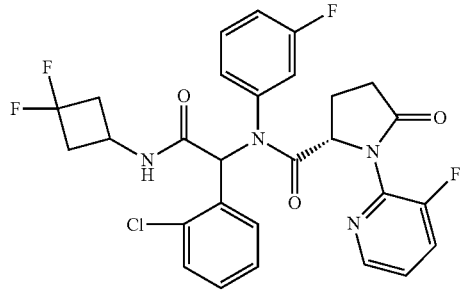

$^1$H NMR (400 MHz, CDCl$_3$): δ 8.27 (m, 1H), 7.64-7.30 (m, 3H), 7.27-6.62 (m, 7H), 6.47-6.30 (m, 1H), 6.28-6.07 (m, 1H), 5.00-4.55 (m, 1H), 4.26 (m, 1H), 3.12-2.67 (m, 3H), 2.65-2.36 (m, 3H), 2.22 (m, 2H). MS: 575.1 (M+1)$^+$.

Compound 34

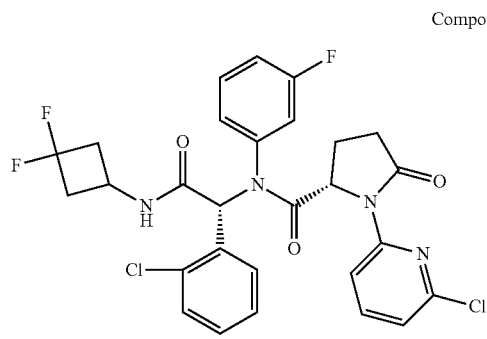

$^1$H NMR (400 MHz, CDCl$_3$): δ 8.37 (t, J=8.9 Hz, 1H), 7.63 (m, 2H), 7.49-6.84 (m, 8H), 6.44 (s, 1H), 5.94 (m, 1H), 5.07-4.74 (m, 1H), 4.25 (d, J=51.6 Hz, 1H), 3.10-2.67 (m, 3H), 2.63-1.85 (m, 5H), 1.25 (s, 1H). MS: 591.1 (M+1)$^+$.

Compound 35

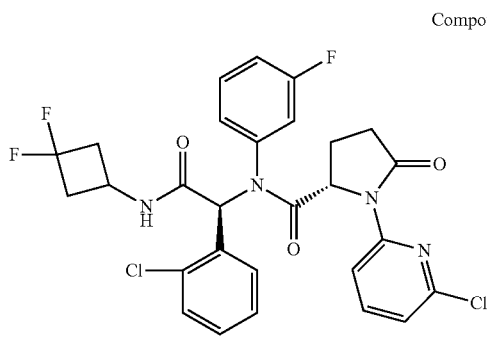

$^1$H NMR (400 MHz, DMSO-d$_6$): δ 8.38 (d, J=8.2 Hz, 1H), 7.86-7.34 (m, 4H), 7.25-6.79 (m, 6H), 6.46 (s, 1H), 5.99 (s, 1H), 4.95 (d, J=9.2 Hz, 1H), 4.34 (s, 1H), 3.12-2.70 (m, 3H), 2.63-1.87 (m, 6H). MS: 591.1 (M+1)$^+$.

Compound 48

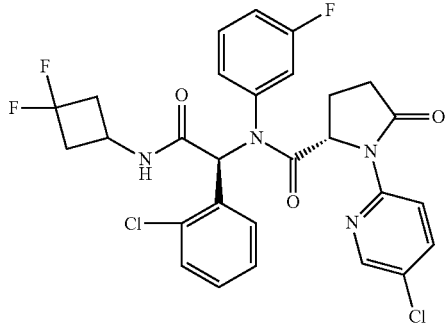

$^1$H NMR (400 MHz, CDCl$_3$): δ 8.59-8.19 (m, 2H), 7.82-7.57 (m, 2H), 7.45-7.34 (m, 2H), 7.01 (m, 4H), 6.45 (s, 1H), 5.94 (s, 1H), 4.89 (dd, J=9.3, 3.1 Hz, 1H), 4.30 (m, 1H), 3.21-2.69 (m, 3H), 2.61-1.88 (m, 5H). MS: 591.1 (M+1)$^+$.

Compound 33

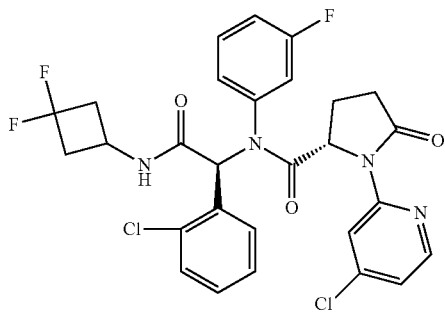

$^1$H NMR (400 MHz, CDCl$_3$): δ 8.63-8.03 (m, 2H), 7.67 (s, 1H), 7.23-6.65 (m, 8H), 6.45-5.93 (m, 2H), 4.84 (m, 1H), 4.23 (m, 1H), 3.04-2.65 (m, 4H), 2.65-1.83 (m, 5H). MS: 591.1 (M+1)$^+$.

Compound 36

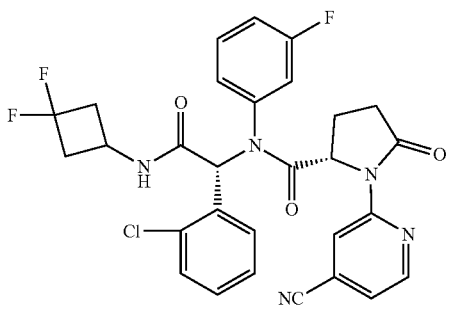

$^1$H NMR (400 MHz, CDCl$_3$): δ 8.79-8.51 (m, 2H), 7.88 (s, 1H), 7.51-7.29 (m, 2H), 7.22 (m, 2H), 7.08 (t, J=7.3 Hz, 1H), 6.99 (t, J=7.2 Hz, 1H), 6.78 (s, 1H), 6.51 (d, J=5.8 Hz, 1H), 6.28 (s, 1H), 4.79 (m, 1H), 4.14 (s, 1H), 3.02-2.66 (m, 3H), 2.55 (m, 1H), 2.33-1.99 (m, 4H). MS: 582.1 (M+1)$^+$.

Compound 37

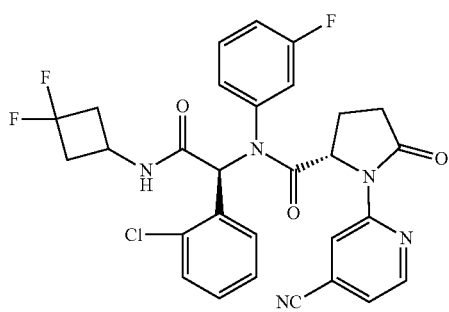

¹H NMR (400 MHz, CDCl₃): δ 8.74 (s, 1H), 8.52 (s, 1H), 7.85-7.30 (m, 3H), 7.24-6.79 (m, 5H), 6.43 (s, 1H), 6.12 (s, 1H), 4.92 (d, J=6.8 Hz, 1H), 4.34 (s, 1H), 2.90 (m, 3H), 2.64-2.46 (m, 1H), 2.46-2.11 (m, 3H), 1.97 (m, 1H). MS: 582.1 (M+1)⁺.

Compound 47

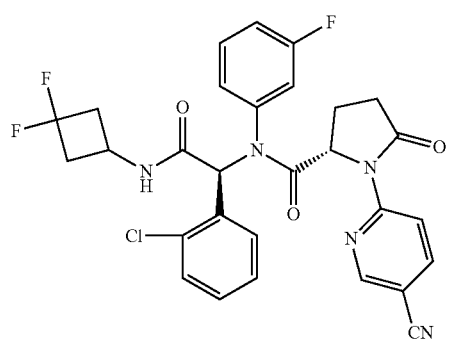

¹H NMR (400 MHz, CDCl₃): δ 8.66-8.38 (m, 2H), 7.90 (d, J=7.0 Hz, 1H), 7.68 (s, 1H), 7.37 (m, 1H), 7.25-6.80 (m, 6H), 6.44 (s, 1H), 5.97 (d, J=6.6 Hz, 1H), 4.91 (d, J=6.7 Hz, 1H), 4.32 (s, 1H), 3.30-2.78 (m, 4H), 2.41 (m, 4H), 2.02 (s, 1H). MS: 582.1 (M+1)⁺.

Compound 16

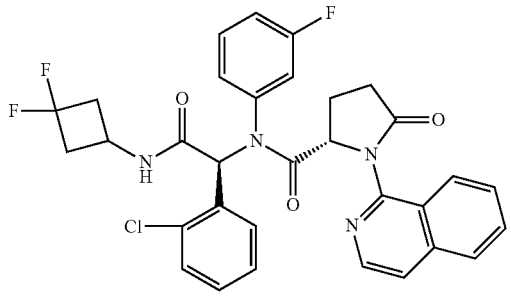

¹H NMR (400 MHz, CDCl₃): δ 8.58 (d, J=9.3 Hz, 1H), 8.11 (d, J=8.7 Hz, 1H), 7.97 (d, J=8.5 Hz, 1H), 7.86-7.59 (m, 3H), 7.48 (m, 2H), 7.18 (m, 3H), 6.97 (m, 3H), 6.38 (s, 1H), 6.11 (s, 1H), 5.20 (s, 1H), 4.30 (s, 1H), 3.09-2.77 (m, 3H), 2.67-2.44 (m, 2H), 2.36-2.21 (m, 2H), 2.10-1.92 (m, 1H). MS: 607.2 (M+1)⁺.

Compound 1

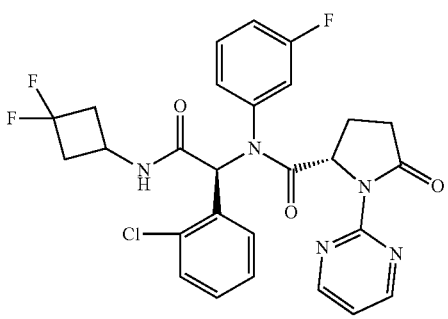

¹H NMR (400 MHz, CDCl₃): δ 8.69 (d, J=4.8 Hz, 2H), 7.71 (s, 1H), 7.31 (m, 1H), 7.18 (m, 1H), 7.13-6.77 (m, 6H), 6.46 (s, 1H), 6.22 (s, 1H), 5.00-4.62 (m, 1H), 4.35 (s, 1H), 3.19-2.71 (m, 3H), 2.69-1.83 (m, 5H). MS: 451.2 (M+1)⁺.

Compound 22

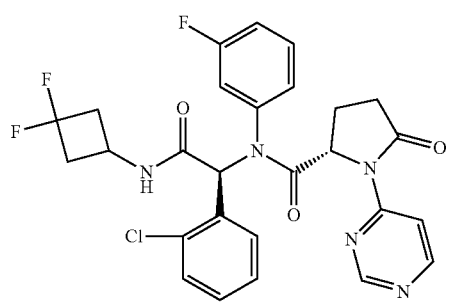

¹H NMR (400 MHz, DMSO-d₆): δ 8.15-8.01 (m, 1H), 7.62-7.52 (m, 1H), 7.31-6.69 (m, 9H), 6.24 (s, 1H), 5.65-4.66 (m, 1H), 2.60 (m, 1H), 2.20-2.05 (m, 3H), 1.76-0.83 (m, 4H). MS: 451.2 (M+1)⁺.

Compound 18

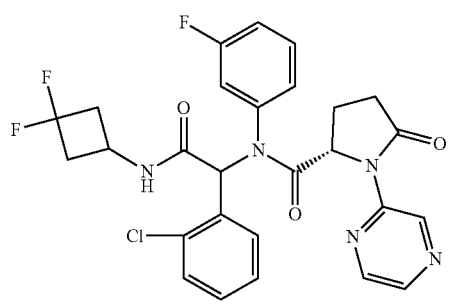

¹H NMR (400 MHz, DMSO-d₆): δ 9.70 (s, 1H), 8.48-8.26 (m, 2H), 7.72 (s, 1H), 7.46-7.31 (m, 1H), 7.28-7.15 (m, 2H), 7.13-6.89 (m, 3H), 6.55-6.14 (m, 2H), 4.82 (m, 1H), 4.26 (m, 1H), 2.90 (m, 3H), 2.64-2.40 (m, 2H), 2.34-1.99 (m, 3H). MS: 558.1 (M+1)⁺.

Compound 13

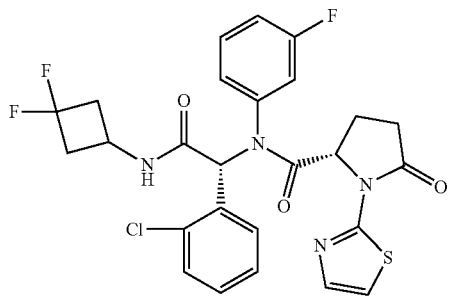

¹H NMR (400 MHz, CDCl₃): δ 7.54 (d, J=3.5 Hz, 1H), 7.45-7.29 (m, 3H), 7.28-6.95 (m, 6H), 6.44 (d, J=6.0 Hz, 1H), 6.24 (s, 1H), 4.92 (m, 1H), 4.25 (s, 1H), 3.11-2.79 (m, 3H), 2.61 (m, 1H), 2.43 (m, 1H), 2.39-2.27 (m, 2H), 2.27-2.11 (m, 1H). MS: 563.1 (M+1)⁺.

Compound 14

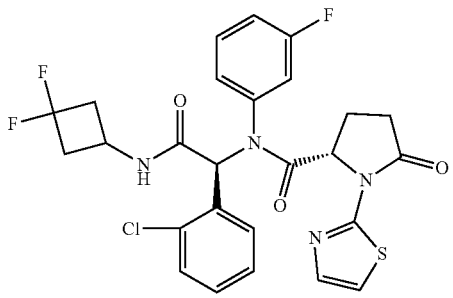

¹H NMR (400 MHz, CDCl₃): δ 7.66 (s, 1H), 7.48 (s, 1H), 7.35 (s, 1H), 7.26-6.82 (m, 8H), 6.43 (s, 1H), 6.09 (d, J=6.3 Hz, 1H), 4.98 (d, J=8.7 Hz, 1H), 4.34 (s, 1H), 3.08-2.84 (m, 2H), 2.63-2.36 (m, 4H), 2.32 (m, 1H), 2.15 (m, 1H). MS: 563.1 (M+1)⁺.

Compound 23

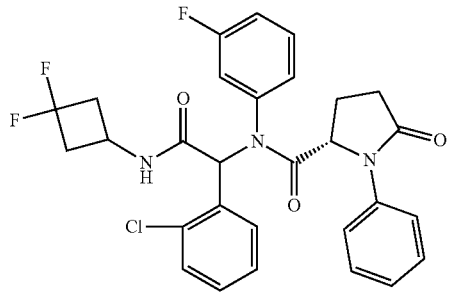

¹H NMR (400 MHz, CDCl₃): δ 7.78-7.49 (m, 2H), 7.39 (m, 4H), 7.24-6.82 (m, 4H), 6.38 (m, 3H), 5.94 (m, 1H), 4.50 (m, 1H), 4.22 (m, 1H), 3.10-2.59 (m, 3H), 2.59-1.99 (m, 6H). MS: 556.2 (M+1)⁺.

Example 3. Preparation of (S)—N—((S)-1-(2-chlorophenyl)-2-(3,3-difluorocyclobutylamino)-2-oxoethyl)-N-(3-fluorophenyl)-5-oxo-1-(thiazol-4-yl)pyrrolidine-2-carboxamide Compounds 42 and 43 were prepared according to the following scheme, using the following protocol.

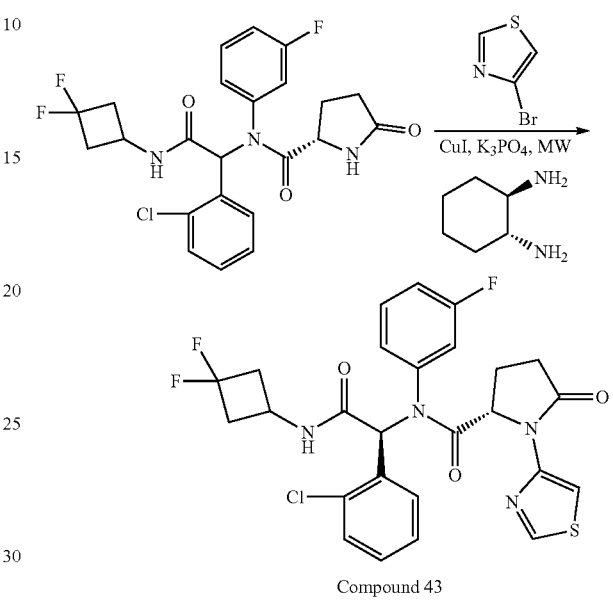

Compound 43

A mixture (2S)—N-(1-(2-chlorophenyl)-2-(3,3-difluorocyclobutylamino)-2-oxoethyl)-N-(3-fluorophenyl)-5-oxopyrrolidine-2-carboxamide (200 mg, 0.417 mmol), 4-bromothiazole (0.045 mL, 0.626 mmol, 1.5 eq), K₃PO₄ (124 mg, 0.585 mmol, 1.4 eq), CuI (8 mg, 0.1 eq) and trans-1,2-diaminocyclohexane (0.24 eq) in dioxane (2 mL) was stirred at 110° C. under microwave for 30 min. The resulting mixture was filtered through a Celite pad. The filtrate was concentrated and the residue was purified by a standard method to give the desired product.

(S)—N—((R)-1-(2-Chlorophenyl)-2-(3,3-difluorocyclobutylamino)-2-oxoethyl)-N-(3-fluorophenyl)-5-oxo-1-(thiazol-4-yl)pyrrolidine-2-carboxamide (Compound 42)

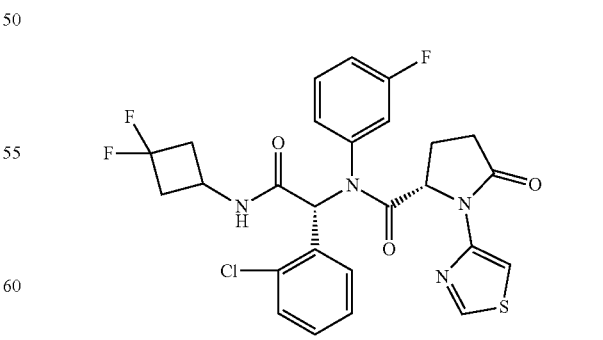

¹H NMR (400 MHz, CDCl₃): δ 8.68 (d, J=2.1 Hz, 1H), 7.65 (m, 5H), 7.30-6.90 (m, 4H), 6.47 (s, 1H), 6.23 (s, 1H), 4.88 (dd, J=9.3, 3.0 Hz, 1H), 4.20 (s, 1H), 3.17-2.63 (m, 3H), 2.58-1.99 (m, 5H). MS: 563.1 (M+1)⁺.

(S)—N—((S)-1-(2-Chlorophenyl)-2-(3,3-difluorocyclobutylamino)-2-oxoethyl)-N-(3-fluorophenyl)-5-oxo-1-(thiazol-4-yl)pyrrolidine-2-carboxamide (Compound 43)

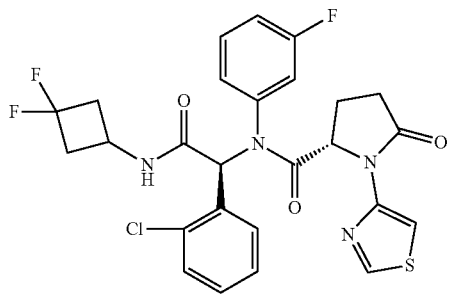 [SMILES: O=C(NC1CC(F)(F)C1)[C@H](c1ccccc1Cl)N(C(=O)[C@@H]1CCC(=O)N1c1cscn1)c1cccc(F)c1]

$^1$H NMR (400 MHz, CDCl$_3$): δ 8.60 (s, 1H), 8.06-7.56 (m, 2H), 7.35 (s, 1H), 7.22-6.79 (m, 5H), 6.42 (s, 1H), 6.13 (s, 1H), 4.96 (d, J=7.8 Hz, 1H), 4.25 (m, 1H), 3.14-2.70 (m, 4H), 2.63-2.21 (m, 4H). MS: 563.1 (M+1)$^+$.

Example 4. Preparation of (S)—N—((S)-1-(2-chlorophenyl)-2-(3,3-difluorocyclobutylamino)-2-oxoethyl)-N-(3-fluorophenyl)-5-oxo-1-(pyridin-2-ylmethyl)pyrrolidine-2-carboxamide Compound 44 was prepared according to the following scheme, using the following protocol.

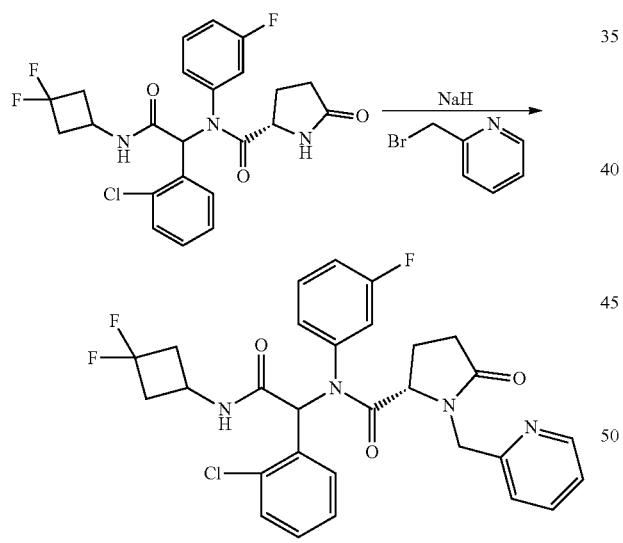

Compound 44.

To a solution of (2S)—N-(1-(2-chlorophenyl)-2-(3,3-difluorocyclobutyl-amino)-2-oxoethyl)-N-(3-fluorophenyl)-5-oxopyrrolidine-2-carboxamide (200 mg, 0.42 mmol) in dry DMF (20 mL) was added NaH (20 mg, 0.84 mmol) at 0° C. The mixture was stirred at this 0° C. for 0.5 h followed by addition of 2-(bromomethyl)pyridine (106 mg, 0.42 mmol). The mixture was then allowed warm to room temperature and stirred overnight. The resulting mixture was slowly added dropwise to 100 mL of water, and then extracted with EtOAc (3×20 mL). The combined organic layers were washed with saturated aq. LiCl, dried over anhydrous Na$_2$SO$_4$ and concentrated in vacuo. The residue was purified by a standard method to afford the desired product. $^1$H NMR (400 MHz, CDCl$_3$): δ 8.51 (s, 1H), 7.88-7.37 (m, 3H), 7.19-5.95 (m, 10H), 5.14 (m, 1H), 4.34 (m, 1H), 4.10 (m, 2H), 3.00 (m, 2H), 2.81-1.57 (m, 6H). MS: 571.2 (M+1)$^+$.

Example 5. Preparation of (S)—N—((S)-1-(2-chlorophenyl)-2-(3,3-difluorocyclobutylamino)-2-oxoethyl)-N-(3-fluorophenyl)-3-hydroxy-2-(pyrimidin-2-ylamino)propanamide Compound 9 was prepared according to the following scheme, using the following protocol.

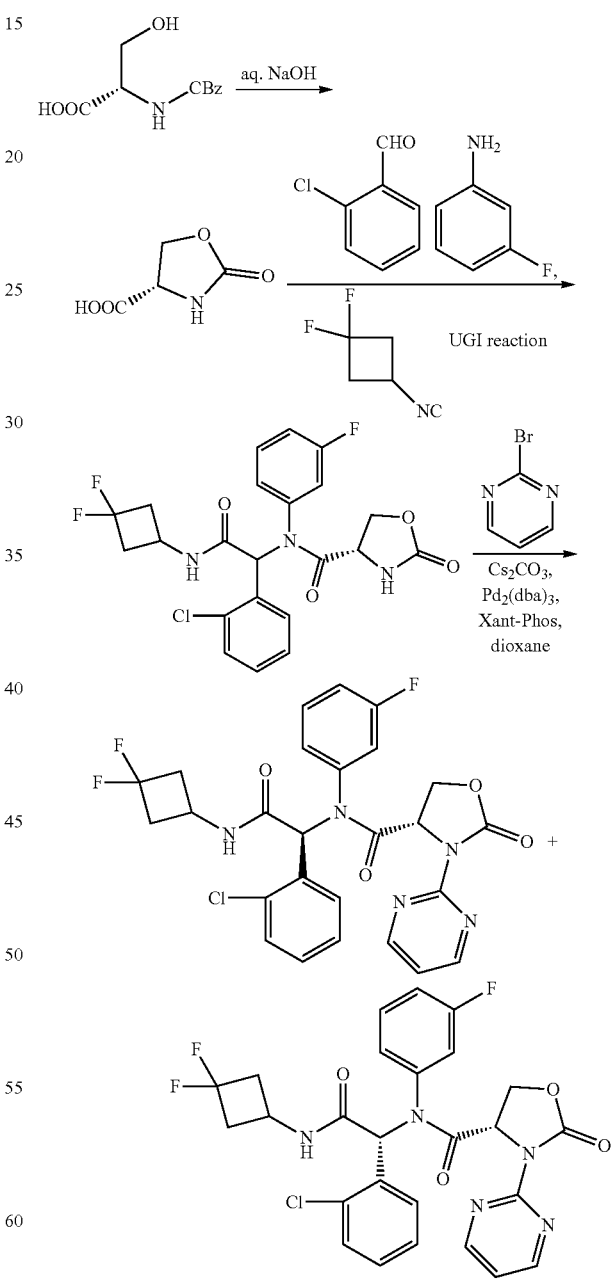

Step A: (S)-2-Oxooxazolidine-4-carboxylic Acid

To a solution of NaOH (0.8 g, 20 mmol) in water (4 mL) was added (S)-2-(benzyloxycarbonylamino)-3-hydroxypropanoic acid (1 g, 4.2 mmol) portionwise at 0° C. over 3 min. The resulting solution was warmed to r.t and stirred for 2 h. After cooling to 0° C., the solution was adjusted to pH=1-2 with 2 N HCl. The mixture was extracted with EtOAc (4×10 mL). The combined organic layers were dried over anhydrous $Na_2SO_4$ and concentrated in vacuo to give the desired product as a white solid. $^1$H NMR (400 MHz, DMSO-$d_6$): δ 13.93-12.30 (m, 1H), 8.15 (s, 1H), 4.49 (t, J=8.6 Hz, 1H), 4.32 (m, 2H); MS: 130.0 (M−1)$^-$.

Step B: (4S)—N-(1-(2-Chlorophenyl)-2-(3,3-difluorocyclobutylamino)-2-oxoethyl)-N-(3-fluoro-phenyl)-2-oxooxazolidine-4-carboxamide 2-Chlorobenzaldehyde (160 mg, 1.14 mmol), 3-fluoroaniline (127 mg, 1.14 mmol), (S)-2-oxooxazolidine-4-carboxylic acid (150 mg, 1.14 mmol) and 1,1-difluoro-3-isocyanocyclobutane (181 mg, 90% of purity, 1.37 mmol) were used in the UGI reaction to give the desired product as a white solid. $^1$H NMR (400 MHz, CDCl$_3$): δ 8.15-8.01 (m, 1H), 7.62-7.52 (m, 1H), 7.31-6.69 (m, 9H), 6.24 (s, 1H), 5.65-4.66 (m, 4H), 2.60 (m, 1H), 2.20-2.05 (m, 3H), 1.76-1.51 (m, 5H), 1.29-0.83 (m, 5H); MS: 482.1 (M+1)+.

Step C: (S)—N—((R)-1-(2-Chlorophenyl)-2-(3,3-difluorocyclobutylamino)-2-oxoethyl)-N-(3-fluorophenyl)-2-oxo-3-(pyrimidin-2-yl)oxazolidine-4-carboxamide and (S)—N—((S)-1-(2-chlorophenyl)-2-(3,3-difluorocyclobutylamino)-2-oxoethyl)-N-(3-fluorophenyl)-2-oxo-3-(pyrimidin-2-yl)oxazolidine-4-carboxamide A mixture of (4S)—N-(1-(2-chlorophenyl)-2-(3,3-difluorocyclo-butylamino)-2-oxoethyl)-N-(3-fluorophenyl)-2-oxooxazolidine-4-carboxamide (350 mg, 0.73 mmol), 2-bromopyrimidine (150 mg, 0.94 mmol), Cs$_2$CO$_3$ (500 mg, 1.52 mmol), Pd$_2$(dba)$_3$ (66 mg, 0.07 mmol) and Xant-Phos (42 mg, 0.07 mmol) in 1,4-dioxane (15 mL) was stirred under N$_2$ at 80° C. for 18 h and then filtered through a Celite pad. The filtrate was concentrated in vacuo and the residue was purified a standard method to give (S)—N—((R)-1-(2-chlorophenyl)-2-(3,3-difluorocyclobutylamino)-2-oxoethyl)-N-(3-fluorophenyl)-2-oxo-3-(pyrimidin-2-yl)oxazolidine-4-carboxamide (8). $^1$H NMR (400 MHz, CDCl$_3$): δ 8.73 (d, J=4.8 Hz, 2H), 7.95 (s, 0.8H), 7.74 (s, 0.2H), 7.41 (d, J=7.5 Hz, 1.6H), 7.24 (t, J=7.2 Hz, 1H), 7.17-6.94 (m, 4.3H), 6.73 (d, J=6.7 Hz, 1H), 6.48 (d, J=73.8 Hz, 2H), 4.93 (s, 1H), 4.41 (dd, J=8.6, 4.8 Hz, 1H), 4.29 (t, J=8.6 Hz, 1H), 4.14 (m, 1H), 2.80 (m, 2H), 2.21 (s, 1H), 2.18-2.07 (m, 1H); MS: 560.1 (M+1)$^+$, and (S)—N—((S)-1-(2-chloro-phenyl)-2-(3,3-difluorocyclo-butylamino)-2-oxoethyl)-N-(3-fluorophenyl)-2-oxo-3-(pyrimidin-2-yl)oxazolidine-4-carboxamide (9). $^1$H NMR (400 MHz, CDCl$_3$): δ 8.68 (d, J=4.8 Hz, 2H), 7.65 (s, 1H), 7.30 (s, 1H), 7.18 (s, 1H), 7.13-6.86 (m, 5H), 6.50 (s, 1H), 6.38 (m, 1H), 5.00 (m, 1H), 4.43 (dd, J=8.7, 4.8 Hz, 1H), 4.32 (m, 1H), 4.20 (m, 1H), 2.99 (m, 2H), 2.50 (m, 2H). MS: 560.1 (M+1)$^+$.

Example 6. Preparation of (S)—N—((S)-1-(2-chlorophenyl)-2-((3,3-difluorocyclobutyl)-amino)-2-oxoethyl)-N-(3-fluorophenyl)-6-oxo-1-(pyrimidin-2-yl)piperidine-2-carboxamide Compounds 19 and 20 were prepared according to the following scheme, using the following protocol.

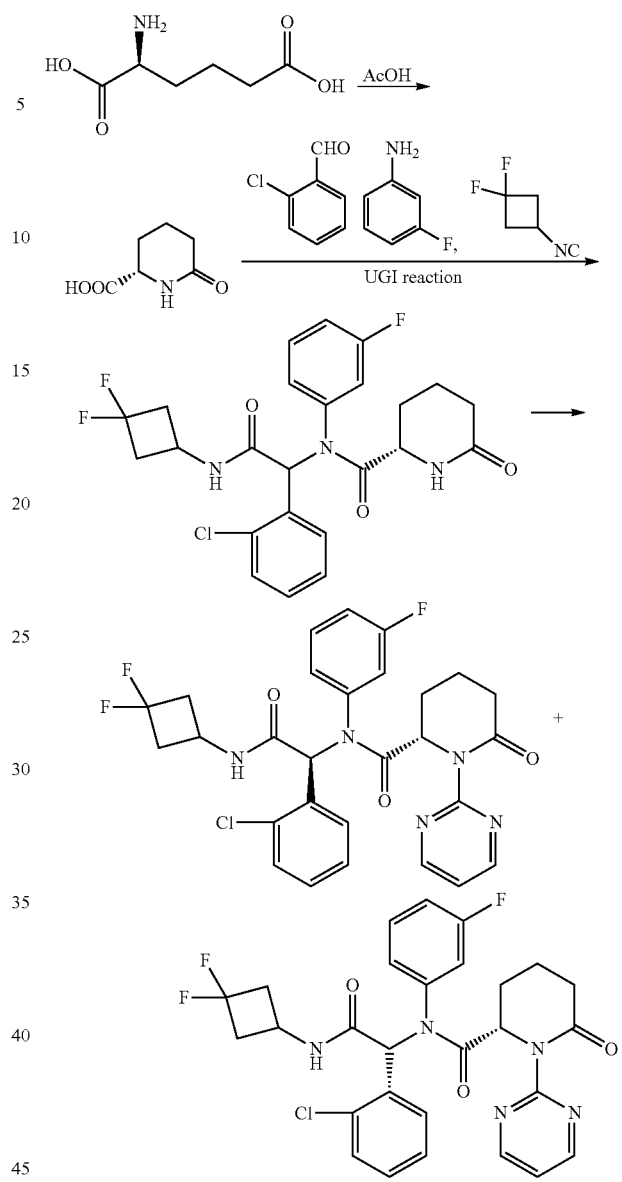

Step A. (S)-6-Oxopiperidine-2-carboxylic Acid

A solution of (S)-2-aminohexanedioic acid (470 mg, 2.9 mmol) in 20% AcOH (5 mL) was stirred at 110° C. overnight. The solvent was removed in vacuo and the residue was dissolved in EtOH (10 mL). The unreacted amino acid was precipitated and filtered off. The filtrate was concentrated to give the crude desired product which was used directly in the next step. MS: 142.1 (M−1)$^-$.

Step B. (S)—N-(1-(2-Chlorophenyl)-2-((3,3-difluorocyclobutyl)amino)-2-oxoethyl)-N-(3-fluorophenyl)-6-oxopiperidine-2-carboxamide 3-Fluoroaniline (217 mg, 1.96 mmol), 2-chlorobenzaldehyde (274 mg, 1.96 mmol), (S)-6-oxopiperidine-2-carboxylic acid (280 mg, 1.96 mmol) and 1,1-difluoro-3-isocyanocyclobutane (280 mg, 1.96 mmol) were used in the UGI reaction to give the desired product. MS: 494.1 (M+1)$^+$.

Step C. (S)—N—((S)-1-(2-Chlorophenyl)-2-((3,3-difluorocyclobutyl)amino)-2-oxoethyl)-N-(3-fluorophenyl)-6-oxo-1-(pyrimidin-2-yl)piperidine-2-carboxamide and (S)—N—((R)-1-(2-chloro-phenyl)-2-((3,3-difluorocyclobutyl)amino)-2-oxoethyl)-N-(3-fluorophenyl)-6-oxo-1-(pyrimidin-2-yl)piperidine-2-carboxamide A mixture consisting of (1R)—N-(1-(2-chlorophenyl)-2-((3,3-difluorocyclobutyl)amino)-2-oxoethyl)-N-(3-fluorophenyl)-3-oxo-2-(pyrimidin-2-yl)cyclohexanecarboxamide (250 mg, 0.51 mmol), 2-bromopyrimidine (121 mg, 0.76 mmol), $Cs_2CO_3$ (331 mg, 1.01 mmol), $Pd_2(dba)_3$ (46 mg, 0.05 mmol) and Xant-Phos (29 mg, 0.04 mmol) in 1,4-dioxane (15 mL) was stirred under $N_2$ at 80° C. overnight and then filtered. The filtrate was concentrated in vacuo and the residue was purified by a standard method to give the desired products.

(S)—N—((S)-1-(2-Chlorophenyl)-2-((3,3-difluorocyclobutyl)amino)-2-oxoethyl)-N-(3-fluoro-phenyl)-6-oxo-1-(pyrimidin-2-yl)piperidine-2-carboxamide (Compound 19)

$^1$H NMR (400 MHz, $CDCl_3$): δ 8.73 (m, 2H), 7.70 (s, 1H), 7.26-6.95 (m, 6H), 6.87 (t, J=7.2 Hz, 1H), 6.53 (s, 1H), 6.33 (s, 1H), 4.77 (d, J=5.3 Hz, 1H), 4.33 (s, 1H), 3.01 (d, J=5.5 Hz, 2H), 2.85-2.28 (m, 4H), 2.05 (m, 2H), 1.81 (s, 2H). MS: 571.1 $(M+1)^+$.

(S)—N—((R)-1-(2-Chloro-phenyl)-2-((3,3-difluorocyclobutyl)amino)-2-oxoethyl)-N-(3-fluoro-phenyl)-6-oxo-1-(pyrimidin-2-yl)piperidine-2-carboxamide (Compound 20)

$^1$H NMR (400 MHz, $CDCl_3$): δ 8.74 (d, J=4.8 Hz, 2H), 7.99 (m, 1H), 7.56-7.32 (m, 1H), 7.27-6.85 (m, 6H), 6.72 (s, 1H), 6.51 (m, 1H), 4.67-4.48 (m, 1H), 4.34-4.01 (m, 1H), 2.95-2.60 (m, 2H), 2.59-2.40 (m, 1H), 2.40-2.19 (m, 2H), 2.15-2.00 (m, 2H), 1.97-1.59 (m, 4H). MS: 571.1 $(M+1)^+$.

Example 7. Preparation of (S)—N—((S)-1-(2-chlorophenyl)-2-((3,3-difluorocyclobutyl)amino)-2-oxoethyl)-N-(3-fluorophenyl)-5-oxo-4-(pyrimidin-2-yl)morpholine-3-carboxamide Compound 30 was prepared according to the following scheme, using the following protocol.

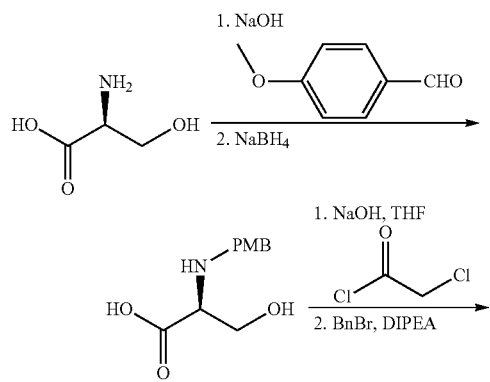

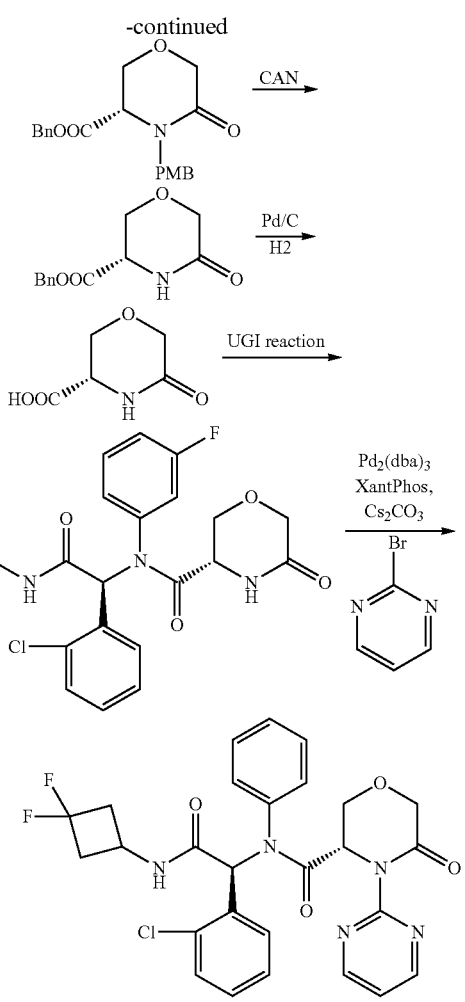

Step A:
(S)-3-Hydroxy-2-(4-methoxybenzylamino)propanoic Acid (S)-2-amino-3-hydroxypropanoic acid (8.4 g, 80 mmol) was dissolved in a solution of NaOH (3.2 g, 80 mmol) in $H_2O$ (40 mL). After cooling to 10° C., 4-methoxybenzaldehyde (21.7 g, 160 mmol) was added dropwise over 10 min. The mixture was stirred at room temperature for 30 min and then cooled to 0° C. $NaBH_4$ (1.67 g, 44 mmol) was added portionwise and the resulting mixture was warmed slowly to r.t and stirred for 2 h. The mixture was washed with $Et_2O$ (2×50 mL). The aqueous phase was adjusted to pH 4.5 with 2 N HCl at 0° C. The precipitate was filtered, washed with petroleum ether (20 mL) and dried in vacuo to give the desired product as a white solid. MS: 226.1 $(M+1)^+$.

Step B: (S)-Benzyl 4-(4-methoxybenzyl)-5-oxomorpholine-3-carboxylate (S)-3-Hydroxy-2-((4-methoxybenzyl)amino)propanoic acid (5.0 g, 22 mmol) was dissolved in a solution of NaOH (1.15 g, 29 mmol) in $H_2O$ (60 mL). After cooling to 0° C., 2-chloroacetyl chloride (3.6 mL, 44 mmol) was added dropwise followed by aq. NaOH (30% wt) to keep pH=13.

After stirring for another 4 h, the reaction was cooled to 0° C. and acidified with 2 N HCl to adjust pH=2-3. The resulting mixture was extracted with EtOAc (2×30 mL). The combined organic layers were dried over anhydrous $Na_2SO_4$ and concentrated. The residue was dissolved in acetone (150 mL) and then treated with BnBr (9.7 g, 51 mmol) and DIPEA (19 mL, 111 mmol). The reaction mixture was stirred for 24 h at room temperature and concentrated in vacuo. The residue was purified by column chromatography to afford the desired product as a white solid. MS: 356.1 $(M+1)^+$.

Step C: (S)-Benzyl 5-oxomorpholine-3-carboxylate

To a solution of (S)-benzyl 4-(4-methoxybenzyl)-5-oxomorpholine-3-carboxylate (200 mg, 0.56 mmol) in $CH_3CN$ (5 mL) and $H_2O$ (5 mL) was added CAN (ceric ammonium nitrate) (1.5 g, 2.8 mmol) at 0° C. The resulting mixture was stirred at 0° C. for 1 h. DIPEA was added at 0° C. to adjust the pH to 6-7 and the mixture was concentrated in vacuo. The residue was purified by column chromatography to afford the desired product as a white solid. MS: 236.1 $(M+1)^+$.

Step D: (S)-5-Oxomorpholine-3-carboxylic Acid

To a mixture of (S)-benzyl 5-oxomorpholine-3-carboxylate (160 mg, 0.7 mmol) in MeOH (8 mL) was added 10% Pd/C (about 5 mg). The reaction was stirred under an atmosphere of hydrogen for 30 min at room temperature. The reaction mixture was filtered through a Celite pad and concentrated in vacuo to afford the desired product as a white solid. MS: 146.1 $(M+1)^+$.

Step E: (S)—N—((S)-1-(2-Chlorophenyl)-2-((3,3-difluorocyclobutyl)amino)-2-oxoethyl)-N-(3-fluorophenyl)-5-oxomorpholine-3-carboxamide 3-Chlorobenzaldehyde (104 mg, 0.74 mmol), 3-fluoroaniline (83 mg, 0.74 mmol), (S)-5-oxomorpholine-3-carboxylic acid (108 mg, 0.74 mmol) and 1,1-difluoro-3-isocyanocyclobutane (248 mg, 1.48 mmol) were used in the UGI reaction to afford the desired product. MS: 496.1 $(M+1)^+$.

Step F: Compound 30

A mixture of (S)—N—((S)-1-(2-chlorophenyl)-2-((3,3-difluoro-cyclobutyl)amino)-2-oxoethyl)-N-(3-fluorophenyl)-5-oxomorpholine-3-carboxamide (100 mg, 0.2 mmol), 2-bromopyrimidine (36 mg, 0.22 mmol), $Pd_2(dba)_3$ (28 mg, 0.03 mmol), XantPhos (16 mg, 0.03 mmol) and $Cs_2CO_3$ (160 mg, 0.5 mmol) in 1,4-dioxane (4 mL) was stirred at 100° C. for 3.5 h under $N_2$. The reaction mixture was then cooled to room temperature and filtered. The solid was washed with DCM (2×20 mL). The filtrate was evaporated and the residue was purified by a standard method to afford the desired product. $^1$H NMR (400 MHz, $CDCl_3$): δ 8.77 (m, 2H), 7.85 (m, 1H), 7.41 (s, 1H), 7.28-7.21 (m, 1H), 7.21-7.10 (m, 2H), 7.09-6.90 (m, 3H), 6.87 (m, 1H), 6.68-6.33 (m, 2H), 4.80 (m, 1H), 4.43-4.22 (m, 2H), 4.13 (m, 2H), 3.94 (m, 1H), 2.99 (m, 1H), 2.86 (m, 1H), 2.63-2.26 (m, 2H). MS: 474.1 $(M+1)^+$.

Example 8

The following analogs were synthesized via the procedure set forth above, using the appropriate aldehyde, amine, carboxylic acid, isocyanide and halo-substituted aromatic ring or heterocyclic (heteroaromatic) ring using the reagents and solvents set forth above, and purified via standard methods.

(2S)—N-(1-(2-Chlorophenyl)-2-((3,3-difluorocyclopentyl)amino)-2-oxoethyl)-N-(3-fluoro phenyl)-5-oxo-1-(pyrimidin-2-yl)pyrrolidine-2-carboxamide (Racemic)—Compound 73

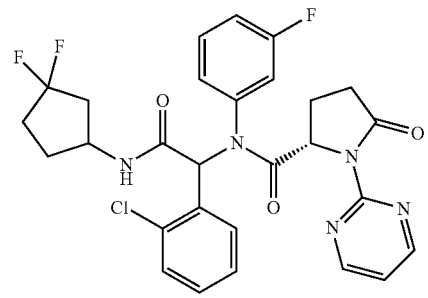

$^1$H NMR (400 MHz, $CDCl_3$): δ 8.71 (d, J=4.8 Hz, 2H), 7.72 (s, 1H), 7.37 (s, 1H), 7.18 (s, 1H), 7.11-6.85 (m, 5H), 6.47 (s, 1H), 5.70 (d, J=7.3 Hz, 1H), 4.86 (d, J=7.0 Hz, 1H), 4.53 (d, J=6.3 Hz, 1H), 3.51 (s, 1H), 2.95-2.88 (m, 1H), 2.64-2.47 (m, 2H), 2.40-1.65 (m, 8H). MS: 572.2 $(M+1)^+$.

(S)—N—((S)-1-(2-Chlorophenyl)-2-(3,3-difluorocyclobutylamino)-2-oxoethyl)-1-(4-cyanopyridin-2-yl)-N-(3-fluorophenyl)-5-oxopyrrolidine-2-carboxamide (Single Enantiomer)—Compound 64

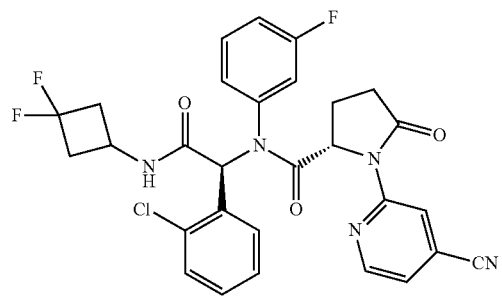 [SMILES: N#Cc1ccnc(N2C(=O)CC[C@H]2C(=O)N(c2cccc(F)c2)[C@H](C(=O)NC2CC(F)(F)C2)c2ccccc2Cl)c1]

$^1$H NMR (400 MHz, $CDCl_3$): δ 8.74 (s, 1H), 8.52 (s, 1H), 7.72 (d, J=7.1 Hz, 1H), 7.43-7.33 (m, 1H), 7.25-7.17 (m, 1H), 7.13-6.81 (m, 4H), 6.43 (s, 1H), 6.12 (s, 1H), 4.92 (d, J=6.8 Hz, 1H), 4.37-4.28 (m, 1H), 3.10-2.82 (m, 3H), 2.59-2.49 (m, 2H), 2.42-2.36 (m, 1H), 2.31-2.22 (m, 1H), 2.06-1.88 (m, 2H). MS: 582.1 $(M+1)^+$.

(S)-1-(4-Cyanopyridin-2-yl)-N—((S)-2-((3,3-difluorocyclobutyl)amino)-2-oxo-1-phenylethyl)-N-(3-fluorophenyl)-5-oxopyrrolidine-2-carboxamide (Single Enantiomer)—Compound 138

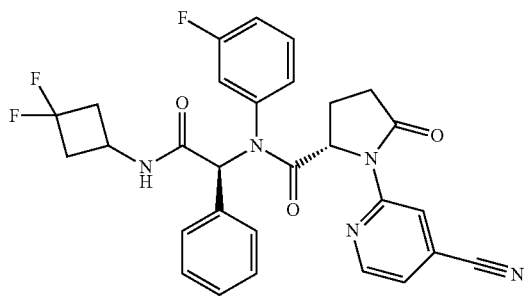 [SMILES: N#Cc1ccnc(N2C(=O)CC[C@H]2C(=O)N(c2cccc(F)c2)[C@H](C(=O)NC2CC(F)(F)C2)c2ccccc2)c1]

¹H NMR (400 MHz, CDCl₃): δ 8.78 (s, 1H), 8.44 (d, J=4.9 Hz, 1H), 7.65 (s, 1H), 7.39-7.15 (m, 6H), 7.14-6.92 (m, 4H), 6.65 (m, 1H), 6.16 (s, 1H), 5.82 (s, 1H), 4.86 (d, J=6.8 Hz, 1H), 4.31 (s, 1H), 3.15-2.77 (m, 3H), 2.68-1.91 (m, 5H). MS: 548.2 (M+1)⁺.

(S)-1-(4-Cyanopyridin-2-yl)-N—((S)-2-((3,3-difluorocyclobutyl)amino)-1-(2-fluorophenyl)-2-oxoethyl)-N-(3-fluorophenyl)-5-oxopyrrolidine-2-carboxamide (Single Enantiomer)—Compound 149

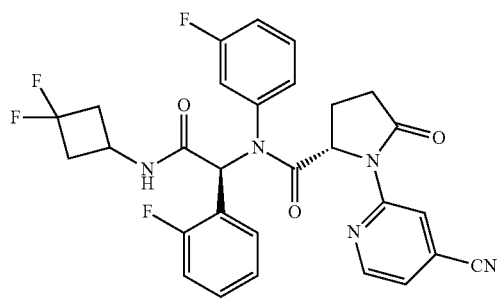 [SMILES: N#Cc1ccnc(N2C(=O)CC[C@H]2C(=O)N(c2cccc(F)c2)[C@H](C(=O)NC2CC(F)(F)C2)c2ccccc2F)c1]

¹H NMR (400 MHz, CDCl₃): δ 8.74 (m, 1H), 8.50 (d, J=4.2 Hz, 1H), 7.65 (s, 1H), 7.45-7.14 (m, 4H), 7.13-6.69 (m, 5H), 6.25 (m, 2H), 4.88 (dd, J=9.2, 3.1 Hz, 1H), 4.33 (s, 1H), 3.21-2.72 (m, 3H), 2.65-1.88 (m, 5H). MS: 566.2 (M+1)⁺.

(S)—N—((S)-1-(2-Chlorophenyl)-2-((3,3-difluorocyclobutyl)amino)-2-oxoethyl)-1-(4-cyanopyrimidin-2-yl)-N-(3-fluorophenyl)-5-oxopyrrolidine-2-carboxamide (Single Enantiomer)—Compound 68

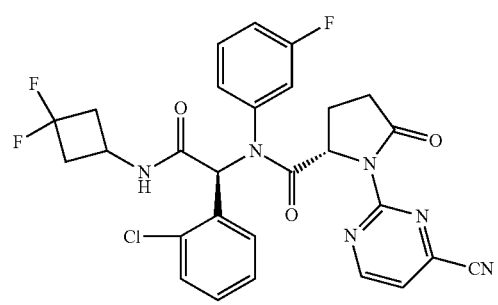 [SMILES: N#Cc1ccnc(N2C(=O)CC[C@H]2C(=O)N(c2cccc(F)c2)[C@H](C(=O)NC2CC(F)(F)C2)c2ccccc2Cl)n1]

¹H NMR (400 MHz, CDCl₃): δ 8.95 (d, J=4.7 Hz, 1H), 7.68 (s, 1H), 7.34 (d, J=4.6 Hz, 2H), 7.16 (s, 1H), 7.04 (d, J=3.6 Hz, 3H), 6.92 (s, 2H), 6.51 (s, 1H), 5.92 (s, 1H), 4.81 (d, J=9.5 Hz, 1H), 4.33 (s, 1H), 2.91 (m, 3H), 2.64-2.26 (m, 4H), 2.01 (s, 1H). MS: 583.1 (M+1)⁺.

(S)—N—((S)-1-(2-Chlorophenyl)-2-((4,4-difluorocyclohexyl)amino)-2-oxoethyl)-1-(4-cyanopyrimidin-2-yl)-N-(3-fluorophenyl)-5-oxopyrrolidine-2-carboxamide (Single Enantiomer)—Compound 85

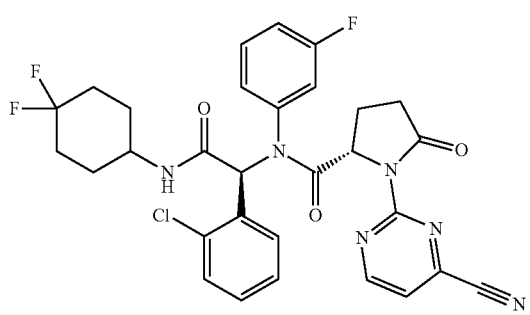 [SMILES: N#Cc1ccnc(N2C(=O)CC[C@H]2C(=O)N(c2cccc(F)c2)[C@H](C(=O)NC2CCC(F)(F)CC2)c2ccccc2Cl)n1]

¹H NMR (400 MHz, CDCl₃): δ 8.98 (d, J=4.7 Hz, 1H), 7.74 (s, 1H), 7.38 (dd, J=11.2, 5.7 Hz, 2H), 7.06 (m, 5H), 6.52 (s, 1H), 5.47 (d, J=7.7 Hz, 1H), 4.85 (d, J=9.2 Hz, 1H), 3.99 (s, 1H), 2.93 (dd, J=18.6, 8.9 Hz, 1H), 2.62 (d, J=9.5 Hz, 1H), 2.36 (s, 1H), 1.97 (m, 7H), 1.57-1.38 (m, 2H). MS: 611.2 (M+1)⁺.

(S)—N—((S)-1-(2-Chlorophenyl)-2-((3,3-difluorocyclobutyl)amino)-2-oxoethyl)-N-(3,5-difluoro-phenyl)-5-oxo-1-(pyrimidin-2-yl)pyrrolidine-2-carboxamide (Single Enantiomer)—Compound 70

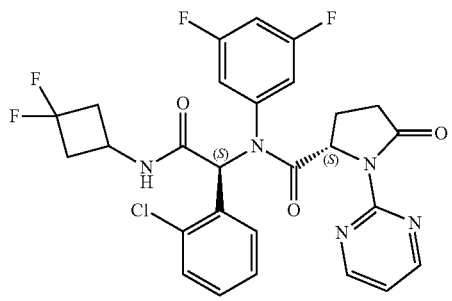

¹H NMR (400 MHz, CDCl₃): δ 8.70 (d, J=4.8 Hz, 2H), 7.60 (s, 1H), 7.37 (d, J=8.0 Hz, 1H), 7.26-7.19 (m, 1H), 7.13-7.04 (m, 2H), 7.03-6.97 (m, 1H), 6.86 (s, 1H), 6.69 (dd, J=9.8, 7.6 Hz, 1H), 6.46 (s, 1H), 6.07 (d, J=6.7 Hz, 1H), 4.87 (dd, J=9.1, 3.1 Hz, 1H), 4.36 (s, 1H), 3.11-2.83 (m, 3H), 2.64-2.34 (m, 3H), 2.21 (m, 1H), 2.10-1.97 (m, 1H). MS: 576.1 (M+1)⁺.

(S)—N—((S)-1-(2-Chlorophenyl)-2-((3,3-difluoro-cyclobutyl)amino)-2-oxoethyl)-1-(4-cyanopyridin-2-yl)-N-(3,5-difluorophenyl)-5-oxopyrrolidine-2-carboxamide (Single Enantiomer)—Compound 71

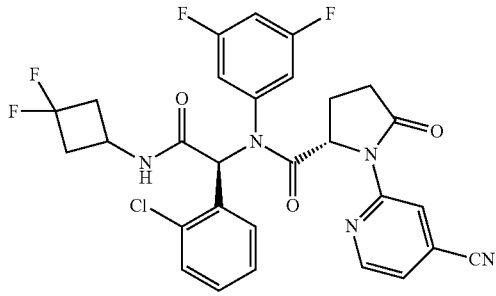 [SMILES: N#Cc1ccnc(N2C(=O)CC[C@H]2C(=O)N(c2cc(F)cc(F)c2)[C@H](C(=O)NC2CC(F)(F)C2)c2ccccc2Cl)c1]

¹H NMR (400 MHz, CDCl₃): δ 8.73 (d, J=7.1 Hz, 1H), 8.60-8.46 (m, 1H), 7.56 (d, J=7.7 Hz, 1H), 7.38-7.32 (m, 1H), 7.31-7.27 (m, 1H), 7.26-7.18 (m, 1H), 7.14-7.00 (m, 1H), 6.96 (m, 1H), 6.85 (s, 1H), 6.69 (m, 1H), 6.40 (s, 1H), 6.02 (d, J=6.6 Hz, 1H), 4.98-4.74 (m, 1H), 4.39-4.10 (m, 1H), 3.11-2.67 (m, 3H), 2.64-1.95 (m, 5H). MS: 600.1 (M+1)⁺.

(S)—N—((S)-1-(2-Chlorophenyl)-2-((3,3-difluoro-cyclobutyl)amino)-2-oxoethyl)-1-(4-cyanopyrimi-din-2-yl)-N-(3,5-difluorophenyl)-5-oxopyrrolidine-2-carboxamide (Single Enantiomer)—Compound 86

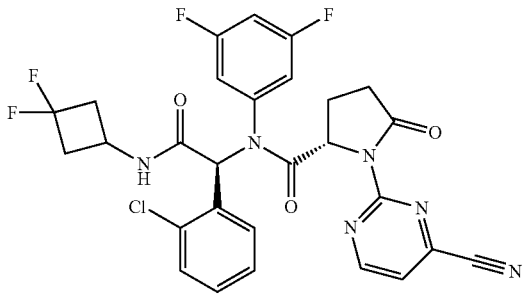 [SMILES: N#Cc1ccnc(N2C(=O)CC[C@H]2C(=O)N(c2cc(F)cc(F)c2)[C@H](C(=O)NC2CC(F)(F)C2)c2ccccc2Cl)n1]

¹H NMR (400 MHz, CDCl₃): δ 8.98 (d, J=4.8 Hz, 1H), 7.56 (s, 1H), 7.40 (m, 2H), 7.23 (t, J=7.0 Hz, 1H), 7.08 (t, J=7.6 Hz, 1H), 7.01-6.84 (m, 2H), 6.71 (t, J=8.6 Hz, 1H), 6.51 (s, 1H), 6.00 (d, J=6.7 Hz, 1H), 4.85 (dd, J=9.3, 2.7 Hz, 1H), 4.36 (s, 1H), 3.15-2.80 (m, 3H), 2.67-2.26 (m, 4H), 2.08 (dt, J=9.7, 8.1 Hz, 1H). MS: 601 (M+1)⁺.

(S)—N—((S)-1-(2-Chlorophenyl)-2-(3,3-difluorocyclobutylamino)-2-oxoethyl)-1-(4-cyanopyridin-2-yl)-5-oxo-N-(3-sulfamoylphenyl)pyrrolidine-2-carboxamide (Single Enantiomer)—Compound 53

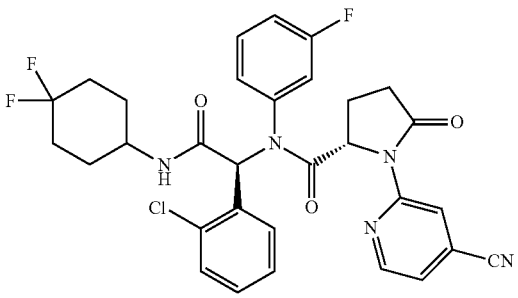 [SMILES: N#Cc1ccnc(N2C(=O)CC[C@H]2C(=O)N(c2cccc(F)c2)[C@H](C(=O)NC2CCC(F)(F)CC2)c2ccccc2Cl)c1]

¹H NMR (400 MHz, CDCl₃): δ 8.74 (s, 1H), 8.50 (s, 1H), 7.73 (d, J=7.5 Hz, 1H), 7.33 (d, J=9.3 Hz, 1H), 7.25-6.80 (m, 6H), 6.40 (s, 1H), 5.61 (d, J=6.9 Hz, 1H), 4.91 (d, J=8.0 Hz, 1H), 3.97 (s, 1H), 2.99-2.79 (m, 1H), 2.55 (dd, J=13.7, 9.9 Hz, 1H), 2.25 (t, J=11.3 Hz, 1H), 2.03-1.74 (m, 5H), 1.56-1.36 (m, 2H). MS: 610.2 (M+1)⁺.

(2S)—N-(1-(2-Chlorophenyl)-2-(4,4-difluorocyclo-hexylamino)-2-oxoethyl)-1-(4-cyanopyridin-2-yl)-N-(3,5-difluorophenyl)-5-oxopyrrolidine-2-carboxamide (Single Enantiomer)—Compound 81

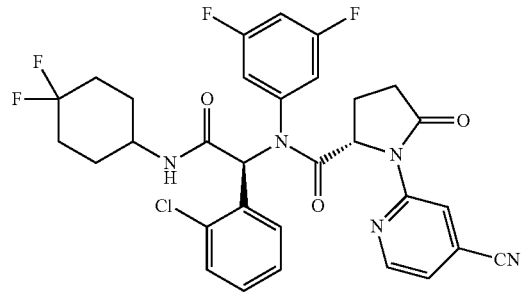 [SMILES: N#Cc1ccnc(N2C(=O)CC[C@H]2C(=O)N(c2cc(F)cc(F)c2)[C@H](C(=O)NC2CCC(F)(F)CC2)c2ccccc2Cl)c1]

¹H NMR (400 MHz, CDCl₃): δ 8.75 (s, 1H), 8.51 (d, J=5.0 Hz, 1H), 7.62 (d, J=9.0 Hz, 1H), 7.37 (d, J=7.9 Hz, 1H), 7.27 (d, J=5.1 Hz, 1H), 7.22 (t, J=7.7 Hz, 1H), 7.06 (t, J=7.5 Hz, 1H), 6.99 (d, J=6.9 Hz, 1H), 6.88 (d, J=7.4 Hz, 1H), 6.69 (t, J=8.6 Hz, 1H), 6.41 (s, 1H), 5.69 (d, J=7.8 Hz, 1H), 4.95 (dd, J=9.3, 3.2 Hz, 1H), 3.98 (m, 1H), 2.95-2.84 (m, 1H), 2.65-2.55 (m, 1H), 2.30-2.20 (m, 1H), 2.05-2.12 (m, 1H), 2.03 (s, 2H), 1.94-1.78 (m, 2H), 1.68-1.35 (m, 3H), 0.85-0.95 (m, 1H). MS: 628.2 (M+1)⁺.

(S)—N—((S)-1-(2-Chlorophenyl)-2-((4,4-difluoro-cyclohexyl)amino)-2-oxoethyl)-1-(4-cyanopyrimi-din-2-yl)-N-(3,5-difluorophenyl)-5-oxopyrrolidine-2-carboxamide (Single Enantiomer)—Compound 87

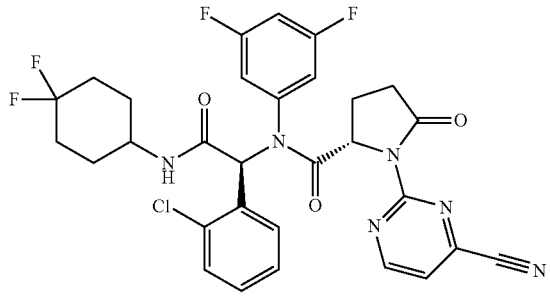 [SMILES: N#Cc1ccnc(N2C(=O)CC[C@H]2C(=O)N(c2cc(F)cc(F)c2)[C@H](C(=O)NC2CCC(F)(F)CC2)c2ccccc2Cl)n1]

¹H NMR (400 MHz, CDCl₃): δ 8.97 (d, J=4.8 Hz, 1H), 7.60 (d, J=8.7 Hz, 1H), 7.46-7.34 (m, 2H), 7.22 (t, J=7.8 Hz, 1H), 7.06 (t, J=7.6 Hz, 1H), 7.00-6.87 (m, 2H), 6.70 (t, J=8.6 Hz, 1H), 6.48 (s, 1H), 5.64 (d, J=7.7 Hz, 1H), 4.86 (dd, J=9.3, 2.7 Hz, 1H), 3.98 (d, J=7.7 Hz, 1H), 2.96-2.86 (m, 1H), 2.63-2.55 (m, 1H), 2.37-2.29 (m, 1H), 2.15-1.99 (m, 5H), 1.96-1.77 (m, 2H), 1.61-1.34 (m, 2H). MS: 629.2 (M+1)⁺.

(S)-1-(4-Cyanopyridin-2-yl)-N—((S)-1-(2,4-dichlo-rophenyl)-2-((3,3-difluorocyclobutyl)-amino)-2-oxoethyl)-N-(3,5-difluorophenyl)-5-oxopyrrolidine-2-carboxamide (Single Enantiomer)—Compound 196

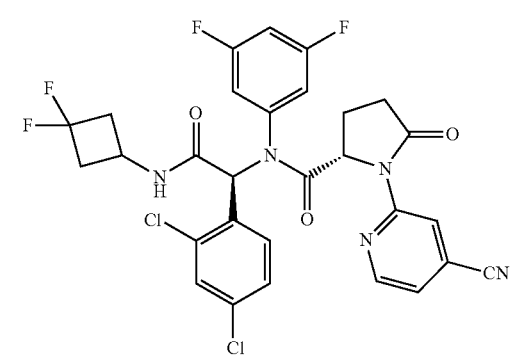 [SMILES: N#Cc1ccnc(N2C(=O)CC[C@H]2C(=O)N(c2cc(F)cc(F)c2)[C@H](C(=O)NC2CC(F)(F)C2)c2ccc(Cl)cc2Cl)c1]

¹H NMR (400 MHz, CDCl₃): δ 8.77 (s, 1H), 8.49 (d, J=5.1 Hz, 1H), 7.56 (s, 1H), 7.40 (d, J=2.1 Hz, 1H), 7.30 (s, 1H), 7.08 (dd, J=8.4, 2.1 Hz, 1H), 6.97 (d, J=8.4 Hz, 1H), 6.90 (s, 1H), 6.79-6.72 (m, 1H), 6.35 (s, 1H), 5.99 (d, J=6.6 Hz, 1H), 4.93 (dd, J=9.3, 3.1 Hz, 1H), 4.33 (s, 1H), 3.12-2.95 (m, 2H), 2.95-2.83 (m, 1H), 2.66-2.32 (m, 3H), 2.24-2.18 (m, 1H), 2.12-1.99 (m, 1H). MS: 634.1 (M+1)⁺.

(S)-1-(4-Cyanopyridin-2-yl)-N—((S)-1-(2,5-dichlorophenyl)-2-((3,3-difluorocyclobutyl)-amino)-2-oxoethyl)-N-(3,5-difluorophenyl)-5-oxopyrrolidine-2-carboxamide (Single Enantiomer)—Compound 201

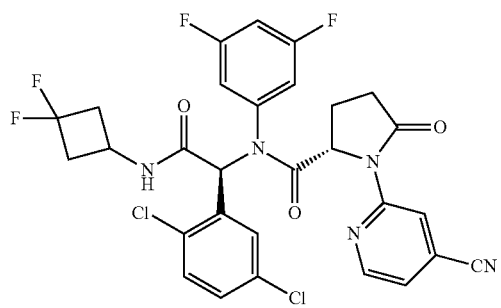 [SMILES: N#Cc1ccnc(N2C(=O)CC[C@H]2C(=O)N(c2cc(F)cc(F)c2)[C@H](C(=O)NC2CC(F)(F)C2)c2cc(Cl)ccc2Cl)c1]

¹H NMR (400 MHz, CDCl₃): δ 8.76 (s, 1H), 8.49 (dd, J=5.0, 0.6 Hz, 1H), 7.58 (s, 1H), 7.30 (t, J=5.2 Hz, 2H), 7.22 (dd, J=8.6, 2.5 Hz, 1H), 7.02 (d, J=2.4 Hz, 1H), 6.88 (s, 1H), 6.76 (tt, J=8.6, 2.3 Hz, 1H), 6.34 (s, 1H), 6.14 (d, J=6.8 Hz, 1H), 4.94 (dd, J=9.3, 3.2 Hz, 1H), 4.43-4.28 (m, 1H), 3.09-3.02 (m, 2H), 2.93-2.84 (m, 1H), 2.65-2.32 (m, 3H), 2.27-2.16 (m, 1H), 2.14-2.00 (m, 1H). MS: 634.1 (M+1)⁺.

(S)-1-(4-Cyanopyridin-2-yl)-N—((S)-1-(2,6-dichlorophenyl)-2-(3,3-difluorocyclobutylamino)-2-oxoethyl)-N-(3-fluorophenyl)-5-oxopyrrolidine-2-carboxamide (Single Enantiomer)—Compound 63

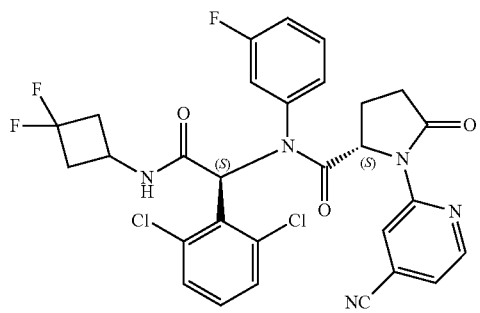

¹H NMR (400 MHz, CDCl₃): δ 8.77 (s, 1H), 8.45 (t, J=5.6 Hz, 1H), 7.88 (t, J=10.0 Hz, 1H), 7.40-7.32 (m, 1H), 7.26-7.21 (m, 2H), 7.10-7.05 (m, 2H), 6.92 (d, J=2.4 Hz, 1H), 6.62 (d, J=8.6 Hz, 1H), 5.53 (d, J=5.3 Hz, 1H), 4.84-4.75 (m, 1H), 4.40 (s, 1H), 3.06-2.92 (m, 3H), 2.65-2.42 (m, 4H), 2.18-2.02 (m, 1H). MS: 616.1 (M+1)⁺.

(S)-1-(4-Cyanopyridin-2-yl)-N—((S)-1-(2,6-dichlorophenyl)-2-((3,3-difluorocyclobutyl)amino)-2-oxoethyl)-N-(3,5-difluorophenyl)-5-oxopyrrolidine-2-carboxamide (Single Enantiomer)—Compound 199

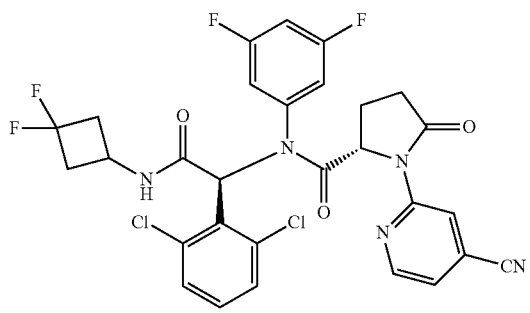 [SMILES: N#Cc1ccnc(N2C(=O)CC[C@H]2C(=O)N(c2cc(F)cc(F)c2)[C@H](C(=O)NC2CC(F)(F)C2)c2c(Cl)cccc2Cl)c1]

¹H NMR (400 MHz, CDCl₃): δ 8.78 (s, 1H), 8.44 (d, J=5.0 Hz, 1H), 7.80-7.22 (m, 5H), 6.91 (s, 1H), 6.81 (tt, J=8.7, 2.3 Hz, 1H), 6.45 (d, J=8.5 Hz, 1H), 5.56 (d, J=6.8 Hz, 1H), 4.83 (dd, J=9.4, 2.7 Hz, 1H), 4.40 (d, J=8.0 Hz, 1H), 3.23-2.92 (m, 3H), 2.69-2.39 (m, 4H), 2.23-2.02 (m, 1H). MS: 634.2 (M+1)⁺.

(2S)-1-(4-Cyanopyridin-2-yl)-N-(1-(2,3-dichlorophenyl)-2-(3,3-difluoro-cyclobutylamino)-2-oxoethyl)-N-(3,5-difluorophenyl)-5-oxopyrrolidine-2-carboxamide (Racemic)—Compound 195

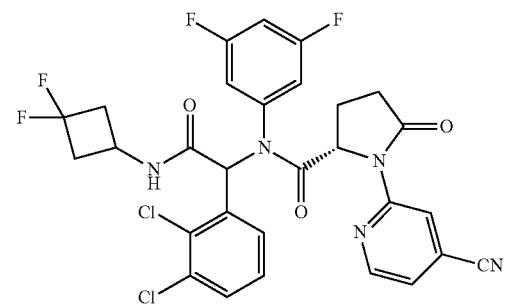 [SMILES: N#Cc1ccnc(N2C(=O)CC[C@H]2C(=O)N(c2cc(F)cc(F)c2)C(C(=O)NC2CC(F)(F)C2)c2cccc(Cl)c2Cl)c1]

¹H NMR (400 MHz, CDCl₃): δ 8.72 (s, 1H), 8.57 (s, 1H), 7.44 (d, J=7.9, 1H), 7.32-7.29 (m, 1H), 7.17-6.68 (m, 4H), 6.53-6.41 (m, 1H), 6.32-6.12 (m, 1H), 4.90-4.65 (m, 1H), 4.41-4.05 (m, 1H), 3.13-2.01 (m, 8H). MS: 634.1 (M+1)⁺.

(S)-1-(4-Cyanopyridin-2-yl)-N—((S)-2-(3,3-difluorocyclobutylamino)-1-(2-fluorophenyl)-2-oxoethyl)-N-(3,5-difluorophenyl)-5-oxopyrrolidine-2-carboxamide (Single Enantiomer)—Compound 208

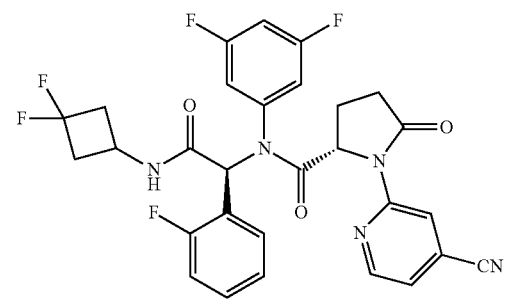 [SMILES: N#Cc1ccnc(N2C(=O)CC[C@H]2C(=O)N(c2cc(F)cc(F)c2)[C@H](C(=O)NC2CC(F)(F)C2)c2ccccc2F)c1]

121

¹H NMR (400 MHz, CDCl₃): δ 8.63 (s, 1H), 8.40 (d, J=4.9 Hz, 1H), 7.43 (s, 1H), 7.20 (s, 1H), 7.16 (d, J=5.0 Hz, 1H), 6.90 (t, J=8.2 Hz, 3H), 6.62 (t, J=8.7 Hz, 2H), 6.20 (s, 1H), 6.14 (d, J=6.4 Hz, 1H), 4.81 (dd, J=9.1, 2.9 Hz, 1H), 4.25 (s, 1H), 2.92 (s, 2H), 2.85-2.70 (m, 1H), 2.56-2.22 (m, 3H), 2.15 (m, 1H), 2.04-1.90 (m, 1H). MS: 584.2 (M+1)⁺.

(S)-1-(4-Cyanopyridin-2-yl)-N—((S)-2-(3,3-difluorocyclobutylamino)-2-oxo-1-phenylethyl)-N-(3,5-difluorophenyl)-5-oxopyrrolidine-2-carboxamide (Single Enantiomer)—Compound 210

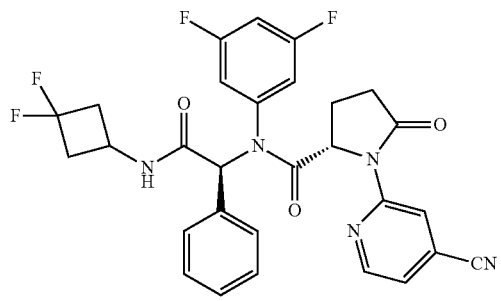 [SMILES: N#Cc1ccnc(N2C(=O)CC[C@H]2C(=O)N(c2cc(F)cc(F)c2)[C@H](C(=O)NC2CC(F)(F)C2)c2ccccc2)c1]

¹H NMR (400 MHz, CDCl₃): δ 8.77 (s, 1H), 8.41 (d, J=5.1 Hz, 1H), 7.49 (s, 1H), 7.27 (dd, J=8.2, 5.0 Hz, 2H), 7.24 (d, J=5.4 Hz, 2H), 7.04 (d, J=6.7 Hz, 2H), 6.71 (t, J=8.8 Hz, 1H), 6.44 (s, 1H), 6.15 (s, 1H), 5.70 (d, J=6.3 Hz, 1H), 4.86 (dd, J=9.3, 2.8 Hz, 1H), 4.29 (s, 1H), 2.99 (m, 2H), 2.90 (m, 1H), 2.62-2.52 (m, 1H), 2.45 (m, 1H), 2.38-2.25 (m, 2H), 2.07 (m, 1H). MS: 566.2 (M+1)⁺.

(S)—N—((S)-1-(3-Chloropyridin-2-yl)-2-(3,3-difluorocyclobutylamino)-2-oxoethyl)-1-(4-cyano pyridin-2-yl)-N-(3,5-difluorophenyl)-5-oxopyrrolidine-2-carboxamide (Single Enantiomer)—Compound 198

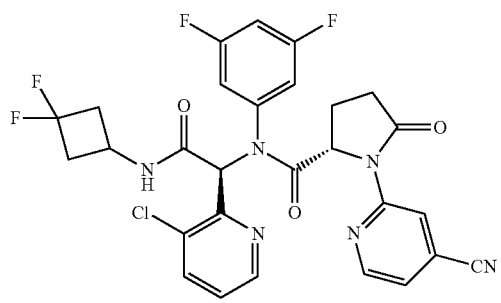 [SMILES: N#Cc1ccnc(N2C(=O)CC[C@H]2C(=O)N(c2cc(F)cc(F)c2)[C@H](C(=O)NC2CC(F)(F)C2)c2ncccc2Cl)c1]

¹H NMR (400 MHz, CDCl₃): δ 8.75 (s, 1H), 8.49 (d, J=5.0 Hz, 1H), 8.31 (d, J=3.4 Hz, 1H), 7.65-7.56 (m, 2H), 7.27 (m, 1H), 7.19-7.15 (m, 1H), 6.98 (m, 1H), 6.76-6.56 (m, 2H), 6.11 (d, J=6.8 Hz, 1H), 5.04-5.01 (m, 1H), 4.38 (m, 1H), 3.05-2.98 (m, 2H), 2.92-2.83 (m, 1H), 2.60-2.52 (m, 1H), 2.51-2.37 (m, 2H), 2.37-2.27 (m, 1H), 2.07-2.02 (m, 1H). MS: 601.1 (M+1)⁺.

122

(S)—N—((S)-1-(2-Chlorophenyl)-2-(3,3-difluorocyclobutylamino)-2-oxoethyl)-1-(4-cyanopyridin-2-yl)-5-oxo-N-(3-sulfamoylphenyl)pyrrolidine-2-carboxamide (Single Enantiomer)—Compound 84

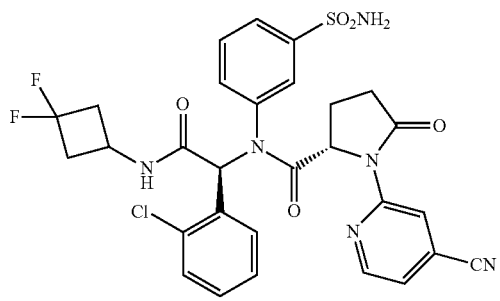 [SMILES: N#Cc1ccnc(N2C(=O)CC[C@H]2C(=O)N(c2cccc(S(N)(=O)=O)c2)[C@H](C(=O)NC2CC(F)(F)C2)c2ccccc2Cl)c1]

¹H NMR (400 MHz, CDCl₃): δ 8.73 (d, J=10.0 Hz, 1H), 8.57-8.45 (d, J=8.0 Hz, 1H), 8.12 (d, J=7.7 Hz, 1H), 7.83-7.76 (m, 2H), 7.61-7.56 (m, 1H), 7.48-7.32 (m, 1H), 7.19 (t, J=7.1 Hz, 1H), 7.05-6.87 (m, 2H), 6.82-6.81 (m, 1H), 6.55-6.43 (m, 1H), 6.27 (d, J=6.7 Hz, 1H), 5.24 (s, 1H), 4.84 (d, J=7.2 Hz, 1H), 4.69 (s, 1H), 4.33 (s, 1H), 2.98-2.87 (m, 3H), 2.63-2.24 (m, 4H), 2.09-2.00 (m, 1H). MS: 643.1 (M+1)⁺.

(S)—N—((S)-1-(2-Chlorophenyl)-2-((3,3-difluorocyclobutyl)amino)-2-oxoethyl)-N-(3-cyano-phenyl)-1-(4-cyanopyridin-2-yl)-5-oxopyrrolidine-2-carboxamide (Single Enantiomer)—Compound 128

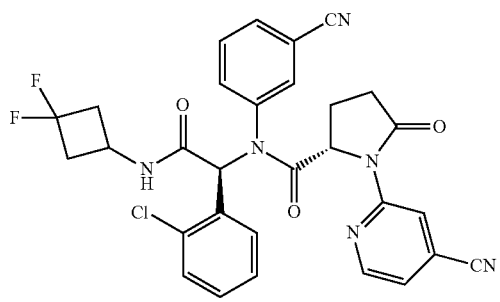 [SMILES: N#Cc1cccc(N(C(=O)[C@@H]2CCC(=O)N2c2cc(C#N)ccn2)[C@H](C(=O)NC2CC(F)(F)C2)c2ccccc2Cl)c1]

¹H NMR (400 MHz, CDCl₃): δ 8.76 (s, 1H), 8.51 (s, 1H), 8.23 (m, 1H), 7.58-7.27 (m, 4H), 6.93 (m, 3H), 6.43 (s, 1H), 5.85 (s, 1H), 4.78 (s, 1H), 4.34 (s, 1H), 3.10-2.82 (m, 3H), 2.37-2.52 (m, 3H), 2.21-2.23 (m, 1H), 1.89-1.99 (m, 1H). MS: 589.1 (M+1)⁺.

(S)—N—((S)-1-(2-Chlorophenyl)-2-((4,4-difluorocyclohexyl)amino)-2-oxoethyl)-N-(3-cyano phenyl)-1-(4-cyanopyridin-2-yl)-5-oxopyrrolidine-2-carboxamide (Single Enantiomer)—Compound 166

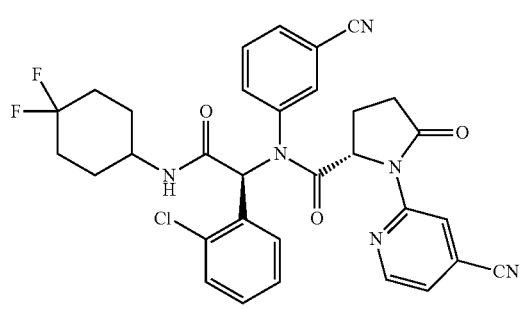 [SMILES: N#Cc1cccc(N(C(=O)[C@@H]2CCC(=O)N2c2cc(C#N)ccn2)[C@H](C(=O)NC2CCC(F)(F)CC2)c2ccccc2Cl)c1]

¹H NMR (400 MHz, CDCl₃): δ 8.77 (s, 1H), 8.49 (d, J=13.9 Hz, 1H), 8.22-8.32 (m, 1H), 7.61-7.27 (m, 4H), 7.17-7.19 (m, 2H), 6.90-7.00 (m, 2H), 6.42 (s, 1H), 5.50 (s, 1H), 4.80 (d, J=9.5 Hz, 1H), 3.97 (s, 1H), 2.99-2.80 (m, 1H), 2.56-2.58 (m, 1H), 2.21-2.24 (m, 1H), 1.70-2.10 (m, 6H), 1.41-1.44 (m, 2H). MS: 617.2 (M+1)⁺.

(S)—N—((S)-1-(2-Chlorophenyl)-2-((3,3-difluorocyclobutyl)amino)-2-oxoethyl)-N-(3-cyano phenyl)-1-(4-cyanopyrimidin-2-yl)-5-oxopyrrolidine-2-carboxamide (Single Enantiomer)—Compound 167

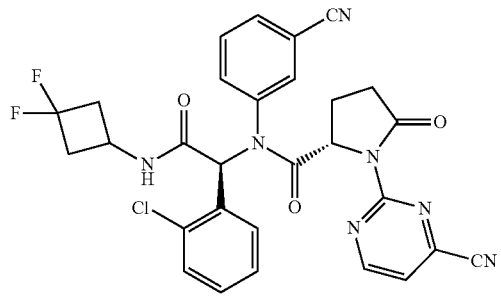 [SMILES: N#Cc1cccc(N(C(=O)[C@@H]2CCC(=O)N2c2nccc(C#N)n2)[C@H](C(=O)NC2CC(F)(F)C2)c2ccccc2Cl)c1]

¹H NMR (400 MHz, CDCl₃): δ 8.91-9.00 (m, 1H), 8.33-8.17 (m, 1H), 7.62-7.32 (m, 5H), 7.20 (t, J=7.0 Hz, 1H), 7.02-7.06 (m, 1H), 6.95-6.83 (m, 1H), 6.55 (s, 1H), 6.05-5.88 (m, 1H), 4.72 (d, J=9.3 Hz, 1H), 4.37 (s, 1H), 2.91-3.05 (m, 3H), 2.70-2.25 (m, 4H), 2.13-1.92 (m, 1H). MS: 590.1 (M+1)⁺.

(S)—N—((S)-1-(2-Chlorophenyl)-2-((4,4-difluorocyclohexyl)amino)-2-oxoethyl)-N-(3-cyanophenyl)-1-(4-cyanopyrimidin-2-yl)-5-oxopyrrolidine-2-carboxamide (Single Enantiomer)—Compound 178

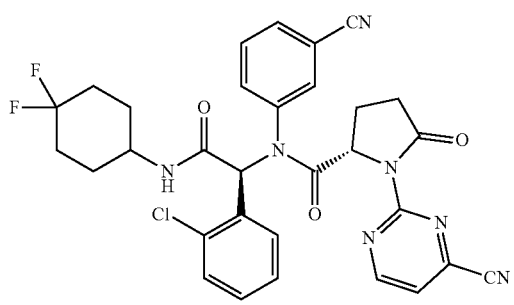

¹H NMR (400 MHz, CDCl₃): δ 8.99 (s, 1H), 8.32 (s, 1H), 7.57 (m, 1H), 7.54-7.28 (m, 2H), 7.19 (t, J=7.2 Hz, 3H), 7.04 (t, J=6.8 Hz, 1H), 6.93 (d, J=7.7 Hz, 1H), 6.53 (s, 1H), 5.64-5.44 (m, 1H), 4.74 (d, J=9.3 Hz, 1H), 3.99 (s, 1H), 2.94 (dd, J=17.8, 9.4 Hz, 1H), 2.62 (m, 1H), 2.41-2.24 (m, 1H), 2.10-1.82 (m, 7H). MS: 618.2 (M+1)⁺.

(S)—N—((S)-1-(2-Chlorophenyl)-2-(3,3-difluorocyclobutylamino)-2-oxoethyl)-N-(3-cyano-5-fluorophenyl)-1-(4-cyanopyridin-2-yl)-5-oxopyrrolidine-2-carboxamide (Single Enantiomer)—Compound 177

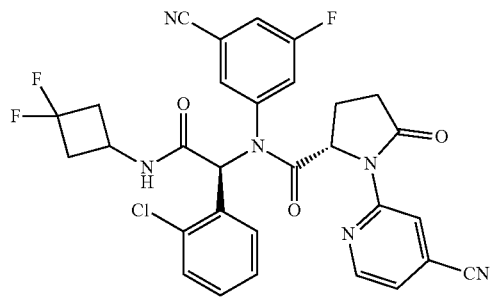 [SMILES: N#Cc1cc(F)cc(N(C(=O)[C@@H]2CCC(=O)N2c2cc(C#N)ccn2)[C@H](C(=O)NC2CC(F)(F)C2)c2ccccc2Cl)c1]

¹H NMR (400 MHz, CDCl₃): δ 8.74 (s, 1H), 8.50 (s, 1H), 8.13-8.08 (m, 1H), 7.44-7.27 (m, 2H), 7.23 (dd, J=12.6, 6.3 Hz, 2H), 7.07 (t, J=7.3 Hz, 1H), 6.93 (t, J=6.4 Hz, 1H), 6.43 (d, J=6.1 Hz, 1H), 6.14 (dd, J=13.9, 6.7 Hz, 1H), 4.81 (dd, J=9.0, 2.3 Hz, 1H), 4.42-4.28 (m, 1H), 3.12-2.94 (m, 2H), 2.94-2.80 (m, 1H), 2.67-2.29 (m, 3H), 2.23-1.92 (m, 2H). MS: 607.1 (M+1)⁺.

(S)—N—((S)-1-(2-Chlorophenyl)-2-((4,4-difluorocyclohexylamino)-2-oxoethyl)-N-(3-cyano-5-fluorophenyl)-1-(4-cyanopyridin-2-yl)-5-oxopyrrolidine-2-carboxamide (Single Enantiomer)—Compound 184

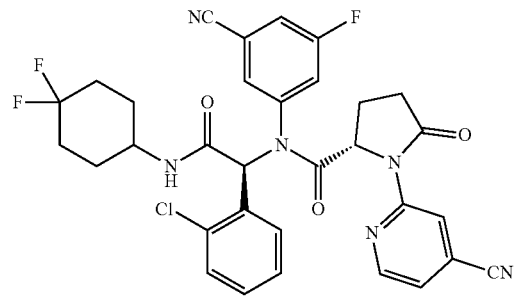 [SMILES: N#Cc1cc(F)cc(N(C(=O)[C@@H]2CCC(=O)N2c2cc(C#N)ccn2)[C@H](C(=O)NC2CCC(F)(F)CC2)c2ccccc2Cl)c1]

¹H NMR (400 MHz, CDCl₃): δ 8.77 (s, 1H), 8.50 (s, 1H), 8.25-8.03 (m, 1H), 7.52-7.28 (m, 2H), 7.22 (t, J=7.7 Hz, 2H), 7.01 (dt, J=14.1, 10.1 Hz, 2H), 6.42 (d, J=6.9 Hz, 1H), 5.58 (t, J=9.9 Hz, 1H), 4.83 (dd, J=9.1, 2.3 Hz, 1H), 4.05-3.86 (m, 1H), 3.04-2.81 (m, 1H), 2.59 (m, 1H), 2.36-1.70 (m, 7H), 1.58-1.31 (m, 3H). MS: 636.2 (M+1)⁺.

(S)—N—((S)-1-(2-Chlorophenyl)-2-((4,4-difluorocyclohexyl)amino)-2-oxoethyl)-N-(3-cyano-5-fluorophenyl)-1-(4-cyanopyrimidin-2-yl)-5-oxopyrrolidine-2-carboxamide (Single Enantiomer)—Compound 185

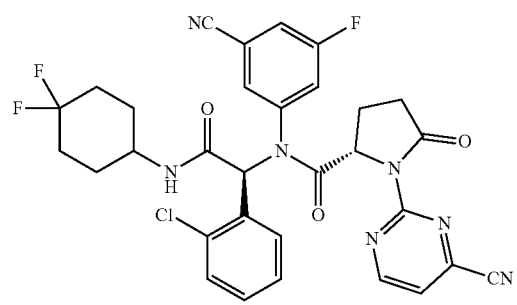 [SMILES: N#Cc1cc(F)cc(N(C(=O)[C@@H]2CCC(=O)N2c2nccc(C#N)n2)[C@H](C(=O)NC2CCC(F)(F)CC2)c2ccccc2Cl)c1]

125

¹H NMR (400 MHz, CDCl₃): δ 8.97 (d, J=4.4 Hz, 1H), 8.12 (m, 1H), 7.50-7.32 (m, 3H), 7.23 (d, J=6.7 Hz, 2H), 7.06 (m, 1H), 6.95 (s, 1H), 6.50 (d, J=8.6 Hz, 1H), 5.60 (d, J=7.5 Hz, 1H), 4.74 (d, J=8.8 Hz, 1H), 3.98 (s, 1H), 2.90 (m, 1H), 2.72-2.49 (m, 1H), 2.28 (s, 1H), 2.17-1.67 (m, 7H), 1.43 (m, 2H). MS: 637.2 (M+1)⁺.

(S)—N-(3-Cyano-5-fluorophenyl)-1-(4-cyanopyridin-2-yl)-N—((S)-2-(3,3-difluorocyclobutyl-amino)-2-oxo-1-phenylethyl)-5-oxopyrrolidine-2-carboxamide (Single Enantiomer)—Compound 211

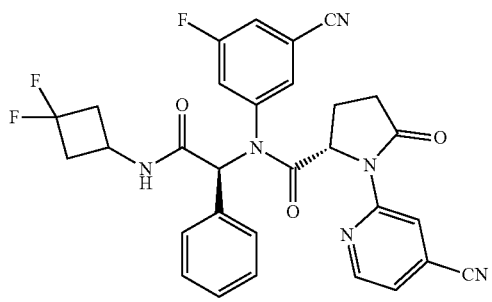 [SMILES: N#Cc1cc(F)cc(N(C(=O)[C@@H]2CCC(=O)N2c2cc(C#N)ccn2)[C@H](C(=O)NC2CC(F)(F)C2)c2ccccc2)c1]

¹H NMR (400 MHz, CDCl₃): δ 8.71 (d, J=10.1 Hz, 1H), 8.38 (s, 1H), 8.02 (m, 1H), 7.23 (m, 5H), 6.97 (d, J=7.3 Hz, 3H), 6.20 (s, 1H), 5.97 (s, 1H), 4.70 (dd, J=9.2, 2.4 Hz, 1H), 4.27 (s, 1H), 2.93 (m, 2H), 2.85 (t, J=8.9 Hz, 1H), 2.59-2.48 (m, 1H), 2.49-2.29 (m, 2H), 2.29-2.20 (m, 1H), 2.08-1.99 (m, 1H). MS: 573.2 (M+1)⁺.

(S)—N-(3-Cyano-5-fluorophenyl)-1-(4-cyanopyridin-2-yl)-N—((S)-2-((3,3-difluorocyclobutyl)amino)-1-(2-fluorophenyl)-2-oxoethyl)-5-oxopyrrolidine-2-carboxamide (Single Enantiomer)—Compound 207

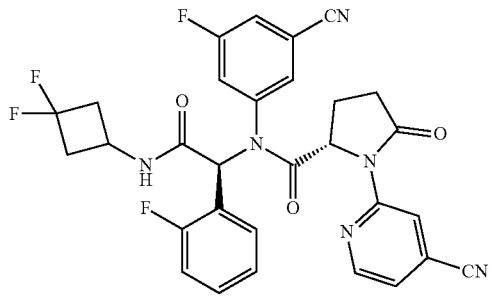 [SMILES: N#Cc1cc(F)cc(N(C(=O)[C@@H]2CCC(=O)N2c2cc(C#N)ccn2)[C@H](C(=O)NC2CC(F)(F)C2)c2ccccc2F)c1]

¹H NMR (400 MHz, DMSO-d₆): δ 8.78 (s, 1H), 8.62 (d, J=5.1 Hz, 1H), 8.48 (s, 1H), 8.04-7.83 (m, 1H), 7.78 (s, 1H), 7.57 (s, 1H), 7.23 (m, 2H), 7.14 (d, J=9.9 Hz, 1H), 6.95 (t, J=7.5 Hz, 1H), 6.84 (s, 1H), 6.20 (s, 1H), 4.72 (s, 1H), 4.04 (s, 1H), 4.00-3.82 (m, 1H), 3.09-2.67 (m, 2H), 2.33 (m, 1H), 1.91 (s, 2H), 1.83 (s, 1H), 1.27-1.05 (m, 1H). MS: 591.2 (M+1)⁺.

126

(2S)—N-(1-(2-Chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Racemic)—Compound

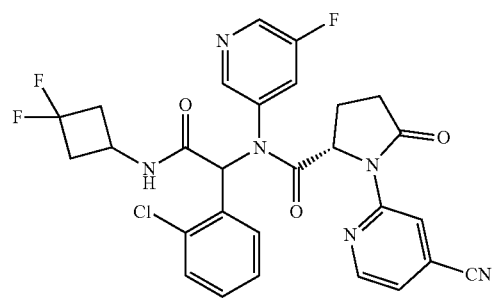 [SMILES: N#Cc1ccnc(N2C(=O)CC[C@H]2C(=O)N(c2cncc(F)c2)C(C(=O)NC2CC(F)(F)C2)c2ccccc2Cl)c1]

¹H NMR (400 MHz, CDCl₃): δ 9.10-8.03 (m, 4H), 7.47-7.39 (m, 2H), 7.27-6.84 (m, 3H), 6.51-6.01 (m, 2H), 4.84-4.70 (m, 1H), 4.36-4.20 (m, 1H), 3.25-1.86 (m, 8H). MS: 583.1 (M+1)⁺.

(S)—N—((S)-1-(2-Chlorophenyl)-2-(3,3-difluorocyclobutylamino)-2-oxoethyl)-1-(4-cyanopyridin-2-yl)-N-(5-fluoropyridin-3-yl)-5-oxopyrrolidine-2-carboxamide (Single Enantiomer)—Compound 176

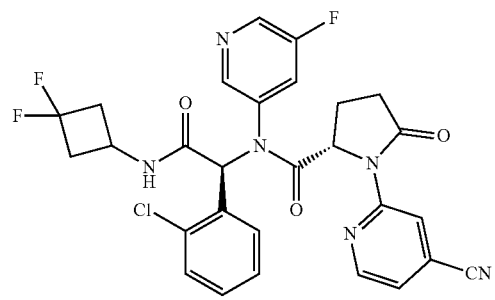 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

¹H NMR (400 MHz, CDCl₃): δ 8.95-8.70 (m, 1H), 8.49 (d, J=4.7 Hz, 1H), 8.36-8.11 (m, 1H), 8.12 (d, J=8.6 Hz, 1H), 7.33 (d, J=8.0 Hz, 1H), 7.21 (t, J=7.8 Hz, 1H), 7.04 (t, J=7.6 Hz, 1H), 6.48-6.41 (m, 1H), 6.30-6.21 (m, 1H), 4.84-6.79 (m, 1H), 4.38-4.30 (m, 1H), 3.11-2.74 (m, 3H), 2.65-1.91 (m, 5H). MS: 583.1 (M+1)⁺.

(S)—N—((S)-1-(2-Chlorophenyl)-2-(4,4-difluorocyclohexylamino)-2-oxoethyl)-1-(4-cyanopyridin-2-yl)-N-(5-fluoropyridin-3-yl)-5-oxopyrrolidine-2-carboxamide (Single Enantiomer)—Compound 193

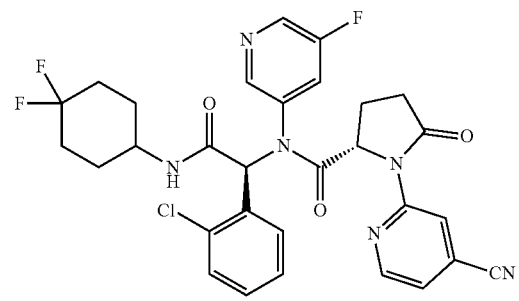 [SMILES: N#Cc1ccnc(N2C(=O)CC[C@H]2C(=O)N(c2cncc(F)c2)[C@H](C(=O)NC2CCC(F)(F)CC2)c2ccccc2Cl)c1]

¹H NMR (400 MHz, CDCl₃): δ 8.77 (s, 1H), 8.49 (d, J=5.2 Hz, 1H), 8.40-8.27 (m, 1H), 8.21-8.04 (m, 1H), 7.41-7.36 (m, 1H), 7.26-7.23 (m, 1H), 7.20 (t, J=6.9 Hz, 1H), 7.04 (t, J=7.2 Hz, 1H), 6.93 (m, 1H), 6.52-6.34 (m, 1H), 5.49 (s, 1H), 4.84 (d, J=7.4 Hz, 1H), 4.01-3.94 (m, 1H), 2.99-2.91 (m, 1H), 2.62-2.54 (m, 1H), 2.22-1.71 (m, 7H), 1.31 (s, 3H). MS: 611.2 (M+1)⁺.

(S)-1-(4-Cyanopyridin-2-yl)-N—((S)-2-((3,3-difluorocyclobutyl)amino)-2-oxo-1-phenylethyl)-N-(5-fluoropyridin-3-yl)-5-oxopyrrolidine-2-carboxamide (Single Enantiomer)—Compound 147

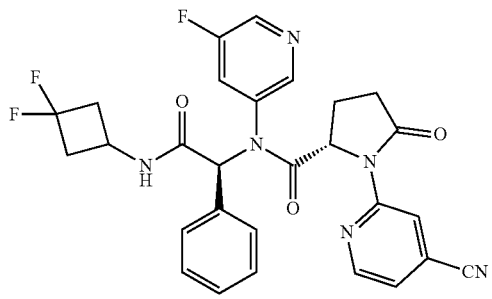 [SMILES: N#Cc1ccnc(N2C(=O)CC[C@H]2C(=O)N(c2cncc(F)c2)[C@H](C(=O)NC2CC(F)(F)C2)c2ccccc2)c1]

¹H NMR (400 MHz, CDCl₃): δ 8.86 (m, 1H), 8.39 (m, 2H), 8.03 (m, 1H), 7.28 (d, J=5.9 Hz, 4H), 6.98 (m, 2H), 6.29 (s, 1H), 5.85 (s, 1H), 4.85 (m, 1H), 4.33 (s, 1H), 3.26-2.82 (m, 3H), 2.69-1.88 (m, 5H). MS: 549.2 (M+1)⁺.

(S)-1-(4-Cyanopyridin-2-yl)-N—((S)-2-((3,3-difluorocyclobutyl)amino)-1-(2-fluorophenyl)-2-oxoethyl)-N-(5-fluoropyridin-3-yl)-5-oxopyrrolidine-2-carboxamide (Single Enantiomer)—Compound 148

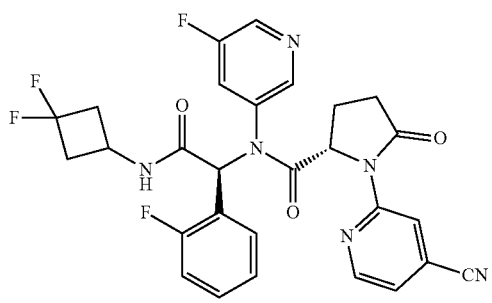 [SMILES: N#Cc1ccnc(N2C(=O)CC[C@H]2C(=O)N(c2cncc(F)c2)[C@H](C(=O)NC2CC(F)(F)C2)c2ccccc2F)c1]

¹H NMR (400 MHz, CDCl₃): δ 8.99-8.60 (m, 1H), 8.55-7.97 (m, 3H), 7.35-7.19 (m, 3H), 7.07-6.89 (m, 3H), 6.36 (m, 1H), 6.12 (s, 1H), 4.80 (s, 1H), 4.35 (s, 1H), 3.22-2.79 (m, 3H), 2.64-1.85 (m, 5H). MS: 567.2 (M+1)⁺.

(S)-1-(4-Cyanopyridin-2-yl)-N—((S)-2-((3,3-difluorocyclobutyl)amino)-2-oxo-1-phenylethyl)-N-(5-isocyanopyridin-3-yl)-5-oxopyrrolidine-2-carboxamide (Single Enantiomer)—Compound 212

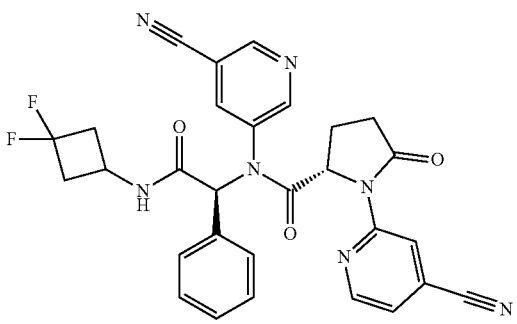 [SMILES: N#Cc1cncc(N(C(=O)[C@@H]2CCC(=O)N2c2cc(C#N)ccn2)[C@H](C(=O)NC2CC(F)(F)C2)c2ccccc2)c1]

¹H NMR (400 MHz, CDCl₃): δ 9.34 (s, 1H), 8.87-8.56 (m, 4H), 8.41 (s, 2H), 8.27 (s, 1H), 7.54 (s, 7H), 7.01 (d, J=6.9 Hz, 3H), 6.35 (s, 2H), 5.73 (s, 2H), 4.66 (s, 2H), 4.35 (s, 2H), 2.99 (m, 5H), 2.73-2.20 (m, 7H), 2.07 (s, 2H). MS: 556.2 (M+1)⁺.

(S)—N—((S)-1-(2-Chlorophenyl)-2-(3,3-difluorocyclobutylamino)-2-oxoethyl)-1-(3-cyano-phenyl)-N-(1H-indazol-7-yl)-5-oxopyrrolidine-2-carboxamide (Single Enantiomer)—Compound 186

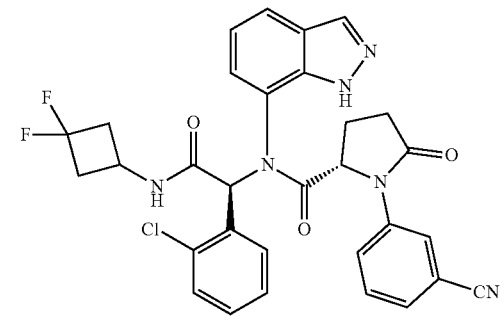 [SMILES: N#Cc1cccc(N2C(=O)CC[C@H]2C(=O)N(c2cccc3cn[nH]c23)[C@H](C(=O)NC2CC(F)(F)C2)c2ccccc2Cl)c1]

¹H NMR (400 MHz, CDCl₃): δ 8.72-8.71 (m, 1H), 8.66 (s, 1H), 8.08 (s, 1H), 7.69 (s, 1H), 7.67 (s, 1H), 7.50-7.49 (m, 1H), 7.36-7.34 (m, 1H), 7.11-7.07 (m, 1H), 7.00-6.96 (m, 1H), 6.83-6.76 (m, 2H), 6.48 (s, 1H), 5.07-5.07 (m, 1H), 4.38-4.33 (m, 1H), 3.05-2.91 (m, 2H), 2.80-2.71 (m, 1H), 2.65-2.60 (m, 1H), 2.53-2.46 (m, 2H), 2.03-1.99 (m, 1H), 1.75-1.67 (m, 1H). MS: 603.2 (M+1)⁺.

(S)—N—((S)-1-(2-Chlorophenyl)-2-(4,4-difluorocyclohexylamino)-2-oxoethyl)-3-(3-cyano phenyl)-N-(1H-indazol-7-yl)-2-oxooxazolidine-4-carboxamide (Single Enantiomer)—Compound 142

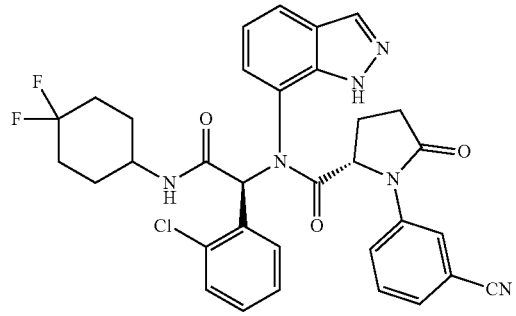 [SMILES: N#Cc1cccc(N2C(=O)CC[C@H]2C(=O)N(c2cccc3cn[nH]c23)[C@H](C(=O)NC2CCC(F)(F)CC2)c2ccccc2Cl)c1]

¹H NMR (400 MHz, CDCl₃): δ 13.03 (s, 1H), 8.73 (s, 1H), 8.55-8.54 (m, 1H), 8.02 (s, 1H), 8.58-8.56 (m, 1H), 8.50-8.48 (m, 1H), 7.27-7.24 (m, 2H), 7.03-6.99 (m, 1H), 6.91-6.87 (m, 1H), 6.80-6.78 (m, 1H), 6.72-6.68 (m, 1H), 6.33 (s, 2H), 5.70-5.69 (m, 1H), 4.99-4.97 (m, 1H), 4.05-4.03 (m, 1H), 2.78-2.95 (m, 1H), 2.47-2.40 (m, 1H), 2.08-4.99 (m, 6H), 1.90-1.82 (m, 2H), 1.67-1.63 (m, 1H), 1.58-1.62 (m, 1H). MS: 633.2 (M+1)⁺.

(2S)—N-(1-(2-Chlorophenyl)-2-((3,3-difluorocyclobutyl)amino)-2-oxoethyl)-1-(4-cyanopyridin-2-yl)-N-(1H-indazol-4-yl)-5-oxopyrrolidine-2-carboxamide (Racemic)—Compound 152

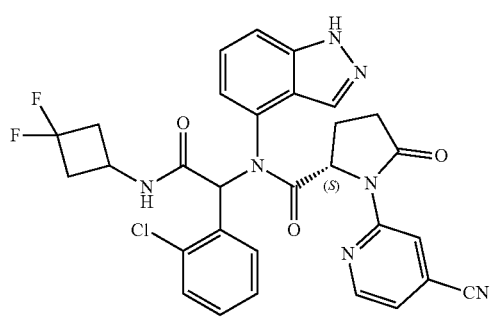

¹H NMR (400 MHz, DMSO-d₆): δ 13.05 (m, 1H), 8.70 (m, 2H), 8.54 (d, J=6.7 Hz, 1H), 8.21 (s, 1H), 7.80 (d, J=6.9 Hz, 1H), 7.63 (d, J=5.0 Hz, 1H), 7.36 (m, 2H), 7.24 (d, J=8.0 Hz, 1H), 7.18-6.97 (m, 1H), 6.92-6.79 (m, 1H), 6.77-6.70 (m, 1H), 6.35 (d, 1H), 4.66 (m, 1H), 4.20-4.01 (m, 1H), 3.05-2.78 (m, 2H), 2.68-2.52 (m, 2H), 2.49-2.26 (m, 2H), 2.22-1.53 (m, 2H). MS: 604.2 (M+1)⁺.

(S)—N-(3-(1H-Pyrazol-4-yl)phenyl)-N—((S)-1-(2-chlorophenyl)-2-(3,3-difluorocyclobutylamino)-2-oxoethyl)-1-(4-cyanopyridin-2-yl)-5-oxopyrrolidine-2-carboxamide (Single Enantiomer)—Compound 200

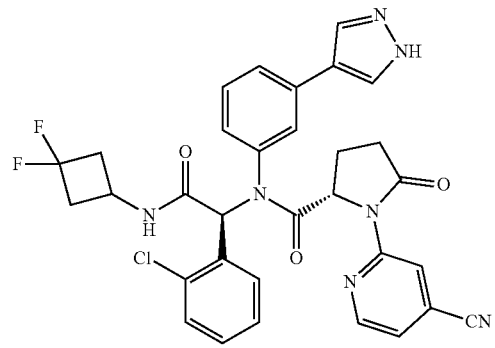 [SMILES: N#Cc1ccnc(N2C(=O)CC[C@H]2C(=O)N(c2cccc(-c3cn[nH]c3)c2)[C@H](C(=O)NC2CC(F)(F)C2)c2ccccc2Cl)c1]

¹H NMR (400 MHz, MeOD): δ 8.73-8.54 (m, 2H), 8.14-7.91 (m, 1H), 7.71 (d, J=7.6 Hz, 1H), 7.56-7.28 (m, 4H), 7.25-6.92 (m, 4H), 6.70 (d, J=7.6 Hz, 1H), 6.54-6.39 (m, 1H), 5.03 (dd, J=9.4, 2.9 Hz, 1H), 4.31-4.05 (m, 1H), 3.00-2.73 (m, 3H), 2.64-2.00 (m, 5H). MS: 630.2 (M+1)⁺.

(2S)—N-(1-(2-Chlorophenyl)-2-((3,3-difluorocyclobutyl)amino)-2-oxoethyl)-1-(4-cyanopyrimidin-2-yl)-5-oxo-N-(3-(trifluoromethoxy)phenyl)pyrrolidine-2-carboxamide (Racemic)—Compound 180

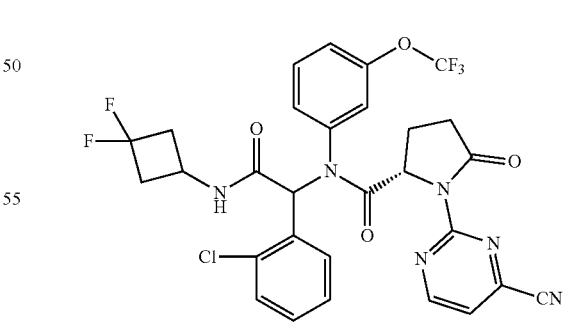

¹H NMR (400 MHz, CDCl₃): δ 8.96 (t, J=5.5 Hz, 1H), 7.88 (s, 1H), 7.44-7.32 (m, 2H), 7.21 (m, 2H), 7.10 (t, J=7.3 Hz, 1H), 7.04-6.95 (m, 1H), 6.91 (m, 1H), 6.52 (m, 1H), 6.18 (m, 1H), 4.89-4.67 (m, 1H), 4.31 (m, 1H), 3.22-2.75 (m, 3H), 2.70-1.92 (m, 5H). MS: 649.1 (M+1)⁺.

(S)—N—((S)-1-(2-Chlorophenyl)-2-((3,3-difluorocyclobutyl)amino)-2-oxoethyl)-1-(4-cyano pyridin-2-yl)-N-(3-(difluoromethoxy)phenyl)-5-oxopyrrolidine-2-carboxamide (Single Enantiomer)—Compound 181

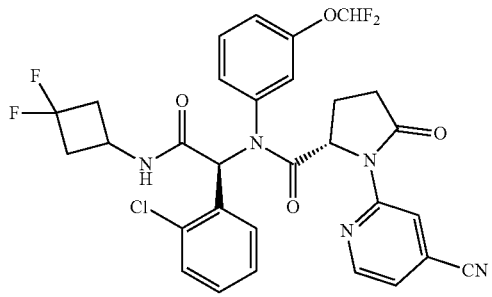 [SMILES: N#Cc1ccnc(N2C(=O)CC[C@H]2C(=O)N(c2cccc(OC(F)F)c2)[C@H](C(=O)NC2CC(F)(F)C2)c2ccccc2Cl)c1]

$^1$H NMR (400 MHz, CDCl$_3$): δ 8.74 (s, 1H), 8.44 (m, 1H), 7.76 (d, J=9.0 Hz, 1H), 7.33 (m, 2H), 7.21-6.83 (m, 6H), 6.44 (t, J=8.8 Hz, 1H), 6.28-6.13 (m, 1H), 4.91 (m, 1H), 4.34 (s, 1H), 3.10-2.66 (m, 3H), 2.65-1.84 (m, 5H). MS: 630.1 (M+1)$^+$.

(S)—N—((S)-1-(2-Chlorophenyl)-2-((3,3-difluorocyclobutyl)amino)-2-oxoethyl)-1-(4-cyano pyrimidin-2-yl)-N-(3-(difluoromethoxy)phenyl)-5-oxopyrrolidine-2-carboxamide (Single Enantiomer)—Compound 194

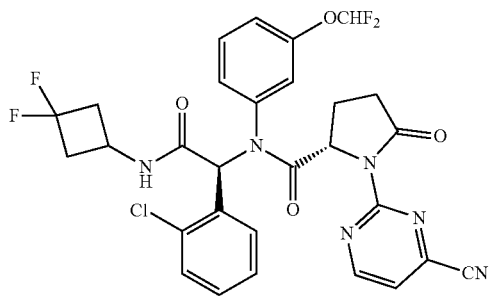 [SMILES: N#Cc1ccnc(N2C(=O)CC[C@H]2C(=O)N(c2cccc(OC(F)F)c2)[C@H](C(=O)NC2CC(F)(F)C2)c2ccccc2Cl)n1]

$^1$H NMR (400 MHz, CDCl$_3$): δ 9.04-8.59 (m, 1H), 7.74 (s, 1H), 7.43-7.26 (m, 4H), 6.96 (m, 3H), 6.36 (m, 2H), 4.81 (t, J=9.3 Hz, 1H), 4.55 (m, 1H), 4.33 (s, 1H), 4.06-3.89 (m, 1H), 3.15-2.69 (m, 2H), 2.69-1.86 (m, 5H). MS: 631.1 (M+1)$^+$.

(S)—N—((S)-1-(2C)-2-((3,3-difluorocyclobutyl)amino)-2-oxoethyl)-1-(4-cyano pyridin-2-yl)-N-(3-methoxyphenyl)-5-oxopyrrolidine-2-carboxamide (Single Enantiomer)—Compound 129

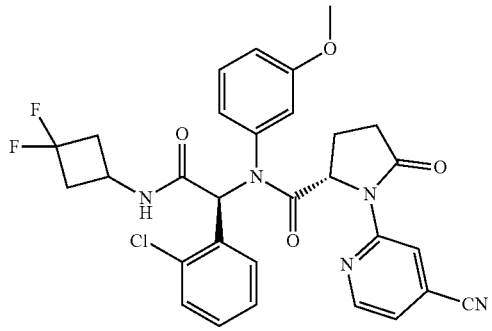 [SMILES: COc1cccc(N(C(=O)[C@@H]2CCC(=O)N2c2cc(C#N)ccn2)[C@H](C(=O)NC2CC(F)(F)C2)c2ccccc2Cl)c1]

$^1$H NMR (400 MHz, CDCl$_3$): δ 8.75 (s, 1H), 8.51 (d, J=5.0 Hz, 1H), 7.47 (m, 1H), 7.38-7.08 (m, 3H), 6.99 (d, J=6.7 Hz, 3H), 6.89-6.66 (m, 2H), 6.41 (s, 1H), 6.09 (d, J=6.6 Hz, 1H), 4.97 (dd, J=9.3, 3.2 Hz, 1H), 4.34 (s, 1H), 3.72 (m, 3H), 3.01 (dd, J=7.5, 4.0 Hz, 3H), 2.65-2.23 (m, 4H), 2.04 (d, J=9.0 Hz, 1H). MS: 594.2 (M+1)$^+$.

(S)—N—((S)-1-(2-Chlorophenyl)-2-(3,3-difluorocyclobutyl-amino)-2-oxoethyl)-1-(4-cyanopyrimidin-2-yl)-N-(3-methoxyphenyl)-5-oxopyrrolidine-2-carboxamide (Single Enantiomer)—Compound 164

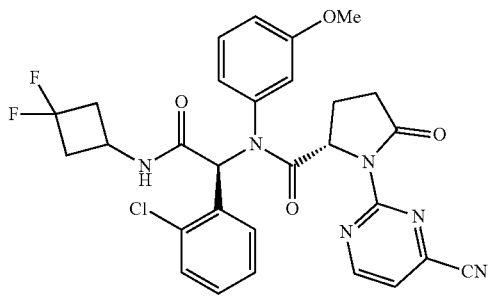 [SMILES: COc1cccc(N(C(=O)[C@@H]2CCC(=O)N2c2nccc(C#N)n2)[C@H](C(=O)NC2CC(F)(F)C2)c2ccccc2Cl)c1]

$^1$H NMR (400 MHz, CDCl$_3$): δ 8.92 (s, 1H), 7.48-7.39 (m, 1H), 7.33-7.26 (m, 2H), 7.22-7.08 (m, 2H), 7.04-6.82 (m, 3H), 6.73 (s, 2H), 6.48 (d, J=9.5 Hz, 1H), 6.18 (m, 1H), 4.88-4.85 (m, 1H), 4.32 (s, 1H), 3.78 (s, 1H), 3.62 (s, 2H), 3.01-2.81 (m, 3H), 2.58-2.49 (m, 2H), 2.42-2.30 (m, 2H), 2.09-1.98 (m, 1H). MS: 595 (M+1)$^+$.

(2S)—N-(1-(2-Chlorophenyl)-2-((3,3-difluorocyclobutyl)amino)-2-oxoethyl)-1-(4-cyanopyrimidin-2-yl)-N-(3-cyclopropoxyphenyl)-5-oxopyrrolidine-2-carboxamide (Racemic)—Compound 192

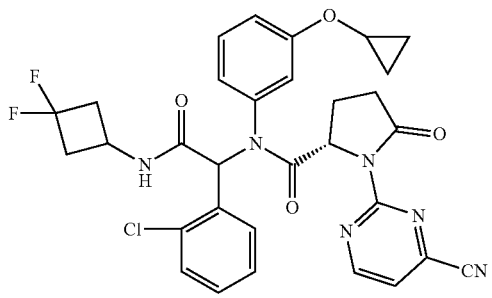 [SMILES: N#Cc1ccnc(N2C(=O)CC[C@H]2C(=O)N(c2cccc(OC3CC3)c2)C(C(=O)NC2CC(F)(F)C2)c2ccccc2Cl)n1]

$^1$H NMR (400 MHz, CDCl$_3$): δ 9.06-8.88 (m, 1H), 7.61-7.30 (m, 4H), 7.27-7.22 (m, 1H), 7.18 (t, J=7.4 Hz, 2H), 7.08-6.92 (m, 1H), 6.87 (dd, J=8.7, 2.1 Hz, 1H), 6.78 (t, J=9.5 Hz, 1H), 6.50 (s, 1H), 6.04 (m, 3H), 5.57-5.14 (m, 2H), 4.88 (m, 1H), 4.77-4.10 (m, 3H), 3.15-2.75 (m, 3H), 2.68-2.47 (m, 2H), 2.45-2.21 (m, 3H), 2.20-1.90 (m, 1H). MS: 621.1 (M+1)$^+$.

(S)—N—((S)-1-(2-Chlorophenyl)-2-(3,3-difluorocyclobutylamino)-2-oxoethyl)-1-(4-cyanopyridin-2-yl)-N-(3-(hydroxymethyl)phenyl)-5-oxopyrrolidine-2-carboxamide (Single Enantiomer)—Compound 131

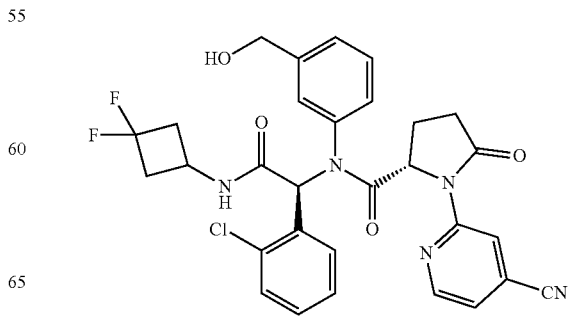

¹H NMR (400 MHz, CDCl₃): δ 8.73 (s, 1H), 8.53 (s, 1H), 7.94-7.70 (m, 1H), 7.31 (s, 1H), 7.26 (dd, J=5.1, 1.3 Hz, 1H), 7.22-7.10 (m, 4H), 7.02-6.87 (m, 2H), 6.44 (d, J=10.5 Hz, 1H), 6.12 (d, J=6.4 Hz, 1H), 4.91 (dd, J=9.3, 3.2 Hz, 1H), 4.69 (s, 1H), 4.48 (s, 1H), 4.42-4.26 (m, 1H), 3.07-2.85 (m, 3H), 2.65-2.17 (m, 4H), 2.01 (s, 2H). MS: 594.2 (M+1)⁺.

(S)—N—((S)-1-(2-Chlorophenyl)-2-(3,3-difluorocyclobutylamino)-2-oxoethyl)-1-(4-cyanopyridin-2-yl)-N-(3-(1-hydroxycyclopropyl)phenyl)-5-oxopyrrolidine-2-carboxamide (Single Enantiomer)—Compound 140

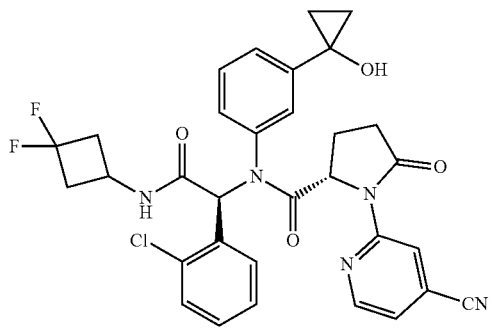 [SMILES: N#Cc1ccnc(N2C(=O)CC[C@H]2C(=O)N(c2cccc(C3(O)CC3)c2)[C@H](C(=O)NC2CC(F)(F)C2)c2ccccc2Cl)c1]

¹H NMR (400 MHz, CDCl₃): δ ¹H NMR (400 MHz, CDCl₃): δ 8.73 (s, 1H), 8.52-8.44 (m, 1H), 7.64-7.30 (m, 3H), 7.22-6.90 (m, 5H), 6.42-6.38 (m, 1H), 6.03 (m, 1H), 4.87 (m, 1H), 4.30 (m, 1H), 3.05-2.82 (m, 3H), 2.60-1.88 (m, 5H), 1.21 (d, J=3.2 Hz, 4H). MS: 620.2 (M+1)⁺.

(S)—N—((S)-1-(2C)-2-((3,3-difluorocyclobutyl)amino)-2-oxoethyl)-1-(4-cyano pyridin-2-yl)-N-(3-(2-hydroxypropan-2-yl)phenyl)-5-oxopyrrolidine-2-carboxamide (Single Enantiomer)—Compound 179

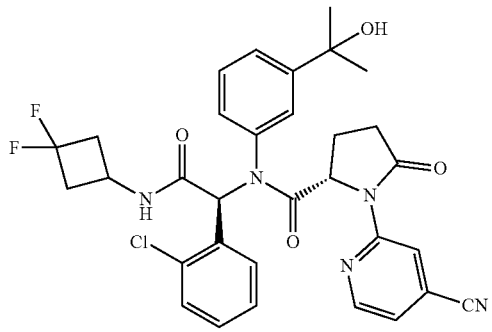 [SMILES: CC(C)(O)c1cccc(N(C(=O)[C@@H]2CCC(=O)N2c2cc(C#N)ccn2)[C@H](C(=O)NC2CC(F)(F)C2)c2ccccc2Cl)c1]

¹H NMR (400 MHz, CDCl₃): δ 8.69 (s, 1H), 8.54 (d, J=5.0 Hz, 1H), 7.93-7.70 (m, 1H), 7.40-7.19 (m, 4H), 7.11 (m, 2H), 7.01-6.72 (m, 2H), 6.45 (m, 2H), 5.05-4.76 (m, 1H), 4.33 (s, 1H), 3.13-2.58 (m, 3H), 2.42 (m, 4H), 2.09-1.83 (m, 1H), 1.33 (s, 6H). MS: 622.2 (M+1)⁺.

(S)—N—((S)-1-(2-Chlorophenyl)-2-(3,3-difluorocyclobutylamino)-2-oxoethyl)-1-(4-cyanopyridin-2-yl)-N-(3-fluoro-5-(2-hydroxypropan-2-yl)phenyl)-5-oxopyrrolidine-2-carboxamide (Single Enantiomer)—Compound 150

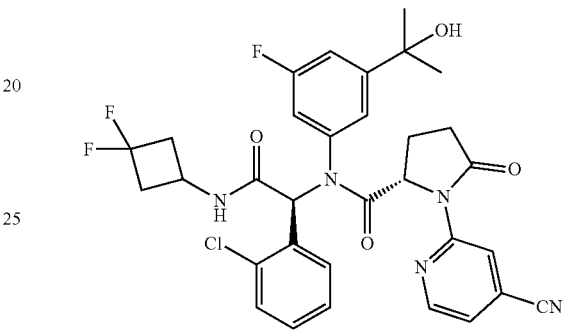

¹H NMR (400 MHz, CDCl₃): δ 8.66 (s, 1H), 8.49 (d, J=4.8 Hz, 1H), 7.73-7.48 (m, 1H), 7.26-6.83 (m, 7H), 6.53-6.42 (m, 2H), 4.91 (d, J=6.4 Hz, 1H), 4.32 (s, 1H), 3.02-2.72 (m, 3H), 2.58-1.85 (m, 6H), 1.63 (s, 2H), 1.51 (d, J=7.0 Hz, 2H), 1.29 (d, J=8.6 Hz, 4H). MS: 640.2 (M+1)⁺.

(S)—N—((S)-1-(2-Chlorophenyl)-2-((3,3-difluorocyclobutyl)amino)-2-oxoethyl)-1-(4-cyanopyridin-2-yl)-N-(3-fluoro-5-(2-hydroxypropan-2-yl)phenyl)-5-oxopyrrolidine-2-carboxamide (Single Enantiomer)—Compound 155

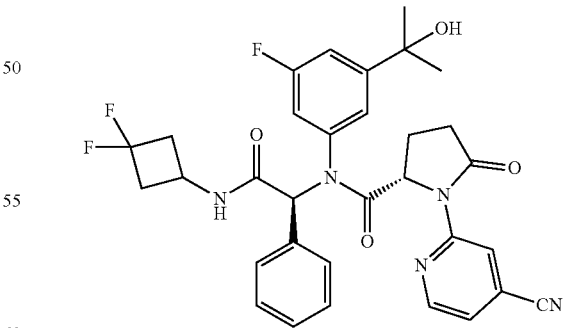

¹H NMR (400 MHz, CDCl₃): δ 8.80 (s, 1H), 8.43 (s, 1H), 7.51 (d, 1H), 7.24 (m, 4H), 7.06 (s, 3H), 6.64 (m, 1H), 6.15 (m, 1H), 5.73 (s, 1H), 4.86 (s, 1H), 4.32 (s, 1H), 3.01 (m, 3H), 2.68-2.27 (m, 4H), 2.12 (s, 1H), 1.44 (s, 1H), 1.29 (d, J=9.0 Hz, 6H). MS: 639.2 (M+1)⁺

135

(S)—N—((S)-1-(2-Chlorophenyl)-2-((3,3-difluorocyclobutyl)amino)-2-oxoethyl)-1-(4-cyanopyridin-2-yl)-N-(3-(2-hydroxyethyl)phenyl)-5-oxopyrrolidine-2-carboxamide (Single Enantiomer)—Compound 160

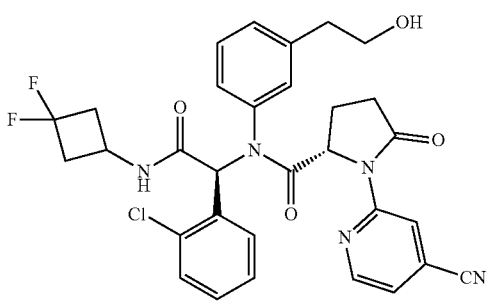 [SMILES: N#Cc1ccnc(N2C(=O)CC[C@H]2C(=O)N(c2cccc(CCO)c2)[C@H](C(=O)NC2CC(F)(F)C2)c2ccccc2Cl)c1]

¹H NMR (400 MHz, CDCl₃): δ 8.76 (s, 1H), 8.52 (d, J=5.0 Hz, 1H), 7.74 (s, 1H), 7.32-7.36 (m, 1H), 7.27-7.11 (m, 2H), 7.09-6.87 (m, 4H), 6.39-6.45 (m, 1H), 6.05 (d, J=6.9 Hz, 1H), 4.33 (s, 1H), 3.82 (s, 1H), 3.59 (s, 1H), 3.12-2.79 (m, 4H), 2.74-2.16 (m, 5H), 1.99-2.07 (m, 1H). MS: 608.2 (M+1)⁺.

(S)—N—((S)-1-(2-Chlorophenyl)-2-((3,3-difluorocyclobutyl)amino)-2-oxoethyl)-1-(4-cyano pyridin-2-yl)-N-(3-(2-hydroxyethoxy)phenyl)-5-oxopyrrolidine-2-carboxamide (Single Enantiomer)—Compound 130

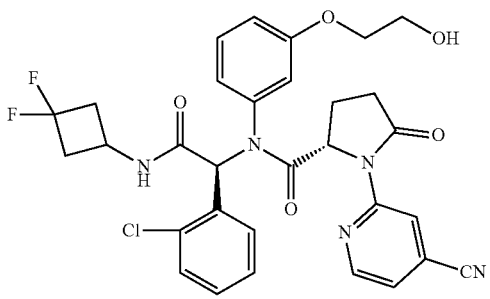 [SMILES: N#Cc1ccnc(N2C(=O)CC[C@H]2C(=O)N(c2cccc(OCCO)c2)[C@H](C(=O)NC2CC(F)(F)C2)c2ccccc2Cl)c1]

¹H NMR (400 MHz, CDCl₃): δ 8.72 (s, 1H), 8.48 (d, J=5.0 Hz, 1H), 7.54-7.28 (m, 2H), 7.18-7.21 (m, 2H), 7.01-6.94 (m, 2H), 6.75-6.77 (m, 2H), 6.39 (s, 1H), 5.99 (s, 1H), 4.94 (dd, J=9.3, 3.4 Hz, 1H), 4.31 (s, 1H), 3.79-4.06 (m, 4H), 3.07-2.80 (m, 3H), 2.58-2.21 (m, 4H), 1.87-2.00 (m, 2H). MS: 624.2 (M+1)⁺.

136

(S)—N—((S)-1-(2-Chlorophenyl)-2-(3,3-difluorocyclobutylamino)-2-oxoethyl)-1-(4-cyanopyridin-2-yl)-N-(3-fluoro-5-((S)-methylsulfinyl)phenyl)-5-oxopyrrolidine-2-carboxamide (Single Enantiomer)—Compound 190

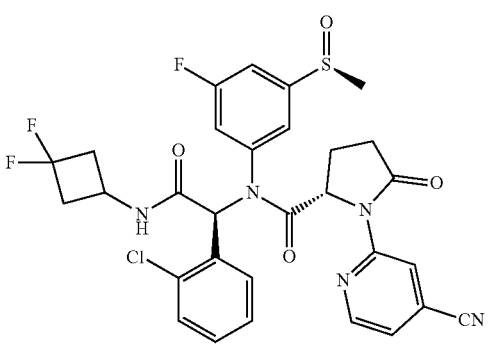 [SMILES: C[S@](=O)c1cc(F)cc(N(C(=O)[C@@H]2CCC(=O)N2c2cc(C#N)ccn2)[C@H](C(=O)NC2CC(F)(F)C2)c2ccccc2Cl)c1]

¹H NMR (400 MHz, CDCl₃): δ 8.75 (s, 1H), 8.54 (m, 1H), 8.02-7.78 (m, 1H), 7.33 (s, 3H), 7.21 (m 1H), 7.06 (t, J=7.4 Hz, 1H), 6.96 (m, 1H), 6.45 (m, 1H), 6.27 (m, 1H), 4.86 (m, 1H), 4.35 (m, 1H), 3.16-2.82 (m, 3H), 2.71 (s, 1H), 2.65-2.47 (m, 2H), 2.41 (m, 3H), 2.22 (m, 1H), 2.09 (m, 1H). MS: 644.1 (M+1)⁺.

(2S)—N-(1-(2-Chlorophenyl)-2-((3,3-difluorocyclobutyl)amino)-2-oxoethyl)-1-(4-cyanopyridin-2-yl)-N-(3-(methylsulfonyl)phenyl)-5-oxopyrrolidine-2-carboxamide (Single Enantiomer)—Compound 96

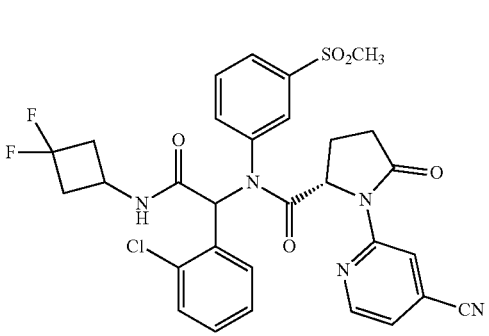 [SMILES: CS(=O)(=O)c1cccc(N(C(=O)[C@@H]2CCC(=O)N2c2cc(C#N)ccn2)C(C(=O)NC2CC(F)(F)C2)c2ccccc2Cl)c1]

¹H NMR (400 MHz, CDCl₃): δ 8.84-8.11 (m, 3H), 7.93-7.35 (m, 4H), 7.25-6.75 (m, 2H), 6.64-5.94 (m, 2H), 4.89-4.69 (m, 1H), 4.28 (d, J=5.7 Hz, 1H), 3.13-2.74 (m, 6H), 2.68-2.48 (m, 2H), 2.46-2.15 (m, 3H), 2.04 (s, 1H). MS: 642.1 (M+1)⁺.

137

(2S)—N-(1-(2-Chlorophenyl)-2-((3,3-difluorocyclobutyl)amino)-2-oxoethyl)-1-(4-cyanopyrimidin-2-yl)-N-(3-(methylsulfonyl)phenyl)-5-oxopyrrolidine-2-carboxamide (Racemic)—Compound 102

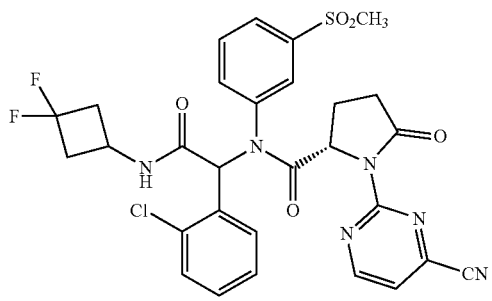 [SMILES: CS(=O)(=O)c1cccc(N(C(=O)[C@@H]2CCC(=O)N2c2nccc(C#N)n2)C(C(=O)NC2CC(F)(F)C2)c2ccccc2Cl)c1]

$^1$H NMR (400 MHz, CDCl$_3$): δ 8.93 (t, J=5.3 Hz, 1H), 8.50-8.15 (m, 1H), 7.94-7.71 (m, 2H), 7.66-7.46 (m, 1H), 7.38 (t, J=6.4 Hz, 1H), 7.28 (t, J=3.6 Hz, 1H), 7.20-7.07 (m, 1H), 7.05-6.87 (m, 2H), 6.74 (m, 1H), 6.52 (m, 1H), 4.72 (dd, J=9.2, 2.5 Hz, 1H), 4.34 (d, J=6.4 Hz, 1H), 3.00 (s, 3H), 2.90-2.75 (m, 3H), 2.56-2.19 (m, 5H), 1.98 (m, 1H). MS: 643.1 (M+1)$^+$.

138

(S)—N—((S)-1-(2C)-2-((4,4-difluorocyclohexyl)amino)-2-oxoethyl)-1-(4-cyanopyrimidin-2-yl)-N-(3-(methylsulfonyl)phenyl)-5-oxopyrrolidine-2-carboxamide (Single Enantiomer)—Compound 103

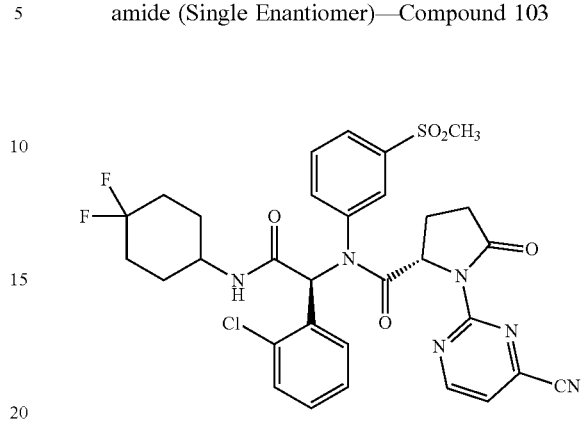

$^1$H NMR (400 MHz, CDCl$_3$): δ 8.94 (dd, J=7.9, 4.8 Hz, 1H), 8.56-8.15 (m, 1H), 7.97-7.62 (m, 2H), 7.56-7.29 (m, 3H), 7.13 (t, J=7.6 Hz, 1H), 7.06-6.84 (m, 2H), 6.51 (d, J=4.2 Hz, 1H), 6.10 (dd, J=3.2, 7.4 Hz, 1H), 4.74 (d, J=6.6 Hz, 1H), 3.98 (s, 1H), 3.01 (s, 1H), 2.93-2.72 (m, 3H), 2.52 (d, J=9.6 Hz, 1H), 2.37-2.20 (m, 1H), 2.13-1.78 (m, 7H), 1.63-1.40 (m, 2H). MS: 671 (M+1)$^+$.

(2S)—N-(1-(2-Chlorophenyl)-2-((4,4-difluorocyclohexyl)amino)-2-oxoethyl)-1-(4-cyanopyridin-2-yl)-N-(3-(methylsulfonyl)phenyl)-5-oxopyrrolidine-2-carboxamide (Racemic)—Compound 95

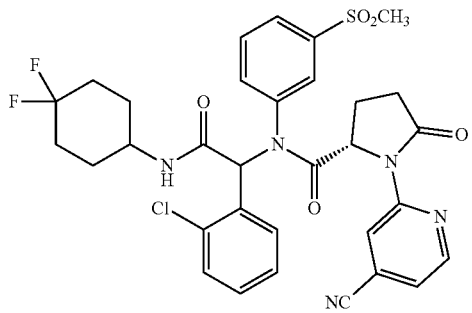

$^1$H NMR (400 MHz, CDCl$_3$): δ 8.87-8.13 (m, 3H), 8.02-7.37 (m, 4H), 7.24-6.87 (m, 2H), 6.51-6.39 (m, 1H), 5.77-5.28 (m, 1H), 4.89-4.65 (m, 1H), 3.94 (d, J=5.2 Hz, 1H), 3.16-2.73 (m, 4H), 2.68-2.53 (m, 1H), 2.44-2.20 (m, 1H), 2.03 (m, 8H), 1.44 (m, 2H). MS: 670.2 (M+1)$^+$.

(2S)—N-(1-(2-Chlorophenyl)-2-((3,3-difluorocyclobutyl)amino)-2-oxoethyl)-1-(4-cyanopyridin-2-yl)-N-(3-fluoro-5-(methylsulfonyl)phenyl)-5-oxopyrrolidine-2-carboxamide (Racemic)—Compound 110

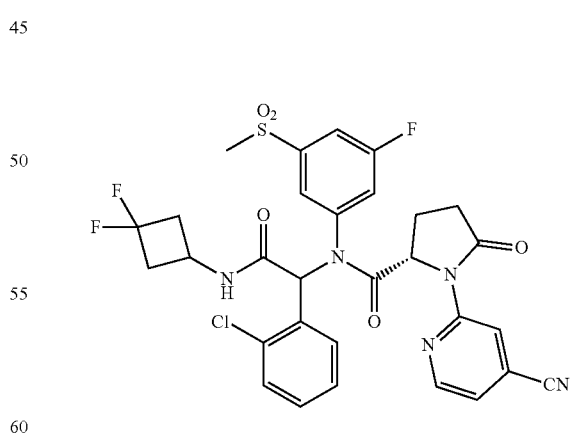

$^1$H NMR (400 MHz, CDCl$_3$): δ 8.45-8.79 (m, 2H), 8.40-8.13 (s, 1H), 8.09-7.67 (m, 1H), 7.63-7.30 (m, 2H), 7.23-6.87 (m, 3H), 6.55-6.30 (m, 1H), 6.22-5.94 (m, 1H), 4.96-4.61 (m, 1H), 4.26 (m, 4H), 3.16-1.87 (m, 7H), 1.27 (d, 1H). MS: 660.1 (M+1)$^+$.

(S)—N—((S)-1-(2-Chlorophenyl)-2-((3,3-difluoro-cyclobutyl)amino)-2-oxoethyl)-1-(4-cyanopyrimidin-2-yl)-N-(3-fluoro-5-(methylsulfonyl)phenyl)-5-oxopyrrolidine-2-carboxamide (Single Enantiomer)—Compound 109

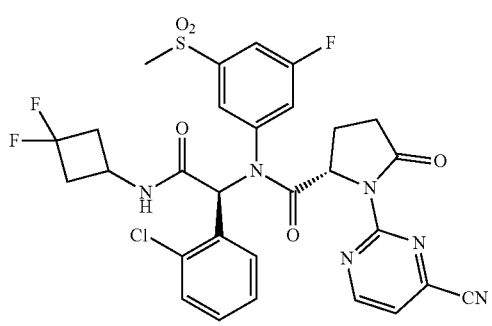 [SMILES: CS(=O)(=O)c1cc(F)cc(N(C(=O)[C@@H]2CCC(=O)N2c2nccc(C#N)n2)[C@H](C(=O)NC2CC(F)(F)C2)c2ccccc2Cl)c1]

$^1$H NMR (400 MHz, CDCl$_3$): δ 8.96 (d, J=4.6 Hz, 3H), 7.99 (d, J=8.5 Hz, 2H), 7.75 (s, 2H), 7.52 (d, J=7.0 Hz, 3H), 7.37 (d, J=4.9 Hz, 5H), 7.19 (t, J=7.7 Hz, 3H), 7.01 (dt, J=7.1 Hz, 6H), 6.40-6.60 (m, 3H), 6.06 (d, J=6.5 Hz, 3H), 4.76 (d, J=9.2 Hz, 1H), 4.35 (m, 4H), 3.14-1.87 (m, 8H). MS: 661.1 (M+1)$^+$.

(2S)—N-(1-(2-Chlorophenyl)-2-((4,4-difluorocyclohexyl)amino)-2-oxoethyl)-1-(4-cyanopyridin-2-yl)-N-(3-fluoro-5-(methylsulfonyl)phenyl)-5-oxopyrrolidine-2-carboxamide (Racemic)—Compound 105

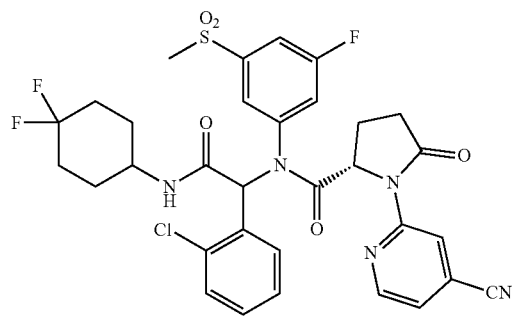 [SMILES: CS(=O)(=O)c1cc(F)cc(N(C(=O)[C@@H]2CCC(=O)N2c2cc(C#N)ccn2)C(C(=O)NC2CCC(F)(F)CC2)c2ccccc2Cl)c1]

$^1$H NMR (400 MHz, CDCl$_3$): δ 8.96 (t, J=4.6 Hz, 1H), 7.53-7.36 (m, 3H), 7.23 (m, J=7.8, 1.5 Hz, 1H), 7.14-6.94 (m, 3H), 6.68 (m, J=8.6, 2.3 Hz, 1H), 6.60 (d, J=3.1 Hz, 1H), 6.07 (d, J=6.7 Hz, 1H), 4.75 (q, J=4.0, 2.1 Hz, 1H), 4.38 (d, J=6.7 Hz, 1H), 3.78-3.67 (m, 2H), 3.39 (m, 1H), 3.26-2.92 (m, 3H), 2.67-2.36 (m, 2H). MS: 688.1 (M+1)$^+$.

(2S)—N-(1-(2-Chlorophenyl)-2-((4,4-difluorocyclohexyl)amino)-2-oxoethyl)-1-(4-cyanopyrimidin-2-yl)-N-(3-fluoro-5-(methylsulfonyl)phenyl)-5-oxopyrrolidine-2-carboxamide (Single Enantiomer)—Compound 108

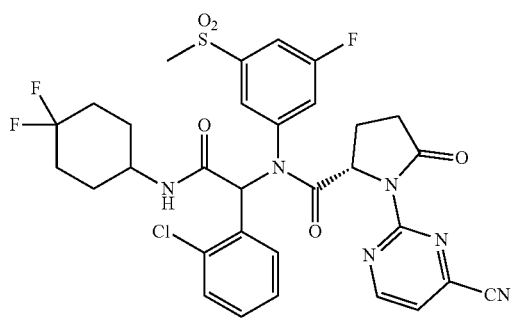 [SMILES: CS(=O)(=O)c1cc(F)cc(N(C(=O)[C@@H]2CCC(=O)N2c2nccc(C#N)n2)C(C(=O)NC2CCC(F)(F)CC2)c2ccccc2Cl)c1]

$^1$H NMR (400 MHz, CDCl$_3$): δ 8.97 (s, 1H), 8.20-8.60 (m, 1H), 8.09-7.68 (m, 1H), 7.63-7.32 (m, 5H), 7.22-6.93 (m, 3H), 6.64-6.03 (m, 2H), 5.62 (s, 1H), 4.60-4.85 (m, 1H), 3.21-1.70 (m, 12H), 1.50-1.14 (m, 2H). MS: 689.1 (M+1)$^+$.

(S)—N—((S)-1-(2-Chlorophenyl)-2-((4,4-difluorocyclohexyl)amino)-2-oxoethyl)-1-(4-cyano pyrimidin-2-yl)-N-(3-fluoro-5-(methylsulfonyl)phenyl)-5-oxopyrrolidine-2-carboxamide (Single Enantiomer)—Compound 168

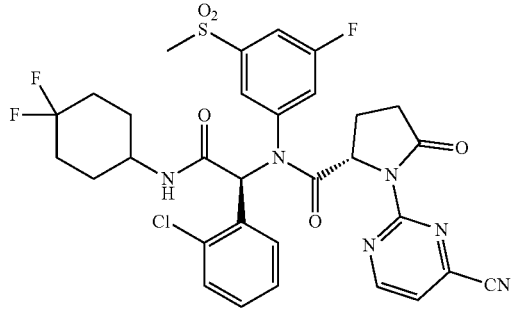 [SMILES: CS(=O)(=O)c1cc(F)cc(N(C(=O)[C@@H]2CCC(=O)N2c2nccc(C#N)n2)[C@H](C(=O)NC2CCC(F)(F)CC2)c2ccccc2Cl)c1]

$^1$H NMR (400 MHz, CDCl$_3$): δ 9.0 (s, 1H), 8.05-8.02 (m, 1H), 7.80 (m, 1H), 7.56-7.00 (m, 7H), 6.58 (m, 1H), 5.65 (m, 1H), 4.80 (m, 1H), 4.14 (m, 1H), 3.00-0.88 (m, 15H). MS: 689.1 (M+1)$^+$.

141

(S)—N—((S)-1-(2-Chlorophenyl)-2-(3,3-difluorocyclobutylamino)-2-oxoethyl)-1-(4-cyanopyridin-2-yl)-N-(3-(methylsulfonamido)phenyl)-5-oxopyrrolidine-2-carboxamide (Single Enantiomer)—Compound 159

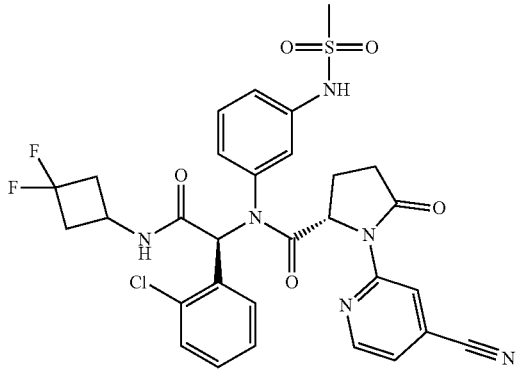 [SMILES: CS(=O)(=O)Nc1cccc(N(C(=O)[C@@H]2CCC(=O)N2c2cc(C#N)ccn2)[C@H](C(=O)NC2CC(F)(F)C2)c2ccccc2Cl)c1]

$^1$H NMR (400 MHz, DMSO-d$_6$): δ 9.78 (s, 1H), 8.84-8.61 (m, 2H), 8.56 (s, 1H), 7.66 (m, 2H), 7.49-7.15 (m, 3H), 7.15-6.79 (m, 4H), 6.25 (m, 1H), 4.89-4.74 (m, 1H), 4.19-4.04 (m, 1H), 3.03-2.83 (m, 3H), 2.72-2.59 (m, 3H), 2.54 (m, 2H), 2.44-2.28 (m, 1H), 1.99 (m, 2H). MS: 657.1 (M+1)$^+$.

(S)—N—((S)-1-(2-Chlorophenyl)-2-(3,3-difluorocyclobutylamino)-2-oxoethyl)-1-(4-cyanopyridin-2-yl)-N-(3-(dimethylamino)phenyl)-5-oxopyrrolidine-2-carboxamide (Single Enantiomer)—Compound 161

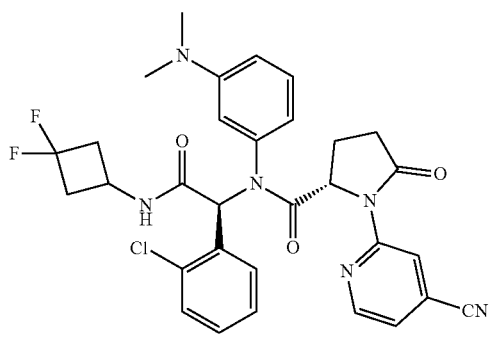 [SMILES: CN(C)c1cccc(N(C(=O)[C@@H]2CCC(=O)N2c2cc(C#N)ccn2)[C@H](C(=O)NC2CC(F)(F)C2)c2ccccc2Cl)c1]

$^1$H NMR (400 MHz, CDCl$_3$): δ 8.71 (d, J=9.9 Hz, 1H), 8.50-8.41 (m, 1H), 7.29 (d, J=7.8 Hz, 1H), 7.22 (dd, J=5.0, 1.3 Hz, 1H), 7.18-7.05 (m, 2H), 6.99-6.86 (m, 3H), 6.56-6.47 (m, 2H), 6.37 (d, J=6.6 Hz, 1H), 6.11 (s, 1H), 5.01 (d, J=9.2 Hz, 1H), 4.34-4.28 (m, 1H), 3.07-2.70 (m, 8H), 2.61-2.42 (m, 2H), 2.35-2.25 (m, 2H), 2.01-1.97 (m, 1H). MS: 607.2 (M+1)$^+$.

142

(S)—N—((S)-1-(2-Chlorophenyl)-2-((3,3-difluorocyclobutyl)amino)-2-oxoethyl)-1-(4-cyanopyridin-2-yl)-N-(2-fluorophenyl)-5-oxopyrrolidine-2-carboxamide (Single Enantiomer)—Compound 187

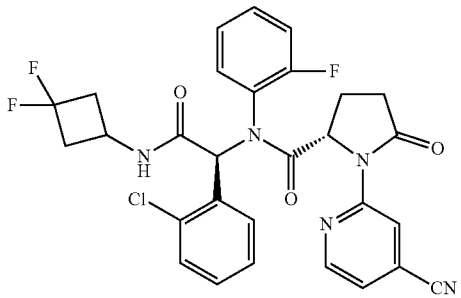 [SMILES: N#Cc1ccnc(N2C(=O)CC[C@H]2C(=O)N(c2ccccc2F)[C@H](C(=O)NC2CC(F)(F)C2)c2ccccc2Cl)c1]

$^1$H NMR (400 MHz, CDCl$_3$): δ 8.74 (m, 1H), 8.48 (m, 1H), 7.96-7.92 (m, 1H), 7.40 (m, 1H), 7.28-6.72 (m, 7H), 6.59-5.79 (m, 2H), 4.86-4.78 (m, 1H), 4.28 (s, 1H), 3.04-2.90 (m, 3H), 2.66-2.01 (m, 5H). MS: 582.1 (M+1)$^+$.

(S)—N—((S)-1-(2-Chlorophenyl)-2-((3,3-difluorocyclobutyl)amino)-2-oxoethyl)-1-(4-cyanopyridin-2-yl)-N-(2,3-difluorophenyl)-5-oxopyrrolidine-2-carboxamide (Single Enantiomer)—Compound 188

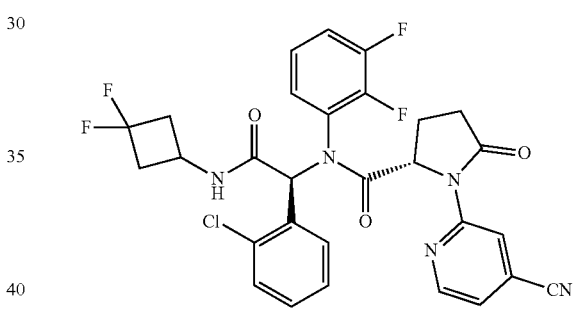

$^1$H NMR (400 MHz, CDCl$_3$): δ 8.73 (m, 1H), 8.47 (d, J=5.0 Hz, 1H), 7.84-7.73 (m, 1H), 7.43 (d, J=8.1 Hz, 1H), 7.28-7.20 (m, 2H), 7.13 (dd, J=8.2, 4.4 Hz, 2H), 7.01-6.83 (m, 2H), 6.62 (s, 1H), 6.42-5.85 (m, 1H), 4.85-4.77 (m, 1H), 4.20 (m, 1H), 3.13-2.78 (m, 3H), 2.68-2.28 (m, 4H), 2.25-2.04 (m, 1H). MS: 600.1 (M+1)$^+$.

(S)—N—((S)-1-(2-Chlorophenyl)-2-((3,3-difluorocyclobutyl)amino)-2-oxoethyl)-1-(4-cyanopyridin-2-yl)-N-(2,5-difluorophenyl)-5-oxopyrrolidine-2-carboxamide (Single Enantiomer)—Compound 197

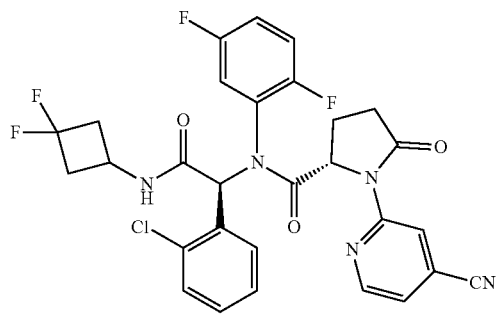 [SMILES: N#Cc1ccnc(N2C(=O)CC[C@H]2C(=O)N(c2cc(F)ccc2F)[C@H](C(=O)NC2CC(F)(F)C2)c2ccccc2Cl)c1]

¹H NMR (400 MHz, CDCl₃): δ 8.73 (m, 1H), 8.54-8.41 (m, 1H), 7.83-7.78 (m, 1H), 7.44-7.39 (m, 1H), 7.28-7.21 (m, 2H), 7.13-6.88 (m, 3H), 6.81-6.80 (m, 1H), 6.61-6.31 (m, 1H), 5.91 (d, J=6.5 Hz, 1H), 4.86-4.79 (m, 1H), 4.29 (dd, J=8.2, 6.7 Hz, 1H), 3.51 (s, 1H), 3.12-2.85 (m, 3H), 2.68-2.56 (m, 1H), 2.54-2.45 (m, 1H), 2.43-2.24 (m, 2H), 2.23-2.06 (m, 1H). MS: 600.1 (M+1)⁺.

(S)—N—((S)-1-(2-Chlorophenyl)-2-((4,4-difluorocyclohexyl)amino)-2-oxoethyl)-1-(4-cyano pyridin-2-yl)-N-(1H-indazol-5-yl)-5-oxopyrrolidine-2-carboxamide (Single Enantiomer)—Compound 203

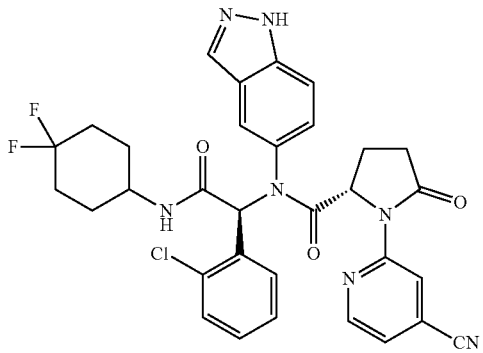 [SMILES: N#Cc1ccnc(N2C(=O)CC[C@H]2C(=O)N(c2ccc3[nH]ncc3c2)[C@H](C(=O)NC2CCC(F)(F)CC2)c2ccccc2Cl)c1]

¹H NMR (400 MHz, CDCl₃): δ 8.78 (s, 1H), 8.56 (m, 1H), 8.39 (s, 1H), 8.13-7.88 (m, 1H), 7.44-7.32 (m, 2H), 7.28-7.00 (m, 4H), 6.99-6.79 (m, 2H), 6.48 (m, 1H), 5.75-5.48 (m, 1H), 5.06-4.75 (m, 1H), 4.00 (s, 1H), 3.10-2.77 (m, 1H), 2.63-2.44 (m, 1H), 2.37-2.20 (m, 1H), 2.15-1.77 (m, 7H), 1.42 (m, 2H). MS: 632.2 (M+1)⁺.

(S)—N—((S)-1-(2-Chlorophenyl)-2-((3,3-difluorocyclobutyl)amino)-2-oxoethyl)-1-(4-cyanopyridin-2-yl)-N-(1H-indazol-6-yl)-5-oxopyrrolidine-2-carboxamide (Single Enantiomer)—Compound 205

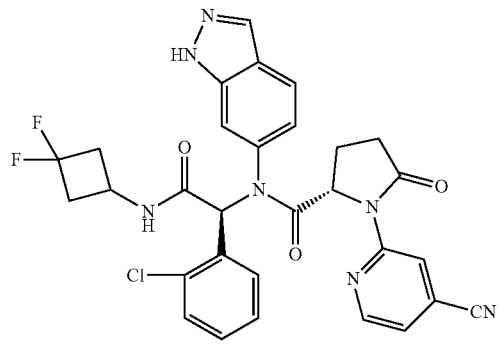 [SMILES: N#Cc1ccnc(N2C(=O)CC[C@H]2C(=O)N(c2ccc3cn[nH]c3c2)[C@H](C(=O)NC2CC(F)(F)C2)c2ccccc2Cl)c1]

¹H NMR (400 MHz, CDCl₃): δ 8.78 (s, 1H), 8.57 (t, J=5.0 Hz, 1H), 8.23-7.76 (m, 2H), 7.54-7.30 (m, 2H), 7.16 (s, 1H), 7.04-6.86 (m, 3H), 6.47 (d, J=11.7 Hz, 1H), 6.02 (d, J=6.1 Hz, 1H), 4.92 (m, 1H), 4.36 (s, 1H), 2.97 (m, 3H), 2.65-2.20 (m, 4H), 1.99 (m, 1H). MS: 604.2 (M+1)⁺.

(S)—N—((S)-1-(2-Chlorophenyl)-2-((4,4-difluorocyclohexyl)amino)-2-oxoethyl)-1-(4-cyanopyridin-2-yl)-N-(1H-indazol-6-yl)-5-oxopyrrolidine-2-carboxamide (Single Enantiomer)—Compound 136

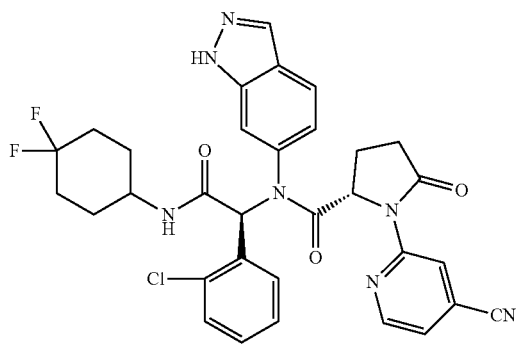 [SMILES: N#Cc1ccnc(N2C(=O)CC[C@H]2C(=O)N(c2ccc3cn[nH]c3c2)[C@H](C(=O)NC2CCC(F)(F)CC2)c2ccccc2Cl)c1]

¹H NMR (400 MHz, CDCl₃): δ 10.41-9.94 (m, 1H), 8.79 (s, 1H), 8.57 (t, J=5.1 Hz, 1H), 8.28-8.09 (m, 1H), 7.93 (m, 1H), 7.52 (s, 1H), 7.40 (d, J=7.9 Hz, 1H), 7.33 (d, J=7.5 Hz, 1H), 7.15-6.98 (m, 1H), 6.46 (d, J=12.7 Hz, 1H), 5.50 (d, J=7.9 Hz, 1H), 5.06-4.76 (m, 1H), 4.02 (s, 1H), 2.92 (dd, 1H), 2.63-2.49 (m, 1H), 2.31 (s, 1H), 2.03 (m, 6H), 1.45 (s, 2H). MS: 632.2 (M+1)⁺.

(S)—N—((S)-1-(2-Chlorophenyl)-2-((3,3-difluorocyclobutyl)amino)-2-oxoethyl)-1-(4-cyanopyridin-2-yl)-N-(1H-indazol-5-yl)-5-oxopyrrolidine-2-carboxamide (Single Enantiomer)—Compound 175

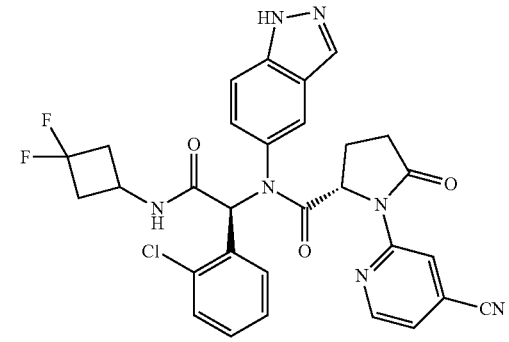 [SMILES: N#Cc1ccnc(N2C(=O)CC[C@H]2C(=O)N(c2ccc3[nH]ncc3c2)[C@H](C(=O)NC2CC(F)(F)C2)c2ccccc2Cl)c1]

¹H NMR (400 MHz, CDCl₃): δ 8.75 (s, 1H), 8.64-8.46 (m, 1H), 8.34 (s, 1H), 8.09 (s, 1H), 7.94-7.92 (m, 1H), 7.42-7.32 (m, 2H), 7.24-7.02 (m, 2H), 6.94-6.85 (m, 2H), 6.49-6.45 (m, 1H), 6.08-6.06 (m, 1H), 5.00-4.76 (m, 1H), 4.35-4.31 (s, 1H), 3.00-2.85 (m, 3H), 2.64-2.11 (m, 4H), 2.01-1.93 (m, 1H). MS: 604.2 (M+1)⁺.

(S)—N—((S)-1-(2-Chlorophenyl)-2-((3,3-difluorocyclobutyl)amino)-2-oxoethyl)-1-(4-cyano pyridin-2-yl)-N-(1H-indol-5-yl)-5-oxopyrrolidine-2-carboxamide (Single Enantiomer)—Compound 206

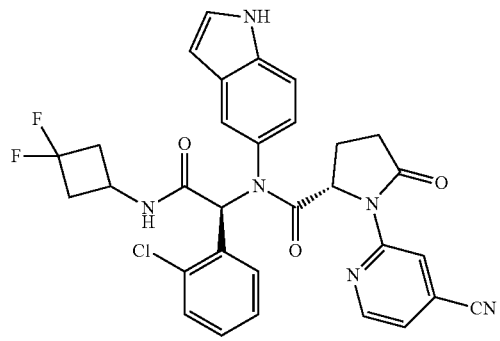 [SMILES: N#Cc1ccnc(N2C(=O)CC[C@H]2C(=O)N(c2ccc3[nH]ccc3c2)[C@H](C(=O)NC2CC(F)(F)C2)c2ccccc2Cl)c1]

¹H NMR (400 MHz, CDCl₃): δ 8.74 (s, 1H), 8.55 (m, 1H), 8.12 (d, J=13.8 Hz, 2H), 7.52-7.29 (m, 2H), 7.18-6.80 (m, 5H), 6.46 (m, 2H), 5.83 (s, 1H), 5.83 (s, 1H), 5.08-4.81 (m, 1H), 4.33 (s, 1H), 2.92 (m, 3H), 2.64-2.16 (m, 4H), 2.01 (m, 1H). MS: 603.2 (M+1)⁺.

(S)—N—((S)-1-(2-Chlorophenyl)-2-((3,3-difluorocyclobutyl)amino)-2-oxoethyl)-1-(4-cyanopyridin-2-yl)-N-(3-cyclopropylphenyl)-5-oxopyrrolidine-2-carboxamide (Single Enantiomer)—Compound 173

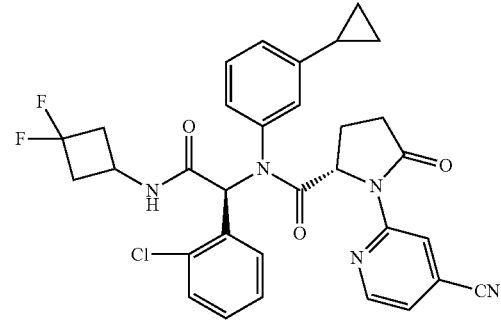

¹H NMR (400 MHz, CDCl₃): δ 8.76 (s, 1H), 8.59 (d, J=4.8 Hz, 1H), 7.50-7.60 (m, 1H), 7.41 (d, J=7.8 Hz, 1H), 7.28-7.19 (m, 2H), 7.14-6.94 (m, 2H), 6.62-6.79 (m, 1H), 6.26-6.07 (m, 2H), 4.86 (dd, J=9.3, 2.9 Hz, 1H), 4.16-4.19 (m, 1H), 3.02-2.76 (m, 3H), 2.57-2.59 (m, 1H), 2.40-2.16 (m, 3H), 2.02-2.12 (m, 1H), 1.28-1.29 (m, 2H), 0.90 (t, J=6.9 Hz, 2H). MS: 604.2 (M+1)⁺.

(S)—N—((S)-1-(2-Chlorophenyl)-2-((3,3-difluorocyclobutyl)amino)-2-oxoethyl)-1-(4-cyano pyridin-2-yl)-N-(1-methyl-1H-indol-5-yl)-5-oxopyrrolidine-2-carboxamide (Single Enantiomer)—Compound 209

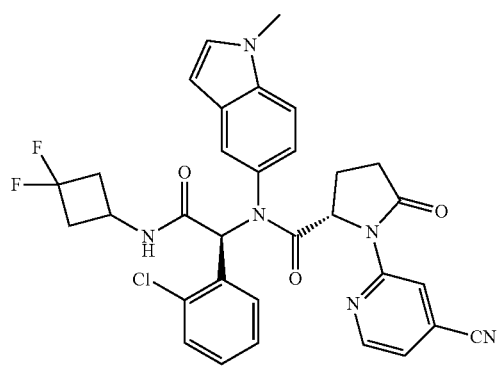 [SMILES: Cn1ccc2cc(N(C(=O)[C@@H]3CCC(=O)N3c3cc(C#N)ccn3)[C@H](C(=O)NC3CC(F)(F)C3)c3ccccc3Cl)ccc21]

¹H NMR (400 MHz, CDCl₃): δ 8.83-8.39 (m, 1H), 8.01 (m, 1H), 7.68-7.32 (m, 1H), 7.28-6.72 (m, 8H), 6.55-6.38 (m, 1H), 5.90 (m, 1H), 5.00-4.73 (m, 1H), 4.33 (s, 1H), 3.80-3.62 (m, 3H), 2.91 (m, 3H), 2.62-1.78 (m, 5H). MS: 617.2 (M+1)⁺.

(S)—N—((S)-1-(2-Chlorophenyl)-2-((3,3-difluorocyclobutyl)amino)-2-oxoethyl)-1-(4-cyanopyrimidin-2-yl)-N-(3-cyclopropylphenyl)-5-oxopyrrolidine-2-carboxamide (Single Enantiomer)—Compound 182

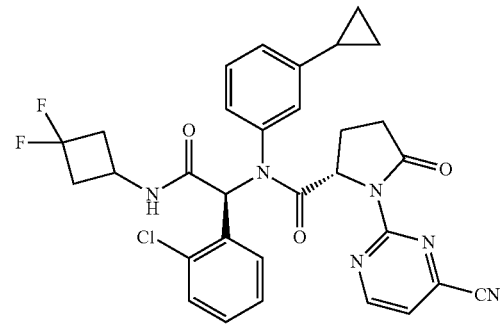 [SMILES: N#Cc1ccnc(N2C(=O)CC[C@H]2C(=O)N(c2cccc(C3CC3)c2)[C@H](C(=O)NC2CC(F)(F)C2)c2ccccc2Cl)n1]

¹H NMR (400 MHz, CDCl₃): δ 8.94 (d, J=4.5 Hz, 1H), 7.57-7.49 (m, 1H), 7.43-7.28 (m, 2H), 7.19-7.14 (m, 2H), 7.05-6.79 (m, 4H), 6.51-6.46 (m, 1H), 6.00-5.97 (m, 1H), 4.82-4.80 (m, 1H), 4.32-4.33 (m, 1H), 3.09-2.81 (m, 3H), 2.64-2.24 (m, 4H), 2.05-1.72 (m, 2H), 0.99-0.76 (m, 4H). MS: 605.2 (M+1)⁺.

147

(S)—N-(3-(tert-Butyl)phenyl)-N—((S)-1-(2-chlorophenyl)-2-((3,3-difluorocyclobutyl)amino)-2-oxoethyl)-1-(4-cyanopyrimidin-2-yl)-5-oxopyrrolidine-2-carboxamide (Single Enantiomer)—Compound 165

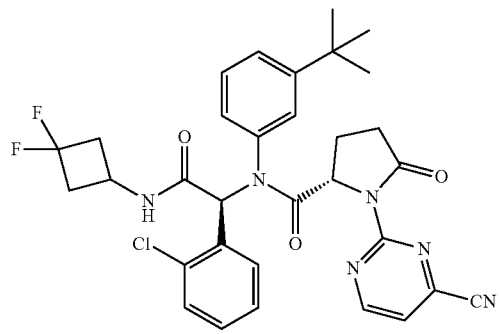 [SMILES: CC(C)(C)c1cccc(N(C(=O)[C@@H]2CCC(=O)N2c2nccc(C#N)n2)[C@H](C(=O)NC2CC(F)(F)C2)c2ccccc2Cl)c1]

$^1$H NMR (400 MHz, CDCl$_3$): δ 8.94 (d, J=4.8 Hz, 1H), 8.00-7.54 (m, 1H), 7.41-7.32 (m, 2H), 7.24-7.15 (m, 2H), 7.14-7.02 (m, 2H), 6.97-6.81 (m, 2H), 6.53 (s, 1H), 6.20 (dd, J=12.7, 6.8 Hz, 1H), 4.86 (m, 1H), 4.34 (s, 1H), 3.15-2.80 (m, 3H), 2.63-2.27 (m, 4H), 2.13-1.92 (m, 1H), 1.29 (s, 9H). MS: 621.2 (M+1)$^+$.

(S)—N—((S)-1-(2-Chlorophenyl)-2-((3,3-difluorocyclobutyl)amino)-2-oxoethyl)-1-(4-cyanopyridin-2-yl)-N-(3-cyclopropyl-5-fluorophenyl)-5-oxopyrrolidine-2-carboxamide (Single Enantiomer)—Compound 204

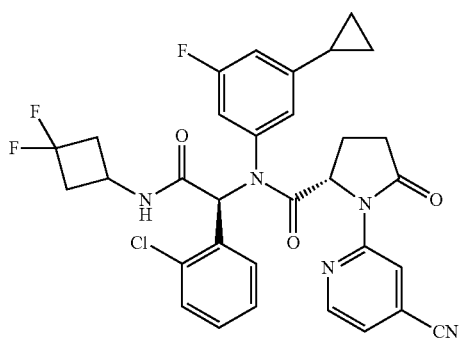 [SMILES: N#Cc1ccnc(N2C(=O)CC[C@H]2C(=O)N(c2cc(F)cc(C3CC3)c2)[C@H](C(=O)NC2CC(F)(F)C2)c2ccccc2Cl)c1]

$^1$H NMR (400 MHz, CDCl$_3$): δ 8.77 (s, 1H), 8.50 (s, 1H), 7.50-7.33 (m, 2H), 7.24-7.17 (m, 1H), 7.01 (m, 2H), 6.68 (m, 2H), 6.39 (m, 1H), 6.00 (s, 1H), 4.93 (s, 1H), 4.34 (s, 1H), 3.15-2.83 (m, 3H), 2.59-2.53 (m, 2H), 2.40-2.37 (m, 2H), 2.07 (s, 1H), 1.27 (s, 1H), 1.05 (s, 1H), 0.91 (d, J=6.7 Hz, 1H), 0.67 (s, 1H), 0.43 (m, 1H). MS: 622.2 (M+1)$^+$.

148

(S)—N—((S)-1-(2-Chlorophenyl)-2-((4,4-difluorocyclohexyl)amino)-2-oxoethyl)-1-(4-cyano pyridin-2-yl)-N-(3-cyclopropyl-5-fluorophenyl)-5-oxopyrrolidine-2-carboxamide (Single Enantiomer)—Compound 202

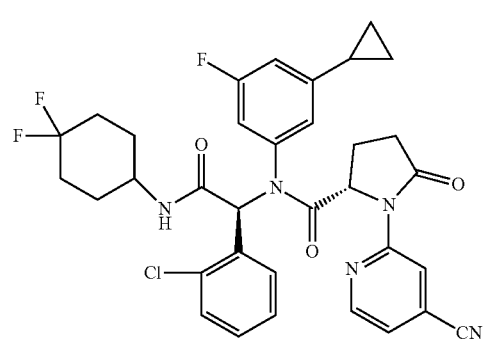 [SMILES: N#Cc1ccnc(N2C(=O)CC[C@H]2C(=O)N(c2cc(F)cc(C3CC3)c2)[C@H](C(=O)NC2CCC(F)(F)CC2)c2ccccc2Cl)c1]

$^1$H NMR (400 MHz, CDCl$_3$): δ 8.79 (s, 1H), 8.50 (s, 1H), 7.40 (m, 2H), 7.15 (m, 1H), 7.01 (m, 3H), 6.84-6.56 (m, 2H), 6.38 (m, 1H), 5.50 (s, 1H), 4.94 (s, 1H), 3.99 (s, 1H), 2.90 (m, 1H), 2.57 (m, 1H), 2.28 (s, 1H), 2.05 (m, 5H), 1.92-1.77 (m, 2H), 1.30 (m, 2H), 0.91 (t, J=6.7 Hz, 2H), 0.67 (s, 2H). MS: 650.2 (M+1)$^+$.

((S)—N—((S)-1-(2-Chlorophenyl)-2-(3,3-difluorocyclobutylamino)-2-oxoethyl)-1-(4-cyanopyridin-2-yl)-N-(3-(N-methylsulfamoyl)phenyl)-5-oxopyrrolidine-2-carboxamide (Single Enantiomer)—Compound 157

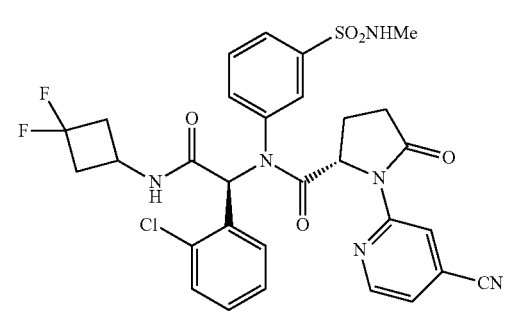

$^1$H NMR (400 MHz, CD$_3$OD): δ 8.89-8.59 (m, 3H), 8.50-8.01 (m, 2H), 7.69-7.31 (m, 5H), 7.17 (t, J=7.6 Hz, 2H), 7.03 (t, J=7.6 Hz, 2H), 6.95 (t, J=7.9 Hz, 2H), 6.51 (s, 1H), 4.98 (s, 1H), 4.24 (s, 2H), 3.01-2.45 (m, 7H), 2.35 (s, 3H), 2.10-2.05 (m, 1H). MS: 657.1 (M+1)$^+$.

149

(S)—N—((S)-1-(2-Chlorophenyl)-2-(3,3-difluorocyclobutylamino)-2-oxoethyl)-1-(4-cyanopyridin-2-yl)-N-(3-(N,N-dimethylsulfamoyl)phenyl)-5-oxopyrrolidine-2-carboxamide (Single Enantiomer)—Compound 156

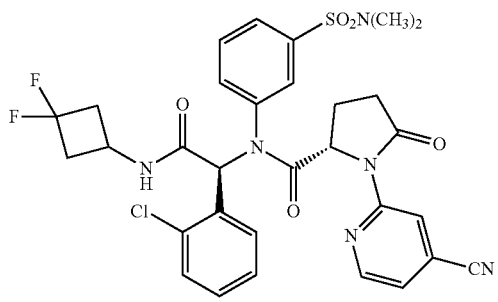

¹H NMR (400 MHz, CDCl₃): δ 8.70 (s, 1H), 8.60 (d, J=4.9 Hz, 1H), 8.17 (d, J=7.7 Hz, 1H), 7.86 (s, 1H), 7.63-7.55 (m, 1H), 7.49 (t, J=7.8 Hz, 1H), 7.27 (s, 1H), 7.20-6.92 (m, 4H), 6.50 (d, J=6.9 Hz, 2H), 4.79 (d, J=7.0 Hz, 1H), 4.32 (s, 1H), 3.05-2.75 (m, 4H), 2.60-1.90 (m, 10H). MS: 671.2 (M+1)⁺.

(S)—N—((S)-1-(2-Chlorophenyl)-2-((3,3-difluorocyclobutyl)amino)-2-oxoethyl)-1-(3-cyanopyridin-2-yl)-N-(3-fluorophenyl)-5-oxopyrrolidine-2-carboxamide (Single Enantiomer)—Compound 69

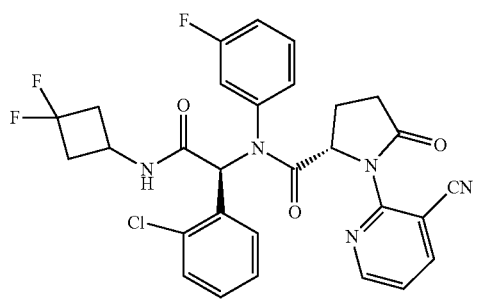 [SMILES: N#Cc1cccnc1N1C(=O)CC[C@H]1C(=O)N(c1cccc(F)c1)[C@H](C(=O)NC1CC(F)(F)C1)c1ccccc1Cl]

¹H NMR (400 MHz, CDCl₃): δ 8.14 (d, J=8.0 Hz, 1H), 7.93 (d, J=4.0 Hz, 1H), 7.92 (m, 1H), 7.17-7.28 (m, 4H), 6.91-7.04 (m, 4H), 6.42 (s, 1H), 6.31 (s, 1H), 4.87-4.91 (m, 1H), 4.35 (m, 1H), 2.97-3.02 (m, 2H), 2.79-2.86 (m, 1H), 2.45-2.57 (m, 3H), 2.23-2.26 (m, 1H), 2.09-2.11 (m, 1H). MS: 582.1 (M+1)⁺.

150

(S)—N—((S)-1-(2-Chlorophenyl)-2-((3,3-difluorocyclobutyl)amino)-2-oxoethyl)-1-(4-cyano-3-fluoropyridin-2-yl)-N-(3-fluorophenyl)-5-oxopyrrolidine-2-carboxamide (Single Enantiomer)—Compound 82

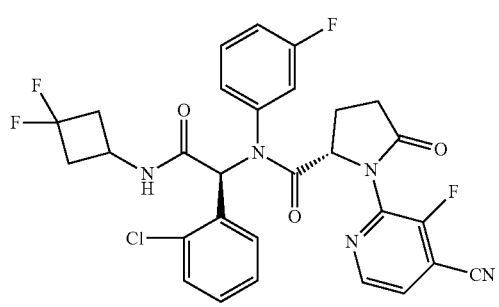 [SMILES: N#Cc1ccnc(N2C(=O)CC[C@H]2C(=O)N(c2cccc(F)c2)[C@H](C(=O)NC2CC(F)(F)C2)c2ccccc2Cl)c1F]

¹H NMR (400 MHz, DMSO-d₆): δ 8.36 (d, J=4.7 Hz, 1H), 7.70 (s, 1H), 7.39 (m, 2H), 7.25-6.63 (m, 5H), 6.39 (s, 1H), 5.96 (s, 1H), 4.85 (s, 1H), 4.34 (s, 1H), 3.12-2.69 (m, 3H), 2.64-2.01 (m, 5H). MS: 600.0 (M+1)⁺.

(S)—N—((S)-1-(2-Chlorophenyl)-2-((4,4-difluorocyclohexyl)amino)-2-oxoethyl)-1-(4-cyano-3-fluoropyridin-2-yl)-N-(3-fluorophenyl)-5-oxopyrrolidine-2-carboxamide (Single Enantiomer)—Compound 83

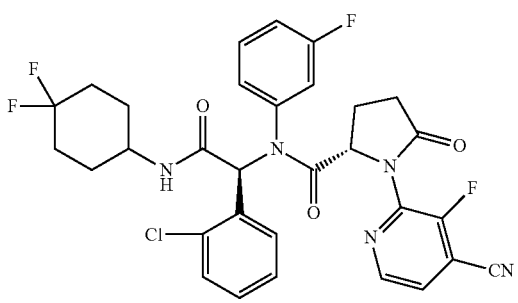 [SMILES: N#Cc1ccnc(N2C(=O)CC[C@H]2C(=O)N(c2cccc(F)c2)[C@H](C(=O)NC2CCC(F)(F)CC2)c2ccccc2Cl)c1F]

¹H NMR (400 MHz, DMSO-d₆): δ 8.37 (d, J=4.6 Hz, 1H), 7.75 (s, 1H), 7.39 (m, 2H), 7.24-6.89 (m, 4H), 6.87-6.65 (d, 1H), 6.50-6.27 (m, 1H), 5.59-5.40 (m, 1H), 4.92-4.75 (m, 1H), 4.05-3.87 (m, 1H), 2.95-2.68 (m, 1H), 2.62-2.43 (m, 1H), 2.41-2.25 (m, 1H), 2.25-2.09 (m, 2H), 2.05-1.74 (m, 4H), 1.59-1.24 (m, 3H). MS: 628.0 (M+1)⁺.

(S)—N—((S)-1-(2-Chlorophenyl)-2-((3,3-difluoro-cyclobutyl)amino)-2-oxoethyl)-1-(4-cyano-3-fluoro-pyridin-2-yl)-N-(3,5-difluorophenyl)-5-oxopyrroli-dine-2-carboxamide (Single Enantiomer)—Compound 88

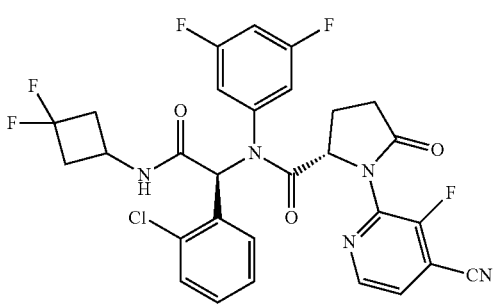 [SMILES: N#Cc1ccnc(N2C(=O)CC[C@H]2C(=O)N(c2cc(F)cc(F)c2)[C@H](C(=O)NC2CC(F)(F)C2)c2ccccc2Cl)c1F]

¹H NMR (400 MHz, DMSO-d₆): δ 8.73 (s, 1H), 8.49 (m, 1H), 7.96 (s, 1H), 7.59-7.30 (m, 3H), 7.26-6.68 (m, 6H), 6.52-6.12 (m, 1H), 5.96 (d, J=10.5 Hz, 1H), 4.95 (s, 1H), 4.63 (m, 1H), 4.49 (m, 1H), 4.22 (s, 1H), 4.14-4.02 (m, 1H), 3.46-2.65 (m, 4H), 2.55-2.00 (m, 2H), 1.69-1.49 (m, 2H). MS: 618.1 (M+1)⁺.

1H), 2.35-2.21 (m, 1H), 2.02 (m, 5H), 1.88 (m, 2H), 1.47-1.19 (m, 2H). MS: 586.2 (M+1)⁺.

2-((S)-1-(2-Chlorophenyl)-2-((3,3-difluorocyclobu-tyl)amino)-2-oxoethyl)(3-fluorophenyl)carbamoyl)-4-hydroxypyrrolidine-1-carboxylate (Single Enantiomer)—Compound 74

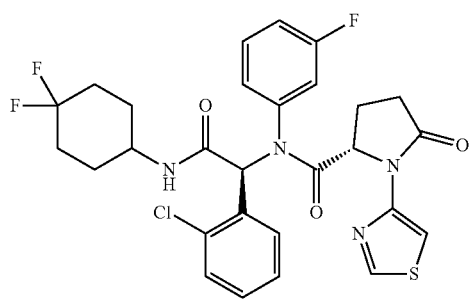 [SMILES: O=C(NC1CCC(F)(F)CC1)[C@H](c1ccccc1Cl)N(C(=O)[C@@H]1CCC(=O)N1c1cscn1)c1cccc(F)c1]

¹H NMR (400 MHz, CDCl₃): δ 8.60 (s, 1H), 7.89 (s, 1H), 7.71 (s, 1H), 7.45-7.29 (m, 2H), 7.25-6.86 (m, 5H), 6.41 (s, 1H), 5.54 (s, 1H), 4.98 (s, 1H), 3.98 (s, 1H), 3.16-2.66 (m, 2H), 2.51 (s, 1H), 2.26 (s, 1H), 1.98 (m, 7H), 1.55 (m, 3H). MS: 591.1 (M+1)⁺.

(S)—N—((S)-1-(2-Chlorophenyl)-2-(4,4-difluorocy-clohexylamino)-2-oxoethyl)-N-(3-fluorophenyl)-5-oxo-1-(pyrazin-2-yl)pyrrolidine-2-carboxamide (Single Enantiomer)—Compound 58

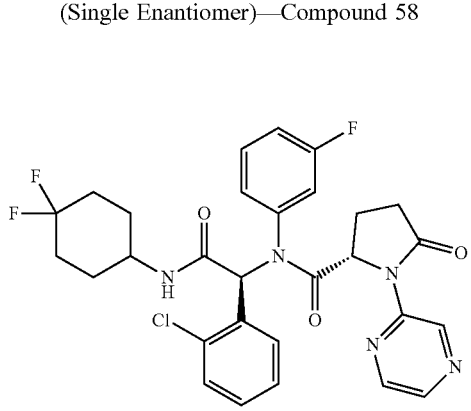

¹H NMR (400 MHz, CDCl₃): δ 9.74 (d, J=1.5 Hz, 1H), 8.32 (m, 2H), 7.71 (s, 1H), 7.36 (m, 1H), 7.16 (m, 1H), 6.97 (m, 4H), 6.41 (s, 1H), 5.44 (d, J=7.0 Hz, 1H), 4.85 (d, J=6.0 Hz, 1H), 3.96 (m, 1H), 2.98-2.82 (m, 1H), 2.61-2.48 (m, (S)—N—((S)-1-(2-Chlorophenyl)-2-((4,4-difluoro-cyclohexyl)amino)-2-oxoethyl)-N-(3-fluoro-phenyl)-2-oxo-3-(pyrimidin-2-yl)oxazolidine-4-carboxamide (Single Enantiomer)—Compound 76

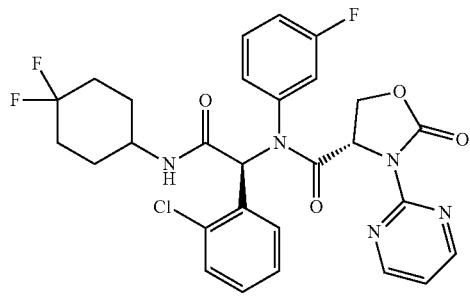 [SMILES: O=C(NC1CCC(F)(F)CC1)[C@H](c1ccccc1Cl)N(C(=O)[C@@H]1COC(=O)N1c1ncccn1)c1cccc(F)c1]

¹H NMR (400 MHz, CDCl₃): δ 8.70 (d, J=4.7 Hz, 2H), 7.67 (d, J=8.0 Hz, 1H), 7.43-7.31 (m, 1H), 7.19 (d, J=7.3 Hz, 1H), 7.13-6.86 (m, 5H), 6.46 (s, 1H), 5.58 (d, J=6.8 Hz, 1H), 5.02 (d, J=4.4 Hz, 1H), 4.47 (dd, J=8.7, 5.0 Hz, 1H), 4.24-4.13 (m, 1H), 3.98 (s, 1H), 2.14-1.79 (m, 6H), 1.57-1.41 (m, 2H). MS: 588.2 (M+1)⁺.

(S)—N—((S)-1-(2-Chlorophenyl)-2-(3,3-difluorocyclobutylamino)-2-oxoethyl)-3-(4-cyanopyridin-2-yl)-N-(3-fluorophenyl)-2-oxooxazolidine-4-carboxamide (Single Enantiomer)—Compound 77

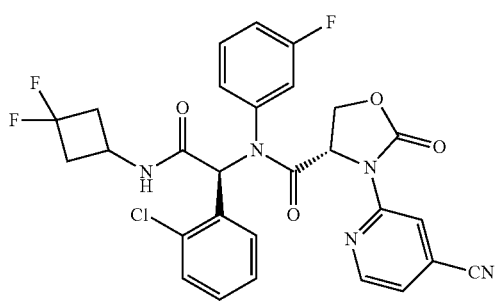 [SMILES: N#Cc1ccnc(N2C(=O)OC[C@H]2C(=O)N(c2cccc(F)c2)[C@H](C(=O)NC2CC(F)(F)C2)c2ccccc2Cl)c1]

¹H NMR (400 MHz, CDCl₃): δ 8.48 (s, 1H), 7.62 (d, J=7.9 Hz, 1H), 7.33 (d, J=8.9 Hz, 1H), 7.19 (d, J=7.2 Hz, 2H), 7.10-6.85 (m, 5H), 6.44 (d, J=5.1 Hz, 1H), 6.20-6.08 (m, 1H), 5.01 (m, 1H), 4.46 (dd, J=8.7, 4.7 Hz, 1H), 4.31-4.20 (m, 2H), 3.09-2.91 (m, 2H), 2.58-2.30 (m, 2H). MS: 584.1 (M+1)⁺.

(S)—N—((S)-1-(2-Chlorophenyl)-2-((4,4-difluorocyclohexyl)amino)-2-oxoethyl)-3-(4-cyano-pyridin-2-yl)-N-(3-fluorophenyl)-2-oxooxazolidine-4-carboxamide (Single Enantiomer)—Compound 78

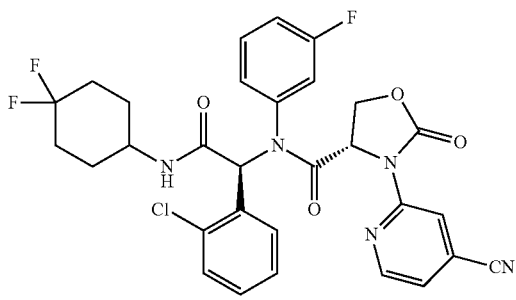 [SMILES: N#Cc1ccnc(N2C(=O)OC[C@H]2C(=O)N(c2cccc(F)c2)[C@H](C(=O)NC2CCC(F)(F)CC2)c2ccccc2Cl)c1]

¹H NMR (400 MHz, CDCl₃): δ 8.55 (s, 1H), 8.50 (t, J=5.8 Hz, 1H), 7.67 (d, J=8.5 Hz, 1H), 7.43-7.29 (m, 2H), 7.20 (d, J=7.6 Hz, 1H), 7.15-6.89 (m, 4H), 6.43 (d, J=4.4 Hz, 1H), 5.54 (d, J=7.9 Hz, 1H), 5.06 (d, J=4.7 Hz, 1H), 4.51 (dd, J=8.8, 5.0 Hz, 1H), 4.25 (m, 1H), 3.98 (s, 1H), 2.19-1.74 (m, 6H), 1.49 (m, 2H). MS: 612.2 (M+1)⁺.

(S)—N—((S)-1-(2-Chlorophenyl)-2-(3,3-difluorocyclobutylamino)-2-oxoethyl)-N-(3-cyano-5-fluorophenyl)-3-(3-cyanophenyl)-2-oxooxazolidine-4-carboxamide (Single Enantiomer)—Compound 134

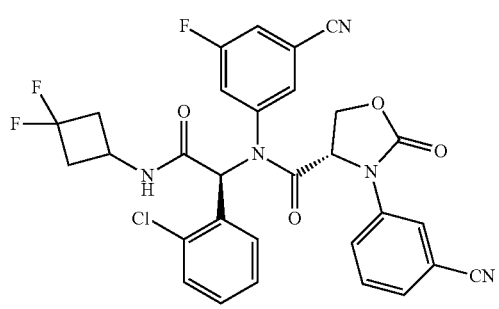 [SMILES: N#Cc1cc(F)cc(N(C(=O)[C@@H]2COC(=O)N2c2cccc(C#N)c2)[C@H](C(=O)NC2CC(F)(F)C2)c2ccccc2Cl)c1]

¹H NMR (400 MHz, CDCl₃): δ 8.51-8.47 (m, 1H), 8.39-8.37 (d, 0.5H), 8.07-7.99 (m, 1H), 7.38 (s, 0.5H), 7.33-7.31 (m, 1H), 7.26-7.22 (m, 1H), 7.08-7.07 (m, 1H), 6.90-6.87 (m, 1H), 6.53-6.46 (m, 2H), 4.94-4.91 (m, 1H), 4.44-4.40 (m, 1H). 4.34-4.32 (m, 1H), 4.28-4.23 (m, 1H), 3.00-2.99 (m, 2H), 2.50-2.43 (m, 2H). MS: 608.1 (M+1)⁺.

(S)—N—((S)-1-(2-Chlorophenyl)-2-((3,3-difluorocyclobutyl)amino)-2-oxoethyl)-3-(4-cyanopyridin-2-yl)-N-(5-fluoropyridin-3-yl)-2-oxooxazolidine-4-carboxamide (Single Enantiomer)—Compound 135

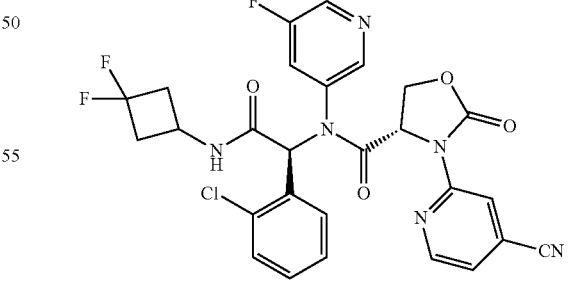

¹H NMR (400 MHz, CDCl₃): δ 8.58-8.28 (m, 3H), 8.08 (d, J=8.5 Hz, 1H), 7.32 (dd, J=5.1, 1.0 Hz, 2H), 7.28-7.20 (m, 1H), 7.07 (m, 1H), 6.91 (m, 1H), 6.66-6.22 (m, 2H), 5.05-4.85 (m, 1H), 4.57-4.09 (m, 3H), 3.02 (m, 2H), 2.69-2.30 (m, 2H). MS: 585.1 (M+1)⁺.

155

(S)—N—((S)-1-(2-Chlorophenyl)-2-((4,4-difluorocyclohexyl)amino)-2-oxoethyl)-3-(4-cyanopyridin-2-yl)-N-(5-fluoropyridin-3-yl)-2-oxooxazolidine-4-carboxamide (Single Enantiomer)—Compound 132

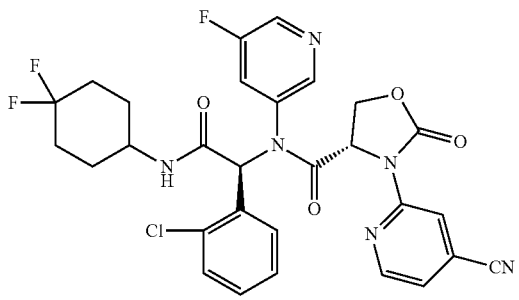 [SMILES: N#Cc1ccnc(N2C(=O)OC[C@H]2C(=O)N(c2cncc(F)c2)[C@H](C(=O)NC2CCC(F)(F)CC2)c2ccccc2Cl)c1]

¹H NMR (400 MHz, CDCl₃): δ 8.91 (s, 1H), 8.41 (m, 4H), 8.11 (s, 1H), 7.23 (s, 1H), 7.05 (s, 1H), 6.91 (s, 1H), 6.52 (m, 1H), 6.05 (m, 1H), 4.95 (m, 1H), 4.37 (m, 2H), 3.95 (s, 1H), 1.71 (m, 10H). MS: 613.2 (M+1)⁺.

(S)—N—((S)-1-(2-Chlorophenyl)-2-((3,3-difluorocyclobutyl)amino)-2-oxoethyl)-N-(3-fluoro phenyl)-2-oxo-3-(thiazol-4-yl)oxazolidine-4-carboxamide (Single Enantiomer)—Compound 72

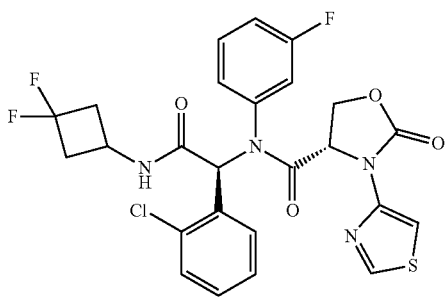 [SMILES: O=C(NC1CC(F)(F)C1)[C@H](c1ccccc1Cl)N(C(=O)[C@@H]1COC(=O)N1c1cscn1)c1cccc(F)c1]

¹H NMR (400 MHz, CDCl₃): δ 8.70-8.47 (m, 1H), 7.69-7.52 (m, 1H), 7.49 (d, J=2.0 Hz, 1H), 7.42-7.26 (m, 1H), 7.25-6.84 (m, 5H), 6.42 (s, 1H), 6.21-6.02 (m, 1H), 5.03 (d, J=4.6 Hz, 1H), 4.42 (m, 1H), 4.38-4.05 (m, 2H), 2.98 (m, 2H), 2.64-2.29 (m, 2H). MS: 565.1 (M+1)⁺.

(4S)—N-(1-(2-Chlorophenyl)-2-(3,3-difluorocyclobutylamino)-2-oxoethyl)-3-(4-cyanopyridin-2-yl)-N-(3-fluoro-5-(2-hydroxypropan-2-yl)phenyl)-2-oxooxazolidine-4-carboxamide (Racemic)—Compound 145

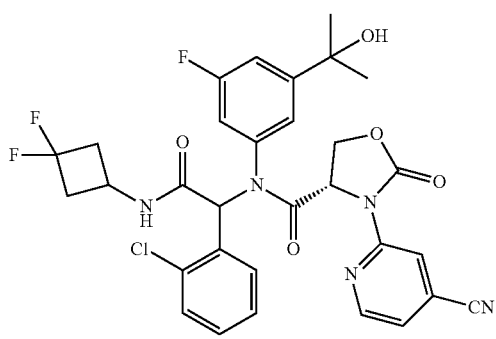 [SMILES: CC(C)(O)c1cc(F)cc(N(C(=O)[C@@H]2COC(=O)N2c2cc(C#N)ccn2)C(C(=O)NC2CC(F)(F)C2)c2ccccc2Cl)c1]

156

¹H NMR (400 MHz, CDCl₃): δ 8.63-8.50 (m, 1H), 8.42 (m, 1H), 7.48-7.40 (m, 1H), 7.29 (d, J=7.0 Hz, 2H), 7.25-7.19 (m, 2H), 7.14-6.95 (m, 3H), 6.89 (m, 1H), 6.67 (d, J=6.9 Hz, 1H), 6.54-6.42 (m, 1H), 5.11-4.96 (m, 1H), 4.51-4.40 (m, 1H), 4.32 (d, J=9.1 Hz, 1H), 4.24-4.09 (m, 1H), 3.12-2.73 (m, 2H), 1.52 (m, 2H), 1.32 (d, J=9.0 Hz, 4H). MS: 642.2 (M+1)⁺.

(4S)—N-(1-(2-Chlorophenyl)-2-(3,3-difluorocyclobutylamino)-2-oxoethyl)-3-(4-cyanopyridin-2-yl)-N-(3-fluorophenyl)-2-oxo-1,3-oxazinane-4-carboxamide (Racemic)—Compound 90

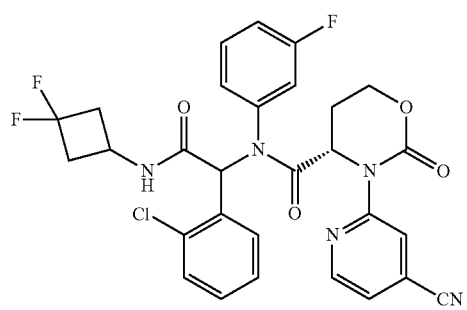 [SMILES: N#Cc1ccnc(N2C(=O)OCC[C@H]2C(=O)N(c2cccc(F)c2)C(C(=O)NC2CC(F)(F)C2)c2ccccc2Cl)c1]

¹H NMR (400 MHz, CDCl₃): δ 8.57 (s, 1H), 8.40 (s, 1H), 7.68 (d, J=8.0 Hz, 1H), 7.25-6.91 (m, 8H), 6.48 (s, 1H), 6.25 (s, 1H), 5.08 (s, 1H), 4.51-4.46 (m, 1H), 4.31 (m, 2H), 3.01 (m, 2H), 2.53-2.50 (m, 2H), 2.29-2.13 (m, 2H). MS: 598.1 (M+1)⁺.

(S)—N—((S)-1-(2-Chlorophenyl)-2-((3,3-difluorocyclobutyl)amino)-2-oxoethyl)-3-(4-cyanopyridin-2-yl)-N-(3,5-difluorophenyl)-2-oxo-1,3-oxazinane-4-carboxamide (Single Enantiomer)—Compound 133

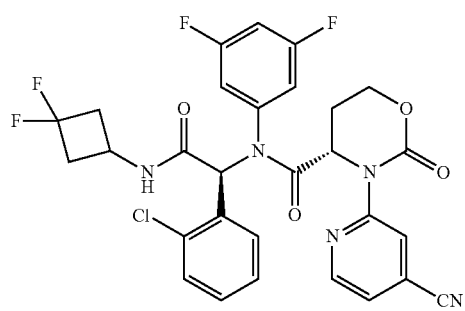 [SMILES: N#Cc1ccnc(N2C(=O)OCC[C@H]2C(=O)N(c2cc(F)cc(F)c2)[C@H](C(=O)NC2CC(F)(F)C2)c2ccccc2Cl)c1]

¹H NMR (400 MHz, CDCl₃): δ 8.55 (d, J=5.0 Hz, 1H), 8.34 (s, 1H), 7.54 (d, J=8.4 Hz, 1H), 7.31 (dd, J=5.0, 1.1 Hz, 1H), 7.26-7.16 (m, 2H), 7.13-7.04 (m, 1H), 6.98 (t, J=6.6 Hz, 2H), 6.72-6.63 (m, 1H), 6.49 (s, 1H), 6.44 (d, J=6.9 Hz, 1H), 5.11 (dd, J=6.4, 3.5 Hz, 1H), 4.51-4.22 (m, 3H), 2.98-3.04 (m, 2H), 2.67-2.41 (m, 2H), 2.33-2.09 (m, 2H). MS: 627.2 (M+1)⁺.

(S)—N—((S)-1-(2-Chlorophenyl)-2-((4,4-difluorocyclohexyl)amino)-2-oxoethyl)-3-(4-cyano pyridin-2-yl)-N-(3,5-difluorophenyl)-2-oxo-1,3-oxazinane-4-carboxamide (Single Enantiomer)—Compound 139

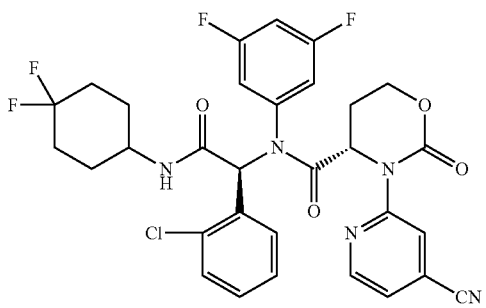 [SMILES: N#Cc1ccnc(N2C(=O)OCC[C@H]2C(=O)N(c2cc(F)cc(F)c2)[C@H](C(=O)NC2CCC(F)(F)CC2)c2ccccc2Cl)c1]

¹H NMR (400 MHz, CDCl₃): δ 8.64 (d, J=5.0 Hz, 1H), 8.47 (s, 1H), 7.45 (d, J=7.4 Hz, 1H), 7.38-7.30 (m, 2H), 7.24 (d, J=7.1 Hz, 1H), 7.15-7.12 (m, 1H), 6.81-6.77 (m, 1H), 6.06 (s, 1H), 5.51 (d, J=7.5 Hz, 1H), 5.05-4.88 (m, 1H), 4.62-4.56 (m, 1H), 4.42-4.30 (m, 1H), 3.87 (s, 1H), 2.35-2.15 (m, 2H), 1.97-1.79 (m, 5H), 1.40 (m, 2H). MS: 643.2 (M+1)⁺.

(S)—N—((S)-1-(2-Chlorophenyl)-2-((4,4-difluorocyclohexyl)amino)-2-oxoethyl)-3-(4-cyano pyrimidin-2-yl)-N-(3,5-difluorophenyl)-2-oxo-1,3-oxazinane-4-carboxamide (Single Enantiomer)—Compound 144

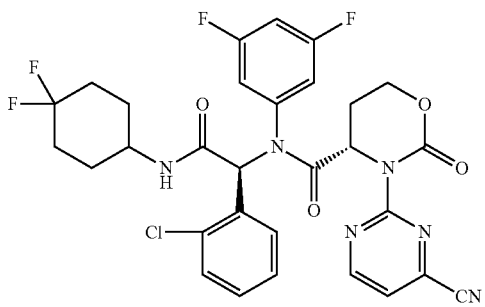 [SMILES: N#Cc1ccnc(N2C(=O)OCC[C@H]2C(=O)N(c2cc(F)cc(F)c2)[C@H](C(=O)NC2CCC(F)(F)CC2)c2ccccc2Cl)n1]

¹H NMR (400 MHz, CDCl₃): δ 8.96 (d, J=4.7 Hz, 1H), 7.56 (d, J=10.0 Hz, 1H), 7.41 (dd, J=9.7, 6.4 Hz, 2H), 7.24-7.22 (m, 1H), 7.14-6.95 (m, 3H), 6.70 (t, J=8.6 Hz, 1H), 6.52 (s, 1H), 5.53 (d, J=7.6 Hz, 1H), 4.96 (dd, J=7.8, 4.0 Hz, 1H), 4.46 (d, J=8.8 Hz, 1H), 4.31 (dd, J=10.7, 5.1 Hz, 1H), 3.99 (s, 1H), 2.49-2.31 (m, 1H), 2.29-2.01 (m, 5H), 1.98-1.78 (m, 2H), 1.49 (dd, J=17.9, 8.5 Hz, 1H). MS: 645.2 (M+1)⁺.

(S)—N—((S)-1-(2-Chlorophenyl)-2-((3,3-difluorocyclobutyl)amino)-2-oxoethyl)-3-(4-cyanopyrimidin-2-yl)-N-(3,5-difluorophenyl)-2-oxo-1,3-oxazinane-4-carboxamide (Single Enantiomer)—Compound 154

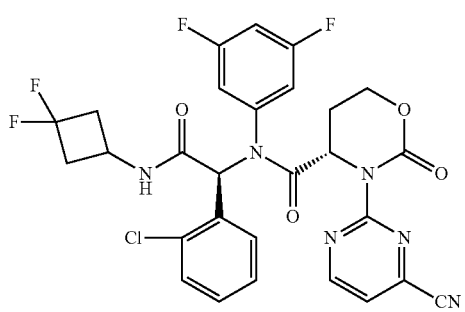 [SMILES: N#Cc1ccnc(N2C(=O)OCC[C@H]2C(=O)N(c2cc(F)cc(F)c2)[C@H](C(=O)NC2CC(F)(F)C2)c2ccccc2Cl)n1]

¹H NMR (400 MHz, CDCl₃): δ 8.89 (d, J=4.8 Hz, 1H), 7.52 (d, J=8.9 Hz, 1H), 7.40 (d, J=4.8 Hz, 1H), 7.22 (dd, J=8.0, 1.2 Hz, 1H), 7.16-7.15 (m, 1H), 7.08-6.97 (m, 2H), 6.94 (dd, J=7.7, 1.5 Hz, 1H), 6.66 (dd, J=9.7, 7.4 Hz, 1H), 6.56 (s, 1H), 6.43 (d, J=6.8 Hz, 1H), 4.91 (dd, J=8.3, 4.5 Hz, 1H), 4.41-4.33 (m, 2H), 4.24-4.20 (m, 1H), 3.06-2.86 (m, 2H), 2.66-2.42 (m, 2H), 2.39-2.25 (m, 1H), 2.24-2.12 (m, 1H). MS: 617.2 (M+1)⁺.

(S)—N—((S)-1-(2-Chlorophenyl)-2-((3,3-difluorocyclobutyl)amino)-2-oxoethyl)-3-(4-cyano pyridin-2-yl)-N-(5-fluoropyridin-3-yl)-2-oxo-1,3-oxazinane-4-carboxamide (Single Enantiomer)—Compound 143

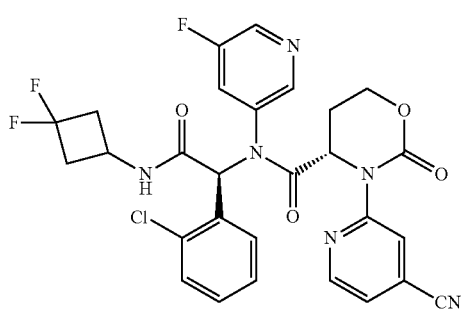 [SMILES: N#Cc1ccnc(N2C(=O)OCC[C@H]2C(=O)N(c2cncc(F)c2)[C@H](C(=O)NC2CC(F)(F)C2)c2ccccc2Cl)c1]

¹H NMR (400 MHz, CDCl₃): δ 9.08-7.79 (m, 3H), 7.62-6.70 (m, 5H), 6.50 (m, 2H), 4.95 (m, 1H), 4.62-4.03 (m, 3H), 2.99 (s, 2H), 2.51 (s, 2H), 2.18 (m, 2H). MS: 599.1 (M+1)⁺.

(S)—N—((S)-1-(2-Chlorophenyl)-2-((4,4-difluorocyclohexyl)amino)-2-oxoethyl)-3-(4-cyano-pyridin-2-yl)-N-(5-fluoropyridin-3-yl)-2-oxo-1,3-oxazinane-4-carboxamide (Single Enantiomer)—Compound 137

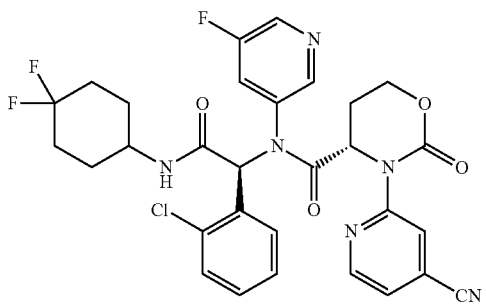 [SMILES: N#Cc1ccnc(N2C(=O)OCC[C@H]2C(=O)N(c2cncc(F)c2)[C@H](C(=O)NC2CCC(F)(F)CC2)c2ccccc2Cl)c1]

¹H NMR (400 MHz, CDCl₃): δ 8.43-8.90 (m, 3H), 8.30 (s, 1H), 7.49-8.13 (m, 1H), 7.29-7.31 (m, 2H), 7.17-7.21 (m, 1H), 6.94-7.08 (m, 2H), 6.45-6.53 (m, 1H), 5.80-593 (m, 1H), 4.96-5.00 (m, 1H), 4.47-4.51 (m, 1H), 4.30-4.33 (m, 1H), 3.96-3.98 (m, 1H), 2.09-2.28 (m, 6H), 1.83-1.95 (m, 2H), 1.49-1.63 (m, 2H). MS: 627.2 (M+1)⁺.

(S)—N—((S)-1-(2-Chlorophenyl)-2-(3,3-difluorocyclobutylamino)-2-oxoethyl)-3-(4-cyanopyridin-2-yl)-N-(3-fluoro-5-(2-hydroxypropan-2-yl)phenyl)-2-oxo-1,3-oxazinane-4-carboxamide (Single Enantiomer)—Compound 146

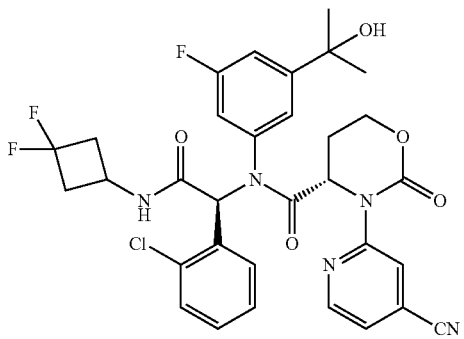 [SMILES: CC(C)(O)c1cc(F)cc(N(C(=O)[C@@H]2CCOC(=O)N2c2cc(C#N)ccn2)[C@H](C(=O)NC2CC(F)(F)C2)c2ccccc2Cl)c1]

¹H NMR (400 MHz, CDCl₃): δ 8.56 (t, J=6.0 Hz, 1H), 8.36 (s, 1H), 7.72-7.45 (m, 1H), 7.23-7.16 (m, 1H), 7.12 (t, J=7.1 Hz, 1H), 7.06-6.86 (m, 3H), 6.38 (s, 1H), 6.28 (d, J=6.9 Hz, 1H), 5.17-5.01 (m, 1H), 4.50-4.44 (m, 1H), 4.30 (m, 2H), 2.99 (d, J=7.8 Hz, 2H), 2.62-2.37 (m, 2H), 2.36-2.06 (m, 2H), 1.49 (d, J=6.2 Hz, 2H), 1.32 (m, 4H). MS: 656.2 (M+1)⁺.

(S)—N—((S)-1-(2-Chlorophenyl)-2-(3,3-difluorocyclobutylamino)-2-oxoethyl)-1-(4-cyanopyridin-2-yl)-N-(3-fluorophenyl)-6-oxopiperidine-2-carboxamide (Single Enantiomer)—Compound 55

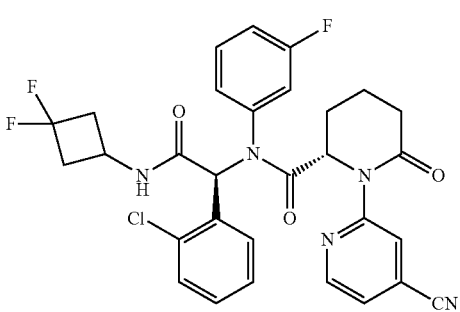

¹H NMR (400 MHz, CDCl₃): δ 8.59 (s, 1H), 8.28 (s, 1H), 7.72 (d, J=7.2 Hz, 1H), 7.43-7.33 (m, 1H) 7.26-7.12 (m, 2H), 7.11-6.96 (m, 2H), 6.89 (dd, J=8.3, 2.2 Hz, 1H), 6.46 (s, 1H), 6.27 (s, 1H), 5.00 (t, J=4.6 Hz, 1H), 4.37-4.28 (m, 1H), 3.13-2.95 (m, 2H), 2.78-2.69 (m, 1H), 2.62-2.35 (m, 3H), 2.15-2.09 (m, 1H), 2.05-1.92 (m, 1H), 1.89-1.70 (m, 3H). MS: 596.2 (M+1)⁺.

(S)—N—((S)-1-(2-Chlorophenyl)-2-((4,4-difluorocyclohexyl)amino)-2-oxoethyl)-1-(4-cyano-pyridin-2-yl)-N-(3-fluorophenyl)-6-oxopiperidine-2-carboxamide (Single Enantiomer)—Compound 75

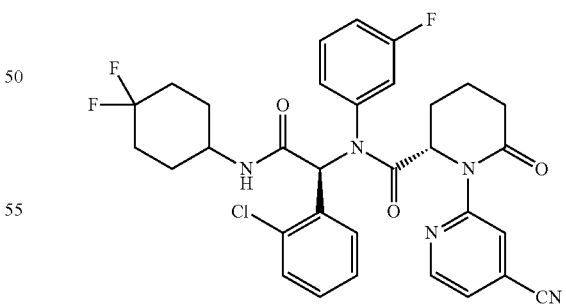

¹H NMR (400 MHz, CDCl₃): δ 8.60 (s, 1H), 8.31 (s, 1H), 7.73-7.75 (m, 1H), 7.30 (m, 1H), 7.00-7.17 (m, 5H), 6.87-6.91 (m, 1H), 6.45 (s, 1H), 5.50 (d, J=7.0 Hz, 1H), 5.00-5.02 (m, 1H), 3.99 (m, 1H), 2.60-2.74 (m, 1H), 2.58-2.60 (m, 1H), 2.01-2.14 (m, 6H), 1.83-1.92 (m, 4H), 1.42-1.46 (m, 3H). MS: 624.2 (M+1)⁺.

161

(2S,4R)—N—((S)-1-(2-Chlorophenyl)-2-((4,4-difluorocyclohexyl)amino)-2-oxoethyl)-1-(4-cyanopyridin-2-yl)-4-fluoro-N-(3-fluorophenyl)-5-oxopyrrolidine-2-carboxamide (Single Enantiomer)— Compound 151

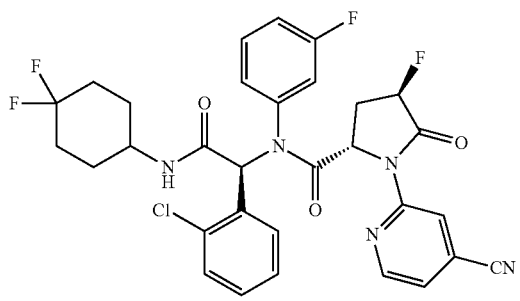 [SMILES: N#Cc1ccnc(N2C(=O)[C@H](F)C[C@H]2C(=O)N(c2cccc(F)c2)[C@H](C(=O)NC2CCC(F)(F)CC2)c2ccccc2Cl)c1]

$^1$H NMR (400 MHz, CDCl$_3$): δ 8.75 (s, 1H), 8.57 (s, 1H), 7.76 (s, 1H), 7.36 (m, 2H), 7.06 (m, 6H), 6.39 (s, 1H), 5.51 (d, J=6.6 Hz, 1H), 5.12 (m, 1H), 4.82 (s, 1H), 3.91 (m, 1H), 2.69-2.26 (m, 2H), 2.05 (m, 6H), 1.53-1.38 (m, 2H). MS: 628.2 (M+1)$^+$.

Example 9. Preparation of (2S)—N-(1-(2-Chlorophenyl)-2-((3,3-difluorocyclobutyl)amino)-2-oxoethyl)-1-(4-cyanopyridin-2-yl)-N-(3,5-dicyanophenyl)-5-oxopyrrolidine-2-carboxamide (Racemic)— Compound 191

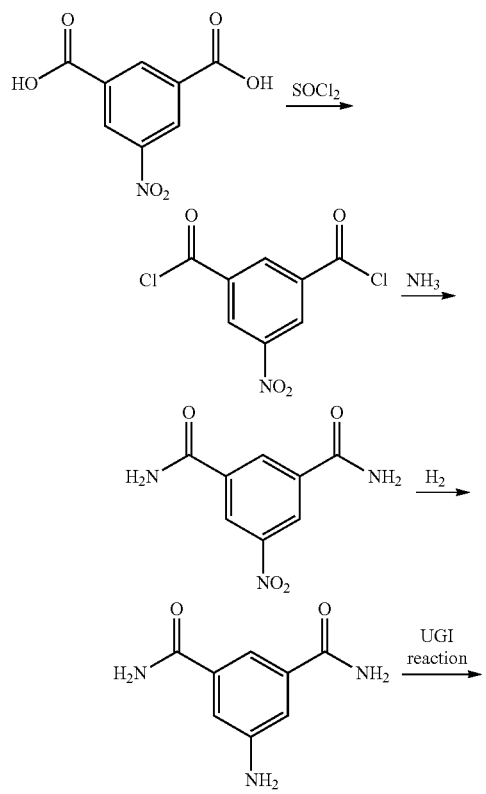

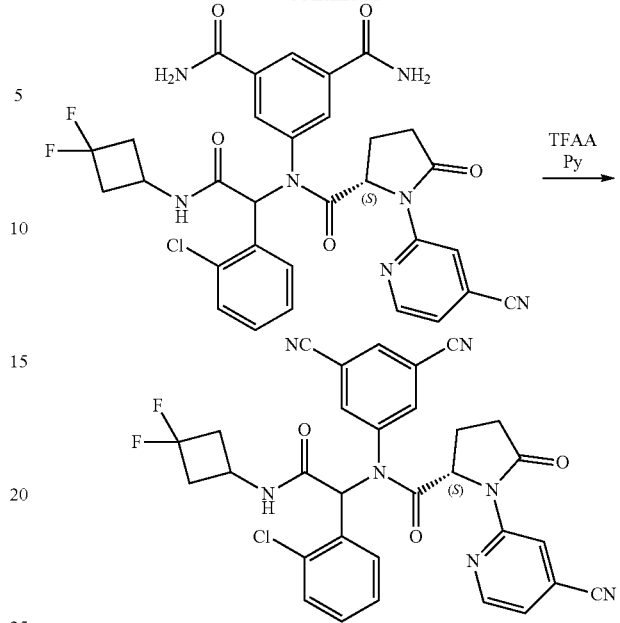

Step A: 5-Nitroisophthaloyl dichloride

To a solution of 5-nitroisophthalic acid (2.3 g, 11 mmol) in SOCl$_2$ (6 mL) was added a drop of DMF and the mixture was stirred at reflux for 3 hr. The resulting reaction mixture was concentrated to give the crude product which was used directly in the next step.

Step B: 5-Nitroisophthalamide

5-Nitroisophthaloyl dichloride (2.7 g, 9.7 mmol) was added portionwise to a cold solution of NH$_3$.H$_2$O (40 mL) at 0° C. The reaction mixture was stirred overnight and a white precipitate formed. The mixture was then filtered, washed with excess of water, and dried at 110° C. to give the crude product which was used directly in the next step.

Step C: 5-Aminoisophthalamide

To a solution of 5-nitroisophthalamide (2 g, 9.6 mmol) in MeOH (200 mL) was added Pd/C (200 mg). The reaction was stirred overnight under a hydrogen atmosphere. The suspension was filtered and the filtrate was concentrated to afford the desired product which was used directly in the next step.

Step D: 5-((2S)—N-(1-(2-Chlorophenyl)-2-((3,3-difluorocyclobutyl)amino)-2-oxoethyl)1-(4cyanopyridin-2-yl)-5-oxopyrrolidine-2-carboxamido) isophthalamide A mixture of 2-chlorobenzaldehyde (1.0 mL, 7.3 mmol) and 5-aminoisophthalamide (1.3 g, 7.3 mmol) was stirred at room temperature for 30 min under N$_2$, followed by addition of (S)-1-(4-cyanopyridin-2-yl)-5-oxopyrrolidine-2-carboxylic acid (1.7 g, 7.3 mmol). After stirring for 10 min, 1,1-difluoro-3-isocyanocyclobutane (854 mg, 7.3 mmol) was added. The mixture was then stirred overnight and filtered and purified by a standard method to give the title product.

Step E: (2S)—N-(1-(2-Chlorophenyl)-2-((3,3-difluorocyclobutyl)amino)-2-oxoethyl)1-(4-cyano pyridin-2-yl)-N-(3,5-dicyanophenyl)-5-oxopyrrolidine-2-carboxamide To a mixture of 5-((2S)—N-(1-(2-chlorophenyl)-2-((3,3-difluorocyclobutyl)amino)-2-oxoethyl)1-(4-cyano pyridin-2-yl)-5-oxopyrrolidine-2-carboxamido)isophthalamide (850 mg, 1.3 mmol) in pyridine (0.62 mL, 7.8 mmol) and DCM (10 mL) was added TFAA (0.9 mL, 6.5 mmol). The reaction solution was stirred at room temperature overnight. The resulting mixture was concentrated and the residue was purified by a standard method to afford the title product. $^1$H NMR (400 MHz, CDCl$_3$): δ 8.77 (s, 1H), 8.62-8.42 (m, 2H), 7.87 (s, 1H), 7.75 (s, 1H), 7.40 (d, J=7.8 Hz, 1H), 7.31 (d, J=4.2 Hz, 1H), 7.25 (d, J=8.1 Hz, 1H), 7.10 (t, J=7.3 Hz, 1H), 6.92 (d, J=7.5 Hz, 1H), 6.47 (s, 1H), 6.11 (d, J=6.6 Hz, 1H), 4.73 (dd, J=9.4, 2.7 Hz, 1H), 4.35 (s, 1H), 3.14-2.82 (m, 3H), 2.68-2.31 (m, 3H), 2.19 (m, 1H), 2.09-1.91 (m, 1H). MS: 614.1 (M+1)$^+$.

The following analogs were synthesized via the procedure set forth above, using the appropriate aldehyde, amine, carboxylic acid, isocyanide and halo-substituted aromatic ring or heterocyclic (heteroaromatic) ring using the reagents and solvents set forth above, and purified via standard methods.

(S)—N—((S)-1-(2-Chlorophenyl)-2-((3,3-difluorocyclobutyl)amino)-2-oxoethyl)-1-(4-cyano pyridin-2-yl)-N-(3,5-dicyanophenyl)-5-oxopyrrolidine-2-carboxamide (Single Enantiomer)—Compound 153

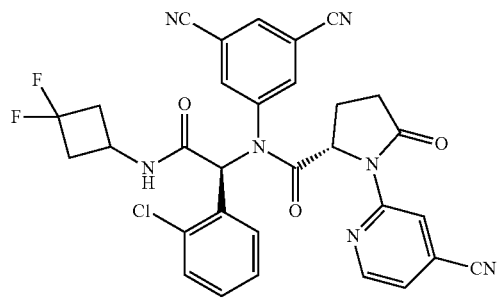 [SMILES: N#Cc1cc(C#N)cc(N(C(=O)[C@@H]2CCC(=O)N2c2cc(C#N)ccn2)[C@H](C(=O)NC2CC(F)(F)C2)c2ccccc2Cl)c1]

$^1$H NMR (400 MHz, CDCl$_3$): δ 8.74 (s, 1H), 8.53 (m, 2H), 7.81 (m, 2H), 7.48-7.16 (m, 4H), 7.09 (t, J=7.5 Hz, 1H), 6.90 (d, J=7.6 Hz, 1H), 6.46 (s, 1H), 6.17 (d, J=6.7 Hz, 1H), 4.72 (dd, J=9.1, 2.3 Hz, 1H), 4.35 (s, 1H), 3.18-2.71 (m, 3H), 2.68-1.83 (m, 5H). MS: 614.1 (M+1)$^+$.

Example 10. Preparation of (S)-tert-butyl 3-(((S)-1-(2-chlorophenyl)-2-((3,3-difluorocyclobutyl)amino)-2-oxoethyl)(3,5-difluorophenyl)carbamoyl)-5-oxopiperazine-1-carboxylate (Single Enantiomer)—Compound 97

Compound 97 was synthesized via the UGI reaction procedure set forth herein, using the appropriate aldehyde, amine, carboxylic acid, isocyanide and halo-substituted aromatic ring or heterocyclic (heteroaromatic) ring and purified via standard methods.

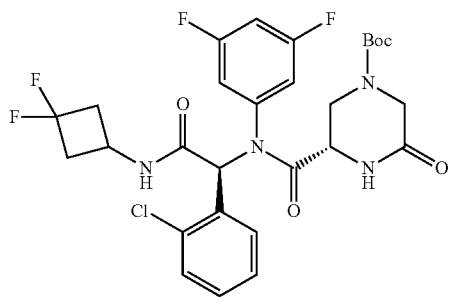 [SMILES: CC(C)(C)OC(=O)N1CC(=O)N[C@H](C(=O)N(c2cc(F)cc(F)c2)[C@H](C(=O)NC2CC(F)(F)C2)c2ccccc2Cl)C1]

$^1$H NMR (400 MHz, CDCl$_3$): δ 8.75-8.44 (m, 2H), 7.81-7.41 (m, 1H), 7.46-7.35 (m, 2H), 7.24 (t, J=7.2 Hz, 1H), 7.16-6.97 (m, 2H), 6.84-6.75 (m, 2H), 6.43-5.82 (m, 1H), 5.09-4.98 (m, 1H), 4.77-4.73 (m, 1H), 4.48 (d, J=13.5 Hz, 1H), 4.27-4.07 (m, 2H), 3.45-2.76 (m, 4H), 1.54 (s, 9H). MS: 613.2 (M+1)$^+$.

Example 11. Preparation of (3S)-tert-butyl 3-((1-(2-chlorophenyl)-2-((3,3-difluorocyclobutyl)amino)-2-oxoethyl)(3,5-difluorophenyl)carbamoyl)-4-(4-cyanopyrimidin-2-yl)-5-oxopiperazine-1-carboxylate (Racemic)—Compound 98

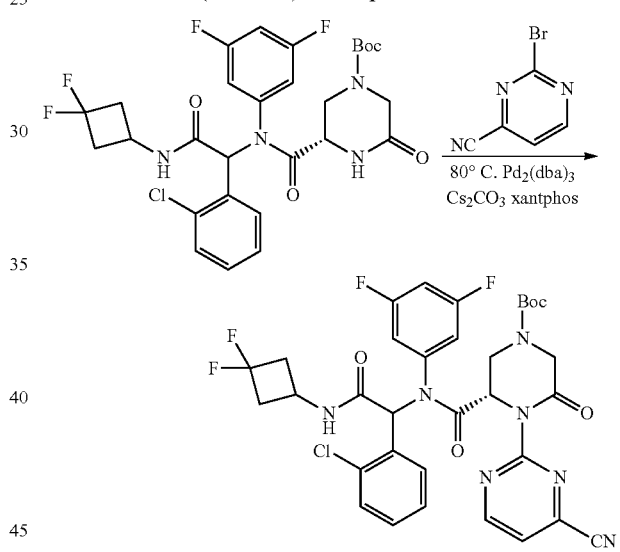

A mixture of (3S)-tert-butyl3-((1-(2-chlorophenyl)-2-((3,3-difluorocyclobutyl)amino)-2-oxoethyl) (3,5-difluorophenyl)carbamoyl)-5-oxopiperazine-1-carboxylate (200 mg, 0.326 mmol), 2-bromopyrimidine-4-carbonitrile (0.489 mmol), Pd$_2$(dba)$_3$ (30.2 mg, 0.0323 mmol), XantPhos (19.1 mg, 0.03 mmol) and Cs$_2$CO$_3$ (148.7 mg, 0.46 mmol) in 1,4-dioxane (10 mL) was stirred at 80° C. for 3 hr under N$_2$. The reaction mixture was cooled to room temperature and filtered. The filtrate was concentrated and the residue was purified by a standard method to afford the desired product. $^1$H NMR (400 MHz, CDCl$_3$): δ 8.97 (d, J=4.3 Hz, 1H), 7.85-7.55 (d, 1H), 7.51-7.39 (m, 2H), 7.25 (t, J=7.6 Hz, 1H), 7.13-6.26 (m, 6H), 5.91 (d, J=7.6 Hz, 1H), 4.92-4.08 (m, 5H), 3.38 (t, J=14.9 Hz, 1H), 3.02 (s, 2H), 2.83-2.22 (d, 2H), 1.61 (s, 9H). MS: 716.1 (M+1)$^+$.

The following analogs were synthesized via the procedure set forth above, using the appropriate aldehyde, amine, carboxylic acid, isocynide and halo-substituted aromatic ring or heterocyclic (heteroaromatic) ring using the reagents and solvents set forth above, and purified via standard methods.

165

(S)-tert-Butyl 3-(((S)-1-(2-chlorophenyl)-2-((4,4-difluorocyclohexyl)amino)-2-oxoethyl)(3,5-difluorophenyl)carbamoyl)-4-(4-cyanopyrimidin-2-yl)-5-oxopiperazine-1-carboxylate (Chiral)—Compound 93

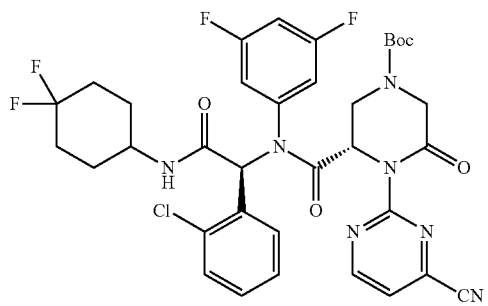 [SMILES: CC(C)(C)OC(=O)N1CC(=O)N(c2nccc(C#N)n2)[C@H](C(=O)N(c2cc(F)cc(F)c2)[C@H](C(=O)NC2CCC(F)(F)CC2)c2ccccc2Cl)C1]

¹H NMR (400 MHz, CDCl₃): δ 8.96 (d, J=4.3 Hz, 1H), 7.83 (s, 1H), 7.43 (m, 2H), 7.21 (t, J=7.4 Hz, 1H), 7.08-6.62 (m, 4H), 6.63-6.37 (m, 1H), 5.93 (m, 1H), 4.85 (t, J=3.6 Hz, 1H), 4.63-4.23 (m, 2H), 4.16 (m, 1H), 3.93 (s, 1H), 3.43 (m, 1H), 2.24-1.91 (m, 5H), 1.79 (m, 3H), 1.60 (m, 1H). MS: 744.2 (M+1)⁺.

(3S)-tert-Butyl 3-((1-(2-chlorophenyl)-2-((3,3-difluorocyclobutyl)amino)-2-oxoethyl)(3-fluorophenyl)carbamoyl)-4-(4-cyanopyridin-2-yl)-5-oxopiperazine-1-carboxylate (Single Enantiomer)—Compound 89

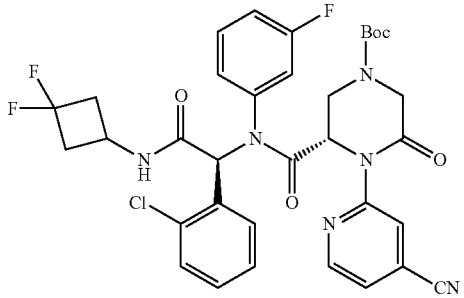 [SMILES: CC(C)(C)OC(=O)N1CC(=O)N(c2cc(C#N)ccn2)[C@H](C(=O)N(c2cccc(F)c2)[C@H](C(=O)NC2CC(F)(F)C2)c2ccccc2Cl)C1]

¹H NMR (400 MHz, DMSO-d₆): δ 8.80-8.37 (m, 1H), 8.05-7.57 (m, 1H), 7.58-7.31 (m, 3H), 7.21 (s, 1H), 7.16-6.89 (m, 3H), 6.90-6.68 (m, 1H), 6.67-6.30 (m, 1H), 6.22-5.84 (m, 1H), 5.09-4.87 (m, 1H), 5.83-4.57 (m, 1H), 4.50 (m, 1H), 4.25 (s, 1H), 4.08 (m, 1H), 3.50-2.70 (m, 4H), 2.60-2.10 (m, 1H), 1.70 (s, 2H), 1.54 (m, 1H). MS: 697.2 (M+1)⁺.

Example 12. Preparation of (S)—N—((S)-1-(2-chlorophenyl)-2-((3,3-difluorocyclobutyl)amino)-2-oxoethyl)-1-(4-cyanopyrimidin-2-yl)-N-(3,5-difluorophenyl)-6-oxopiperazine-2-carboxamide (Single Enantiomer)—Compound 99

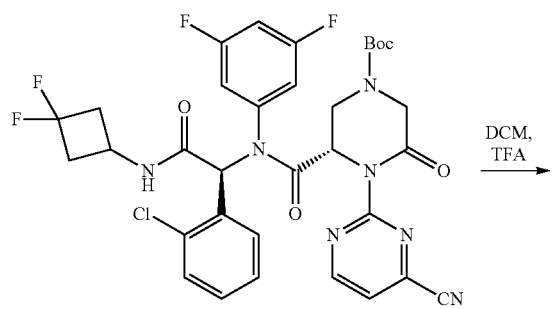

166

-continued

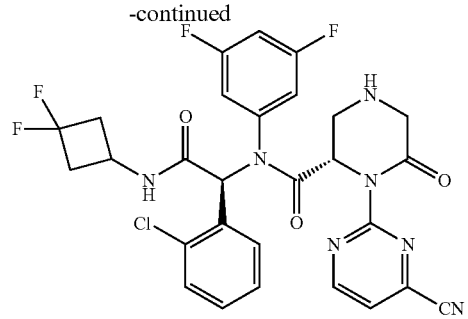

TFA (0.3 mL) was added to a solution of (S)-tert-butyl 3-(((R)-1-(2-chlorophenyl)-2-((3,3-difluorocyclobutyl)amino)-2-oxoethyl)(3,5-difluorophenyl)carbamoyl)-4-(4-cyanopyridin-2-yl)-5-oxopiperazine-1-carboxylate (60 mg, 0.08 mmol) in DCM (1.0 mL) at 0° C. The mixture was warmed to room temperature and stirred for 1 hr, and then concentrated. The residue was purified by a standard method to give the desired product. ¹H NMR (400 MHz, CDCl₃): δ 8.94 (t, J=4.6 Hz, 1H), 7.48-7.36 (m, 3H), 7.21 (m, J=7.8, 1.5 Hz, 1H), 7.12-6.94 (m, 3H), 6.71-6.55 (m, 2H), 6.05 (d, J=6.7 Hz, 1H), 4.73 (q, J=4.0, 2.1 Hz, 1H), 4.36 (d, J=6.7 Hz, 1H), 3.77-3.65 (m, 2H), 3.50-3.35 (m, 1H), 3.18 (m, 1H), 3.12-2.96 (m, 2H), 2.64-2.35 (m, 2H). MS: 616.1 (M+1)⁺.

The following compound was synthesized via the procedure set forth above, using the appropriate aldehyde, amine, carboxylic acid, isocyanide and halo-substituted aromatic ring or heterocyclic (heteroaromatic) ring using the reagents and solvents set forth above, and purified via standard methods.

(S)—N—((S)-1-(2-Chlorophenyl)-2-((3,3-difluorocyclobutyl)amino)-2-oxoethyl)-1-(4-cyano pyridin-2-yl)-N-(3,5-difluorophenyl)-6-oxopiperazine-2-carboxamide (Single Enantiomer)—Compound 100

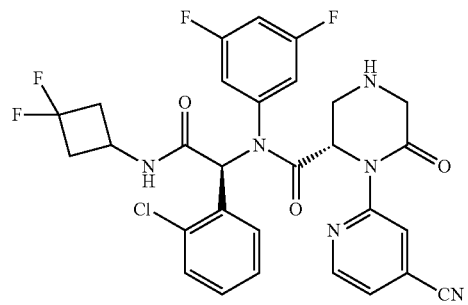 [SMILES: N#Cc1ccnc(N2C(=O)CNC[C@H]2C(=O)N(c2cc(F)cc(F)c2)[C@H](C(=O)NC2CC(F)(F)C2)c2ccccc2Cl)c1]

¹H NMR (400 MHz, CDCl₃): δ 8.68-8.28 (m, 1H), 7.61-7.28 (m, 2H), 7.20 (dd, J=7.9, 1.3 Hz, 0H), 7.02-6.90 (m, 1H), 6.66 (tt, J=8.6, 2.3 Hz, 1H), 6.49 (d, J=2.7 Hz, 0H), 6.09 (m, 1H), 4.90 (dd, J=3.8, 2.0 Hz, 1H), 4.42-4.16 (m, 1H), 3.71 (m, 1H), 3.50-3.23 (m, 1H), 3.18-2.78 (m, 2H), 2.63-2.13 (m, 2H). MS: 615.2 (M+1)⁺.

Example 13. (S)-4-Acetyl-N—((S)-1-(2-chlorophenyl)-2-(3,3-difluorocyclobutylamino)-2-oxoethyl)-1-(4-cyanopyridin-2-yl)-N-(3-fluorophenyl)-6-oxopiperazine-2-carboxamide (Single Enantiomer)—Compound 92

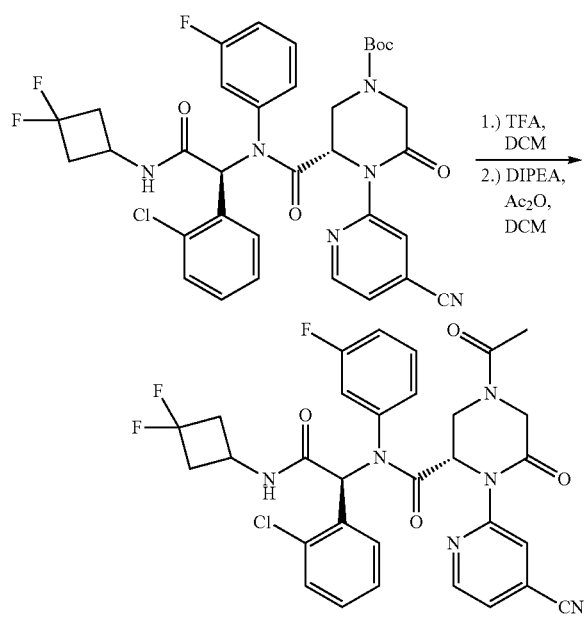

To a solution of (3S)-tert-butyl 3-((1-(2-chlorophenyl)-2-(3,3-difluorocyclobutylamino)-2-oxoethyl)(3-fluorophenyl)carbamoyl)-4-(4-cyanopyridin-2-yl)-5-oxopiperazine-1-carboxylate (100 mg, 0.14 mmol) in DCM (3 mL) was added TFA dropwise (1 mL) at 0° C. The mixture was stirred at room temperature for 2 hr and then concentrated. The residue was dissolved in DCM and cooled to 0° C. DIPEA (0.055 mL, 0.34 mmol) was added to the mixture followed by Ac₂O (0.031 mL, 0.34 mmol) at 0° C. Then the mixture was stirred at room temperature for 2 hr. The solution was concentrated and the residue was purified by a standard method to afford the desired product. $^1$H NMR (400 MHz, CDCl₃): δ 8.54 (s, 2H), 7.70-7.44 (m, 2H), 7.36 (m, 2H), 7.20 (t, J=7.2 Hz, 1H), 7.14-6.99 (m, 2H), 6.94 (t, J=7.4 Hz, 1H), 6.80 (s, 1H), 6.66 (d, J=7.8 Hz, 1H), 6.58-6.42 (m, 1H), 5.09 (dt, J=5.2, 3.1 Hz, 1H), 4.93 (m, 1H), 4.63 (m, 1H), 4.54-4.41 (m, 1H), 4.35-4.31 (m, 1H), 3.16 (s, 1H), 3.12-2.96 (m, 3H), 2.86 (s, 1H), 2.25 (s, 3H). MS: 639.2 (M+1)⁺.

Example 14. Preparation of (S)—N—((S)-1-(2-chlorophenyl)-2-((3,3-difluorocyclobutyl)amino)-2-oxoethyl)-1-(4-cyanopyridin-2-yl)-4-cyclopropyl-N-(3,5-difluorophenyl)-6-oxopiperazine-2-carboxamide (Single Enantiomer)—Compound 106

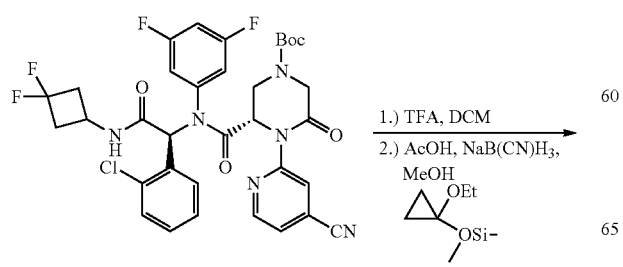

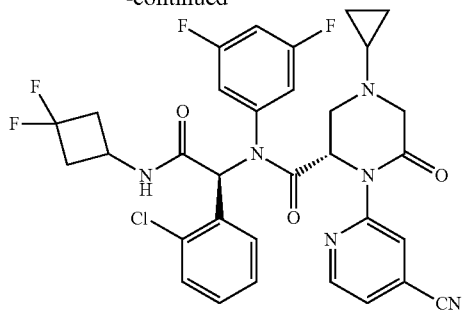

TFA (0.3 mL) was added to a solution of (S)-tert-butyl 3-(((R)-1-(2-chlorophenyl)-2-((3,3-difluorocyclobutyl)amino)-2-oxoethyl)(3,5-difluorophenyl)carbamoyl)-4-(4-cyanopyridin-2-yl)-5-oxopiperazine-1-carboxylate (60 mg, 0.084 mmol) in DCM (1.0 mL) at 0° C. The mixture was stirred at room temperature for 1 hr then concentrated. The residue was dissolved in MeOH (2 mL) followed by addition of (1-ethoxycyclopropoxy)trimethylsilane (88 mg, 0.50 mmol), AcOH (50 mg, 0.84 mmol) and NaBH₃(CN) (27 mg, 0.42 mmol). The resulting suspension was stirred at 80° C. under N₂ for 1.5 hr. The reaction mixture was partitioned between EtOAc and H₂O. The organic layer was separated, washed with brine, dried over anhydrous Na₂SO₄ and concentrated. The residue was purified by a standard method to afford the desired product. $^1$H NMR (400 MHz, CDCl₃): δ 7.64 (d, J=7.8 Hz, 1H), 7.30 (d, J=5.3 Hz, 2H), 7.19 (s, 1H), 7.07 (s, 3H), 6.66 (s, 1H), 6.32 (s, 1H), 6.09 (m, 1H), 5.09 (s, 1H), 4.28 (s, 1H), 3.76-3.59 (m, 1H), 3.46-3.33 (m, 1H), 3.08-2.89 (m, 4H), 2.59-2.31 (m, 2H), 0.94 (s, 1H), 0.61-0.37 (m, 4H). MS: 655.2 (M+1)⁺.

Example 15. Preparation of (S)—N—((S)-1-(2-chlorophenyl)-2-((3,3-difluorocyclobutyl)amino)-2-oxoethyl)-1-(4-cyanopyridin-2-yl)-N-(3,5-difluorophenyl)-4-methyl-6-oxopiperazine-2-carboxamide (Single Enantiomer)—Compound 101

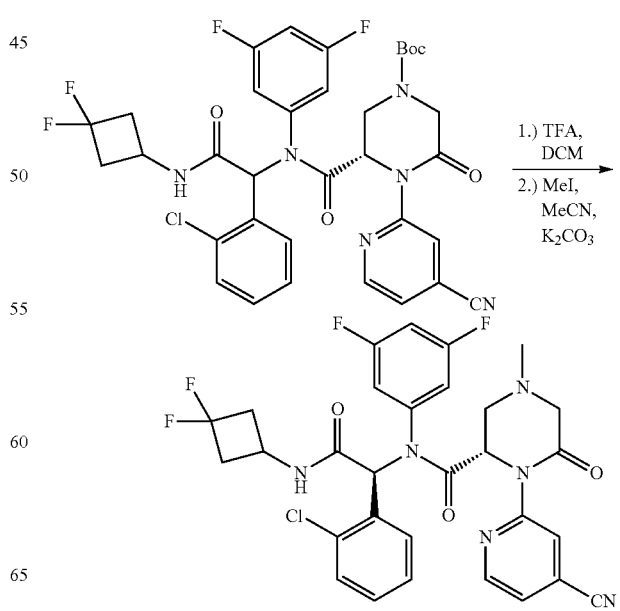

TFA (0.6 mL) was added to a solution of (3S)-tert-butyl 3-((1-(2-chlorophenyl)-2-((3,3-difluorocyclobutyl)amino)-2-oxoethyl)(3,5-difluorophenyl)carbamoyl)-4-(4-cyanopyridin-2-yl)-5-oxopiperazine-1-carboxylate (30 mg, 0.042 mmol) in DCM (2 mL) at 0° C. The mixture was stirred at room temperature for 1 hr and then concentrated. The residue was dissolved in MeCN (4 mL) followed by addition of K$_2$CO$_3$ (10 mg, 0.072 mmol) and iodomethane (2 mL). The resulting mixture was stirred at room temperature for 2 hr and then concentrated. The residue was purified by a standard method to afford the desired product. $^1$H NMR (400 MHz, CDCl3): δ 8.60 (m, 2H), 7.80 (s, 1H), 7.45 (d, J=7.9 Hz, 1H), 7.33 (m, 1H), 7.07 (d, J=4.3 Hz, 2H), 6.74 (t, J=8.6 Hz, 1H), 6.48-5.91 (m, 3H), 4.92 (t, J=4.7 Hz, 1H), 4.20 (m, 1H), 3.61-3.40 (m, 1H), 3.14 (m, 1H), 3.02-2.77 (m, 3H), 2.71 (m, 1H), 2.42-2.26 (m, 5H), 2.04 (d, J=9.0 Hz, 1H). MS: 629 (M+1)$^+$.

Example 16. Preparation of (S)—N—((S)-1-(2-chlorophenyl)-2-((3,3-difluorocyclobutyl)amino)-2-oxoethyl)-1-(4-cyanopyridin-2-yl)-N-(3,5-difluorophenyl)-4-(2-hydroxyethyl)-6-oxopiperazine-2-carboxamide (Single Enantiomer)—Compound 107

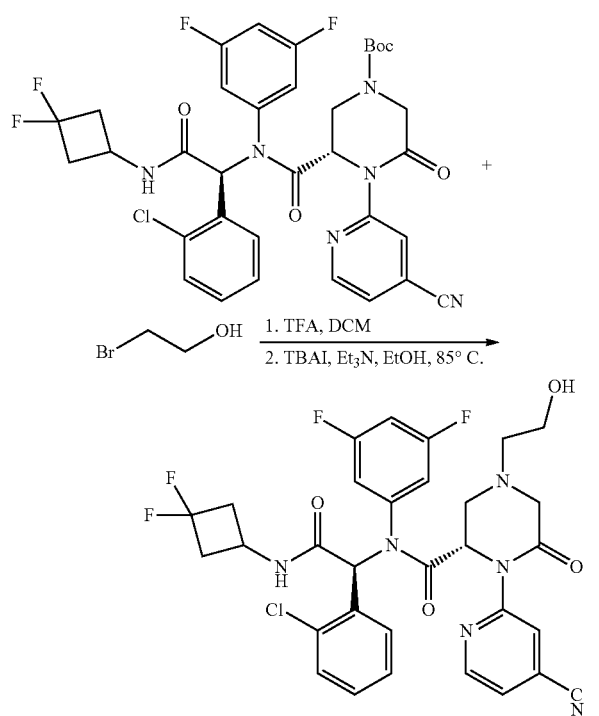

To a solution of (S)-tert-butyl 3-(((S)-1-(2-chlorophenyl)-2-((3,3-difluorocyclobutyl)amino)-2-oxoethyl)(3,5-difluorophenyl)carbamoyl)-4-(4-cyanopyridin-2-yl)-5-oxopiperazine-1-carboxylate (30 mg, 0.04 mmol) in DCM (3 mL) was added TFA (1 mL) at 0° C. The mixture was stirred at room temperature for 1 hr and concentrated in vacuo. The residue was dissolved in EtOH (3 mL) followed by addition of TBAI (16 mg, 0.04 mmol), Et$_3$N (10 mg, 0.1 mol) and 2-bromoethanol (7 mg, 0.056 mmol). The resulting mixture was stirred at 85° C. for 3 hr and then filtered. The filtrate was concentrated and the residue was purified by a standard method to afford the desired product. $^1$H NMR (400 MHz, CDCl$_3$): δ 8.96 (t, J=4.6 Hz, 1H), 7.53-7.36 (m, 3H), 7.23 (m, J=7.8, 1.5 Hz, 1H), 7.14-6.94 (m, 3H), 6.68 (m, J=8.6, 2.3 Hz, 1H), 6.60 (d, J=3.1 Hz, 1H), 6.07 (d, J=6.7 Hz, 1H), 4.75 (q, J=4.0, 2.1 Hz, 1H), 4.38 (d, J=6.7 Hz, 1H), 3.78-3.67 (m, 2H), 3.39 (m, 1H), 3.26-2.92 (m, 3H), 2.67-2.36 (m, 2H). MS: 659.2 (M+1)$^+$.

The following compound was synthesized via the procedure set forth above, using the appropriate aldehyde, amine, carboxylic acid, isocyanide and halo-substituted aromatic ring or heterocyclic (heteroaromatic) ring using the reagents and solvents set forth above, and purified via standard methods.

Compound 104

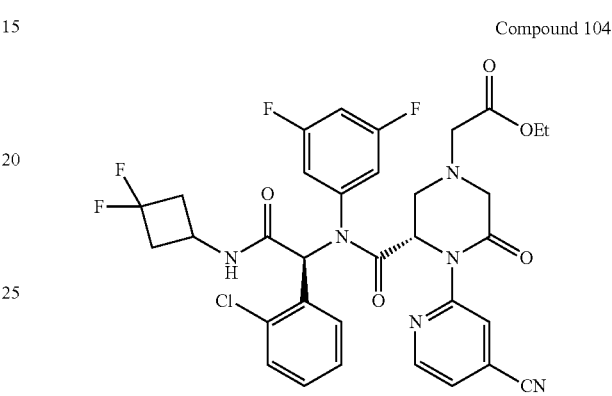

$^1$H NMR (400 MHz, CDCl$_3$): δ 8.60-8.56 (m, 2H), 7.47-7.28 (m, 3H), 7.22-7.01 (m, 4H), 6.72-6.67 (m, 1H), 6.54-6.44 (m, 2H), 5.24 (m, 1H), 4.37-4.13 (m, 3H), 3.63-2.97 (m, 8H), 2.44-2.06 (m, 2H), 1.34-1.28 (m, 3H). MS: 701.2 (M+1)$^+$.

Example 17. Preparation of (S)—N—((S)-1-(2-chlorophenyl)-2-((3,3-difluorocyclobutyl)amino)-2-oxoethyl)-1-(5-cyanooxazol-2-yl)-N-(3,5-difluorophenyl)-5-oxopyrrolidine-2-carboxamide (Single Enantiomer)—Compound 162

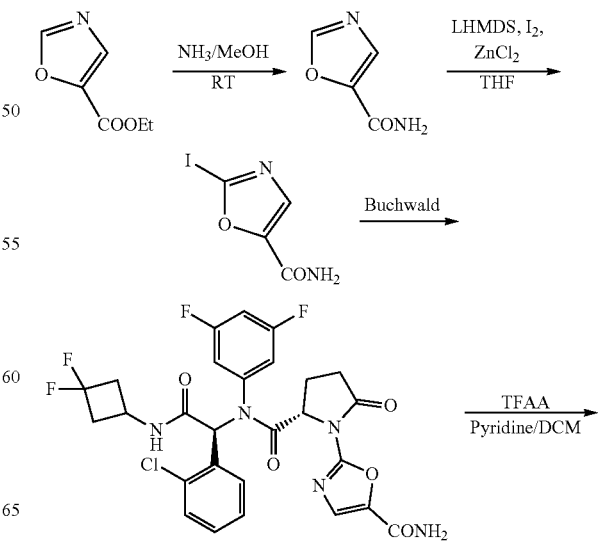

-continued

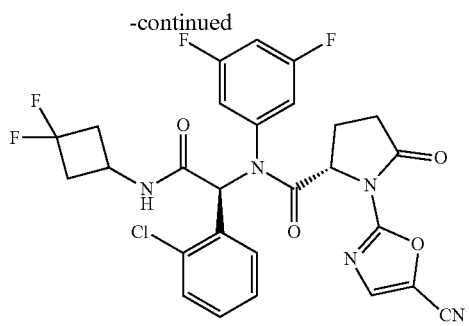

Step A: Oxazole-5-carboxamide

Ethyl oxazole-5-carboxylate (2 g, 14.2 mmol) was dissolved in NH₃ solution (7 M in MeOH, 25 mL). The solution was stirred at room temperature for 2 hr and filtered. The solid was dried to give the desired product (1.5 g, 92% yield) as a white powder which was used directly in the next step.

Step B: 2-Iodooxazole-5-carboxamide

Oxazole-5-carboxamide (560 mg, 5.0 mmol) was dissolved in anhydrous THF (7.5 mL) and flushed with $N_2$. The solution was cooled to −42° C. and treated with fresh LiHMDS (15 mL, 1 M in THF). The solution became dark yellow was stirred for 20 min and followed by the addition of a solution of $ZnCl_2$ (30 mL, 0.5 M in THF). The reaction was warmed to 0° C. for 1 hr. After solid iodine (1.65 g, 6.5 mmol) was added, the reaction mixture was stirred at room temperature for another 1 hr and then poured into saturated $Na_2S_2O_3$ solution containing 25% aq. $NH_3$ solution. The resulting mixture was extracted with EtOAc (3×30 mL). The combined organic layers were washed with brine, dried over anhydrous $Na_2SO_4$ and concentrated. The resulting residue was purified by a standard method to give the desired product. MS: 239.0 $(M+1)^+$.

Step C: 2-((S)-2-(((S)-1-(2-Chlorophenyl)-2-((3,3-difluorocyclobutyl)amino)-2-oxoethyl)(3,5-difluorophenyl)carbamoyl)-5-oxopyrrolidin-1-yl)oxazole-5-carboxamide The product was prepared by the general procedure for the Buchwald reaction. ¹H NMR (400 MHz, CDCl₃): δ 7.59 (s, 1H), 7.53 (s, 1H), 7.37 (d, J=7.9 Hz, 1H), 7.20 (t, J=7.0 Hz, 1H), 7.04 (t, J=7.6 Hz, 1H), 6.96 (d, J=7.9 Hz, 2H), 6.68 (t, J=8.7 Hz, 1H), 6.46 (s, 1H), 6.36 (d, J=6.4 Hz, 1H), 5.68 (s, 1H), 4.82 (dd, J=9.3, 2.6 Hz, 1H), 4.33 (s, 1H), 4.16-4.09 (m, 1H), 3.03-3.00 (m, 2H), 2.90-2.77 (m, 1H), 2.62-2.35 (m, 3H), 2.29-2.28 (m, 1H), 2.19-2.08 (m, 1H). MS: 608.1 $(M+1)^+$.

Step D: (S)—N—((S)-1-(2-Chlorophenyl)-2-((3,3-difluorocyclobutyl)amino)-2-oxoethyl)-1-(5-cyanooxazol-2-yl)-N-(3,5-difluorophenyl)-5-oxopyrrolidine-2-carboxamide 2-((S)-2-(((S)-1-(2-Chlorophenyl)-2-((3,3-difluorocyclobutyl)amino)-2-oxoethyl)(3,5-difluoro-phenyl)carbamoyl)-5-oxopyrrolidin-1-yl)oxazole-5-carboxamide (100 mg, 0.16 mmol) was dissolved in DCM (3 mL) and dry pyridine (0.8 mL). TFAA (0.1 mL) was added and the reaction solution was stirred for 25 min at room temperature and then concentrated in vacuo. The residue was dissolved in EtOAc and washed with H₂O, saturated aq. NaHCO₃ and brine. The organic phase was separated, dried over anhydrous Na₂SO₄, and concentrated. The residue was purified by a standard method to give the desired product. ¹H NMR (400 MHz, CDCl₃): δ 7.63 (s, 1H), 7.55 (d, J=7.0 Hz, 1H), 7.41 (d, J=7.1 Hz, 1H), 7.25 (td, J=7.8, 1.5 Hz, 1H), 7.08 (t, J=7.6 Hz, 1H), 6.98-6.91 (m, 1H), 6.80 (d, J=6.7 Hz, 1H), 6.71 (dd, J=9.7, 7.4 Hz, 1H), 6.49 (s, 1H), 5.97 (d, J=6.8 Hz, 1H), 4.80 (dd, J=9.3, 2.8 Hz, 1H), 4.36 (s, 1H), 3.06-3.03 (m, 2H), 2.92-2.79 (m, 1H), 2.62-2.29 (m, 4H), 2.18-2.12 (m, 1H). MS: 590.1 $(M+1)^+$.

Example 18. Preparation of (2S,4R)—N-(1-(2-chlorophenyl)-2-((3,3-difluorocyclobutyl)amino)-2-oxoethyl)-N-(3-cyano-phenyl)-1-(4-cyanopyridin-2-yl)-4-hydroxy-5-oxopyrrolidine-2-carboxamide (Racemic)—Compound 170

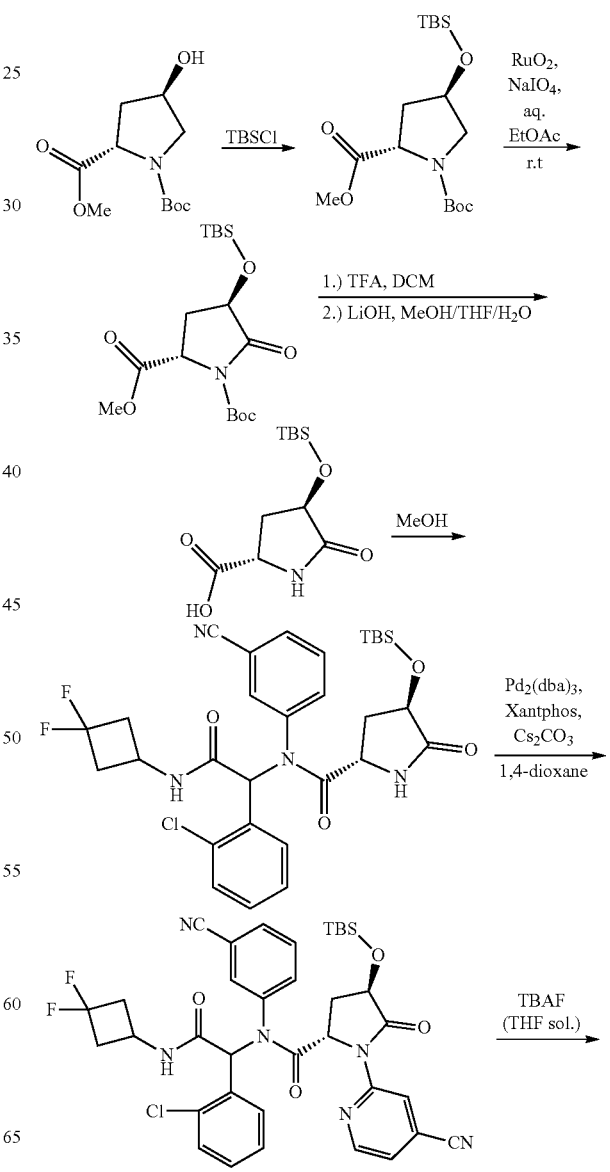

-continued

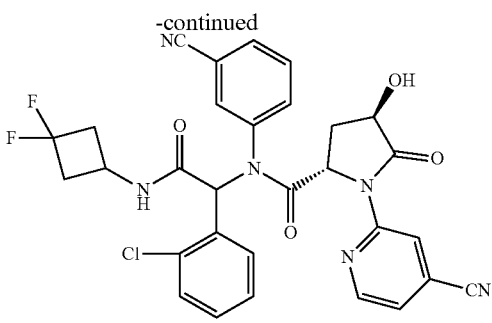

Step A: (2S,4R)-1-tert-Butyl 2-methyl 4-((tert-butyldimethylsilyl)oxy)pyrrolidine-1,2-dicarboxylate Imidazole (2.8 g, 40.8 mmol) was added to a solution of (2S,4R)-1-tert-butyl 2-methyl 4-hydroxypyrrolidine-1,2-dicarboxylate (5.0 g, 20.4 mmol) and TBSCl (4.6 g, 30.6 mmol) in anhydrous DMF (100 mL). The mixture was stirred at room temperature overnight and then partitioned between EtOAc and $H_2O$. The organic layer was separated, washed with aq. LiCl (10%) and brine, dried over anhydrous $Na_2SO_4$, and then concentrated. The residue was purified by column chromatography to afford the desired product as a colorless oil. MS: 360.2 $(M+1)^+$.

Step B: (2S,4R)-1-tert-Butyl 2-methyl 4-((tert-butyldimethylsilyl)oxy)-5-oxopyrrolidine-1,2-dicarboxylate To a solution of $NaIO_4$ (7.5 g, 35.0 mmol) in water (80 mL) was added $RuO_2$ (370 mg, 2.8 mmol) under the atmosphere of nitrogen. The resulting green-yellow solution was stirred for 5 min followed by addition of (2S,4R)-1-tert-butyl-2-methyl4-((tert-butyldimethyl silyl)oxy)pyrrolidine-1,2-dicarboxylate (5.0 g, 14.0 mmol) in EtOAc (44 mL) in one portion. The mixture was stirred at room temperature overnight. The resulting mixture was then diluted with EtOAc and filtered through a pad of Celite. The organic layer was separated and washed with saturated aq. $NaHSO_3$, which resulted in precipitation of Ru black. The organic layer was then washed with brine and dried over anhydrous $Na_2SO_4$. Evaporation of the solvent gave the desired product as a colorless oil. MS: 374.2 $(M+1)^+$.

Step C: (2S,4R)-4-((tert-Butyldimethylsilyl)oxy)-5-oxopyrrolidine-2-carboxylic Acid TFA (6 mL) was added to a solution of (2S,4R)-1-tert-butyl 2-methyl 4-((tert-butyldimethylsilyl)oxy)-5-oxopyrrolidine-1,2-dicarboxylate (2.5 g, 6.68 mmol) in DCM (18 mL) at 0° C. The mixture was stirred at room temperature for 1 h then concentrated. The residue was dissolved in MeOH/THF (10 mL/10 mL) followed by addition of a solution of LiOH (842 mg, 20.1 mmol) in water (5 mL). The resulting mixture was stirred at room temperature for 1 h and then partitioned between EtOAc and $H_2O$. The aqueous layer was separated and then adjusted to pH=6 with 1 N HCl aq. and extracted with EtOAc (3×20 mL). Combined organic layers were washed with brine, dried over anhydrous $Na_2SO_4$, and then concentrated to afford the desired product. $^1$H NMR (400 MHz, DMSO-$d_6$): δ 12.87 (s, 1H), 8.17 (s, 1H), 4.21 (t, J=8.0 Hz, 1H), 4.02 (d, J=8.4 Hz, 1H), 2.39-2.23 (m, 1H), 2.09 (m, 1H), 0.84 (s, 9H), 0.07 (s, 6H). MS: 260.1 $(M+1)^+$.

Step D

The same as general procedure for UGI reaction set forth herein.

Step E

The same as general procedure for Buchwald reaction set forth herein.

Step F: (2S,4R)—N-(1-(2-Chlorophenyl)-2-((3,3-difluorocyclobutyl)amino)-2-oxoethyl)-N-(3-cyanophenyl)-1-(4-cyanopyridin-2-yl)-4-hydroxy-5-oxopyrrolidine-2-carboxamide TBAF in THF (1N, 0.3 mL) was added to a solution of (2S,4R)-4-((tert-butyldimethylsilyl)oxy)-N-(1-(2-chlorophenyl)-2-((3,3-difluorocyclobutyl)amino)-2-oxoethyl)-N-(3-cyanophenyl)-1-(4-cyano pyridin-2-yl)-5-oxopyrrolidine-2-carboxamide (0.15 mmol) in THF at 0° C. and the reaction solution was stirred at this temperature for 20 min. The resulting mixture was concentrated and the residue was purified by a standard method to afford the desired product. $^1$H NMR (400 MHz, CDCl$_3$): δ 8.82-8.43 (m, 2H), 8.40-8.17 (m, 1H), 7.63-7.30 (m, 3H), 7.26-6.66 (m, 4H), 6.68-6.34 (m, 2H), 6.65-6.31 (m, 2H), 4.87-4.56 (m, 2H), 4.23 (m, 1H), 4.01-3.76 (m, 1H), 3.15-1.96 (m, 6H). MS: 605.1 $(M+1)^+$.

The following analogs were synthesized via the procedure set forth herein, using the appropriate aldehyde, amine, carboxylic acid, isocyanide and halo-substituted aromatic ring or heterocyclic (heteroaromatic) ring using the reagents and solvents set forth herein, and purified via various standard methods.

(2S,4R)—N—((S)-1-(2-Chlorophenyl)-2-(3,3-difluorocyclobutylamino)-2-oxoethyl)-1-(4-cyanopyridin-2-yl)-N-(3-fluorophenyl)-4-hydroxy-5-oxopyrrolidine-2-carboxamide (Single Enantiomer)—Compound 113

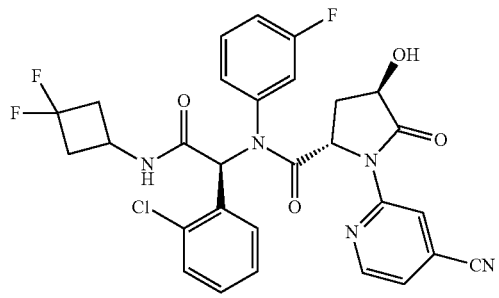 [SMILES: N#Cc1ccnc(N2C(=O)[C@H](O)C[C@H]2C(=O)N(c2cccc(F)c2)[C@H](C(=O)NC2CC(F)(F)C2)c2ccccc2Cl)c1]

$^1$H NMR (400 MHz, CDCl$_3$): δ 8.70 (m, 1H), 8.53 (s, 1H), 7.72 (d, J=7.5 Hz, 1H), 7.32 (d, J=4.9 Hz, 2H), 7.18 (d, J=6.0 Hz, 1H), 7.09-6.85 (m, 4H), 6.43 (s, 1H), 6.20 (d, J=5.3 Hz, 1H), 4.89 (s, 1H), 4.74 (t, J=9.2 Hz, 1H), 4.37-4.32 (m, 1H), 3.40 (s, 1H), 3.11-2.87 (m, 2H), 2.77-2.14 (m, 3H), 2.03-1.91 (m, 1H). MS: 598.1 $(M+1)^+$.

(2S,4R)—N—((S)-1-(2-Chlorophenyl)-2-((3,3-difluorocyclobutyl)amino)-2-oxoethyl)-1-(4-cyanopyrimidin-2-yl)-N-(3-fluorophenyl)-4-hydroxy-5-oxopyrrolidine-2-carboxamide—Compound 120

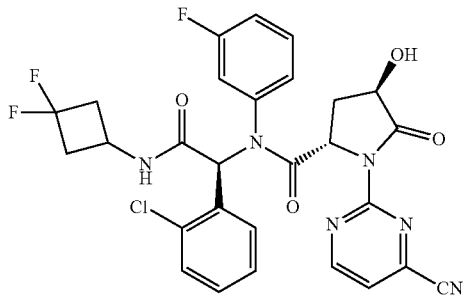 [SMILES: N#Cc1ccnc(N2C(=O)[C@H](O)C[C@H]2C(=O)N(c2cccc(F)c2)[C@H](C(=O)NC2CC(F)(F)C2)c2ccccc2Cl)n1]

¹H NMR (400 MHz, CDCl₃): δ 8.98 (d, J=4.4 Hz, 1H), 7.70 (s, 1H), 7.39 (d, J=4.9 Hz, 2H), 7.20-6.86 (m, 4H), 6.50 (s, 1H), 5.75 (s, 1H), 5.35 (s, 1H), 4.92-4.63 (m, 2H), 4.34 (s, 1H), 2.91 (m, 3H), 2.21 (m, 4H). MS: 599.1 (M+1)⁺.

(2S,4R)—N—((S)-1-(2-Chlorophenyl)-2-((4,4-difluorocyclohexyl)amino)-2-oxoethyl)-1-(4-cyanopyridin-2-yl)-N-(3-fluorophenyl)-4-hydroxy-5-oxopyrrolidine-2-carboxamide (Single Enantiomer)—Compound 121

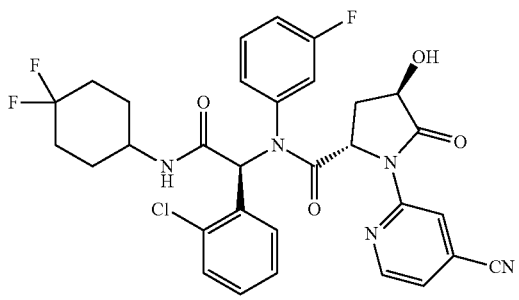 [SMILES: N#Cc1ccnc(N2C(=O)[C@H](O)C[C@H]2C(=O)N(c2cccc(F)c2)[C@H](C(=O)NC2CCC(F)(F)CC2)c2ccccc2Cl)c1]

¹H NMR (400 MHz, CDCl₃): δ 8.78 (s, 1H), 8.54 (s, 1H), 7.77 (d, J=8.1 Hz, 1H), 7.45-7.30 (m, 2H), 7.25-6.83 (m, 5H), 6.42 (s, 1H), 5.49 (d, J=7.4 Hz, 1H), 4.83 (m, 2H), 4.00 (s, 1H), 3.02 (s, 1H), 2.74 (m, 1H), 2.25-1.74 (m, 7H), 1.56-1.33 (m, 2H). MS: 626.2 (M+1)⁺.

(2S,4R)—N—((R)-1-(2-Chlorophenyl)-2-((4,4-difluorocyclohexyl)amino)-2-oxoethyl)-1-(4-cyanopyrimidin-2-yl)-N-(3-fluorophenyl)-4-hydroxy-5-oxopyrrolidine-2-carboxamide (Single Enantiomer)—Compound 122

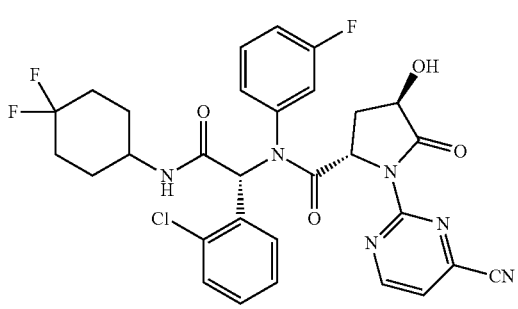 [SMILES: N#Cc1ccnc(N2C(=O)[C@H](O)C[C@H]2C(=O)N(c2cccc(F)c2)[C@@H](C(=O)NC2CCC(F)(F)CC2)c2ccccc2Cl)n1]

¹H NMR (400 MHz, CDCl₃): δ 9.00 (d, J=4.8 Hz, 1H), 7.83 (m, 1H), 7.42 (t, J=6.6 Hz, 2H), 7.22 (m, 2H), 7.18-7.08 (m, 1H), 7.08-6.67 (m, 2H), 6.17 (m, 1H), 5.70 (d, J=7.6 Hz, 1H), 4.93-4.66 (m, 2H), 3.88 (d, J=7.7 Hz, 1H), 3.37 (s, 1H), 2.71 (m, 1H), 2.03 (m, 5H), 1.88-1.64 (m, 4H). MS: 627.2 (M+1)⁺.

(2S,4R)—N—((S)-1-(2-Chlorophenyl)-2-((4,4-difluorocyclohexyl)amino)-2-oxoethyl)-1-(4-cyanopyrimidin-2-yl)-N-(3-fluorophenyl)-4-hydroxy-5-oxopyrrolidine-2-carboxamide—Compound 123

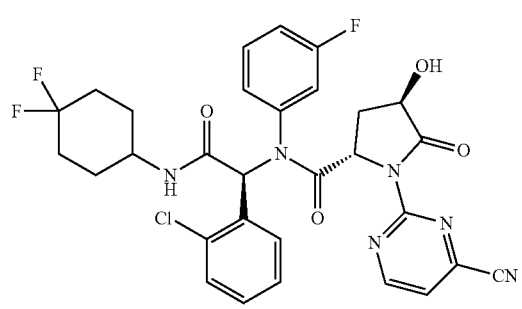 [SMILES: N#Cc1ccnc(N2C(=O)[C@H](O)C[C@H]2C(=O)N(c2cccc(F)c2)[C@H](C(=O)NC2CCC(F)(F)CC2)c2ccccc2Cl)n1]

¹H NMR (400 MHz, CDCl₃): δ 8.99 (d, J=4.4 Hz, 1H), 7.74 (d, J=7.9 Hz, 1H), 7.47-7.29 (m, 3H), 7.08 (m, 6H), 6.51 (s, 1H), 5.61 (s, 1H), 4.81 (m, 2H), 4.02 (d, J=7.2 Hz, 1H), 3.38 (s, 1H), 2.89-2.65 (m, 1H), 2.23-1.81 (m, 8H), 1.58-1.48 (m, 1H). MS: 627.2 (M+1)⁺.

(2S,4R)—N—((R)-1-(2-Chlorophenyl)-2-((3,3-difluorocyclobutyl)amino)-2-oxoethyl)-1-(4-cyanopyridin-2-yl)-N-(3,5-difluorophenyl)-4-hydroxy-5-oxopyrrolidine-2-carboxamide (Single Enantiomer)—Compound 114

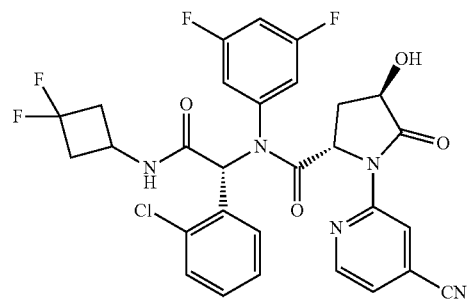 [SMILES: N#Cc1ccnc(N2C(=O)[C@H](O)C[C@H]2C(=O)N(c2cc(F)cc(F)c2)[C@@H](C(=O)NC2CC(F)(F)C2)c2ccccc2Cl)c1]

¹H NMR (400 MHz, CDCl₃): δ 8.71 (d, J=5.8 Hz, 1H), 8.64-8.50 (m, 1H), 7.94-7.56 (m, 1H), 7.47-7.31 (m, 2H), 7.29 (d, J=2.2 Hz, 1H), 7.26-7.18 (m, 1H), 7.16-6.95 (m, 2H), 6.88-6.65 (m, 1H), 6.44-6.35 (m, 1H), 6.29 (s, 1H), 6.11 (d, J=6.7 Hz, 1H), 4.77 (m, 2H), 4.40-4.08 (m, 1H), 3.27 (s, 1H), 3.09-2.58 (m, 3H), 2.54-2.12 (m, 2H), 2.10-1.95 (m, 1H). MS: 616 (M+1)⁺.

(2S,4R)—N—((S)-1-(2-Chlorophenyl)-2-((3,3-difluorocyclobutyl)amino)-2-oxoethyl)-1-(4-cyanopyridin-2-yl)-N-(3,5-difluorophenyl)-4-hydroxy-5-oxopyrrolidine-2-carboxamide (Single Enantiomer)—Compound 115

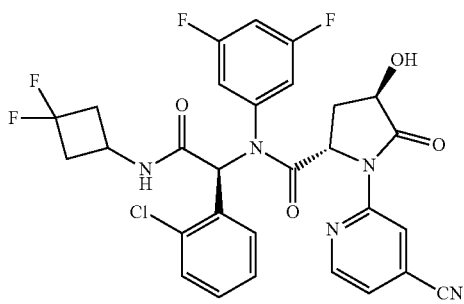 [SMILES: N#Cc1ccnc(N2C(=O)[C@H](O)C[C@H]2C(=O)N(c2cc(F)cc(F)c2)[C@H](C(=O)NC2CC(F)(F)C2)c2ccccc2Cl)c1]

1H NMR (400 MHz, MeOD): δ 8.65-8.50 (m, 2H), 7.54 (d, J=9.5 Hz, 1H), 7.43-7.32 (m, 1H), 7.22-7.12 (m, 2H), 7.03 (m, 1H), 6.97-6.87 (m, 1H), 6.84-6.75 (m, 2H), 6.36 (d, J=8.5 Hz, 1H), 4.89 (d, J=8.6 Hz, 1H), 4.65-4.49 (m, 2H), 4.13 (m, 1H), 2.93-2.72 (m, 2H), 2.57-2.26 (m, 3H), 1.85 (m, 1H). MS: 616.1 (M+1)+.

(2S,4R)—N—((S)-1-(2-Chlorophenyl)-2-((3,3-difluorocyclobutyl)amino)-2-oxoethyl)-1-(4-cyanopyrimidin-2-yl)-N-(3,5-difluorophenyl)-4-hydroxy-5-oxopyrrolidine-2-carboxamide—Compound 117

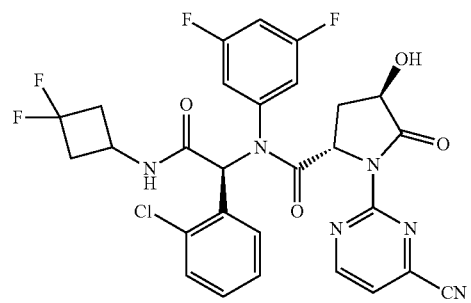

¹H NMR (400 MHz, MeOD): δ 8.88 (d, J=4.9 Hz, 1H), 7.56 (m, 2H), 7.34 (dd, J=8.0, 1.1 Hz, 1H), 7.16 (td, J=7.8, 1.6 Hz, 1H), 7.09-7.00 (m, 1H), 6.98-6.85 (m, 2H), 6.81 (m, 1H), 6.42 (s, 1H), 4.87 (d, J=8.8 Hz, 1H), 4.59-4.42 (m, 2H), 4.27-4.09 (m, 1H), 2.98-2.74 (m, 2H), 2.46 (m, 3H), 2.02-1.76 (m, 1H). MS: 617.1 (M+1)+.

(2S,4R)—N—((R)-1-(2-Chlorophenyl)-2-((3,3-difluorocyclobutyl)amino)-2-oxoethyl)-1-(4-cyanopyrimidin-2-yl)-N-(3,5-difluorophenyl)-4-hydroxy-5-oxopyrrolidine-2-carboxamide (Single Enantiomer)—Compound 116

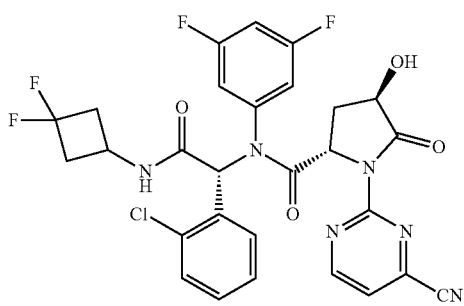 [SMILES: N#Cc1ccnc(N2C(=O)[C@H](O)C[C@H]2C(=O)N(c2cc(F)cc(F)c2)[C@@H](C(=O)NC2CC(F)(F)C2)c2ccccc2Cl)n1]

¹H NMR (400 MHz, CDCl₃): δ 8.98 (t, J=5.0 Hz, 1H), 7.88 (s, 1H), 7.88 (s, 1H), 7.50-7.37 (m, 2H), 7.33-7.20 (m, 2H), 7.19-7.06 (m, 2H), 6.83-6.66 (m, 1H), 6.48 (m, 2H), 6.27 (s, 1H), 4.23 (s, 1H), 3.32 (s, 1H), 2.87 (m, 2H), 2.66 (m, 1H), 2.35-2.02 (m, 3H). MS: 617.1 (M+1)+.

(2S,4R)—N—((R)-1-(2-Chlorophenyl)-2-(4,4-difluorocyclohexylamino)-2-oxoethyl)-1-(4-cyanopyridin-2-yl)-N-(3,5-difluorophenyl)-4-hydroxy-5-oxopyrrolidine-2-carboxamide (Single Enantiomer)—Compound 124

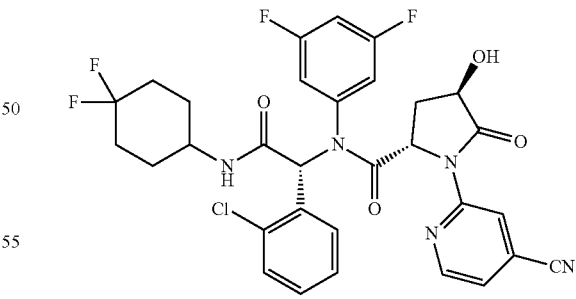

¹H NMR (400 MHz, CDCl₃): δ 8.71 (s, 1H), 8.64 (d, J=5.0 Hz, 1H), 7.79 (s, 1H), 7.45 (d, J=7.8 Hz, 1H), 7.35 (dd, J=5.0, 1.0 Hz, 1H), 7.30-7.24 (m, 1H), 7.16 (d, J=6.3 Hz, 1H), 7.14-7.05 (m, 1H), 6.79-6.68 (m, 2H), 6.27 (s, 1H), 5.87 (d, J=7.5 Hz, 1H), 4.82 (t, J=6.9 Hz, 1H), 4.74 (t, J=9.2 Hz, 1H), 3.90-3.71 (m, 1H), 3.27 (s, 1H), 2.65 (m, 1H), 2.15-1.72 (m, 8H), 1.57-1.43 (m, 1H). MS: 644.2 (M+1)+.

(2S,4R)—N—((S)-1-(2-Chlorophenyl)-2-(4,4-difluorocyclohexylamino)-2-oxoethyl)-1-(4-cyanopyridin-2-yl)-N-(3,5-difluorophenyl)-4-hydroxy-5-oxopyrrolidine-2-carboxamide (Single Enantiomer)—Compound 125

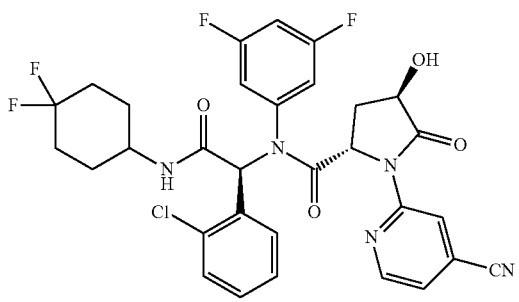 [SMILES: N#Cc1ccnc(N2C(=O)[C@H](O)C[C@H]2C(=O)N(c2cc(F)cc(F)c2)[C@H](C(=O)NC2CCC(F)(F)CC2)c2ccccc2Cl)c1]

¹H NMR (400 MHz, CDCl₃): δ 8.83-8.47 (m, 2H), 7.62 (d, J=8.0 Hz, 1H), 7.38 (d, J=8.0 Hz, 1H), 7.32 (d, J=5.0 Hz, 1H), 7.21 (t, J=7.1 Hz, 1H), 7.05 (t, J=7.5 Hz, 1H), 6.98 (d, J=7.7 Hz, 1H), 6.85 (d, J=7.7 Hz, 1H), 6.68 (t, J=8.6 Hz, 1H), 6.40 (s, 1H), 5.62 (d, J=7.7 Hz, 1H), 4.96-4.70 (m, 2H), 4.01 (d, J=7.6 Hz, 1H), 3.37 (s, 1H), 2.70 (m, 1H), 2.14-1.74 (m, 8H), 155-1.41 (m, 1H). MS: 644.2 (M+1)⁺.

(2S,4R)—N—((S)-1-(2-Chlorophenyl)-2-(4,4-difluorocyclohexylamino)-2-oxoethyl)-1-(4-cyanopyrimidin-2-yl)-N-(3,5-difluorophenyl)-4-hydroxy-5-oxopyrrolidine-2-carboxamide (Single Enantiomer)—Compound 127

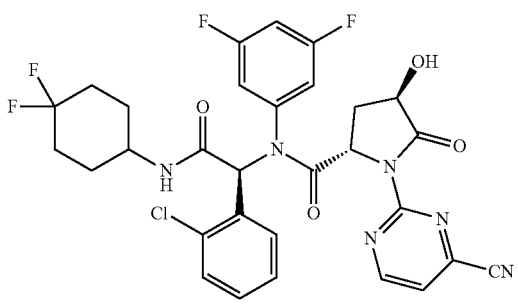

¹H NMR (400 MHz, CDCl₃): δ 8.99 (d, J=4.8 Hz, 1H), 7.62 (d, J=8.7 Hz, 1H), 7.49-7.35 (m, 2H), 7.22 (td, J=7.8, 1.5 Hz, 1H), 7.07 (t, J=7.1 Hz, 1H), 6.98 (dd, J=7.8, 1.3 Hz, 1H), 6.91 (d, J=8.2 Hz, 1H), 6.72 (tt, J=8.6, 2.2 Hz, 1H), 6.48 (s, 1H), 5.64 (d, J=7.7 Hz, 1H), 4.94-4.69 (m, 2H), 4.11-3.91 (m, 1H), 3.46 (s, 1H), 2.79 (m, 1H), 2.19-1.85 (m, 7H), 1.61-1.40 (m, 2H). MS: 645.2 (M+1)⁺.

(2S,4R)—N—((R)-1-(2-Chlorophenyl)-2-(4,4-difluorocyclohexylamino)-2-oxoethyl)-1-(4-cyanopyrimidin-2-yl)-N-(3,5-difluorophenyl)-4-hydroxy-5-oxopyrrolidine-2-carboxamide (Single Enantiomer)—Compound 126

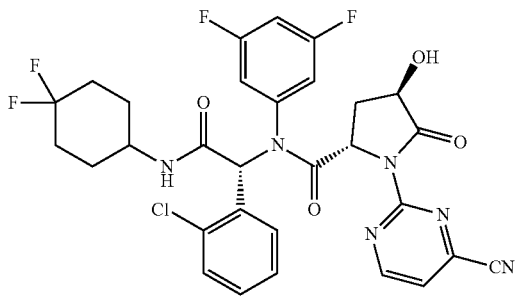 [SMILES: N#Cc1ccnc(N2C(=O)[C@H](O)C[C@H]2C(=O)N(c2cc(F)cc(F)c2)[C@@H](C(=O)NC2CCC(F)(F)CC2)c2ccccc2Cl)n1]

¹H NMR (400 MHz, CDCl₃): δ 8.98 (dd, J=4.7, 2.1 Hz, 1H), 7.63 (d, J=7.3 Hz, 1H), 7.50-7.33 (m, 2H), 7.28-6.87 (m, 3H), 6.84-6.38 (m, 2H), 6.19 (s, 1H), 5.82 (d, J=7.6 Hz, 1H), 4.94-4.65 (m, 2H), 3.86 (d, J=7.5 Hz, 1H), 3.57-3.49 (m, 1H), 2.68 (m, 1H), 2.16-1.86 (m, 6H), 1.81-1.77 (m, 2H). MS: 645.2 (M+1)⁺.

(2S,4R)—N-(1-(2-Chlorophenyl)-2-(3,3-difluorocyclobutylamino)-2-oxoethyl)-N-(3-cyano-5-fluorophenyl)-1-(4-cyanopyridin-2-yl)-4-hydroxy-5-oxopyrrolidine-2-carboxamide (Racemic)—Compound 169

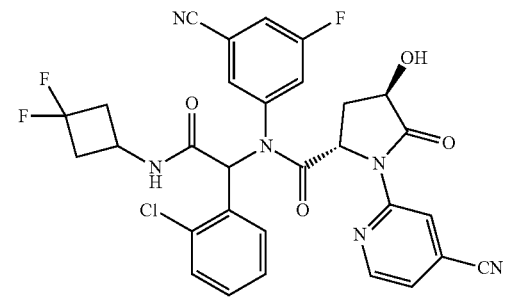 [SMILES: N#Cc1cc(F)cc(N(C(=O)[C@@H]2C[C@@H](O)C(=O)N2c2cc(C#N)ccn2)C(C(=O)NC2CC(F)(F)C2)c2ccccc2Cl)c1]

¹H NMR (400 MHz, CDCl₃): δ 8.87-8.72 (m, 1H), 8.67-8.48 (m, 1H), 8.26-8.01 (m, 1H), 7.56-7.30 (m, 4H), 7.27-7.17 (m, 1H), 7.10 (m, 1H), 6.95 (t, J=7.3 Hz, 1H), 6.52-6.28 (m, 1H), 6.21-5.95 (m, 1H), 4.88-4.64 (m, 2H), 4.30 (m, 1H), 3.21-2.81 (m, 3H), 2.74-2.19 (m, 3H), 2.13-1.91 (m, 1H). MS: 623.1 (M+1)⁺.

181

(2S,4S)—N—((S)-1-(2-Chlorophenyl)-2-(3,3-difluorocyclobutylamino)-2-oxoethyl)-1-(4-cyano-pyridin-2-yl)-N-(3-fluorophenyl)-4-hydroxy-5-oxopyrrolidine-2-carboxamide (Single Enantiomer)—Compound 118

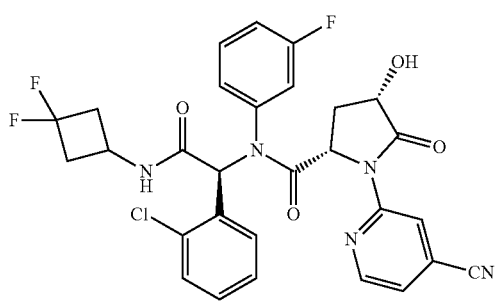 [SMILES: N#Cc1ccnc(N2C(=O)[C@@H](O)C[C@H]2C(=O)N(c2cccc(F)c2)[C@H](C(=O)NC2CC(F)(F)C2)c2ccccc2Cl)c1]

$^1$H NMR (400 MHz, CD$_3$OD): δ 8.97 (d, J=4.7 Hz, 1H), 7.81-7.62 (m, 2H), 7.41-7.35 (m, 2H), 7.26-6.96 (m, 5H), 6.46 (d, J=12.0 Hz, 1H), 4.81-4.75 (m, 1H), 4.37-4.28 (m, 1H), 4.25-4.15 (m, 1H), 2.91 (s, 2H), 2.60-2.37 (m, 3H), 2.00-1.87 (m, 1H). MS: 598.1 (M+1)$^+$.

182

(2S,4S)—N—((S)-1-(2-Chlorophenyl)-2-((4,4-difluorocyclohexyl)amino)-2-oxoethyl)-1-(4-cyano-pyridin-2-yl)-N-(3-fluorophenyl)-4-hydroxy-5-oxopyrrolidine-2-carboxamide (Single Enantiomer)—Compound 172

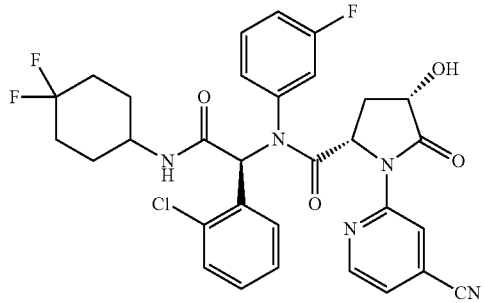

$^1$H NMR (400 MHz, CDCl$_3$): δ 8.87-8.57 (m, 2H), 7.96 (s, 1H), 7.50-7.30 (m, 3H), 7.26-7.12 (m, 2H), 7.09-6.96 (m, 2H), 6.28 (s, 1H), 5.67 (d, J=7.6 Hz, 1H), 4.74 (dd, J=8.1, 4.6 Hz, 1H), 4.42-4.36 (m, 1H), 4.04 (s, 1H), 3.87 (d, J=7.8 Hz, 1H), 2.54-2.41 (m, 1H), 2.22-1.76 (m, 8H), 1.50-1.32 (m, 2H). MS: 626.2 (M+1)$^+$.

(2S,4S)—N—((S)-1-(2-Chlorophenyl)-2-(3,3-difluorocyclobutylamino)-2-oxoethyl)-1-(4-cyanopyrimidin-2-yl)-N-(3-fluorophenyl)-4-hydroxy-5-oxopyrrolidine-2-carboxamide (Single Enantiomer)—Compound 119

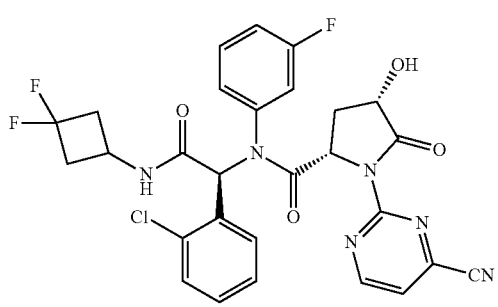 [SMILES: N#Cc1ccnc(N2C(=O)[C@@H](O)C[C@H]2C(=O)N(c2cccc(F)c2)[C@H](C(=O)NC2CC(F)(F)C2)c2ccccc2Cl)n1]

$^1$H NMR (400 MHz, CD$_3$OD): δ 8.97 (d, J=4.7 Hz, 1H), 7.81-7.62 (m, 2H), 7.41-7.35 (m, 2H), 7.26-6.96 (m, 5H), 6.46 (d, J=12.0 Hz, 1H), 4.81-4.75 (m, 1H), 4.37-4.28 (m, 1H), 4.25-4.15 (m, 1H), 2.91 (s, 2H), 2.60-2.37 (m, 3H), 2.00-1.87 (m, 1H). MS: 599.1 (M+1)$^+$.

(2S,4S)—N—((S)-1-(2-Chlorophenyl)-2-((4,4-difluorocyclohexyl)amino)-2-oxoethyl)-1-(4-cyanopyrimidin-2-yl)-N-(3-fluorophenyl)-4-hydroxy-5-oxopyrrolidine-2-carboxamide (Single Enantiomer)—Compound 189

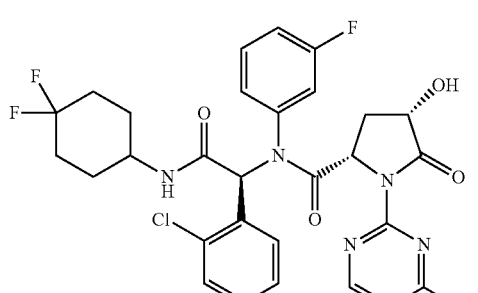

$^1$H NMR (400 MHz, CDCl$_3$): δ 9.00 (d, J=4.7 Hz, 1H), 7.76 (s, 1H), 7.47-7.30 (m, 2H), 7.24-6.88 (m, 6H), 6.47 (d, J=6.7 Hz, 1H), 5.54 (s, 1H), 4.74 (s, 1H), 4.35 (s, 1H), 3.99 (s, 1H), 3.72 (d, J=34.8 Hz, 1H), 2.58-2.18 (m, 2H), 1.88 (m, 4H), 1.56-1.42 (m, 2H). MS: 627.2 (M+1)$^+$.

(2S,4S)—N—((S)-1-(2-Chlorophenyl)-2-((3,3-difluorocyclobutyl)amino)-2-oxoethyl)-1-(4-cyanopyridin-2-yl)-N-(3,5-difluorophenyl)-4-hydroxy-5-oxopyrrolidine-2-carboxamide (Single Enantiomer)—Compound 171

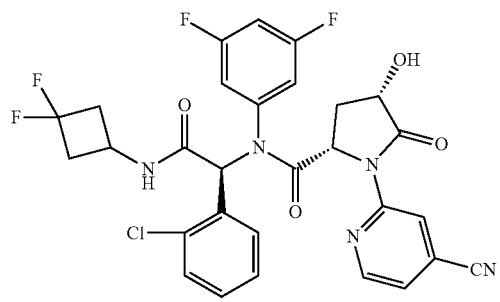 [SMILES: N#Cc1ccnc(N2C(=O)[C@@H](O)C[C@H]2C(=O)N(c2cc(F)cc(F)c2)[C@H](C(=O)NC2CC(F)(F)C2)c2ccccc2Cl)c1]

$^1$H NMR (400 MHz, CDCl$_3$): δ 8.68 (s, 1H), 8.52 (d, J=5.0 Hz, 1H), 7.60 (d, J=8.2 Hz, 1H), 7.45-7.17 (m, 4H), 7.15-6.91 (m, 2H), 6.84 (d, J=8.7 Hz, 1H), 6.69 (t, J=8.7 Hz, 1H), 6.54-6.36 (m, 2H), 4.87-4.60 (m, 1H), 4.31 (m, 2H), 3.99-3.77 (m, 1H), 3.15-2.78 (m, 2H), 2.62-2.26 (m, 3H), 2.26-2.08 (m, 1H). MS: 616.1 (M+1)$^+$.

(2S,4S)—N—((S)-1-(2-Chlorophenyl)-2-((4,4-difluorocyclohexyl)amino)-2-oxoethyl)-1-(4-cyanopyridin-2-yl)-N-(3,5-difluorophenyl)-4-hydroxy-5-oxopyrrolidine-2-carboxamide (Single Enantiomer)—Compound 174

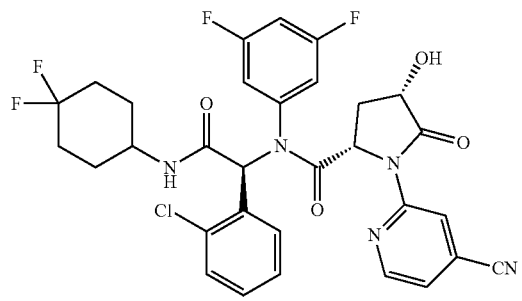 [SMILES: N#Cc1ccnc(N2C(=O)[C@@H](O)C[C@H]2C(=O)N(c2cc(F)cc(F)c2)[C@H](C(=O)NC2CCC(F)(F)CC2)c2ccccc2Cl)c1]

$^1$H NMR (400 MHz, CDCl$_3$): δ 8.75 (s, 1H), 8.53 (d, J=4.5 Hz, 1H), 7.62 (s, 1H), 7.44-7.18 (m, 3H), 7.09-6.96 (m, 2H), 6.86 (s, 1H), 6.71 (t, J=8.7 Hz, 1H), 6.38 (s, 1H), 5.58 (d, J=7.6 Hz, 1H), 4.80 (dd, J=8.0, 5.2 Hz, 1H), 4.37 (d, J=5.6 Hz, 1H), 3.96 (s, 1H), 3.61 (d, J=7.7 Hz, 1H), 2.62-2.29 (m, 1H), 2.13 (m, 6H), 1.48 (m, 2H). MS: 644.2 (M+1)$^+$.

Example 19. Preparation of (2S)—N—((R)-1-(2-chlorophenyl)-2-(3,3-difluorocyclobutylamino)-2-oxoethyl)-1-(4-cyanopyridin-2-yl)-N-(3-fluorophenyl)-4-hydroxy-4-methyl-5-oxopyrrolidine-2-carboxamide (Single Enantiomer)—Compound 183

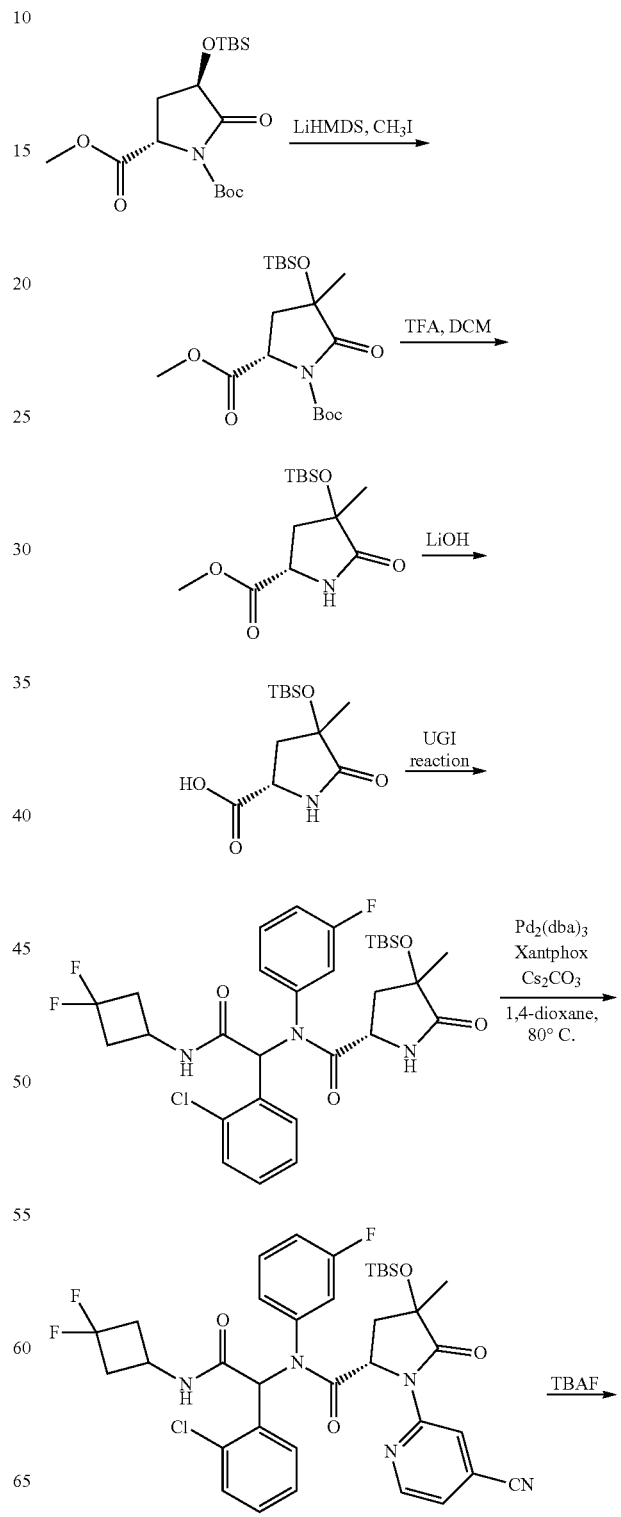

-continued

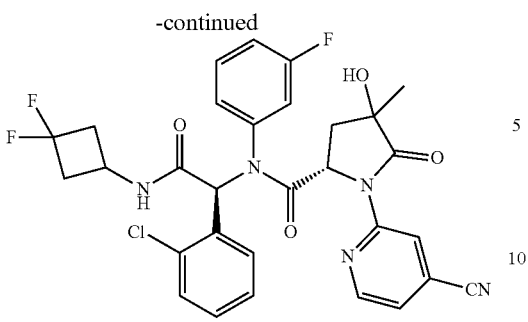

Step A. (2S)-1-tert-Butyl 2-methyl 4-(tert-butyldimethylsilyloxy)-4-methyl-5-oxopyrrolidine-1,2-dicarboxylate LiHMDS (1 M in THF, 22.6 mL, 22.6 mmol) was added into a mixture of (2S,4R)-1-tert-butyl 2-methyl 4-(tert-butyldimethylsilyloxy)-5-oxopyrrolidine-1,2-dicarboxylate (6.5 g, 17.4 mmol) in THF (60 mL) at −78° C. under $N_2$. The mixture was stirred at −78° C. for 1 hr. A solution of iodomethane (2.7 g, 19.1 mmol) in THF (10 mL) was added dropwise to the above mixture over 30 min. Then the solution was stirred at −78° C. for another 25 min. The resulting mixture was allowed to warm to room temperature and stirred overnight. The mixture was quenched with $NH_4Cl$ and extracted by ethyl acetate (60 mL×3). The combined organic layers were dried and concentrated. The residue was purified by column chromatography to give the desired product. MS: 388 $(M+1)^+$.

Step B. (2S,4S)-Methyl 4-((tert-butyldimethylsilyl)oxy)-5-oxopyrrolidine-2-carboxylate A solution of (2S)-1-tert-butyl 2-methyl 4-(tert-butyldimethylsilyloxy)-4-methyl-5-oxopyrrolidine-1,2-dicarboxylate (960 mg, 25 mmol) in TFA/DCM (V:V=1:3) was stirred at room temperature for 1 h. The mixture was then concentrated to give the desired product which was used directly in the next step. MS: 288 $(M+1)^+$.

Step C. (2S)-4-(tert-Butyldimethylsilyloxy)-4-methyl-5-oxopyrrolidine-2-carboxylic Acid To a solution of (2S)-methyl 4-(tert-butyldimethylsilyloxy)-4-methyl-5-oxopyrrolidine-2-carboxylate (400 mg, 1.4 mmol) in MeOH/THF/$H_2O$ (V:V:V=2:2:1) was added LiOH (50 mg, 2.1 mmol). The mixture was stirred at room temperature for 1 hr and then concentrated. The residue was partitioned between ethyl acetate and water. The aqueous phase was separated and adjusted to pH=3-4 with 1N HCl solution. The aqueous layer was then extracted with ethyl acetate (2×20 mL). The combined organic layers were dried over anhydrous $Na_2SO_4$ and concentrated to give the desired product. MS: 274 $(M+1)^+$.

Step D. (2S)-4-(tert-Butyldimethylsilyloxy)-N-(1-(2-chlorophenyl)-2-(3,3-difluorocyclobutylamino)-2-oxoethyl)-N-(3-fluorophenyl)-4-methyl-5-oxopyrrolidine-2-carboxamide A solution of 3-fluoroaniline (83 mg, 0.75 mmol) and 2-chlorobenzaldehyde (105 mg, 0.75 mmol) in MeOH (5 mL) was stirred for 30 min at room temperature, followed by addition of (2S)-4-(tert-butyldimethylsilyloxy)-4-methyl-5-oxopyrrolidine-2-carboxylic acid (205 mg, 0.75 mmol). The resulting mixture was stirred for 10 min and followed by the addition of 1,1-difluoro-3-isocyanocyclobutane (105 mg, 0.9 mmol). The mixture was stirred at room temperature overnight and concentrated, and then the residue was purified by a standard method to give the desired product. MS: 624 $(M+1)^+$.

Step E. (2S)-4-(tert-Butyldimethylsilyloxy)-N-(1-(2-chlorophenyl)-2-(3,3-difluorocyclobutyl-amino)-2-oxoethyl)-1-(4-cyanopyridin-2-yl)-N-(3-fluorophenyl)-4-methyl-5-oxopyrrolidine-2-carboxamide A mixture consisting of (2S)-4-(tert-butyldimethylsilyloxy)-N-(1-(2-chlorophenyl)-2-(3,3-difluorocyclobutylamino)-2-oxoethyl)-N-(3-fluorophenyl)-4-methyl-5-oxopyrrolidine-2-carboxamide (200 mg, 0.32 mmol), 2-bromoisonicotinonitrile (88 mg, 0.48 mmol), $Cs_2CO_3$ (146 mg, 0.45 mmol), $Pd_2(dba)_3$ (29 mg, 0.032 mmol), Xant-Phos (19 mg, 0.032 mmol) and 1,4-dioxane (5 mL) was stirred under $N_2$ at 80° C. overnight. After filtration, the filtrate was concentrated in vacuo and the residue was purified by a standard method to give desired product. MS: 726 $(M+1)^+$.

Step F. (2S)—N—((R)-1-(2-Chlorophenyl)-2-(3,3-difluorocyclobutylamino)-2-oxoethyl)-1-(4-cyanopyridin-2-yl)-N-(3-fluorophenyl)-4-hydroxy-4-methyl-5-oxopyrrolidine-2-carboxamide To a solution of (2S)-4-(tert-butyldimethylsilyloxy)-N-(1-(2-chlorophenyl)-2-(3,3-difluorocyclobutylamino)-2-oxoethyl)-1-(4-cyanopyridin-2-yl)-N-(3-fluorophenyl)-4-methyl-5-oxopyrrolidine-2-arboxamide (50 mg, 0.07 mmol) in THF (2 mL) was added TBAF (36 mg, 0.14 mmol) at 0° C. The solution was stirred at 0° C. for 30 min and then partitioned between water and EtOAc. Combined organic layers were separated, dried, and concentrated in vacuo. The resulting residue was purified by a standard method to give the desired product. $^1$H NMR (400 MHz, $CDCl_3$): δ 8.57 (d, J=5.0 Hz, 1H), 8.48 (d, J=3.8 Hz, 1H), 7.54-7.17 (m, 5H), 6.98-6.84 (m, 3H), 6.67 (dd, J=8.6 Hz, 1H), 6.33 (d, J=5.2 Hz, 1H), 6.08-6.01 (m, 1H), 4.55-4.48 (m, 1H), 4.29 (s, 1H), 3.22-2.35 (m, 6H), 1.93-1.80 (m, 1H), 1.27 (s, 3H). MS: 612.2 $(M+1)^+$.

Example 20. Preparation of (2S)—N-(1-(2-chlorophenyl)-2-(3,3-difluorocyclobutylamino)-2-oxoethyl)-1-(4-cyanopyridin-2-yl)-N-(3-fluoro-5-sulfamoylphenyl)-5-oxopyrrolidine-2-carboxamide (Racemic)—Compound 158

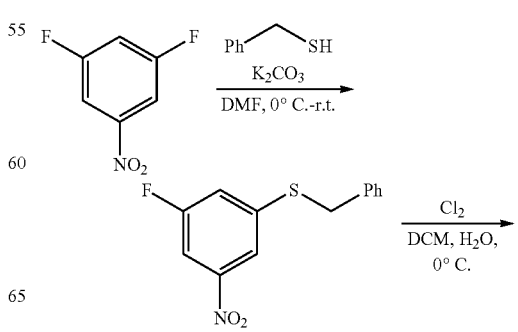

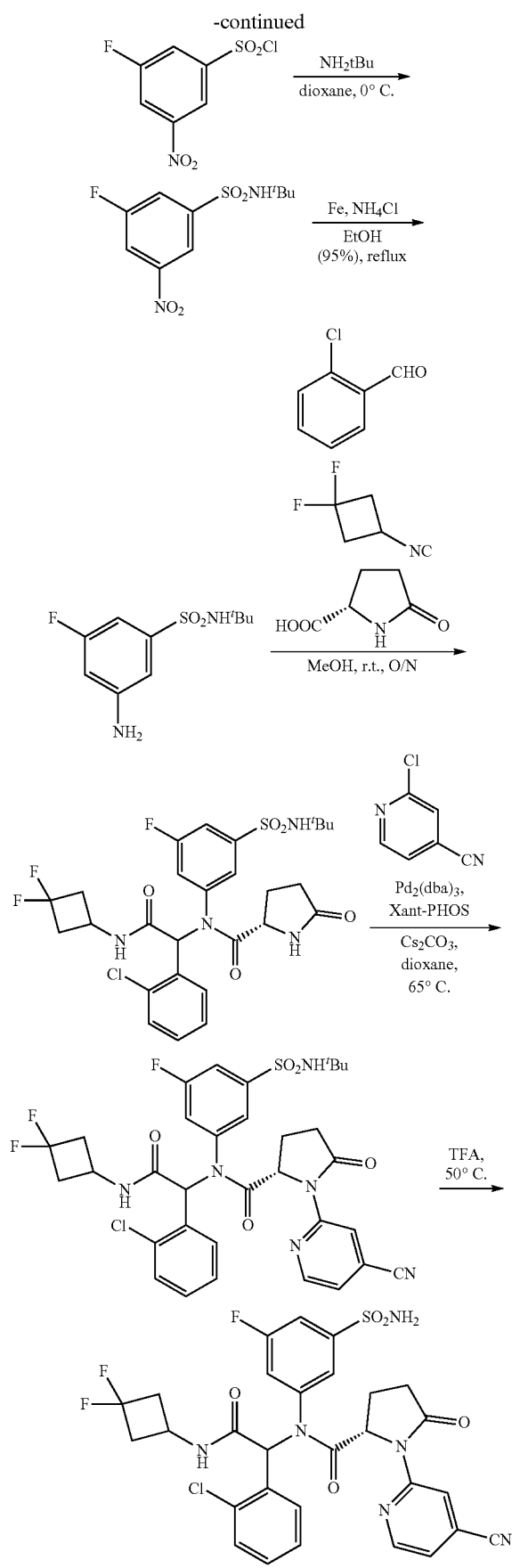

Step A. Benzyl(3-fluoro-5-nitrophenyl)sulfane

To a solution of 1,3-difluoro-5-nitrobenzene (15.9 g, 100 mmol) in DMF (160 mL) was added $K_2CO_3$ (15.8 g, 110 mmol) and phenylmethanethiol (12.4 g, 100 mmol) at 0° C. The reaction was stirred at room temperature for 2 hr and then quenched with $H_2O$. The resulting mixture extracted with EtOAc (3×100 mL). The combined organic layers were dried over anhydrous $Na_2SO_4$ and concentrated in vacuo to afford the crude product as a yellow oil which was used in the next step without further purification.

Step B. 3-Fluoro-5-nitrobenzene-1-sulfonyl chloride

To a solution of benzyl(3-fluoro-5-nitrophenyl)sulfane (3.0 g) in DCM (30 mL) was added deionized water (30 mL). Then chlorine was bubbled slowly into the mixture until the complete consumption of the starting material was observed (monitored by TLC). The organic layer was separated, washed with sat. aq. $Na_2S_2O_3$ solution, dried and concentrated to afford the crude product which was used in the next step without further purification.

Step C. N-tert-butyl-3-fluoro-5-nitrobenzenesulfonamide

To a solution of 3-fluoro-5-nitrobenzene-1-sulfonyl chloride in dry dioxane (30 mL) was slowly added tert-butylamine (10 mL) at 0° C. The reaction was allowed to warm to room temperature and stirred for 2 hr. The mixture was then concentrated and the residue was purified by column chromatography to afford the desired product. $^1$H NMR (400 MHz, DMSO-$d_6$): δ 8.43 (s, 1H), 8.40-8.32 (m, 1H), 8.10-8.05 (m, 1H), 7.99 (s, 1H), 1.12 (s, 9H).

Step D. 3-Amino-N-tert-butyl-5-fluorobenzenesulfonamide

N-tert-butyl-3-fluoro-5-nitrobenzenesulfonamide (1.0 g, 3.6 mmol), iron powder (1.0 g, 18 mmol) and $NH_4Cl$ (1.0 g, 18 mmol) were mixed in EtOH (95%, 10 mL). The mixture was refluxed for 16 hr then filtered. The filtrate was concentrated and the residue was purified by a standard method to afford the desired product. $^1$H NMR (400 MHz, DMSO-$d_6$): δ 7.45 (s, 1H), 6.88-6.85 (m, 1H), 6.66-6.62 (m, 1H), 6.48-6.42 (m, 1H), 5.89 (s, 2H), 1.11 (s, 9H).

Step E

The same as general procedures for UGI reaction set forth herein.

Step F

The same as general procedures for Buchwald reaction set forth herein.

Step G. (S)—N—((S)-1-(2-Chlorophenyl)-2-(3,3-difluorocyclobutylamino)-2-oxoethyl)-1-(4-cyanopyridin-2-yl)-N-(3-fluoro-5-sulfamoylphenyl)-5-oxopyrrolidine-2-carboxamide To a solution of (2S)—N-(3-(N-tert-butylsulfamoyl)-5-fluorophenyl)-N-(1-(2-chlorophenyl)-2-(3,3-difluorocyclobutylamino)-2-oxoethyl)-1-(4-cyanopyridin-2-yl)-5-oxopyrrolidine-2-carboxamide (80 mg, 0.11 mmol) in DCM (1 mL) was added TFA (1 mL). The reaction was stirred at room temperature for 16 hr and neutralized with saturated aq. NaHCO$_3$. The mixture was then extracted with EtOAc (3×10 mL). The combined organic layers were dried and concentrated. The residue was purified by a standard method to afford the target compound. $^1$H NMR (400 MHz, DMSO-d$_6$): δ 8.90-8.84 (m, 1H), 8.67-8.62 (m, 1H), 8.55 (s, 1H), 8.19 (s, 1H), 7.87-7.76 (m, 1H), 7.65-7.60 (m, 2H), 7.45-7.40 (m, 3H), 7.21 (d, J=7.0 Hz, 2H), 7.11-7.04 (m, 1H), 6.93-6.86 (m, 1H), 6.33-6.26 (m, 1H), 4.83 (m, 1H), 4.13 (s, 1H), 2.94 (m, 2H), 2.63-2.53 (m, 3H), 2.42-2.32 (m, 1H), 1.97 (s, 2H). MS: 661 (M+1)$^+$.

Example 21. Preparation of (2S)—N-(1H-benzo[d]imidazol-7-yl)-N-(1-(2-chlorophenyl)-2-((4,4-difluorocyclohexyl)amino)-2-oxoethyl)-1-(4-cyanopyridin-2-yl)-5-oxopyrrolidine-2-carboxamide (Racemic)—Compound 141

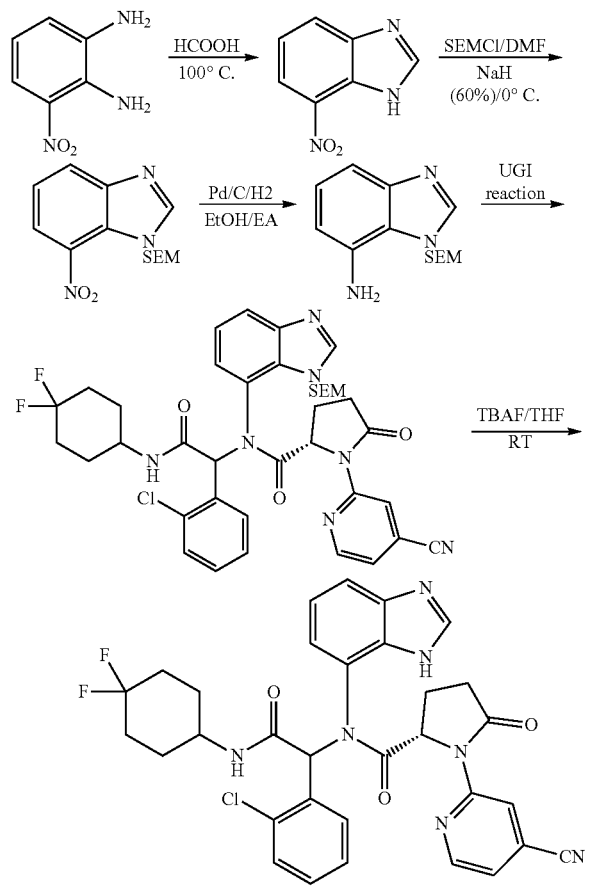

Step A: 7-Nitro-1H-benzo[d]imidazole

A solution of 3-nitrobenzene-1,2-diamine (900 mg, 5.88 mmol) in AcOH (12 mL) was stirred at 100° C. overnight. The mixture was neutralized with aq. NaHCO$_3$ to pH=8 at 0° C. and the precipitate was collected by filtration. The precipitate was dried in vacuo to afford the desired product.

Step B: 7-Nitro-1-((2-(trimethylsilyl)ethoxy)methyl)-1H-benzo[d]imidazole

NaH (331 mg, 8.28 mmol) was added to a solution of 7-nitro-1H-benzo[d]imidazole (900 mg, 5.52 mmol) in DMF (7 mL) at 0° C. under N$_2$. After stirring at 0° C. for 1 hr, SEMCl (1.38 g, 8.28 mmol) was added and the resulting mixture was stirred at room temperature for 2 hr. The reaction mixture was quenched with H$_2$O and extracted with EtOAc (3×30 mL). The combined organic layers were washed with brine, dried over anhydrous Na$_2$SO$_4$, and concentrated. The residue was purified by column chromatography to afford the desired product as a yellow oil.

Step C: 1-((2-(Trimethylsilyl)ethoxy)methyl)-1H-benzo[d]imidazol-7-amine

To a solution of 7-nitro-1-((2-(trimethylsilyl)ethoxy)methyl)-1H-benzo[d]imidazole (600 mg, 2.05 mmol) in EtOH/EtOAc (10 mL/2 mL) was added Pd/C (60 mg). After stifling under a hydrogen atmosphere at room temperature overnight, the reaction mixture was filtered and the filtrate was concentrated. The residue was purified by a standard method to afford the desired product.

Step D

The same as general procedure for UGI reaction set forth herein.

Step E: (2S)—N-(1H-Benzo[d]imidazol-7-yl)-N-(1-(2-chlorophenyl)-2-((4,4-difluorocyclohexyl)amino)-2-oxoethyl)-1-(4-cyanopyridin-2-yl)-5-oxopyrrolidine-2-carboxamide TBAF (1 M in THF, 3 mL) was added to a solution of (2S)—N-(1-(2-chlorophenyl)-2-((4,4-difluoro-cyclohexyl)amino)-2-oxoethyl)-1-(4-cyanopyridin-2-yl)-5-oxo-N-(1-((2-(trimethylsilyl)ethoxy)-methyl)-1H-benzo[d]imidazol-7-yl)pyrrolidine-2-carboxamide in THF (0.5 mL) at 0° C. under N$_2$. After stirring at room temperature for 7 hr, the reaction was quenched with water at 0° C. The resulting mixture was extracted with EtOAc (3×10 mL). The combined organic layers were washed with brine, dried over anhydrous Na$_2$SO$_4$ and concentrated. The resulting residue was purified by a standard method to afford the desired product. $^1$H NMR (400 MHz, CDCl$_3$): δ 13.08 (s, 1H), 8.92-8.39 (m, 2H), 8.19 (m, 1H), 7.82 (m, 1H), 7.51-7.31 (m, 2H), 7.25 (d, J=5.2 Hz, 1H), 7.13-6.70 (m, 3H), 6.41 (m, 1H), 6.20-5.29 (m, 1H), 4.85 (m, 1H), 3.86 (s, 1H), 2.97-2.39 (m, 2H), 2.36-1.70 (m, 9H), 1.40 (m, 2H). MS: 632.2 (M+1)$^+$.

Example 22. Preparation of (4S)—N-(1-(2-chlorophenyl)-2-((3,3-difluorocyclobutyl)amino)-2-oxoethyl)-3-(4-cyanopyridin-2-yl)-N-(3-fluorophenyl)-1-methyl-2-oxoimidazolidine-4-carboxamide (Racemic)—Compound 79

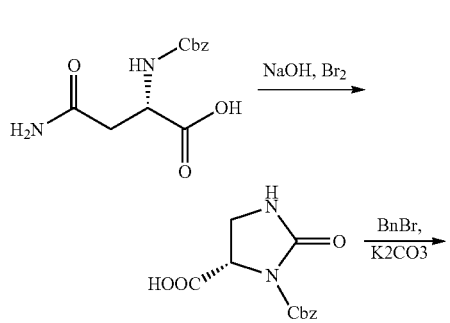

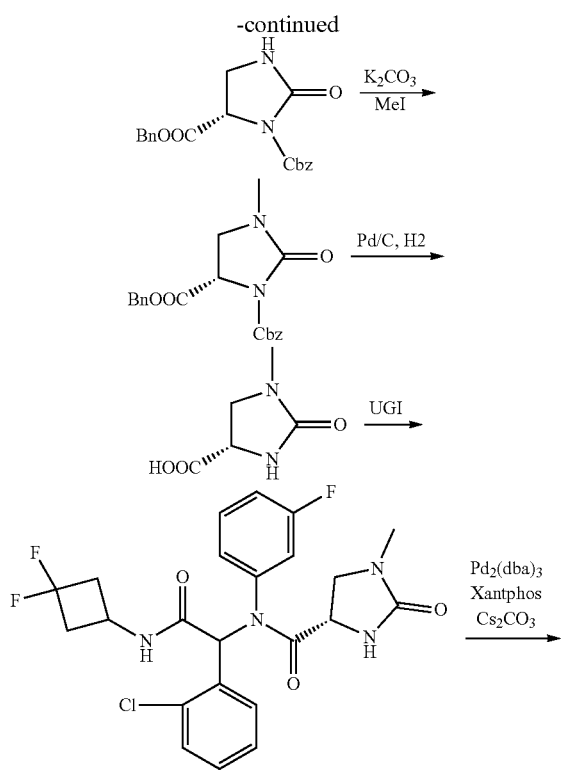

Step A: (S)-3-(Benzyloxycarbonyl)-2-oxoimidazolidine-4-carboxylic Acid

To a solution of 6.6 g of sodium hydroxide in 140 mL of water at 0° C., 8.8 g of bromine was added dropwise, followed by addition of (S)-4-amino-2-(benzyloxycarbonylamino)-4-oxobutanoic acid (13.4 g, 50 mmol) portionwise over 3 min. The resulting yellow solution was heated to 50° C. for 1 hr and then cooled to room temperature. After addition of sodium thiosulfate (2.0 g), the reaction mixture was washed with ether (2×30 mL). The aqueous layer was acidified to pH 1-2 with 6 N HCl. After the precipitate was formed, the suspension was filtered. The sticky material was collected and re-crystallized in MeOH to afford the desired product as a white solid. $^1$H NMR (400 MHz, DMSO-$d_6$): δ 13.29 (s, 1H), 7.57 (s, 1H), 7.40-7.27 (m, 4H), 5.27-5.04 (m, 2H), 4.66 (dd, J=10.2, 3.2 Hz, 1H), 3.63 (t, J=10.0 Hz, 1H), 3.20 (dd, J=9.7, 3.2 Hz, 1H).

Step B: (S)-Dibenzyl 2-oxoimidazolidine-1,5-dicarboxylate

To a 500 mL-flask were added (S)-3-(benzyloxycarbonyl)-2-oxoimidazolidine-4-carboxylic acid (5.3 g, 20 mmol), BnBr (2.8 mL, 23 mmol), $K_2CO_3$ (8.28 g, 60 mmol), and acetonitrile (250 mL). The reaction solution was heated to reflux for 6 hr, cooled and then filtered. The filtrate was concentrated in vacuo and the residue was purified by column chromatography to afford the desired product as white solid. $^1$H NMR (400 MHz, CDCl$_3$): δ 7.41-7.25 (m, 10H), 6.36 (s, 1H), 5.30-5.05 (m, 4H), 4.80 (dd, J=10.2, 3.6 Hz, 1H), 3.74 (t, J=10.0 Hz, 1H), 3.41 (dd, J=9.7, 3.7 Hz, 1H).

Step C: (S)-Dibenzyl 3-methyl-2-oxoimidazolidine-1,5-dicarboxylate

To a dry 100 mL-flask were added (S)-dibenzyl 2-oxoimidazolidine-1,5-dicarboxylate (1.5 g, 4.24 mmol), $K_2CO_3$ (1.17 g, 8.47 mmol), MeI (5.2 mL, 84.7 mmol), and acetone (50 mL). The reaction solution was heated to reflux and stirred overnight. The resulting reaction mixture was cooled and filtered. The filtrate was concentrated in vacuo and the residue was purified by column chromatography to afford the desired product as a white solid. $^1$H NMR (400 MHz, CDCl$_3$): δ 7.40-7.26 (m, 10H), 5.27-5.07 (m, 4H), 4.70 (dd, J=10.2, 3.8 Hz, 1H), 3.63 (dd, J=10.1, 9.7 Hz, 1H), 3.31 (dd, J=9.6, 3.8 Hz, 1H), 2.84 (s, 3H). MS: 369 (M+1)$^+$.

Step D: (S)-1-Methyl-2-oxoimidazolidine-4-carboxylic Acid

To a dry 50 mL-flask were added (S)-dibenzyl 2-oxoimidazolidine-1,5-dicarboxylate (0.5 g, 1.36 mmol), Pd/C (10%, 100 mg) and MeOH (15 mL). The suspension was stirred overnight at room temperature under a hydrogen atmosphere. The resulting reaction mixture was filtered. The filtrate was concentrated in vacuo to afford the desired product as an off-white solid. $^1$H NMR (400 MHz, CD$_3$OD): δ 4.21 (dd, J=9.9, 4.8 Hz, 1H), 3.70 (t, J=9.6 Hz, 1H), 3.55 (dd, J=9.3, 4.8 Hz, 1H), 2.74 (s, 3H). MS: 145 (M+1)$^+$.

Step E: (4S)—N-(1-(2-Chlorophenyl)-2-(3,3-difluorocyclobutylamino)-2-oxoethyl)-N-(3-fluorophenyl)-1-methyl-2-oxoimidazolidine-4-carboxamide A mixture of 2-chlorobenzaldehyde (165 mg, 1.18 mmol) and 3-fluorobenzenamine (131 mg, 1.18 mmol) in MeOH (3 mL) was stirred at room temperature for 30 min. Then (S)-1-methyl-2-oxoimidazolidine-4-carboxylic acid (170 mg, 1.18 mmol) was added and the reaction mixture was stirred for another 15 min, followed by addition of 1,1-difluoro-3-isocyanocyclobutane (138 mg, 1.18 mmol). The reaction mixture was stirred overnight and concentrated in vacuo. The residue was purified by a standard method to give the desired product. MS: 495 (M+1)$^+$.

Step F

The same as the Buchwald reaction procedure set forth herein. $^1$H NMR (400 MHz, CDCl$_3$): δ 8.64-8.34 (m, 2H), 7.94-7.59 (m, 1H), 7.50-6.61 (m, 8H), 6.34-6.07 (m, 1H), 4.94-4.67 (m, 1H), 4.3-4.2 (m, 1H), 3.49 (m, 1H), 3.46-3.22 (m, 1H), 3.02-2.83 (m, 2H), 2.87 (s, 3H), 2.5-2.2 (m, 2H). MS: 597 (M+1)$^+$.

Example 23. Preparation of (S)—N—((S)-1-(2-chlorophenyl)-2-(3,3-difluorocyclobutylamino)-2-oxoethyl)-3-(4-cyanopyridin-2-yl)-N-(3-fluorophenyl)-2-oxoimidazolidine-4-carboxamide (Single Enantiomer)—Compound 80

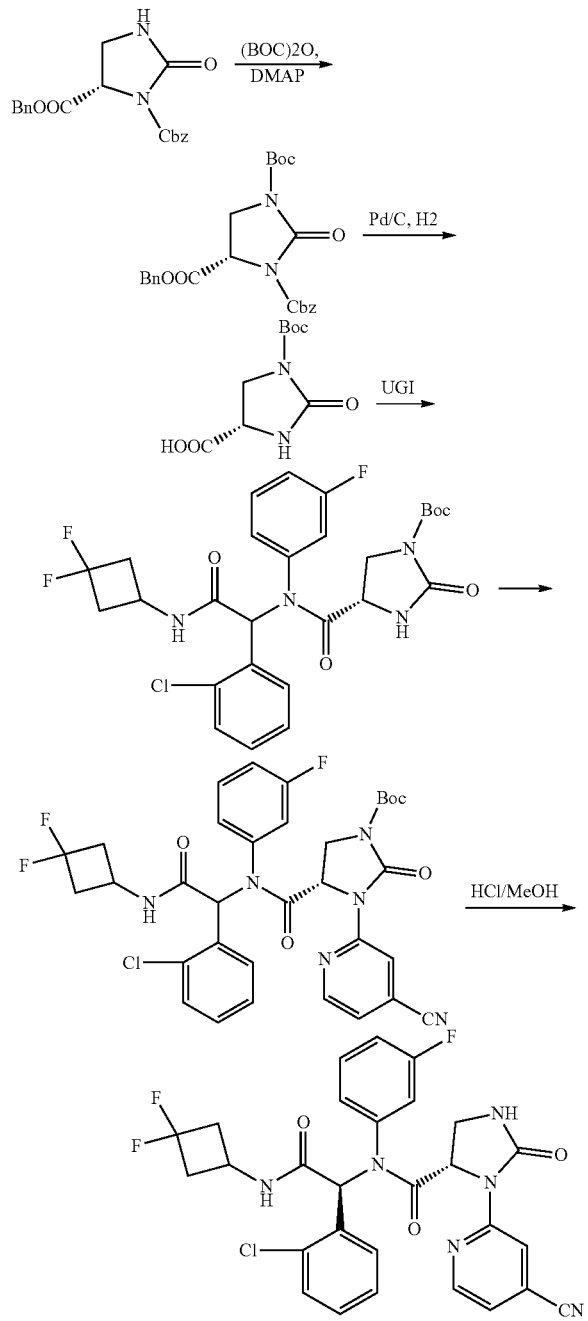

Step A: (S)-3,4-Dibenzyl 1-tert-butyl 2-oxoimidazolidine-1,3,4-tricarboxylate To a 25 mL-flask were added (S)-dibenzyl 2-oxoimidazolidine-1,5-dicarboxylate (40 mg, 0.11 mmol), (BOC)₂O (26 mg, 0.12 mmol), TEtOAc (0.06 mL, 0.3 mmol), DMAP (cat.) and CH$_2$Cl$_2$ (2 mL). The mixture was stirred overnight. The solvent was then removed in vacuo and the residue was purified by column chromatography to give the desired product. $^1$H NMR (400 MHz, CDCl$_3$): δ 7.39-7.27 (m, 10H), 5.24 (s, 2H), 5.16 (s, 2H), 4.67 (dd, J=10.2, 3.5 Hz, 1H), 3.94 (dd, J=11.1, 10.3 Hz, 1H), 3.74 (dd, J=11.2, 3.5 Hz, 1H), 1.51 (s, 9H).

Step B: (S)-1-(tert-Butoxycarbonyl)-2-oxoimidazolidine-4-carboxylic Acid

To a dry 50 mL-flask were added (S)-3,4-dibenzyl 1-tert-butyl 2-oxoimidazolidine-1,3,4-tricarboxylate (1.24 g, 2.73 mmol), Pd/C (10%, 200 mg) and MeOH (30 mL). The suspension was stirred overnight at room temperature under a hydrogen atmosphere. The reaction mixture was filtered, and the filtrate was concentrated in vacuo to afford the desired product. $^1$H NMR (400 MHz, DMSO-d$_6$): δ 6.06 (s, 2H), 4.31 (s, 1H), 4.25-3.94 (m, 2H), 1.52 (s, 9H).

Step C: (4S)-tert-Butyl 4-((1-(2-chlorophenyl)-2-(3,3-difluorocyclobutylamino)-2-oxoethyl)(3-fluorophenyl)carbamoyl)-2-oxoimidazolidine-1-carboxylate A mixture of 2-chlorobenzaldehyde (122 mg, 0.87 mmol) and 3-fluorobenzenamine (97 mg, 0.87 mmol) in MeOH (2 mL) was stirred at room temperature for 30 min. Then (S)-1-(tert-butoxycarbonyl)-2-oxoimidazolidine-4-carboxylic acid (200 mg, 0.87 mmol) was added and the reaction mixture was stirred for another 15 min followed by addition of 1,1-difluoro-3-isocyanocyclobutane (102 mg, 0.87 mmol). The reaction mixture was further stirred at room temperature overnight and then concentrated in vacuo. The residue was purified by a standard method to give the desired product. $^1$H NMR (400 MHz, CDCl$_3$): δ 7.46-6.59 (m, 8H), 6.45 (s, 1H), 4.41-4.04 (m, 2H), 4.01-3.78 (m, 1H), 3.64-3.30 (m, 1H), 2.92 (m, 2H), 2.71-2.27 (m, 2H), 1.46 (s, 9H). MS: 581 (M+1)$^+$.

Step D: (4S)-tert-Butyl 4-((1-(2-chlorophenyl)-2-(3,3-difluorocyclobutylamino)-2-oxoethyl)(3-fluorophenyl)carbamoyl)-3-(4-cyanopyridin-2-yl)-2-oxoimidazolidine-1-carboxylate To a 25 mL flask charged with 1,4-dioxane (4.5 mL) were added (4S)-tert-butyl 4-((1-(2-chlorophenyl)-2-(3,3-difluoro cyclo butylamino)-2-oxoethyl)(3-fluoro-phenyl)carbamoyl)-2-oxoimidazolidine-1-carboxylate (250 mg, 0.43 mmol), 2-bromoisonicotinonitrile (122 mg, 0.65 mmol), Cs$_2$CO$_3$ (281 mg, 0.862 mmol), Xant-Phos (25 mg, 0.043 mmol) and Pd$_2$(dba)$_3$ (40 mg, 0.043 mmol). The mixture was degassed and refilled with nitrogen, and then heated to 100° C. for 3 hr. The resulting mixture was cooled and filtered. The filtrate was concentrated in vacuo and the residue was purified by a standard method to give both epimers. The epimers were further separated by a standard method to give the desired product. $^1$H NMR (400 MHz, CDCl$_3$): δ 8.58 (s, 1H), 8.48 (t, J=5.9 Hz, 1H), 7.71 (d, J=8.4 Hz, 1H), 7.37-7.16 (m, 4H), 7.15-6.76 (m, 4H), 6.56-6.31 (m, 2H), 4.95-4.75 (m, 1H), 4.31 (s, 1H), 3.86 (dd, J=10.8, 5.1 Hz, 1H), 3.66 (m, 1H), 2.99 (m, 2H), 2.61-2.27 (m, 2H), 1.56 (s, 9H). MS: 683 (M+1)$^+$.

Step E: (S)—N—((S)-1-(2-Chlorophenyl)-2-(3,3-difluorocyclo butylamino)-2-oxoethyl)-3-(4-cyanopyridin-2-yl)-N-(3-fluorophenyl)-2-oxoimidazolidine-4-carboxamide To a solution of 2N HCl/MeOH (2 mL) at 0° C. was added 50 mg of (S)-tert-butyl-4-(((S)-1-(2-chlorophenyl)-2-(3,3- difluorocyclobutylamino)-2-oxoethyl)(3-fluorophenyl) carbamoyl)-3-(4-cyanopyridin-2-yl)-2-oxoimidazolidine-1-carboxylate. The reaction mixture was warmed to room temperature and stirred for 5 hr. The solvent was removed in vacuo and the residue was purified by a standard method to give the desired product. $^1$H NMR (400 MHz, CD$_3$OD): δ 8.50 (d, J=4.5 Hz, 1H), 7.65 (d, J=8.6 Hz, 1H), 7.50-6.81 (m, 8H), 6.47 (d, J=11.6 Hz, 1H), 5.04-4.92 (m, 1H), 4.22 (m, 1H), 3.59-3.46 (m, 1H), 3.39 (dd, J=9.9, 4.5 Hz, 1H), 2.91 (m, 2H), 2.63-2.36 (m, 2H). MS: 583 (M+1)$^+$.

Example 24. Preparation of (4S)—N-(1-(2-chlorophenyl)-2-(3,3-difluorocyclobutyl-amino)-2-oxoethyl)-3-(4-cyanopyridin-2-yl)-N-(3-fluorophenyl)-1-(2-hydroxyeth-yl)-2-oxoimidazolidine-4-carboxamide (Racemic)

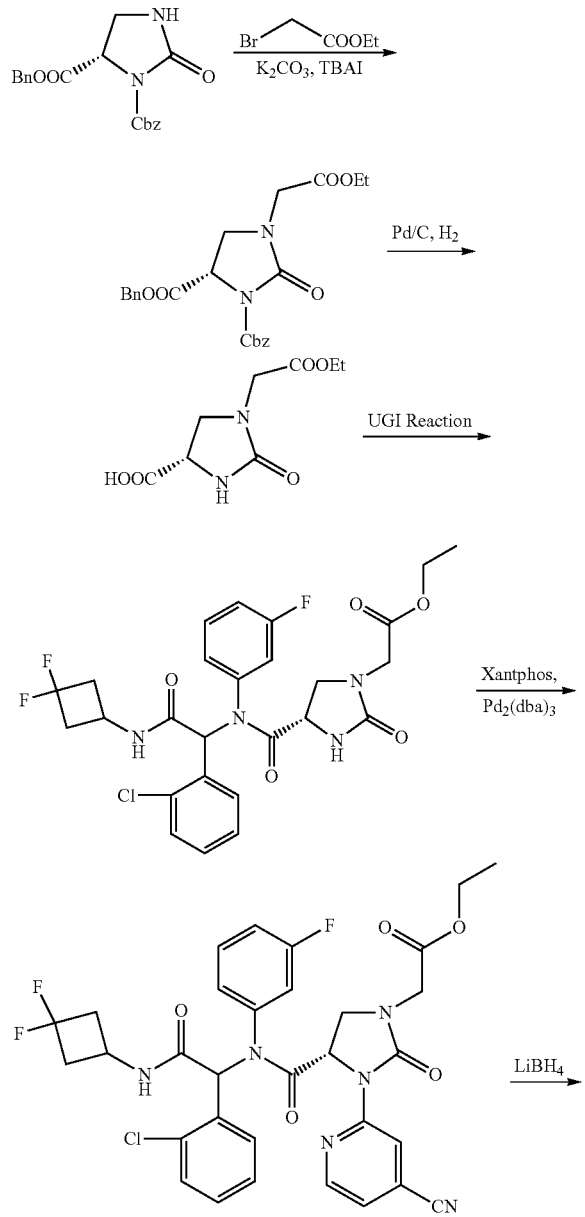

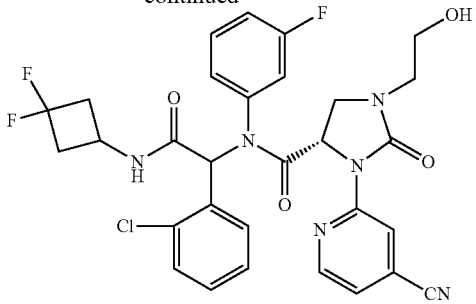

Step A: (S)-Dibenzyl 3-(2-ethoxy-2-oxoethyl)-2-oxoimidazolidine-1,5-dicarboxylate To a dry 50 mL-flask charged with DME (5 mL) were added (S)-dibenzyl 2-oxoimidazolidine-1,5-dicarboxylate (200 mg, 0.56 mmol), K$_2$CO$_3$ (156 mg, 1.13 mmol), and ethyl 2-bromoacetate (0.13 mL, 1.13 mmol). The mixture was heated to reflux for 3 hr. The reaction mixture was cooled and filtered. The filtrate was concentrated in vacuo and the residue was purified by column chromatography to afford the desired product as a colorless oil. $^1$H NMR (400 MHz, CDCl$_3$): δ 7.45-7.25 (m, 10H), 5.41-5.05 (m, 4H), 4.80 (dd, J=10.2, 3.5 Hz, 2H), 4.29-4.08 (m, 3H), 3.90 (dd, J=12.2, 7.2 Hz, 2H), 3.45 (dd, J=9.2, 3.5 Hz, 1H), 1.28 (td, J=7.1, 2.1 Hz, 3H).

Step B: (S)-1-(2-Ethoxy-2-oxoethyl)-2-oxoimidazolidine-4-carboxylic Acid

To a dry 50 mL-flask were added (S)-dibenzyl 3-(2-ethoxy-2-oxoethyl)-2-oxoimidazolidine-1,5-dicarboxylate (170 mg, 0.386 mmol), Pd/C (10%, 35 mg) and MeOH (4 mL). The suspension was stirred at room temperature overnight under a hydrogen atmosphere. The reaction mixture was filtered, and the filtrate was concentrated in vacuo to afford the desired product as an off-white solid. $^1$H NMR (400 MHz, CD$_3$OD): δ 4.30 (dd, J=10.0, 4.8 Hz, 1H), 4.20 (q, J=7.1 Hz, 2H), 4.05-3.91 (m, 2H), 3.91-3.85 (m, 1H), 3.69 (dd, J=9.0, 4.8 Hz, 1H), 1.29 (t, J=7.1 Hz, 3H).

Step C: Ethyl 2-((4S)-4-((1-(2-chlorophenyl)-2-(3,3-difluorocyclobutylamino)-2-oxoethyl)(3-fluorophenyl)carbamoyl)-2-oxoimidazolidin-1-yl)acetate A mixture of 2-chlorobenzaldehyde (518 mg, 3.70 mmol) and 3-fluorobenzenamine (411 mg, 3.7 mmol) in MeOH (12 mL) was stirred at room temperature for 30 min. Then (S)-1-(2-ethoxy-2-oxoethyl)-2-oxoimidazolidine-4-carboxylic acid (800 mg, 3.7 mmol) was added and the reaction mixture was stirred for another 30 min, followed by addition of 1,1-difluoro-3-isocyanocyclobutane (600 mg, 3.7 mmol). The reaction mixture was stirred overnight and concentrated in vacuo. The residue was purified by a standard method to give the desired product. MS: 567: (M+1)$^+$.

Step D: Ethyl 2-((4S)-4-((1-(2-chlorophenyl)-2-((3,3-difluorocyclobutyl)amino)-2-oxoethyl)(3-fluorophenyl)carbamoyl)-3-(4-cyanopyridin-2-yl)-2-oxoimidazolidin-1-yl)acetate—Compound 94

To a 25 mL-flask were added ethyl 2-((4S)-4-((1-(2-chlorophenyl)-2-(3,3-difluorocyclobutylamino)-2-oxoethyl)

(3-fluoro-phenyl)carbamoyl)-2-oxoimidazolidin-1-yl)acetate (50 mg, 0.0882 mmol), 2-bromoisonicotinonitrile (21 mg, 0.115 mmol), Cs$_2$CO$_3$ (58 mg, 0.176 mmol), Xant-Phos (5.2 mg, 0.009 mmol), Pd$_2$(dba)$_3$ (8.2 mg, 0.009 mmol) and 1,4-dioxane (1 mL). The mixture was degassed and refilled with nitrogen, and then heated to 100° C. for 3 hr. The resulting mixture was cooled and filtered and then the filtrate was concentrated in vacuo. The residue was purified by a standard method to give both epimers. $^1$H NMR (400 MHz, CDCl$_3$): δ 8.63-8.57 (S, 1H), 8.55-8.38 (m, 1H), 7.63 (s, 1H), 7.46-6.84 (m, 8H), 6.45-6.37 (m, 1H), 6.22-5.94 (m, 1H), 5.06-4.77 (m, 1H), 4.43-4.37 (m, 1H), 4.32-4.20 (m, 1H), 4.21 (q, J=7.1 Hz, 2H), 3.82-3.46 (m, 3H), 3.12-2.82 (m, 2H), 2.66-2.25 (m, 2H), 1.29 (t, J=7.1 Hz, 3H). MS: 669 (M+1)$^+$.

Step E: (4S)—N-(1-(2-Chlorophenyl)-2-(3,3-difluorocyclobutyl-amino)-2-oxoethyl)-3-(4-cyanopyridin-2-yl)-N-(3-fluorophenyl)-1-(2-hydroxyeth-yl)-2-oxoimidazolidine-4-carboxamide—Compound 112

To a solution of ethyl 2-((4S)-4-((1-(2-chlorophenyl)-2-(3,3-difluorocyclobutylamino)-2-oxoethyl)(3-fluorophenyl) carbamoyl)-2-oxo-3-(pyrimidin-2-yl)imidazolidin-1-yl)acetate (100 mg, 0.155 mmol) in DME (2 mL) at 0° C. was added LiBH$_4$ (22 mg) in two portions. The mixture was stirred for 0.5 hr, then warmed to room temperature. The resulting mixture was stirred for another 2 hr and quenched with H$_2$O (2 mL) at 0° C. The resulting mixture was extracted with EtOAc (2×10 mL). The combined organic layers were combined, washed with brine, dried over anhydrous Na$_2$SO$_4$, and concentrated in vacuo. The residue was purified by a standard method to give the desired product. $^1$H NMR (400 MHz, CDCl$_3$): δ 8.62-8.55 (m, 2H), 7.63 (d, J=8.1 Hz, 1H), 7.40-6.85 (m, 8H), 6.47-6.2 (m, 2H), 4.90-4.69 (m, 1H), 4.30-4.15 (m, 1H), 3.87-3.72 (m, 2H), 3.71-3.19 (m, 5H), 3.08-2.85 (m, 2H), 2.63-2.35 (m, 2H). MS: 603 (M+1)$^+$.

The following compound was synthesized via the procedure set forth above, using the appropriate aldehyde, amine, carboxylic acid, isocyanide and halo-substituted aromatic ring or heterocyclic (heteroaromatic) ring using the reagents and solvents set forth above, and purified via standard methods.

Ethyl 2-((4S)-4-((1-(2-chlorophenyl)-2-((3,3-difluorocyclobutyl)amino)-2-oxoethyl)(3-fluorophenyl) carbamoyl)-3-(4-cyanopyrimidin-2-yl)-2-oxoimidazolidin-1-yl)acetate (Racemic)—Compound 111

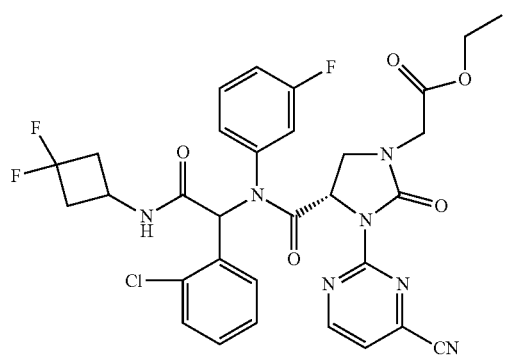 [SMILES: CCOC(=O)CN1C[C@@H](C(=O)N(c2cccc(F)c2)C(C(=O)NC2CC(F)(F)C2)c2ccccc2Cl)N(c2nccc(C#N)n2)C1=O]

$^1$H NMR (400 MHz, CDCl$_3$): δ 8.90-8.82 (m, 1H), 7.62-7.57 (m, 1H), 7.46-6.82 (m, 8H), 6.52-6.48 (m, 1H), 6.15-5.85 (m, 2H), 4.88-4.82 (m, 1H), 4.45-4.35 (m, 1H), 4.32-4.13 (m, 2H), 3.86-3.46 (m, 3H), 3.05-2.85 (m, 2H), 2.56-2.32 (m, 2H), 1.29 (t, J=7.1 Hz, 3H). MS: 670 (M+1)$^+$.

Example A: In Vitro Assays for IDH1m (R132H or R132C) Inhibitors

A test compound is prepared as 10 mM stock in DMSO and diluted to 50× final concentration in DMSO, for a 50 μl reaction mixture. IDH enzyme activity converting alpha-ketoglutarate to 2-hydroxyglutaric acid is measured using a NADPH depletion assay. In the assay the remaining cofactor is measured at the end of the reaction with the addition of a catalytic excess of diaphorase and resazurin, to generate a fluorescent signal in proportion to the amount of NADPH remaining. IDH1-R132 homodimer enzyme is diluted to 0.125 μg/ml in 40 μl of Assay Buffer (150 mM NaCl, 20 mM Tris-Cl pH 7.5, 10 mM MgCl$_2$, 0.05% BSA, 2 mM b-mercaptoethanol); 1 μl of test compound dilution in DMSO is added and the mixture is incubated for 60 minutes at room temperature. The reaction is started with the addition of 10 μl of Substrate Mix (20 μl NADPH, 5 mM alpha-ketoglutarate, in Assay Buffer) and the mixture is incubated for 90 minutes at room temperature. The reaction is terminated with the addition of 25 μl of Detection Buffer (36 μg/ml diaphorase, 30 mM resazurin, in 1× Assay Buffer), and is incubated for 1 minute before reading on a SpectraMax platereader at Ex544/Em590.

Compounds are assayed for their activity against IDH1 R132C following the same assay as above with the following modifications: Assay Buffer is (50 mM potassium phosphate, pH 6.5; 40 mM sodium carbonate, 5 mM MgCl$_2$, 10% glycerol, 2 mM b-mercaptoethanol, and 0.03% BSA). The concentration of NADPH and alpha-ketoglutarate in the Substrate Buffer is 20 μM and 1 mM, respectively.

Representative compounds of formula I set forth in Table 1 were tested in this assay or a similar assay and the results are set forth below in Table 2. As used in Table 2, "A" refers to an inhibitory activity against IDH1 R132H or IDH1 R132C with an IC$_{50}$≤0.1 μM; "B" refers to an inhibitory activity against IDH1 R132H or IDH1 R132C with an IC$_{50}$ between 0.1 μM and 0.5 μM; "C" refers to an inhibitory activity against IDH1 R132H or IDH1 R132C with an IC$_{50}$ between 0.5 μM and 1 μM; "D" refers to an inhibitory activity against IDH1 R132H or IDH1 R132C with an IC$_{50}$ between 1 μM and 2 μM.

TABLE 2

| | Inhibitory Activities of Representative Compounds of formula I | | | |
|---|---|---|---|---|
| Cpd No | IDH R132C IC50 (uM) | IDH R132H IC50 (uM) | HT1080 IC50 (uM) | U87MG IC50 (uM) |
| 1 | A | A | A | B |
| 2 | D | B | | |
| 3 | B | B | B | |
| 4 | A | A | A | A |
| 5 | A | A | A | B |
| 6 | A | B | B | |
| 7 | A | A | A | A |
| 8 | B | C | | |
| 9 | A | A | A | A |
| 10 | B | B | | |
| 11 | B | B | | |

TABLE 2-continued

Inhibitory Activities of Representative Compounds of formula I

| Cpd No | IDH R132C IC50 (uM) | IDH R132H IC50 (uM) | HT1080 IC50 (uM) | U87MG IC50 (uM) |
|---|---|---|---|---|
| 12 | A | B | B | |
| 13 | C | C | | |
| 14 | A | A | A | B |
| 15 | A | A | B | B |
| 16 | B | B | B | C |
| 17 | B | B | C | D |
| 18 | A | A | A | A |
| 19 | B | C | | |
| 20 | A | A | B | B |
| 21 | A | A | A | B |
| 22 | B | B | | |
| 23 | A | B | B | B |
| 24 | C | D | | |
| 25 | B | C | | |
| 26 | A | B | B | |
| 27 | A | A | | |
| 28 | A | B | A | |
| 29 | A | A | | A |
| 30 | A | A | | B |
| 31 | A | B | C | |
| 32 | B | D | | |
| 33 | A | A | A | B |
| 34 | A | B | C | |
| 35 | A | B | B | |
| 36 | B | B | | |
| 37 | A | A | A | A |
| 38 | C | D | | |
| 39 | C | D | | |
| 40 | A | A | B | B |
| 41 | A | B | C | |
| 42 | B | C | | |
| 43 | A | A | A | A |
| 44 | B | B | | |
| 45 | A | A | B | B |
| 46 | C | D | | |
| 47 | A | A | A | B |
| 48 | A | A | B | B |
| 49 | A | A | B | B |
| 50 | C | D | | |
| 51 | A | B | B | B |
| 52 | A | A | | |
| 53 | A | A | A | A |
| 54 | B | B | | |
| 55 | A | A | A | A |
| 56 | A | A | | |
| 57 | B | C | | |
| 58 | A | A | A | A |
| 59 | B | C | | |
| 60 | B | B | | |
| 61 | B | B | | |
| 62 | A | B | | |
| 63 | A | A | A | A |
| 64 | A | A | A | A |
| 68 | A | A | A | A |
| 69 | A | A | A | A |
| 70 | A | A | A | A |
| 71 | A | A | A | A |
| 72 | A | A | A | A |
| 73 | A | A | A | A |
| 74 | A | A | A | A |
| 75 | A | A | A | A |
| 76 | A | A | A | A |
| 77 | A | A | A | A |
| 78 | A | A | A | A |
| 79 | A | A | A | A |
| 80 | A | A | A | A |
| 81 | A | A | A | A |
| 82 | A | A | A | A |
| 83 | A | A | A | A |
| 84 | A | A | A | B |
| 85 | A | A | A | A |
| 86 | A | A | A | A |
| 87 | A | A | A | A |
| 88 | A | A | A | A |
| 89 | A | A | A | A |
| 90 | A | A | A | A |
| 91 | A | A | A | A |
| 92 | A | A | A | A |
| 93 | A | A | A | A |
| 94 | A | A | A | A |
| 95 | A | A | A | A |
| 96 | A | A | A | A |
| 97 | A | A | A | A |
| 98 | A | A | A | A |
| 99 | A | A | A | A |
| 100 | A | A | A | A |
| 101 | A | A | A | A |
| 102 | A | A | A | B |
| 103 | A | A | A | B |
| 104 | A | A | A | A |
| 105 | A | A | A | A |
| 106 | A | A | A | A |
| 107 | A | A | A | A |
| 108 | A | A | A | A |
| 109 | A | A | A | B |
| 110 | A | A | A | A |
| 111 | A | A | A | A |
| 112 | A | A | A | A |
| 113 | A | A | A | A |
| 114 | A | A | A | A |
| 115 | A | A | A | A |
| 116 | A | A | A | B |
| 117 | A | A | A | A |
| 118 | A | A | A | A |
| 119 | A | A | A | B |
| 120 | A | A | A | B |
| 121 | A | A | A | A |
| 122 | A | A | A | B |
| 123 | A | A | A | A |
| 124 | A | A | A | A |
| 125 | A | A | A | A |
| 126 | A | A | A | B |
| 127 | A | A | A | A |
| 128 | A | A | A | A |
| 129 | A | A | A | A |
| 130 | A | A | A | A |
| 131 | A | A | A | A |
| 132 | A | A | A | A |
| 133 | A | A | A | A |
| 134 | A | A | A | A |
| 135 | A | A | A | A |
| 136 | A | A | A | A |
| 137 | A | A | A | A |
| 138 | A | A | A | A |
| 139 | A | A | A | A |
| 140 | A | A | A | A |
| 141 | A | A | A | A |
| 142 | A | A | A | A |
| 143 | A | A | A | A |
| 144 | A | A | A | A |
| 145 | A | A | A | A |
| 146 | A | A | A | A |
| 147 | A | A | A | A |
| 148 | A | A | A | A |
| 149 | A | A | A | A |
| 150 | A | A | A | A |
| 151 | A | A | A | A |
| 152 | A | A | A | A |
| 153 | A | A | A | A |
| 154 | A | A | A | A |
| 155 | A | A | A | A |
| 156 | A | A | A | A |
| 157 | A | A | A | A |
| 158 | A | A | A | A |

TABLE 2-continued

Inhibitory Activities of Representative Compounds of formula I

| Cpd No | IDH R132C IC50 (uM) | IDH R132H IC50 (uM) | HT1080 IC50 (uM) | U87MG IC50 (uM) |
|---|---|---|---|---|
| 159 | A | A | A | A |
| 160 | A | A | A | A |
| 161 | A | A | A | A |
| 162 | A | A | A | A |
| 163 | A | A | A | A |
| 164 | A | A | A | A |
| 165 |   | A | A | A |
| 166 | A | A | A | A |
| 167 |   | A | A | A |
| 168 | A | A | A | A |
| 169 |   | A | A | A |
| 170 |   | A | A | A |
| 171 |   | A | A | A |
| 172 |   | A | A | A |
| 173 |   | A | A | A |
| 174 | A | A | A | A |
| 175 | A | A | A | A |
| 176 | A | A | A | A |
| 177 | A | A | A | A |
| 178 | A | A | B | A |
| 179 | A | A | A | A |
| 180 | A | A | A | A |
| 181 | A | A | A | A |
| 182 | A | A | A | A |
| 183 |   | A | A | A |
| 184 | A | A | A | A |
| 185 | A | A | A | A |
| 186 | A | A | A | A |
| 187 | A | A | A | A |
| 188 | A | A | A | A |
| 189 |   | A | A | A |
| 190 | A | A | A | A |
| 191 | A | A | A | A |
| 192 |   | A | A | A |
| 193 | A | A | A | A |
| 194 |   | A | A | A |
| 195 |   | A | A | A |
| 196 |   | A | A | A |
| 197 | A | A | A | A |
| 198 | A | A | A | A |
| 199 | A | A | A | A |
| 200 | A | A | A | A |
| 201 | A | A | A | A |
| 202 |   | A | A | A |
| 203 |   | A | A | A |
| 204 | A | A | A | A |
| 205 | A | A | A | A |
| 206 |   | A | A | A |
| 207 | A | A | A | A |
| 208 | A | A | A | A |
| 209 | A | A | A | A |
| 210 | A | A | A | A |
| 211 | A | A | A | A |
| 212 | A | A | A | A |

Example B: Cellular Assays for IDH1m (R132H or R132C) Inhibitors

Cells (HT1080 or U87MG) are grown in T125 flasks in DMEM containing 10% FBS, 1× penicillin/streptomycin and 500 ug/mL G418 (present in U87MG cells only). They are harvested by trypsin and seeded into 96 well white bottom plates at a density of 5000 cell/well in 100 ul/well in DMEM with 10% FBS. No cells are placed in columns 1 and 12. Cells are incubated overnight at 37° C. in 5% $CO_2$. The next day test compounds are made up at 2× the final concentration and 100 ul are added to each cell well. The final concentration of DMSO is 0.2% and the DMSO control wells are plated in row G. The plates are then placed in the incubator for 48 hours. At 48 hours, 100 ul of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 ul of Promega Cell Titer Glo reagent is added to each well of media. The cell plate is then placed on an orbital shaker for 10 minutes and then allowed to sit at room temperature for 20 minutes. The plate is then read for luminescence with an integration time of 500 ms.

The $IC_{50}$ for inhibition of 2-HG production (concentration of test compound to reduce 2HG production by 50% compared to control) in these two cell lines for various compounds of formula I is set forth in Table 2 above. As used in Table 2, "A" refers to an $IC_{50}$ for inhibition of 2-HG production ≤0.1 μM; "B" refers to an $IC_{50}$ for inhibition of 2-HG production between 0.1 μM and 0.5 μM; "C" refers to an $IC_{50}$ for inhibition of 2-HG production between 0.504 and 1 μM; "D" refers to an $IC_{50}$ for inhibition of 2-HG production between 1 μM and 2 μM.

Example C: Metabolic Stabilities of Compounds of Formula I

Metabolic stabilities of compounds of formula I can be tested with the following assay and species specific liver microsomes (LM) extraction ratio (Eh) can be calculated:
1. Buffer A: 1.0 L of 0.1 M monobasic Potassium Phosphate buffer containing 1.0 mM EDTA; Buffer B: 1.0 L of 0.1 M Dibasic Potassium Phosphate buffer containing 1.0 mM EDTA; Buffer C: 0.1 M Potassium Phosphate buffer, 1.0 mM EDTA, pH 7.4 by titrating 700 mL of buffer B with buffer A while monitoring with the pH meter.
2. Reference compounds (Ketanserin) and test compounds spiking solution:
500 μM spiking solution: add 10 μL, of 10 mM DMSO stock solution into 190 μL, CAN; 1.5 μM spiking solution in microsomes (0.75 mg/mL): add 1.5 μL of 500 μM spiking solution and 18.75 μL of 20 mg/mL liver microsomes into 479.75 μL of Buffer C.
3. NADPH stock solution (6 mM) is prepared by dissolving NADPH into buffer C.
4. Dispense 30 μL 1.5× compound/liver microsome solution in 96-well plate and immediately add 135 μL ACN containing IS before adding 15 uL Buffer C to prepare real 0 minute samples.
5. Add 15 μL of NADPH stock solution (6 mM) to the wells designated as Time 30, and start timing.
6. At the end of incubation (0 min), add 135 μL of ACN containing the internal standard Osalmid) to all the wells (30 min, and 0 min). Then add 15 μL of NADPH stock solution (6 mM) to the wells designated as Time 0.
7. After quenching, centrifuge the reaction mixtures at 3220 g for 10 min.
8. Transfer 50 μL of the supernatant from each well into a 96-well sample plate containing 50 μL of ultra pure water (Millipore) for LC/MS analysis.

The invention claimed is:
1. A method of making a compound of structural formula (A) or a pharmaceutically acceptable salt, tautomer or hydrate thereof, wherein:

(A)

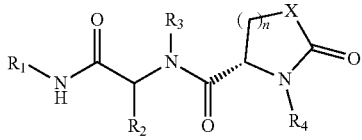

$R^1$ is optionally substituted $C_4$-$C_6$ carbocyclyl;
each $R^2$ and $R^3$ is independently selected from optionally substituted aryl or optionally substituted heteroaryl;
$R^4$ is optionally substituted aryl or optionally substituted heteroaryl,
n is 1 or 2; and
X is —$CH_2$—, O, —NH—, —CH(OH)—, or —CH(F)—,
the method comprising:
reacting a compound of formula B:

(B)

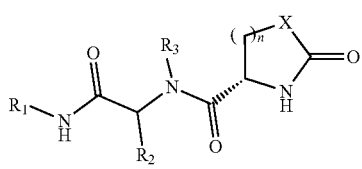

with $R^4$—Br under Buchwald conditions to provide the compound of structural formula (A).

2. The method of claim 1 wherein the Buchwald conditions comprise use of a palladium catalyst, a ligand and a base in an organic solvent.

3. The method of claim 2 wherein the solvent is dioxane, the palladium catalyst is $Pd_2(dba)_3$, the ligand is Xphos and the base is cesium carbonate.

4. A method of making a compound of structural formula (B) or a pharmaceutically acceptable salt, tautomer, or hydrate thereof, (B)

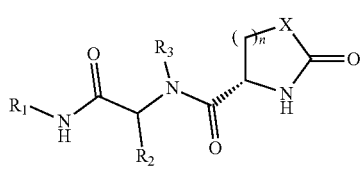

the method comprising:
reacting a compound of structural formula (C):

(C)

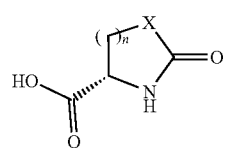

with $R^1NC$, $R^2CHO$ and $R^3$—$NH_2$ under Ugi coupling reaction conditions to provide the compound of structural formula (B).

5. The method of claim 4 wherein the Ugi coupling takes place in a solvent.

6. The method of claim 5 wherein the solvent is methanol.

* * * * *